(12) United States Patent
Bombrun et al.

(10) Patent No.: US 9,150,519 B2
(45) Date of Patent: Oct. 6, 2015

(54) 6-AMINO-PYRIMIDINE-4-CARBOXAMIDE DERIVATIVES AND RELATED COMPOUNDS WHICH BIND TO THE SPHINGOSINE 1-PHOSPHATE (S1P) RECEPTOR FOR THE TREATMENT OF MULTIPLE SCLEROSIS

(71) Applicant: MERCK SERONO SA, Coinsins, Vaud (CH)

(72) Inventors: Agnes Bombrun, Chambesy (CH); Matthias Schwarz, Gland (CH); Stefano Crosignani, St. Genis-Pouilly (FR); David Covini, Feigeres (FR); Delphine Marin, Arthaz-Pont-Notre Dame (FR)

(73) Assignee: MERCK SERONO SA, Coinsins, Vaud (CH)

( * ) Notice: Subject to any disclaimer, the term of this patent is extended or adjusted under 35 U.S.C. 154(b) by 169 days.

(21) Appl. No.: 13/711,893

(22) Filed: Dec. 12, 2012

(65) Prior Publication Data

US 2013/0109669 A1   May 2, 2013

Related U.S. Application Data

(62) Division of application No. 12/671,996, filed as application No. PCT/EP2008/059933 on Jul. 29, 2008, now Pat. No. 8,399,448.

(60) Provisional application No. 60/964,864, filed on Aug. 15, 2007.

(30) Foreign Application Priority Data

Aug. 8, 2007 (EP) .................................... 07113992

(51) Int. Cl.
| | | |
|---|---|---|
| *A61K 31/397* | (2006.01) | |
| *A61K 31/535* | (2006.01) | |
| *A61K 31/497* | (2006.01) | |
| *A61K 31/415* | (2006.01) | |
| *A61K 31/4164* | (2006.01) | |
| *C07D 239/42* | (2006.01) | |
| *C07D 413/12* | (2006.01) | |
| *C07D 401/12* | (2006.01) | |
| *C07D 403/12* | (2006.01) | |

(52) U.S. Cl.
CPC ............ *C07D 239/42* (2013.01); *C07D 401/12* (2013.01); *C07D 403/12* (2013.01); *C07D 413/12* (2013.01)

(58) Field of Classification Search
CPC .. C07D 239/42; C07D 413/12; C07D 401/12; C07D 403/12; A61K 31/397; A61K 31/535; A61K 31/497; A61K 31/415; A61K 31/4164
USPC .......... 514/210.2, 210.18, 235.8, 252.14, 256
See application file for complete search history.

(56) References Cited

U.S. PATENT DOCUMENTS

| 2004/0138257 A1 | 7/2004 | Bouchard et al. |
| 2013/0065858 A1 * | 3/2013 | Chen et al. ...................... 514/86 |

FOREIGN PATENT DOCUMENTS

| WO | WO 00/18738 | 4/2000 |
| WO | WO 03/105840 | 12/2003 |
| WO | WO 2005/037801 | 4/2005 |
| WO | WO 2005/066147 | 7/2005 |
| WO | WO 2006/053109 | 5/2006 |

OTHER PUBLICATIONS

Li, X. et al. "Luminescent pyrimidine hydrazide oligomers with peptide affinity" *Bioorganic & Medicinal Chemistry*, 2006, pp. 6075-6084, vol. 14, No. 17. XP-002468102.
Daves, G. D. et al. "Pyrimidines. II. Orotic Acid Analogs" *J. Org. Chem.*, 1961, pp. 2755-2763, vol. 26, XP-002468103.
Database Belstein, Accession No. BR 10576474, Miltschizky et al., *Heterocycles*, 2006, pp. 1-5, XP-002468104.
Database Belstein, Accession Nos. BR 797890, 790240, 786838, and 808565, Britkova et al., *Chem. Heterocycl. Compd.*, 1966, pp. 1-5, XP-002468106.
Written Opinion in International Application No. PCT/EP2008/059933, Oct. 9, 2008, pp. 1-8.

* cited by examiner

*Primary Examiner* — James O Wilson
*Assistant Examiner* — Ebenezer O Sackey
(74) *Attorney, Agent, or Firm* — Saliwanchik, Lloyd & Eisenschenk

(57) ABSTRACT

The invention relates to compounds of formula (I):

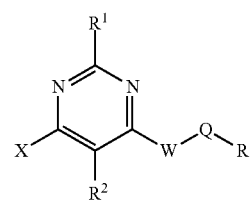

wherein X, W, Q, R, $R^1$ and $R^2$ have the meanings given in claim 1. The compounds are useful e.g. in the treatment of autoimmune disorders, such as multiple sclerosis.

4 Claims, No Drawings

6-AMINO-PYRIMIDINE-4-CARBOXAMIDE DERIVATIVES AND RELATED COMPOUNDS WHICH BIND TO THE SPHINGOSINE 1-PHOSPHATE (S1P) RECEPTOR FOR THE TREATMENT OF MULTIPLE SCLEROSIS

CROSS-REFERENCE TO RELATED APPLICATIONS

This application is a divisional of U.S. patent application Ser. No. 12/671,996, filed Feb. 3, 2010, now allowed, which is the U.S. national stage application of International Patent Application No. PCT/EP2008/059933, filed Jul. 29, 2008, which claims the benefit of U.S. Provisional Patent Application No. 60/964,864, filed Aug. 15, 2007, the disclosures of which are hereby incorporated by reference in their entirety, including all figures, tables and amino acid or nucleic acid sequences.

The present invention relates to pyrimidine derivatives, their use as medicaments and their use for treating multiple sclerosis and other diseases.

In particular, the invention relates to compounds of formula (I):

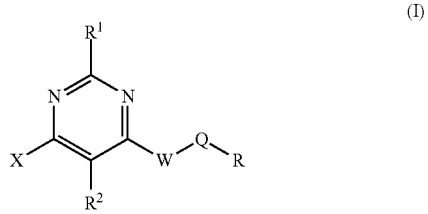

(I)

wherein

X is $NR^aR^b$, $SR^b$ or Hal, $R^a$ is H or A, $R^b$ is A,

A is branched or linear alkyl having 1 to 12 C-atoms, wherein one or more, preferably 1 to 7 H-atoms may be replaced by Hal, $OR^3$, $COOR^3$, CN or $N(R^3)_2$ and wherein one or more, preferably 1 to 7 non-adjacent $CH_2$-groups may be replaced by O, $NR^3$, S or $SO_2$ and/or by —CH=CH— groups, or denotes cycloalkyl or cycloalkylalkylene having 3-7 ring C atoms.

Hal is F, Cl, Br or I,

W is C=O, C=S, $SO_2$ or SO,

Q is $NR^3$, —O— or —S—,

R is H, A, Ar, Het,

Ar denotes a monocyclic or bicyclic, saturated, unsaturated or aromatic carbocyclic ring having 6 to 14 carbon atoms which may be unsubstituted or monosubstituted, disubstituted or trisubstituted by Hal, A, $OR^3$, $—[C(R^3)_2]_n—OR^3$, $N(R^3)_2$, $—[C(R^3)_2]n—N(R^3)_2$, $NO_2$, CN, $COOR^3$, $CF_3$, $OCF_3$, $CON(R^3)_2$, $NR^3COA$, $NR^3CON(R^3)_2$, $—[C(R^3)_2]_n$-Het, $—[C(R^3)_2]_n—Ar$, $—[C(R^3)_2]_n$-cycloalkyl, $—[C(R^3)_2]_n—CON(R^3)_2$, $—[C(R^3)_2]_n—COOR^3$, $—[C(R^3)_2]_n—NR^3—[C(R^3)_2]_n—CO_2R^3$, $—[C(R^3)_2]_n—NR^3—[C(R^3)_2]_n—OR^3$, $—SO_2—[C(R^3)_2]_n—CO_2R^3$, $—SO_2—N(R^3)_2—[C(R^3)_2]_n—CO_2R^3$, $—CO_2R^3$, $—[C(R^3)_2]_n—SO_2—$ $[C(R^3)_2]_n—CO_2R^3$, $—SO_2—[C(R^3)_2]_n—OR^3$, $—SO_2—N(R^3)_2—[C(R^3)_2]_n—$ $[C(R^3)_2]_n—SO_2—[C(R^3)_2]_n—OR^3$, $NR^3CON(R^3)_2$, $NR^3SO_2A$, $COR^3$, $SO_2N(R^3)_2$, $SO_2N(R^3)A$, SOA, $SONR^3A$, or $SO_2A$, and/or $—O[C(R^3)_2]_n—COOR^3$, Het denotes a monocyclic or bicyclic, saturated, unsaturated or aromatic heterocyclic ring having 1 to 4 N, O and/or S atoms which may be unsubstituted or monosubstituted, disubstituted or trisubstituted by Hal, A, $OR^3$, $—[C(R^3)_2]_n—OR^3$, $N(R^3)_2$, $—[C(R^3)_2]_n$, $—N(R^3)_2$, $NO_2$, CN, $COOR^3$, $CF_3$, $OCF_3$, $CON(R^3)_2$, $NR^3COA$, $NR^3CON(R^3)_2$, $—[C(R^3)_2]_n$—Het, $—[C(R^3)_2]_n—Ar$, $—[C(R^3)_2]_n$-cycloalkyl, $—[C(R^3)_2]_n—CON(R^3)_2$, $—[C(R^3)_2]_n—COOR^3$, $—[C(R^3)_2]$, $—NR^3—[C(R^3)_2]_n—CO_2R^3$, $—[C(R^3)_2]_n—NR^3—[C(R^3)_2]_n—OR^3$, $—SO_2—[C(R^3)_2]_n—CO_2R^3$, $—SO_2—N(R^3)_2—[C(R^3)_2]_n—CO_2R^3[C(R^3)_2]_n—SO_2—[C(R^3)_2]_n—CO_2R^3$, $—SO_2—[C(R^3)_2]_n—OR^3$, $—SO_2—N(R^3)_2—[C(R^3)_2]_nOR^3$, $—[C(R^3)_2]_n—SO_2—[C(R^3)_2]—OR^3$, $NR^3CON(R^3)_2$, $NR^3SO_2A$, $COR^3$, $SO_2N(R^3)_2—SO_2N(R^3)A$, SOA, $SONR^3A$, or $SO_2A$, and/or $—O[C(R^3)_2]_n—COOR^3$, $R^1$ denotes H or A, $R^2$ denotes H, A or Hal, $R^3$ is H or A, N is 0, 1, 2, 3, 4, 5, 6, 7 or 8, and pharmaceutically acceptable derivatives, solvates, tautomers, salts and stereoisomers thereof, including mixtures thereof in all ratios.

In a preferred embodiment, the invention relates to compounds of structure (I')

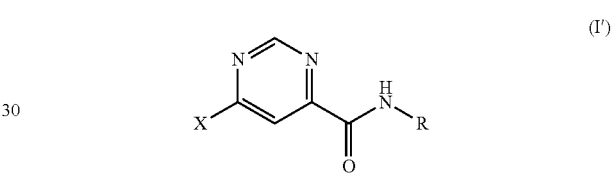

(I')

wherein

X and R are as above defined, and pharmaceutically acceptable derivatives, solvates, tautomers, salts and stereoisomers thereof, including mixtures thereof in all ratios.

Preferably, R in I' is Ar or Het.

In another preferred embodiment, the invention relates to compounds of Formula (I")

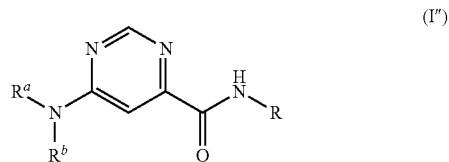

(I")

wherein $R^a$, $R^b$ and R are as above defined.

More particularly, $R^a$ is H, $(C_1-C_{12})$alkyl, $(C_1-C_{12})$alkylcycloalkyl, $(C_1-C_{12})$cycloalkyl, or $(C_1-C_{12})$alkyl-O-alkyl $R^b$ is $(C_1-C_{12})$alkyl, $(C_1-C_{12})$alkylcycloalkyl, $(C_1-C_{12})$cycloalkyl or $(C_1-C_{12})$alkyl-O-alkyl, R is Ar, Het, Ar, Het are as above defined and pharmaceutically acceptable derivatives, solvates, tautomers, salts and stereoisomers thereof, including mixtures thereof in all ratios.

In one embodiment, the invention relates to compounds of formula I, wherein Ar is substituted by an aminosulfonyl or a hydroxyl group.

In a preferred embodiment, the invention relates to compounds of formula I, wherein X is $NR^aR^b$ and $R^a$ is hydrogen, alkyl or cycloalkyl, $R^b$ is cycloalkyl, R is selected from 4-aminosulfonyl-2-methyl-phenyl, 4-aminosulfonyl-phenyl, 4-(2-hydroxyethyl)amino-sulfonyl-phenyl, 4-(2,3-dihydroxypropyl)aminosulfonyl-phenyl, 4-(2-methoxyethyl)aminosulfonyl-phenyl and 4-(ethylaminosulfonyl)-phenyl, W is CO, Q is $NR^3$, and $R^1$, $R^2$ are H.

In another preferred embodiment, the invention relates to compounds of formula I, wherein X is $NR^aR^b$, $R^a$ is alkyl, $R^b$ is cycloalkyl or alkyl, R is selected from 4-hydroxy-phenyl, 4 hydroxy-2-methyl-phenyl, W is CO, Q is $NR^3$ and $R^1$, $R^2$ are H.

In a very preferred embodiment, the invention relates compounds of formula I, wherein X is O, $R^b$ is cycloalkyl, R is selected from 4-hydroxyphenyl and 4-hydroxy-2-methyl-phenyl, W is CO, Q is $NR^3$ and $R^1$, $R^2$ are H.

In a more preferred embodiment, the invention relates to compounds of formula I, wherein X is $NR^aR^b$, $R^a$ is hydrogen or alkyl, $R^b$ is alkyl or cycloalkyl, R is selected from 1H-indazol-5-yl and 6-methyl-1H-indazol-5-yl, W is CO, Q is $NR^3$ and $R^1$, $R^2$ are H. Also compounds of Formula (I) wherein X is $OR^b$ are preferred.

In another embodiment, the invention relates to compounds of formula (I), wherein X is $NR^aR^b$, $R^a$ is alkyl, $R^b$ is alkyl or cycloalkyl, R is 4-(aminomethyl)phenyl, W is CO, Q is $NR^3$ and $R^1$, $R^2$ are H. Also compounds of formula (I) wherein $R^1$ is Hal are preferred.

In another embodiment, the invention relates to compounds of formula (I), wherein X is $NR^aR^b$, $R^a$ is hydrogen, $R^b$ is cycloalkyl, R is selected from 2-fluoro-4-hydroxy-phenyl, 2-chloro-4-hydroxyphenyl or 4-hydroxy-2-methyl-phenyl, W is CO, Q is $NR^3$ and $R^1$, $R^2$ are H.

More preferably, the invention relates to compounds of formula (I), wherein X is $NR^aR^b$, $R^a$ is hydrogen, $R^b$ is alkyl, R is selected from 4-hydroxy-napthyl, W is CO, Q is $NR^3$ and $R^1$, $R^2$ are H.

Most preferably, the invention relates to compounds of formula (I), wherein X is $NR^aR^b$, $R^a$ is hydrogen or alkyl, $R^b$ is alkyl, R is selected from quinolin-4-yl and pyridine-4-yl, W is CO, Q is $NR^3$ and $R^1$, $R^2$ are H.

In another embodiment, the invention relates to compounds of formula (I), wherein X is $NR^aR^b$, $R^a$ is alkyl, $R^b$ is alkyl or cycloalkyl, R is 4-(aminocarbonyl)phenyl, W is CO, Q is $NR^3$ and $R^1$, $R^2$ are H.

In another embodiment, the invention relates to compounds of formula (I), wherein X is $NR^aR^b$, $R^a$ is hydrogen, $R^b$ is alkyl, R is selected from 4-hydroxyphenyl, 4-hydroxy-3-methyl-phenyl, 3-chloro-4-hydroxy-phenyl, 2,3-dimethyl-phenyl, 2,5-dimethyl-phenyl or 3-fluoro-4-hydroxy-phenyl, W is CO, Q is $NR^3$ and $R^1$, $R^2$ are H.

In another embodiment, the invention relates to compounds of formula (I) having a EC50 in GTPγS for the binding to the $S1P_1$ receptor of less than about 5 μM.

In another embodiment, the invention relates to a pharmaceutical composition comprising at least one compound according to one or more of Formulae I, I' and I" and/or pharmaceutically usable derivatives, tautomers, salts, solvates and stereoisomers thereof, including mixtures thereof in all ratios, and at least one further active ingredient.

In another embodiment, the invention relates to the use of compounds according to one or more of Formulae I, I' and I", and pharmaceutically usable derivatives, salts, tautomers, solvates and stereoisomers thereof, including mixtures thereof in all ratios, for the preparation of a medicament for the treatment and/or prophylaxis of diseases in which the inhibition, activation, regulation, and/or modulation of $S1P_1$ receptor signal transduction plays a role.

In another embodiment, the invention relates to the use of compounds of one or more of Formulae I, I' and I", wherein the sphingosine 1-phosphate-(1) associated disorder is an autoimmune disorder or condition associated with an overactive immune response.

The compounds of formula I are preferably binding on receptors for sphingosine 1-phosphate (S1P). S1P is a bioactive sphingolipid metabolite that is secreted by hematopoietic cells and stored and released from activated platelets. It acts as an agonist on a family of G protein-coupled receptors (GPCR). Five sphingosine 1-phosphate receptors have been identified ($S1P_1$, $S1P_2$, $S1P_3$, $S1P_4$, and $S1P_5$, also known as endothelial differentiation genes, which are Edg1, Edg5, Edg3, Edg6 and Edg8 respectively), that have widespread cellular and tissue distribution and are well conserved in human and rodent species.

S1P is involved in a number of cellular functions such as survival, proliferation and immunological responses. The compounds of the present invention are preferably acting as $S1P_1$/Edg1 receptor agonists and thus have immunosuppressive activities by modulating leukocyte trafficking, sequestering lymphocytes in secondary lymphoid tissues, and interfering with cell-cell interactions required for an efficient immune response. The invention is also directed to pharmaceutical compositions containing such compounds and methods of treatment or prevention.

FTY720 or fingolimod, a non selective S1P1 agonist, exerts immunosuppressive activity and shows therapeutic effects in the treatment of relapsing-remitting multiple sclerosis. Numerous publications have been already published using this compound: Cyster JG Annu Rev Immunol 23:127-59, 2005, Rosen H Nat Rev Immunol 5:560-570, 2005, Rosen H Trends Immunol 28:102-107, 2007, Yopp AC Clin Transplant 20:788-795, 2006, Kappos L N Engl J Med 355:1124-1140, 2006, Massberg S N Engl J Med 355:1088-1089, 2006.

Immunosuppressive agents are further useful in a wide variety of autoimmune and chronic inflammatory diseases, including systemic lupus erythematosus, chronic rheumatoid arthritis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves ophthalmopathy, atopic dermatitis and asthma. They are also useful as part of chemotherapeutic regimens for the treatment of cancers, lymphomas and leukemias.

It has been found that the compounds of the present invention are selective $S1P_1$ agonists with improved pharmacological and/or other properties.

Thus, the present invention preferably comprises compounds, which are agonists of the $S1P_1$/Edg1 receptor, especially having selectivity over the $S1P_3$/Edg3 receptor. An $S1P_1$/Edg1 receptor selective agonist has advantages over current therapies and extends the therapeutic window of lymphocyte sequestration agents, allowing better tolerability with higher dosing and thus improving efficacy.

The term "selectivity" is taken to mean, $IC_{50}$ of the compounds toward the receptor $S1P1/Edg_1$ substantially higher than $IC_{50}$ toward the receptor $S1P_3/Edg3$, for instance, 10 to $10^7$ fold higher and more preferably $10^3$ to $10^7$ fold higher.

The invention further relates to the manufacture of a medicament for the improvement of vascular function, either alone or in combination with other active compounds or therapies.

The pyrimidine compounds according to formula I may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The following abbreviations refer respectively to the definitions below: aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), BOC (tert-butoxy-carbonyl), CBZ (carbobenzoxy), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethylcarbodiimide), ESI (Electrospray ionization), EtOAc (ethyl acetate), $Et_2O$ (diethyl ether), EtOH (ethanol), FMOC (fluorenylmethyloxycarbonyl), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), $K_2CO_3$ (potassium carbonate), LC (Liquid Chromatography), MeOH (methanol), $MgSO_4$ (magnesium sulfate), MS (mass spectrometry), MTBE (Methyl tert-butyl ether), Mtr. (4-Methoxy-2,3,6-trimethylbenzensulfonyl), $NaHCO_3$ (sodium bicarbonate), $NaBH_4$ (sodium borohydride), NMM (N-methyl morpholine), NMR (Nuclear Magnetic Resonance), POA (phenoxyacetate), PyBOP® (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoroborate), TEA (triethylamine), TFA (trifluoroacetic acid), THF (tetrahydrofuran), TLC (Thin Layer Chromatography), UV (Ultraviolet).

Depending on the nature of X, W, Q, $R^1$, $R^2$ and R in Formula I, different synthetic strategies may be selected for the synthesis of compounds of Formula I. In the process illustrated in the following schemes X, W, Q, $R^1$, $R^2$, $R^3$ and R are as above-defined in the description.

In general, the pyrimidine compounds according to Formula I of this invention may be prepared from readily available starting materials. If such starting materials are not commercially available they may be prepared by standard synthetic techniques. The following general methods and procedures described hereinafter in the examples may be employed to prepare compounds of Formula I.

Generally, compounds of Formula I can by prepared by coupling a pyrimidine carboxylic acid of Formula IV with an aryl amine of Formula V, wherein X, $R^1$, $R^2$, $R^3$ and R are defined as above, as outlined in Scheme 1. General protocols for such coupling are given below in the Examples, using conditions and methods well known to those skilled in the art to prepare an amide bond from an aryl amine and a carboxylic acid, with standard coupling agents, such as but not limited to 1-alkyl-2-chloropyridinium salt or preferably polymer-supported 1-alkyl-2-chloropyridinium salt (polymer-supported Mukaiyama's reagent), 1-methyl-2-chloropyridinium iodide (Mukaiyama's reagent), in the presence or absence of bases such as TEA, DIEA, NMM in a suitable solvent such as DCM, THF or DMF, at a temperature between 20° C. to 50° C., preferably at room temperature, for a few hours, e.g. one hour to 24 h. Alternatively, a carboxylic acid derivative (e.g. acyl chloride) may be coupled with the amine, using conditions and methods well known to those skilled in the art, in the presence of bases such as TEA, DIEA, NMM in a suitable solvent such as DCM, THF or DMF, at a temperature rising from 20° C. to 50° C., preferably at room temperature, for a few hours, e.g. one hour to 24 h.

Scheme 1

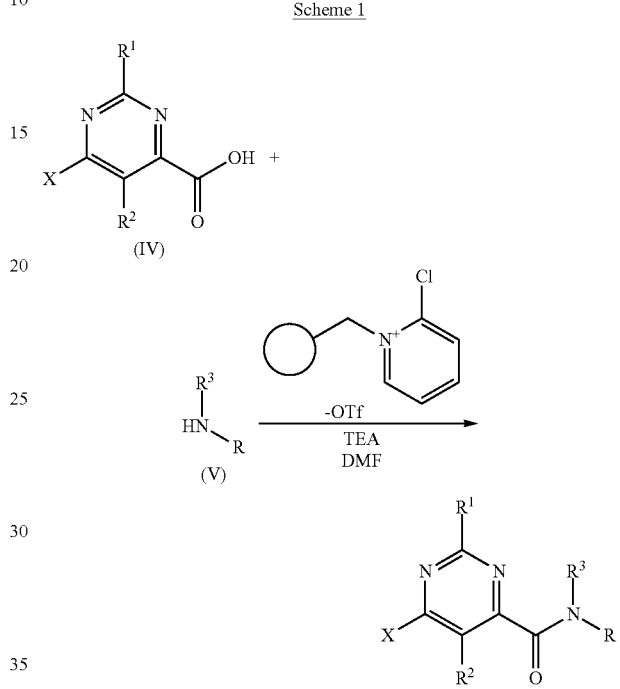

The compounds of Formula IV, wherein X, A, $R^1$ and $R^2$ are defined as above, can be obtained in a 2-step protocol as outlined in Scheme 2. The first step, preferably consists in the reaction of an amine or an alcohol with methyl 2,4-dichloropyrimidine-6-carboxylate (Apollo, OR2558), in the presence or absence of bases such as TEA, DIEA, NMM, sodium hydride, sodium (0) or sodium tert-butoxide, at a temperature between 20° C. to 50° C., preferably at room temperature, for a few hours, e.g. one hour to 24 h. The hydrolysis of the ester VII to give the compounds of Formula IV can be accomplished using conditions and methods well known to those skilled in the art, such as but not limited to the use of a metal hydroxide, e.g. lithium hydroxide, sodium hydroxide or potassium hydroxide, in a suitable solvent such as THF, methanol or water or mixtures thereof, at a temperature rising from 20° C. to 50° C., preferably at room temperature, for a few hours, e.g. one hour to 24 h.

Scheme 2

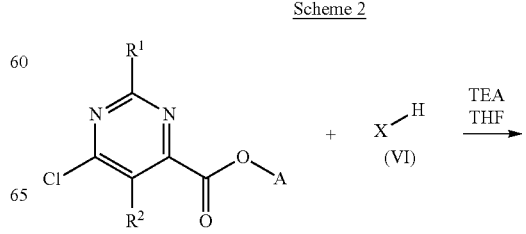

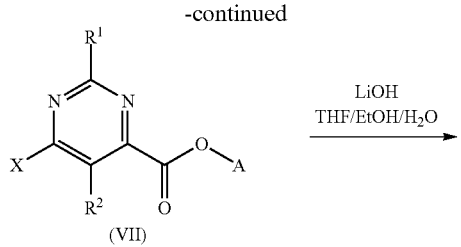

(VII)

LiOH
THF/EtOH/H₂O
→

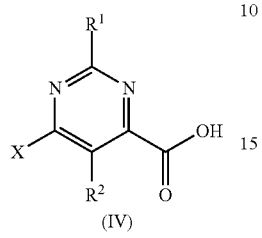

(IV)

Compounds of formula IV, wherein $R^1$ is H are preferably obtained according to scheme 2a. The first and third steps are carried out as described above. The reduction of the chloropyrimidine VIIa can be accomplished with an appropriate reducing agent, such as hydrogen (gas) in the presence of a suitable catalyst (e.g. palladium on charcoal) and a suitable base, such as TEA or DIEA, at a temperature between 20° C. to 50° C., preferably at room temperature, for a few hours, e.g. one hour to 24 h.

Scheme 2a

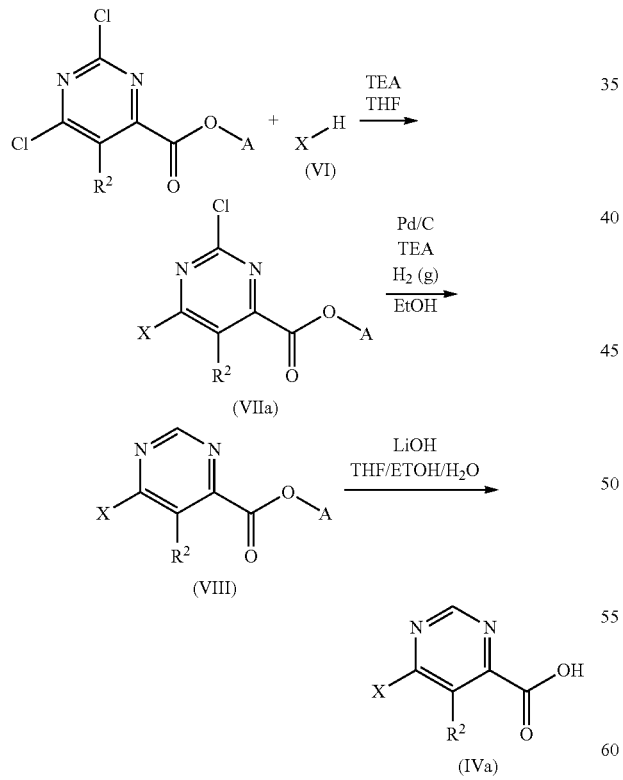

Compounds of Formula V, wherein R and $R^3$ are defined as above, are either commercially available or may be prepared by standard synthetic techniques, as hereinafter described in the examples, for example by reduction of the corresponding nitroaryl derivatives.

An alternative route for the preparation of compounds of Formula II, wherein $R^a$, $R^b$, $R^1$, $R^2$, $R^3$ and R are defined as above, may be the coupling of an amine of Formula VIa with the 6-chloropyrimidine-4-carboxamido derivatives of Formula IX, as outlined in Scheme 3, in the presence of a suitable solvent, such as ethanol, methanol or tetrahydrofuran, at a temperature between 20° C. and 200° C., or using possibly a microwave oven, for a time between 5 minutes and five days, preferably for 1 hour.

Scheme 3

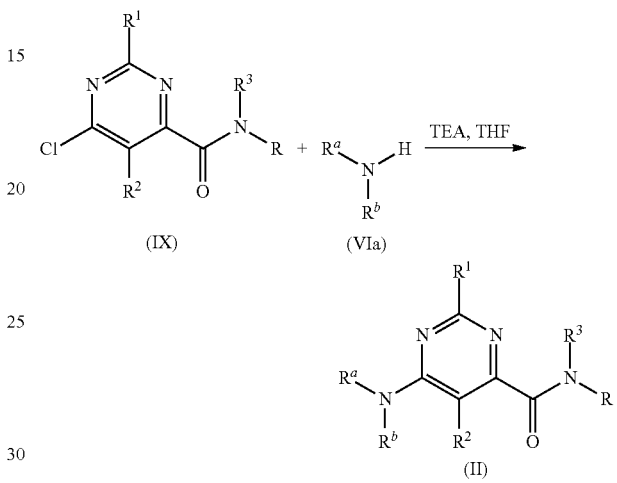

An alternative route for the preparation of compounds of Formula III, wherein $R^a$, $R^b$, $R^1$, $R^2$, $R^3$ and R are defined as above, may be the coupling of an alcohol of Formula VIb with the 6-chloropyrimidine-4-amido derivatives of Formula IX, as outlined in Scheme 4, in the presence of a suitable base, such as sodium (0) or sodium hydride, neat or using a suitable solvent such as THF or DMF.

Scheme 4

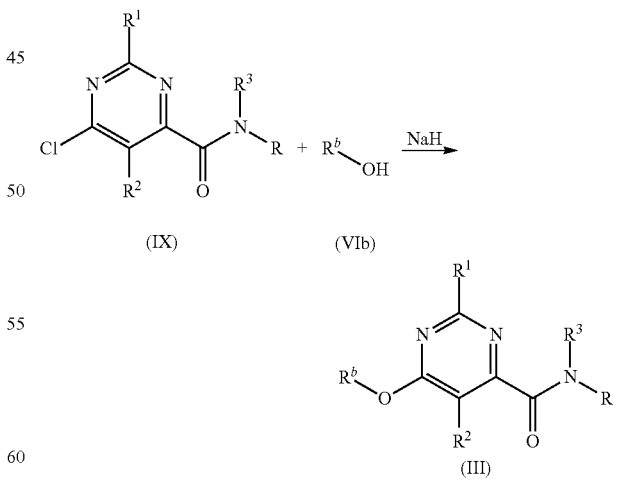

Compounds of Formula IX, wherein $R^1$, $R^2$, $R^3$, and R are defined as above, can be prepared by coupling of an arylamine of Formula V with 6-hydroxypyrimidine-4-carboxylic acid derivatives, prepared according to the method described by Daves, G. C.; Baiocchi, F.; Robins, R. K.; Cheng, C. C. in J.

Org. Chem. 1961, 26, 2755-2763", via conversion to an appropriate derivative, e.g. acyl chloride, followed by reaction with the arylamine in the presence or absence of bases such as TEA, DIEA, NMM in a suitable solvent such as DCM, THF or DMF, at a temperature between 20° C. to 50° C., preferably at room temperature, for a few hours, e.g. one hour to 24 h, as outlined in Scheme 5 below.

Alternatively, the reaction of 4-chloropyrimidine-2-carboxylic acid with an arylamine of Formula V may be obtained using standard coupling agents, such as but not limited to 1-methyl-2-chloropyridinium iodide (Mukaiyama's reagent), polymer-supported 1-alkyl-2-chloropyridinium salt (polymer-supported Mukaiyama's reagent), or others in the presence or absence of bases such as TEA, DIEA, NMM in a suitable solvent such as DCM, THF or DMF, at a temperature between 20° C. and 200° C., for a time between 5 minutes and five days.

Scheme 5

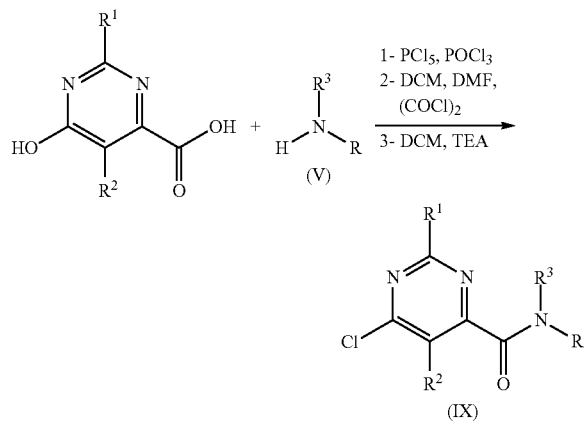

Compounds of Formula XII, wherein X, $R^1$, $R^2$, $R^3$, are defined as above and $R^x$, $R^y$ denote A or together with the N atom form a Het group, can be prepared by reductive amination of an aldehyde of Formula X with an amine of Formula XI (Scheme 6), using standard reductive amination reagents, such as but not limited to sodium borohydride, sodium triacetoxyborohydride, sodium cyanoborohydride or hydrogen (gas) in the presence of a suitable catalyst such as Palladium on charcoal or others, in the presence or absence of an acid such as acetic acid, a suitable solvent such as DCM, THF or toluene, at a temperature between 20° C. and 200° C., preferentially at RT, for a time between 5 minutes and five days, with or without isolation of the imine intermediate.

Scheme 6

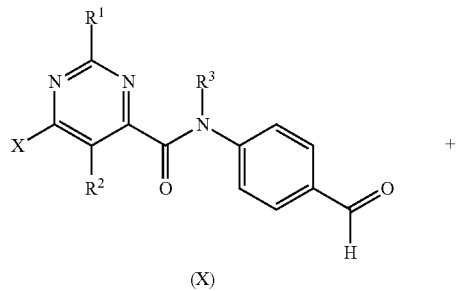

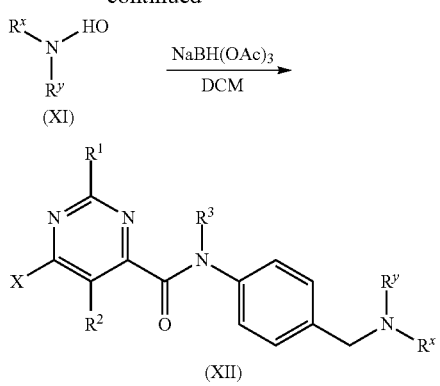

Compounds of Formula (X), wherein X, $R^1$, $R^2$, $R^3$, are defined as above, can be obtained as outlined in Scheme 7. The first step consists in the coupling of an acid of Formula (IV) with an arylamine of Formula (XIII) using standard coupling agents, such as but not limited to 1-methyl-2-chloropyridinium iodide (Mukaiyama's reagent), polymer-supported 1-alkyl-2-chloropyridinium salt (polymer-supported Mukaiyama's reagent), or others in the presence or absence of bases such as TEA, DIEA, NMM in a suitable solvent such as DCM, THF or DMF, at a temperature between about 20° C. and about 200° C., for a time between 5 minutes and five days. Alternatively, a carboxylic acid derivative (e.g. acyl chloride) may be coupled with the amine, using conditions and methods well known to those skilled in the art, in the presence of bases such as TEA, DIEA, NMM in a suitable solvent such as DCM, THF or DMF, at a temperature rising from about 20° C. to about 50° C., preferably at room temperature, for a few hours, e.g. one hour to 24 h. The second step consists in the oxidation of the compound (XIV) to give the corresponding aldehyde of Formula (X), which can be carried out with a number of oxidating agents, as is well known to those skilled in the art, such as but not limited to manganese dioxide, Dess-Martin periodinane, 2-iodoxybenzoic acid or polymer-supported 2-iodoxybenzoic acid.

Scheme 7

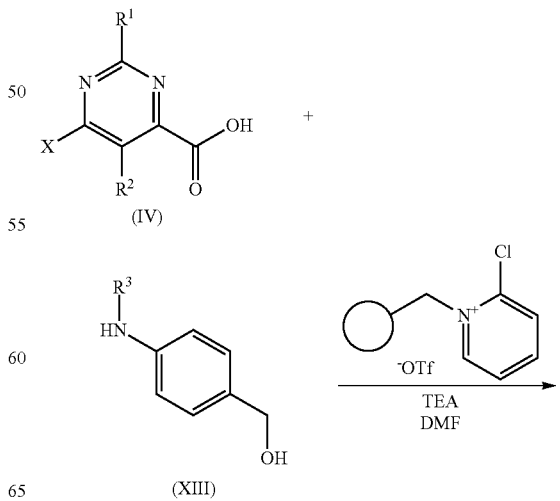

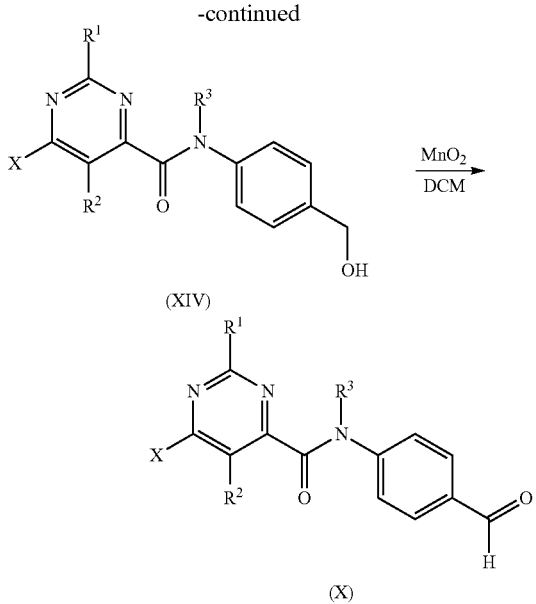

Sulfonamides of Formula (XVI) wherein X, $R^1$, $R^2$, $R^3$, $R^x$ and $R^y$ are defined as above, can be prepared by reaction of an amine of Formula (XI) with a sulfonyl chloride of Formula (XV) wherein $R^1$, $R^2$, $R^3$ and X are as defined above, in the presence of bases such as TEA, DIEA, NMM in a suitable solvent such as DCM, THF or DMF, at a temperature rising from 20° C. to 50° C., preferably at room temperature, for a few hours, e.g. one hour to 24 h.

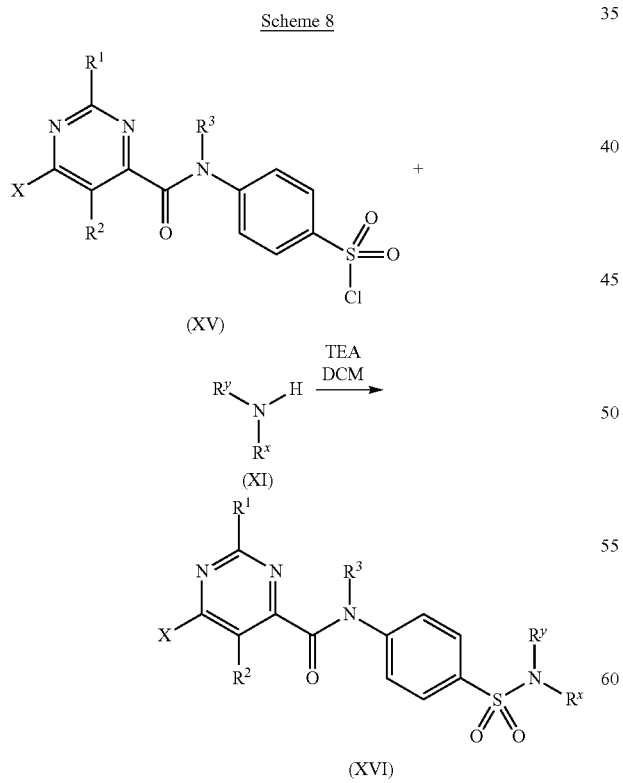

The sulfonyl chlorides of Formula (XVa) wherein X, $R^a$, $R^b$, $R^1$, $R^2$, $R^3$ are defined as above, can be prepared as outlined in Scheme 9. The first step consists in the coupling of an arylamine of Formula XVII with 6-hydroxypyrimidine-4-carboxylic acid derivatives, prepared according to the method described by Daves, G. C.; Baiocchi, F.; Robins, R. K.; Cheng, C. C. in J. Org. Chem. 1961, 26, 2755-2763, via conversion to an appropriate derivative, e.g. acyl chloride, followed by reaction with the arylamine in the presence or absence of bases such as TEA, DIEA, NMM in a suitable solvent such as DCM, THF or DMF, at a temperature between about 20° C. to about 50° C., preferably at room temperature, for a few hours, e.g. one hour to 24 h. The second step consists in the coupling of an amine of Formula (VIa) with the 6-chloropyrimidine-4-carboxamido derivatives of Formula (XVIII), in the presence of a suitable solvent, such as ethanol, methanol or tetrahydrofuran, at a temperature between about 20° C. and about 200° C., or using possibly a microwave oven, for a time between 5 minutes and five days, preferably for 1 hour. The last step consists in the chlorosulfonylation of the compound of Formula (XIX), which can be accomplished by reaction with chlorosulfonic acid in a suitable inert solvent such as DCM at a temperature between 0° C. and 100° C., preferentially at room temperature, for a time between 5 minutes and five days.

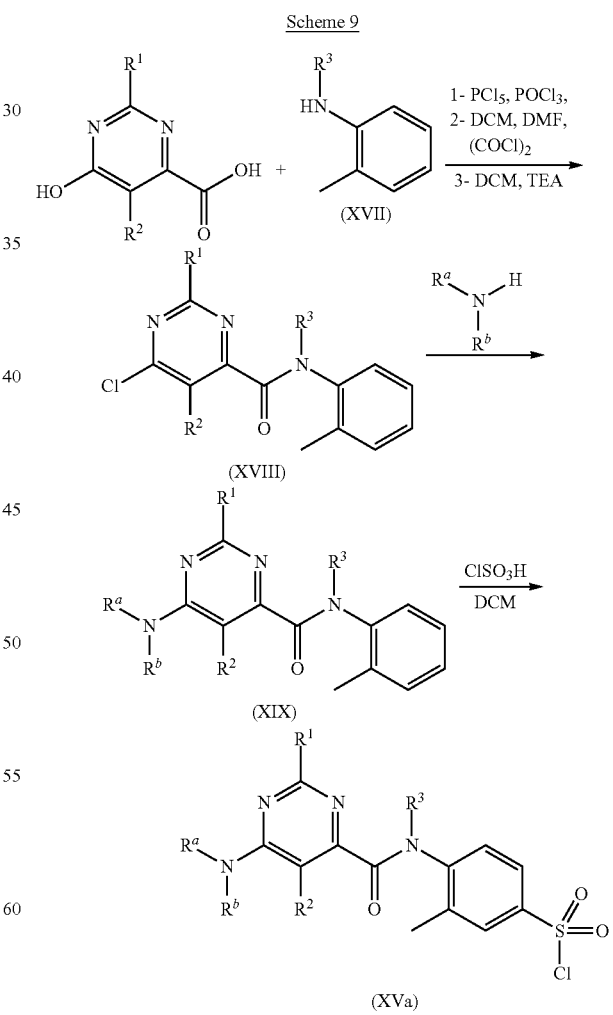

Alternatively, the sulfonamides of Formula (XVI) wherein $R^a$, $R^b$, $R^1$, $R^2$, $R^3$, $R^x$ and $R^y$ are defined as above can be prepared as outlined in Scheme 10. Starting from the Compounds of Formula (XVIII), which can be prepared as described above (Scheme 9), the first step consists in the reaction with chlorosulfonic acid in a suitable inert solvent such as DCM at a temperature between about 0° C. and about 100° C., preferentially at room temperature, for a time between 5 minutes and five days. The second step consists in the reaction with an amine of Formula (XI), in the presence of bases such as TEA, DIEA, NMM in a suitable solvent such as DCM, THF or DMF, at a temperature rising from about 20° C. to about 50° C., preferably at room temperature, for a few hours, e.g. one hour to 24 h. The last step consists in the reaction of the compounds of Formula (XXI) with an amine of Formula (VIa) in the presence of a suitable solvent, such as ethanol, methanol or tetrahydrofuran, at a temperature between about 20° C. and about 200° C., or using possibly a microwave oven, for a time between 5 minutes and five days, preferably for 1 hour.

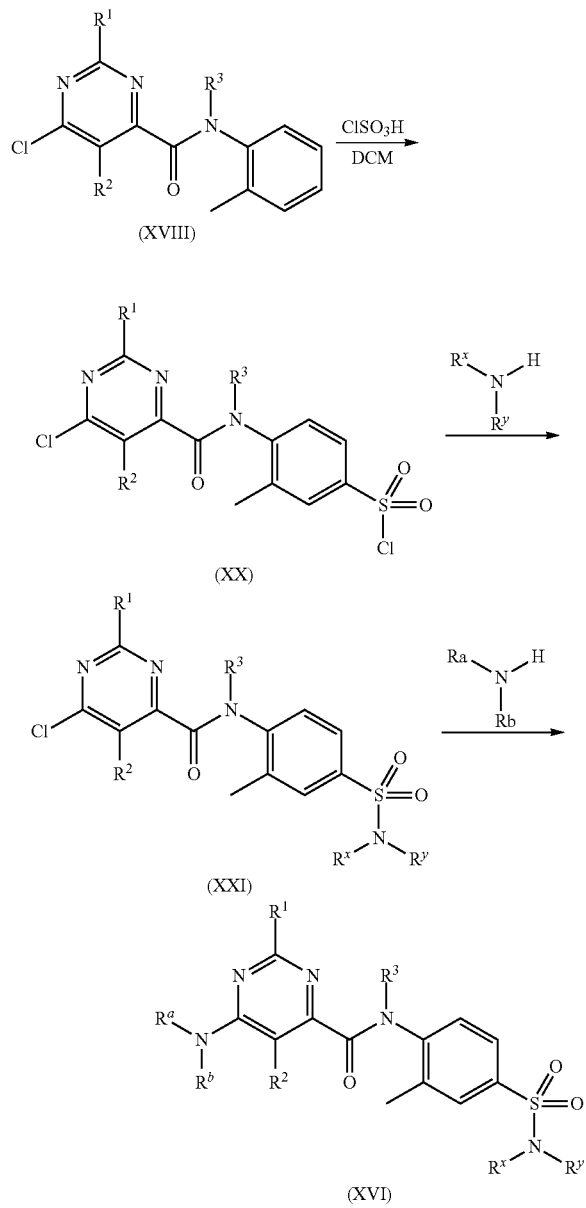

The above set out general synthetic methods may be modified for the obtention of compounds of Formula (I), since various suitable methods of preparation known by a person skilled in the art are available.

According to a further general process, compounds of Formula (I), (II), (III) (XII) and (XVI) can be converted to alternative compounds of Formula (I), (II) (III), (XII) and (XVI), employing suitable interconversion techniques well known by a person skilled in the art.

Suitable methods of preparation for the compounds and intermediates of the invention as known by a person skilled in the art should be used. In general, the synthesis pathways for any individual compound of Formula I will depend on the specific substituents of each molecule and upon the ready availability of intermediates necessary; again such factors being appreciated by those of ordinary skill in the art.

Compounds of this invention can be isolated in association with solvent molecules by crystallization through evaporation of an appropriate solvent. The pharmaceutically acceptable acid addition salts of the compounds of Formula I, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula I, which contain an acid center, with a suitable base. Both types of salts may be formed or interconverted preferably using ion-exchange resin techniques.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of the formula I can furthermore be obtained by liberating compounds of the formula I from one of their functional derivatives by treatment with a solvolysing or hydrogenolysing agent.

Preferred starting materials for the solvolysis or hydrogenolysis are those which conform to the formula I, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula I, but carry a —COOR" group, in which R" denotes a hydroxylprotecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group"

is to be understood in the broadest sense in connection with the present process. It includes acyl groups derived from aliphatic, araliphatic, aromatic or hetero-cyclic carboxylic acids or sulfonic acids, and, in particular, alkoxy-carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxy-carbonyl) and 2-iodoethoxycarbonyl; aralkoxycarbonyl, such as CBZ ("carbo-benz-oxy"), 4-methoxybenzyloxycarbonyl and FMOC; and aryl-sulfonyl, such as Mtr. Preferred amino-protecting groups are BOC and Mtr, further-more CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitro-benzoyl, p-toluenesulfonyl, tert-butyl and acetyl, where benzyl and tert-butyl are particularly preferred.

The compounds of the formula (I) are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OBut and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, tri-fluoro-methylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using LiOH, NaOH or KOH in water, water/THF, water/THF/ethanol or water/dioxane, at temperatures between 0 and 100° C.

Free amino groups can furthermore be acylated in a conventional manner using an acid chloride or anhydride or alkylated using an unsubstituted or substituted alkyl halide or reacted with $CH_3$—C(=NH)—OEt, advantageously in an inert solvent, such as dichloromethane or THF and/or in the presence of a base, such as triethylamine or pyridine, at temperatures between −60° C. and +30° C.

Therefore, the invention also relates to the preparation of the compounds of formula (I), and salts thereof, characterized in that a) a compound of formula A

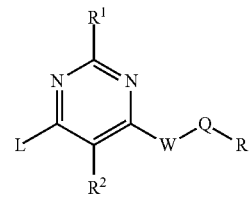

A wherein $R^1$, $R^2$, W, Q, R have the meanings given above and L is a leaving group, such as Cl, Br, I, phenylsulfonate, tosylate, besylate, mesylate or triflate, is reacted with a compound of formula XH, wherein X is as defined above, preferably in the presence of a suitable base, such as an amine like TEA, DIEA, NMM, or an alkalicarbonate, such as sodium- or potassiumcarbonate or b) a compound of formula B

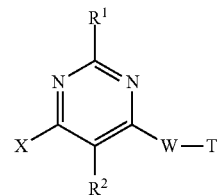

B wherein X, $R^1$, $R^2$ and W have the meanings given above and T is OH, OA, Cl, Br or another leaving group, such as $ACO_2$—, $ArCO_2$—, $ASO_2$—, $ArSO_2$— is reacted with $HNR^3R$, HOR or HSR, wherein R and $R^3$ have the meaning given above, and optionally transforming the groups $R^1$ and/or $R^2$ into different groups $R^1$ and $R^2$ by methods known in the art and/or a base or acid of the formula (I) is converted into one of its salts.

The invention also relates to a process for the preparation of the compounds of formula (I) wherein $R^1$ is H, and salts thereof, characterized in that a) a compound of formula C

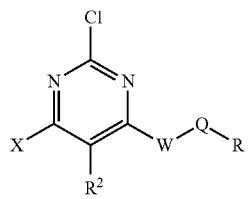

C wherein X, $R^2$, W, Q, R have the meanings given above is hydrogenated, in the presence of a suitable catalyst and a suitable base. Preferably, in formula C the group —W-Q-R denote COOH or COOA, wherein A is as defined above.

In the compounds of the formula A, L denotes a leaving group. Throughout the specification, the term leaving group preferably denotes Cl, Br, I or a reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

The formula (I) also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the formula I and so-called prodrug compounds.

The term "prodrug derivatives" is taken to mean compounds of the formula I which have been modified with, for example, alkyl or acyl groups, sugars or oligopeptides and which are rapidly cleaved in the organism to form the active compounds.

These also include biodegradable polymer derivatives of the compounds according to the invention, as described, for example, in Int. J. Pharm. 115, 61-67 (1995).

The formula (I) also encompasses mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Preference is given to the compounds of the present invention selected from the following group I-1 to I-175:

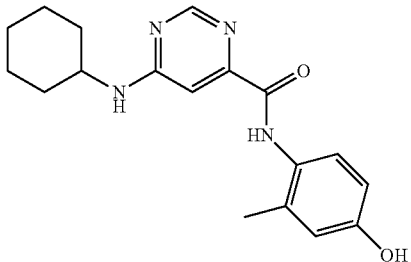

I-1

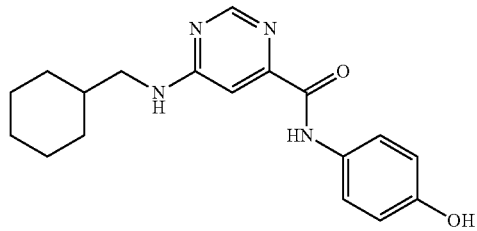

I-2

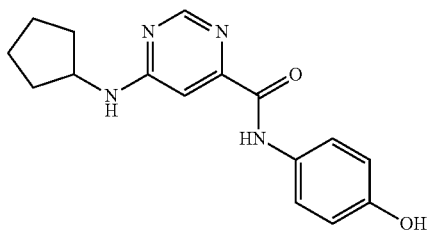

I-3

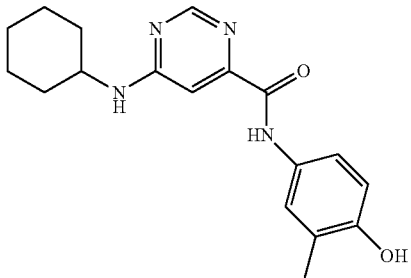

I-4

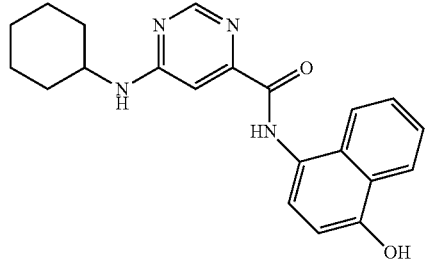

I-5

I-6
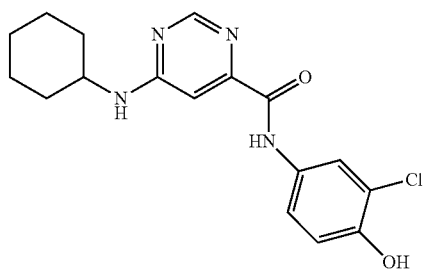
I-7
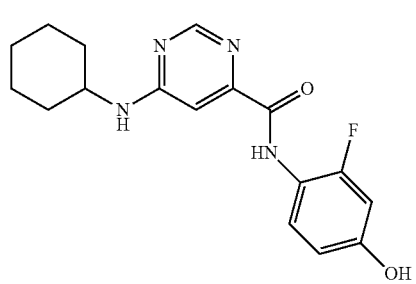
I-8
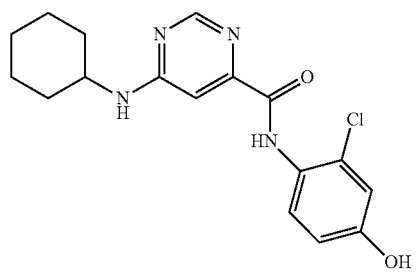
I-9
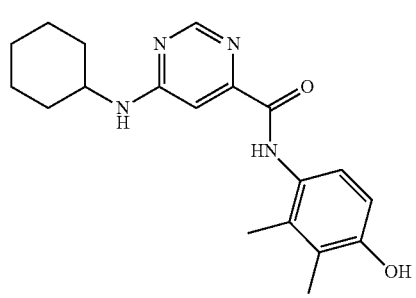
I-10
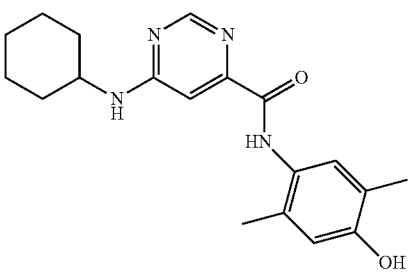
I-11
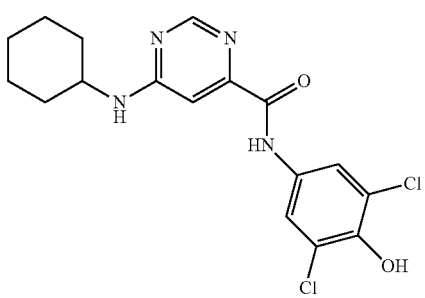
I-12
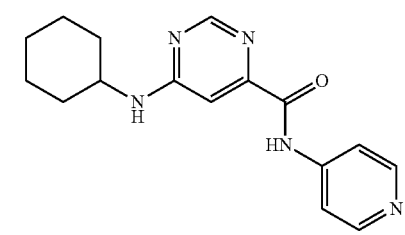
I-13
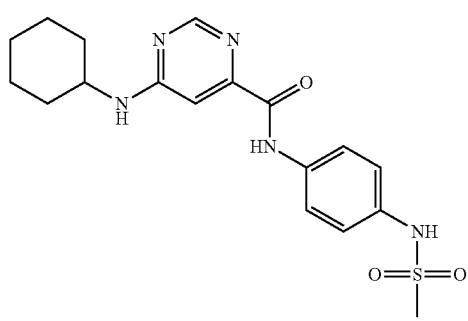
I-14
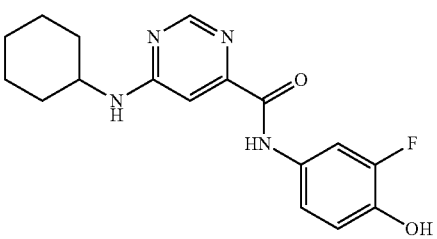
I-15
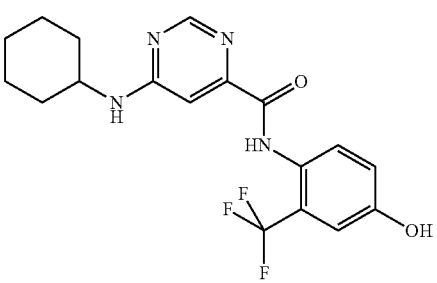
I-16
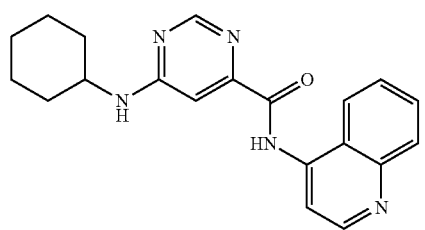

I-17 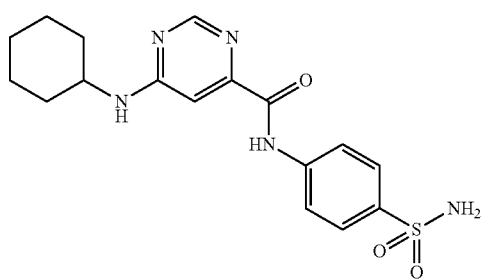
I-18 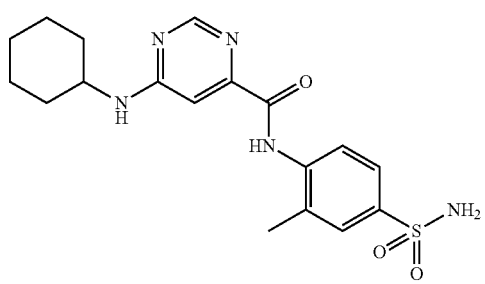
I-19 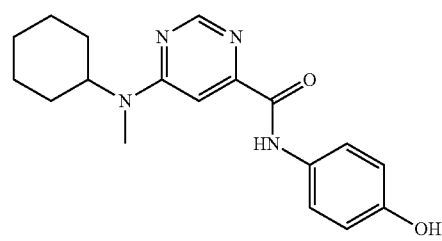
I-20 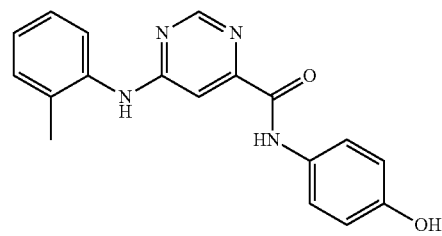
I-21 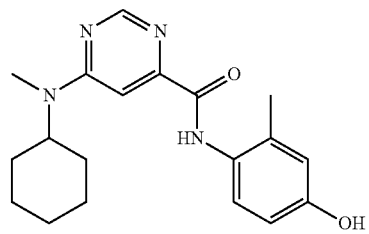
I-22 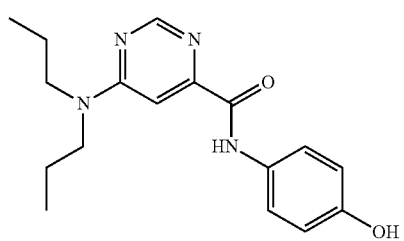
I-23 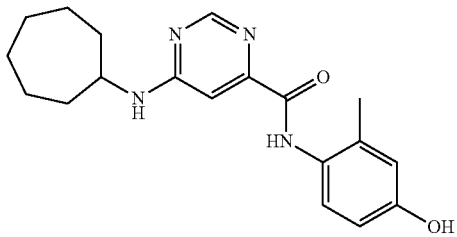
I-24 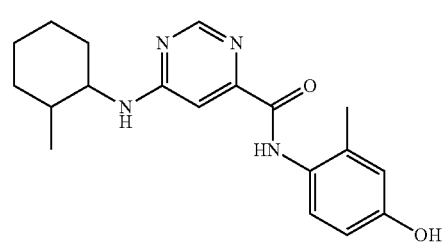
I-25 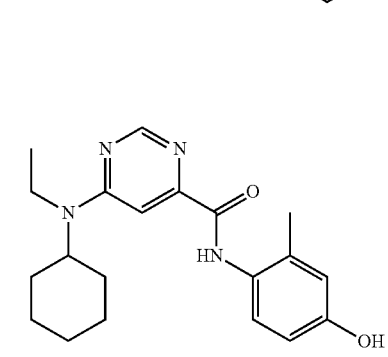
I-26 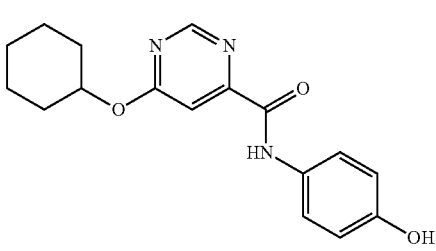
I-27 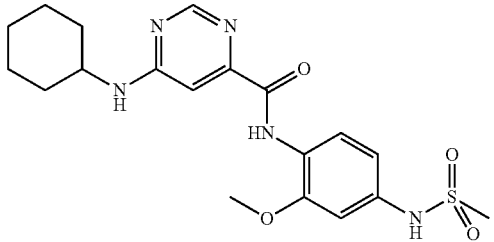
I-28 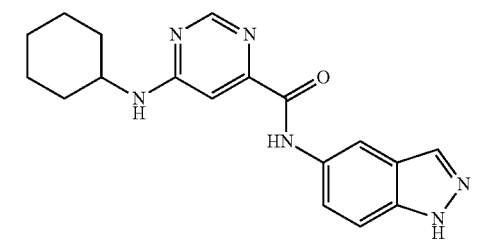

-continued
I-29
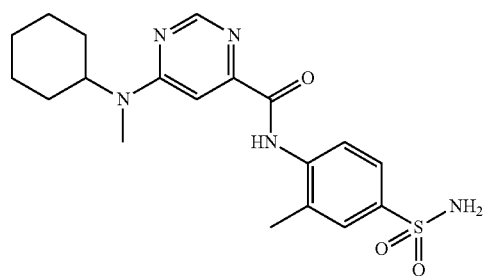
I-30
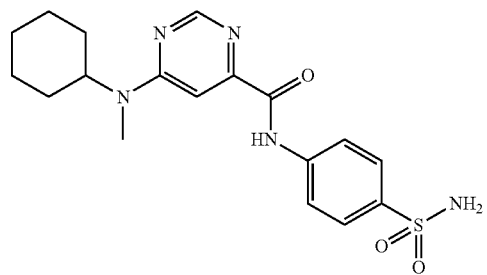
I-31
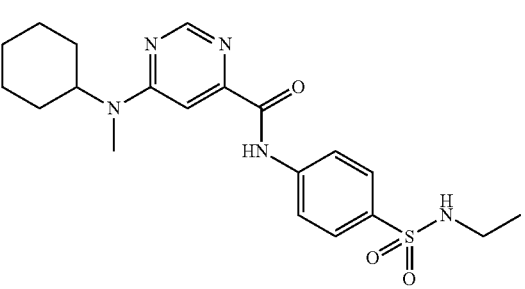
I-32
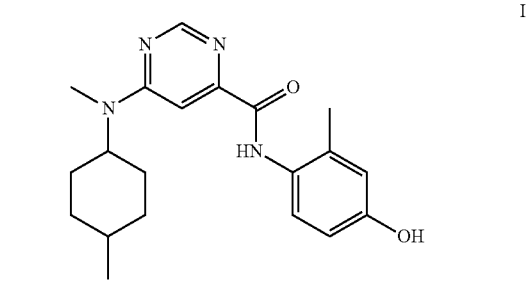
I-33
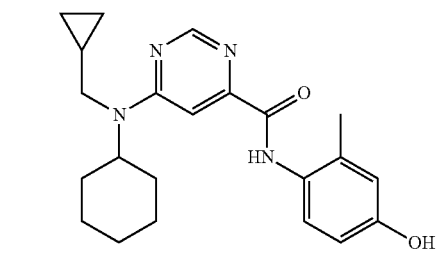
I-34
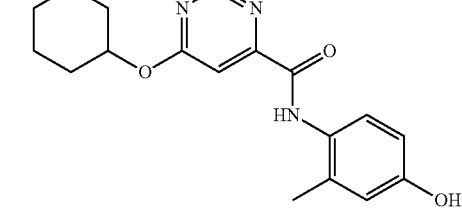
-continued
I-35
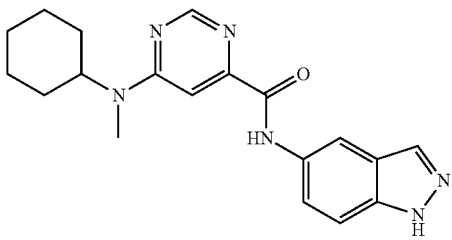
I-36
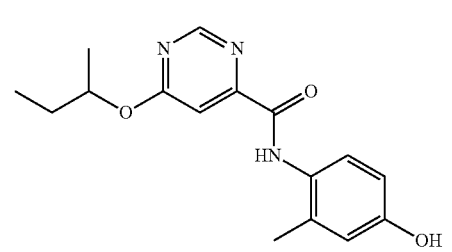
I-37
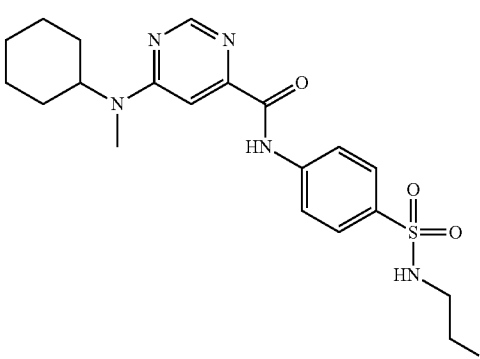
I-38
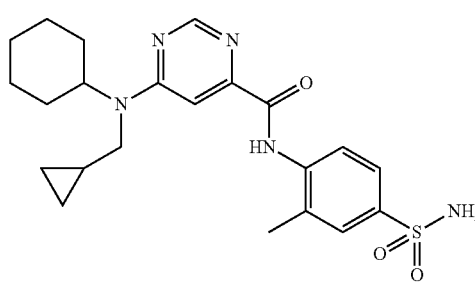
I-39
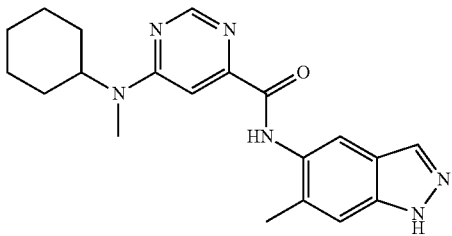
I-40
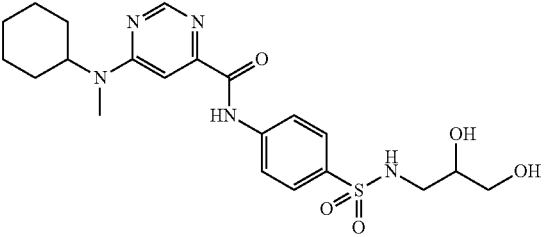

-continued
I-41
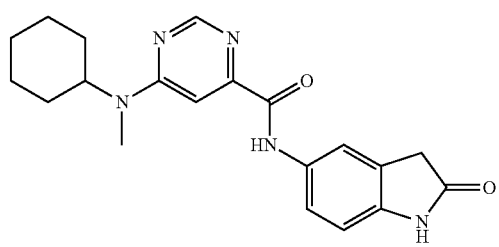
I-42
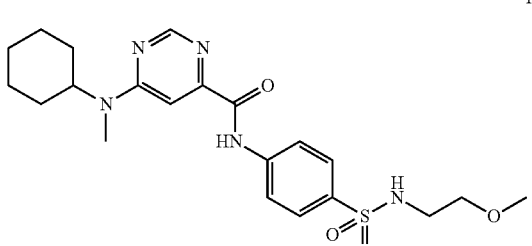
I-43
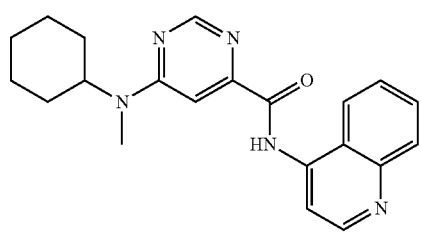
I-44
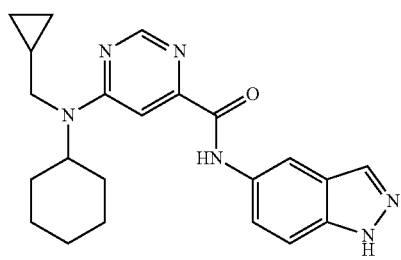
I-45
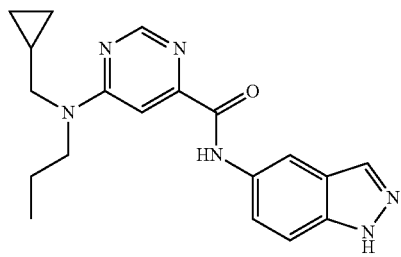
I-46
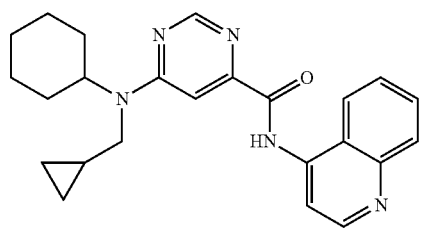
-continued
I-47
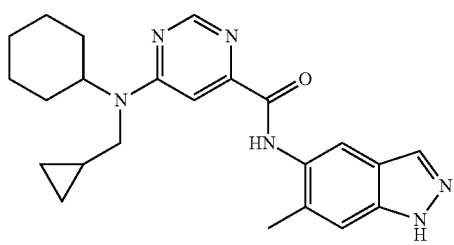
I-48
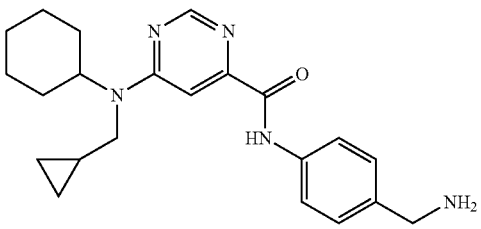
I-49
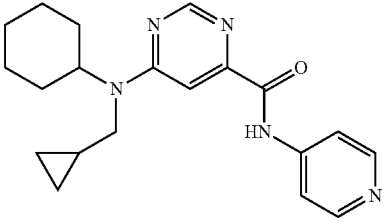
I-50
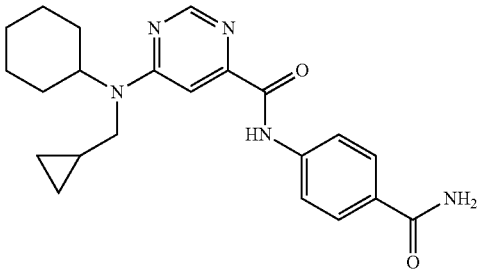
I-51
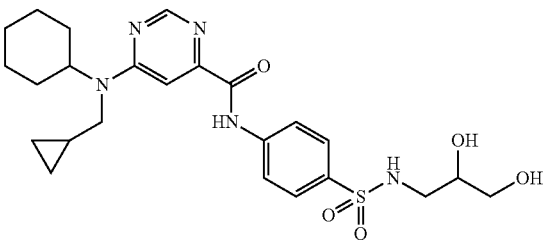
I-52
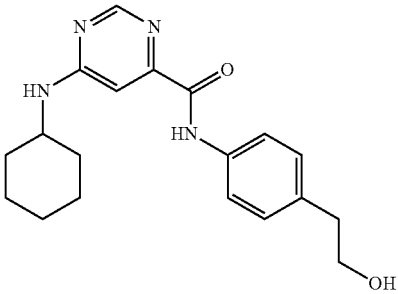

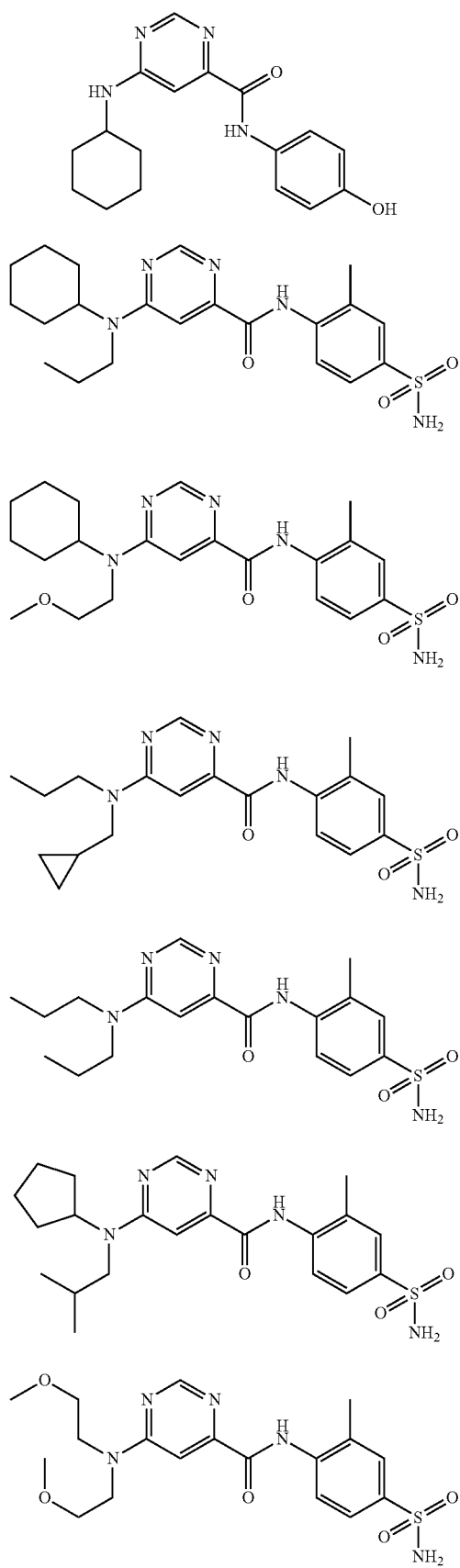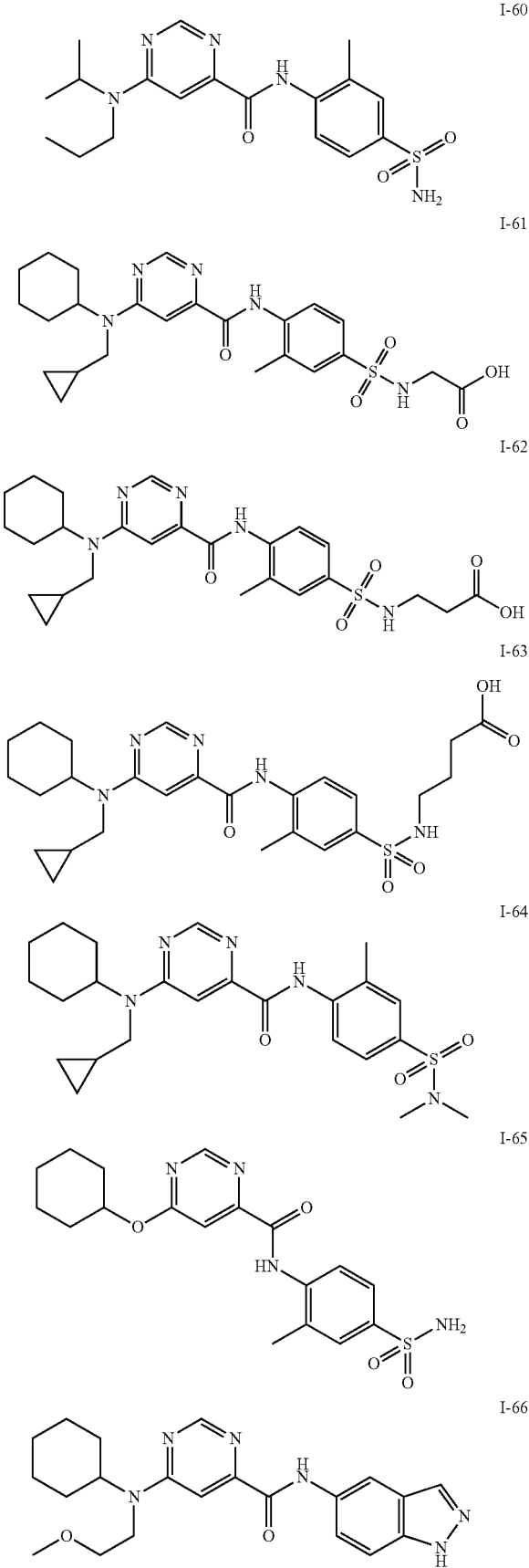

I-67 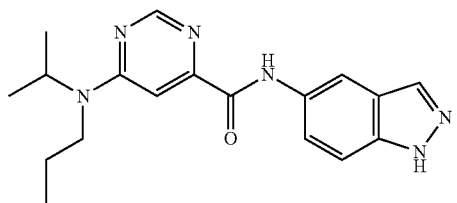
I-68 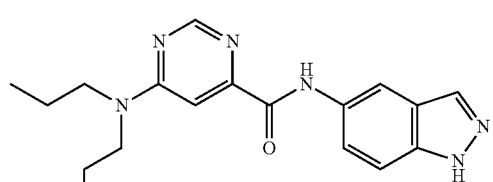
I-69 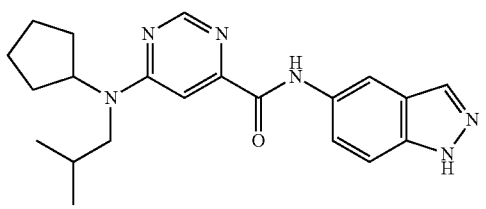
I-70 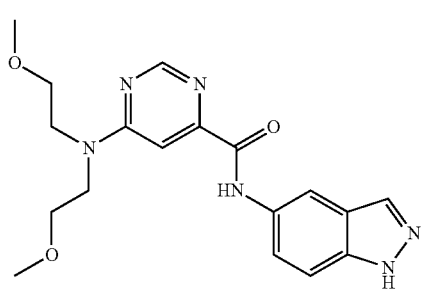
I-71 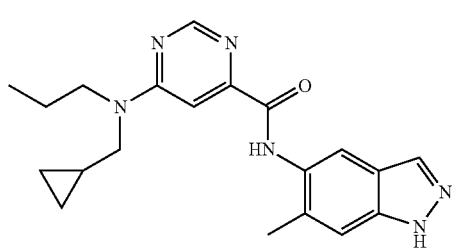
I-72 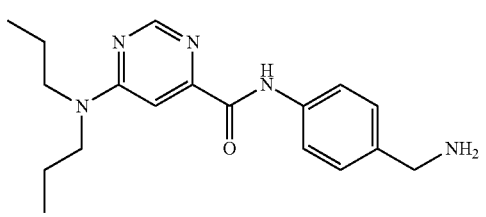
I-73 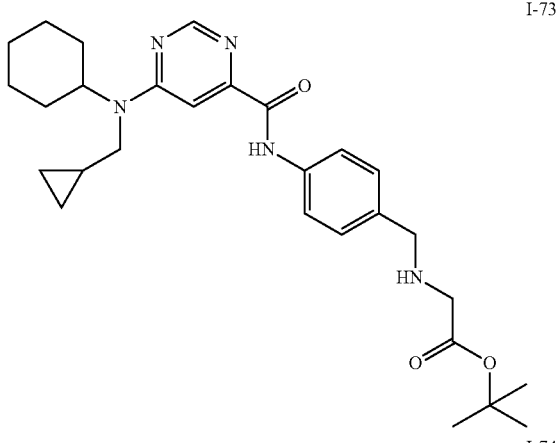
I-74 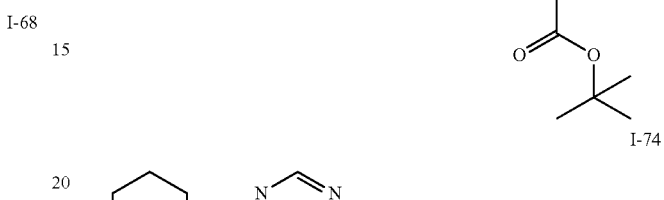
I-75 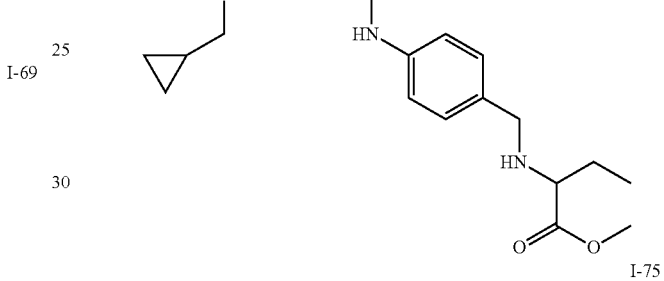
I-76 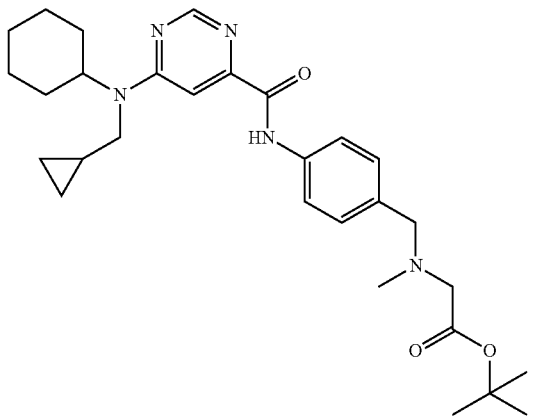

-continued
I-77
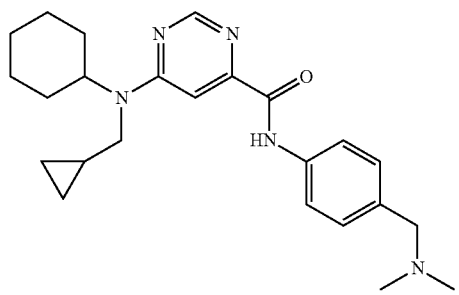
I-78
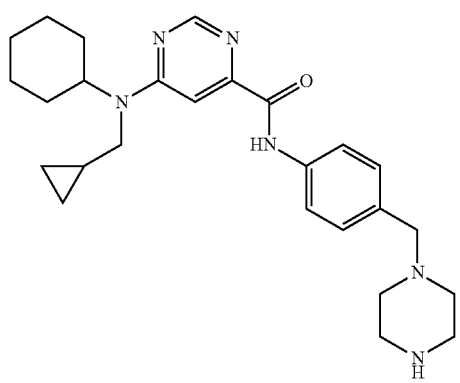
I-79
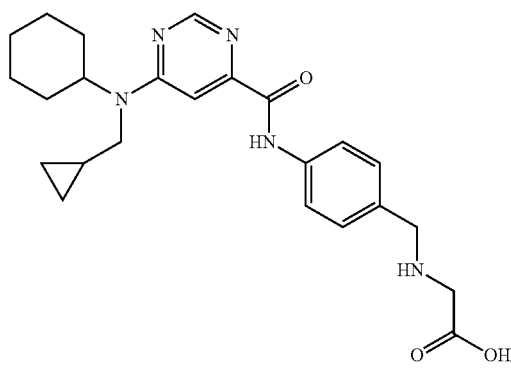
I-80
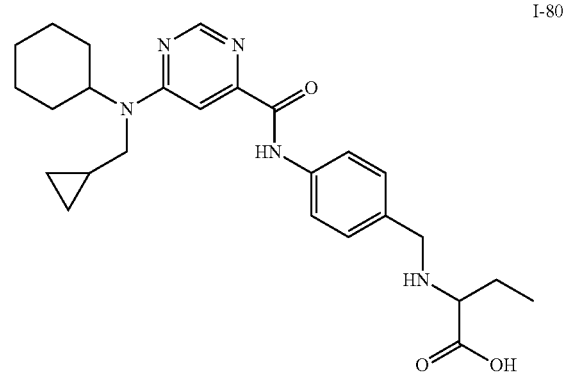
-continued
I-81
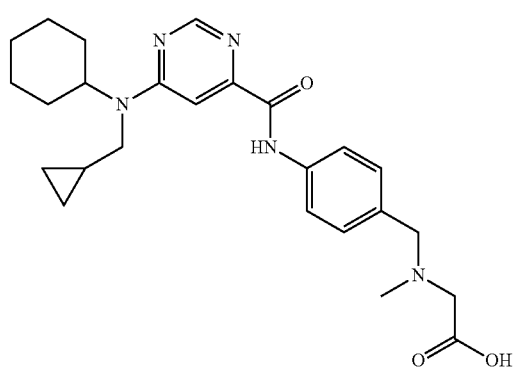
I-82
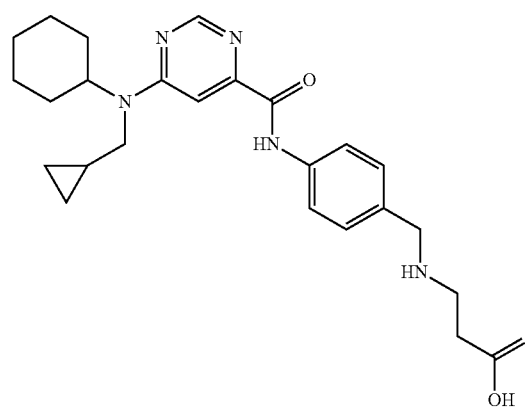
I-83
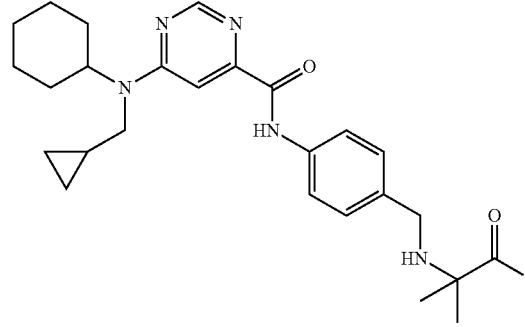
I-84
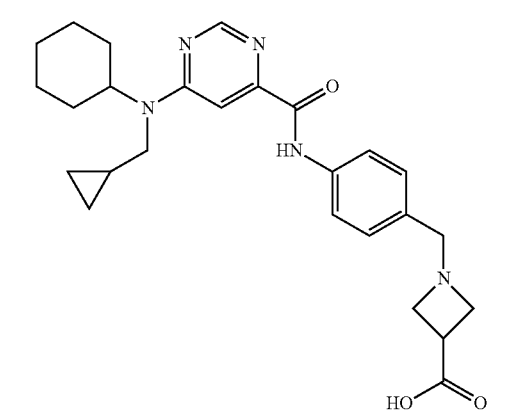

I-85 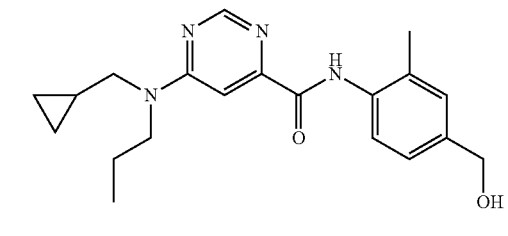
I-86 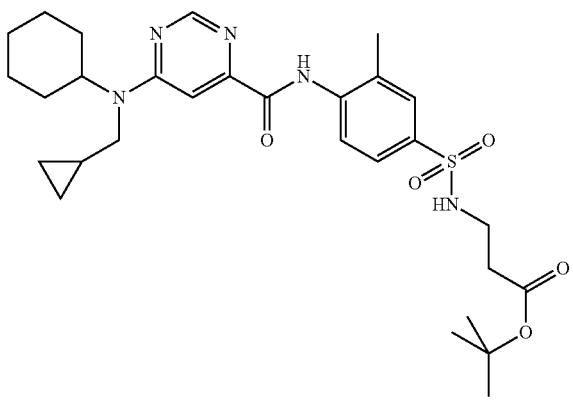
I-87 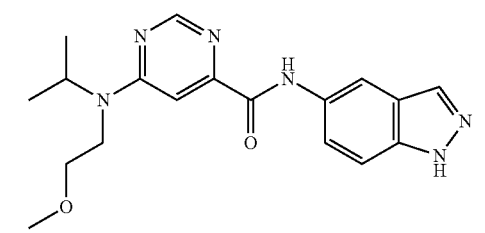
I-88 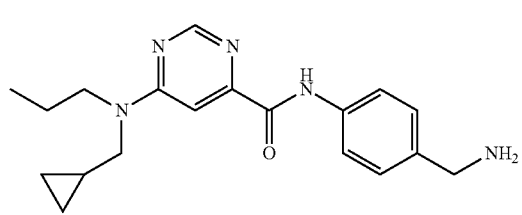
I-89 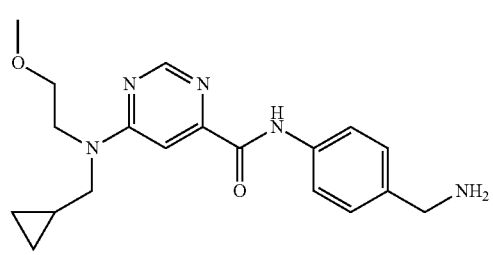
I-90 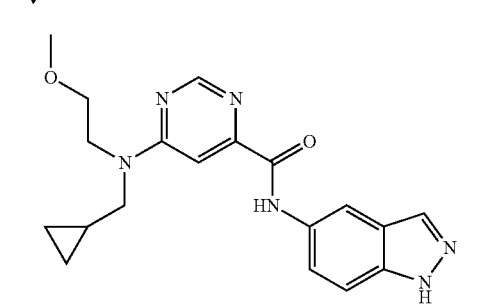
I-91 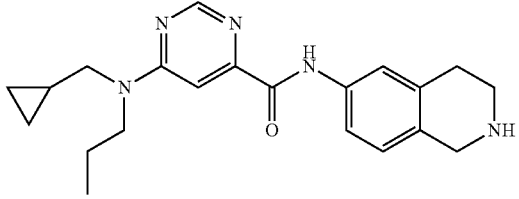
I-92 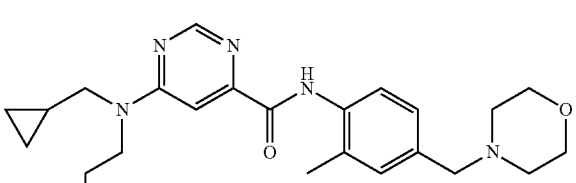
I-93 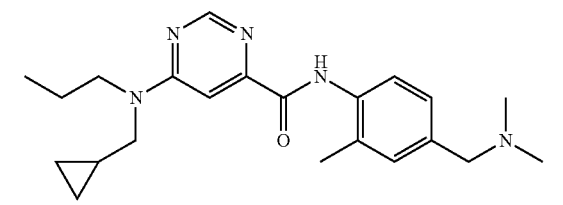
I-94 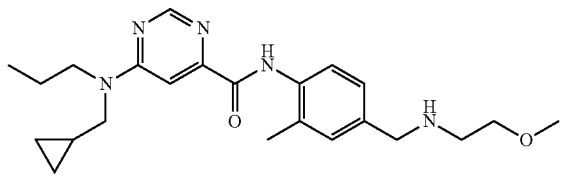
I-95 
I-96 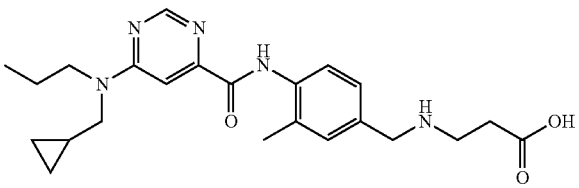
I-97

I-98
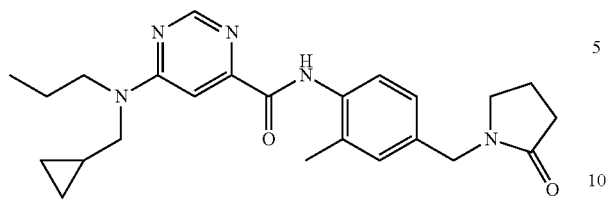
I-99
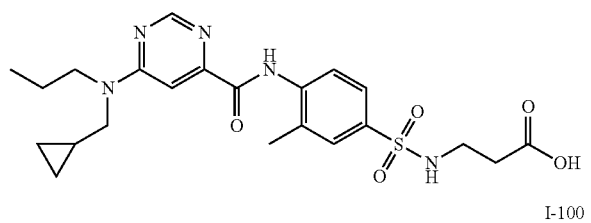
I-100
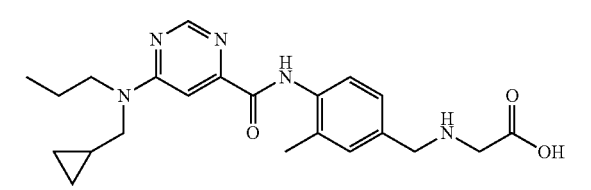
I-101
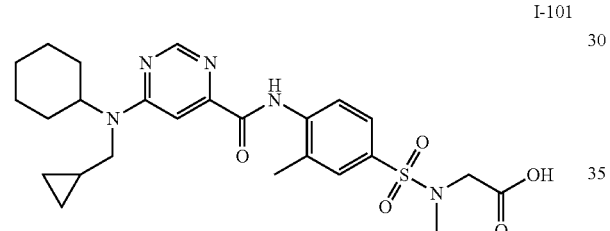
I-102
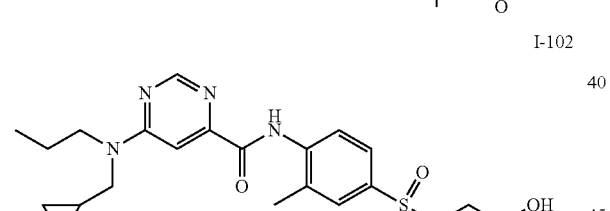
I-103
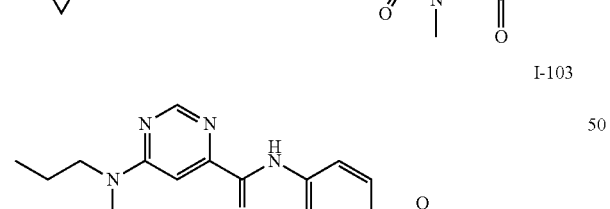
I-104
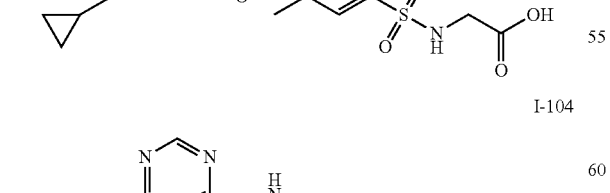
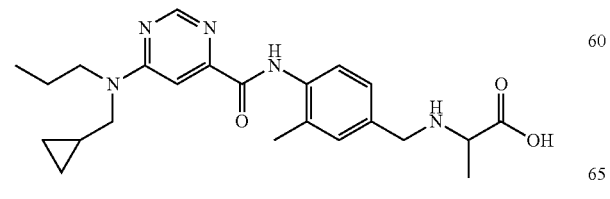
I-105

I-106
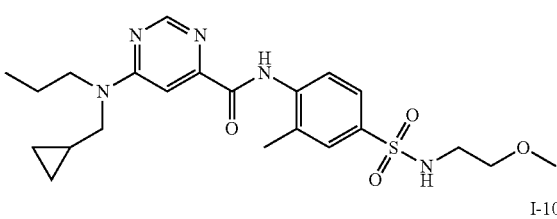
I-107
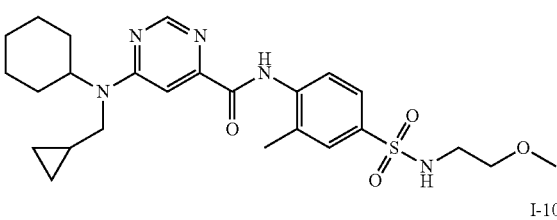
I-108
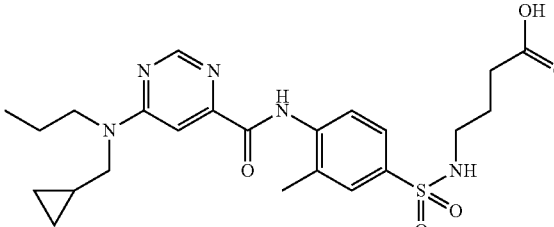
I-109
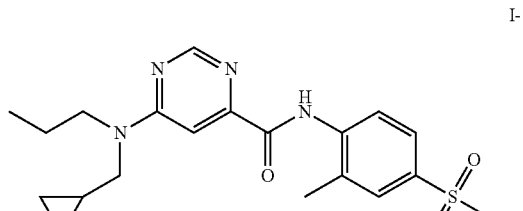
I-110
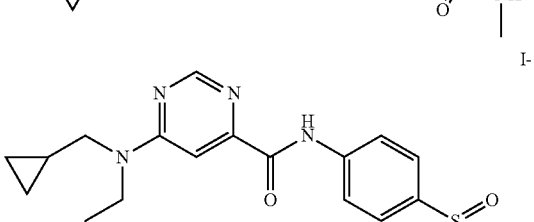
I-111

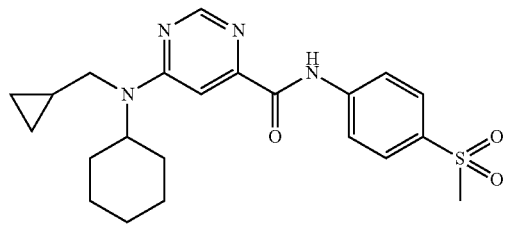
I-112
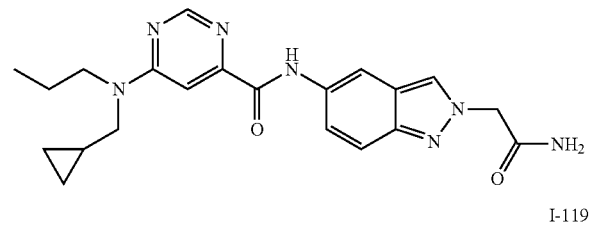
I-118
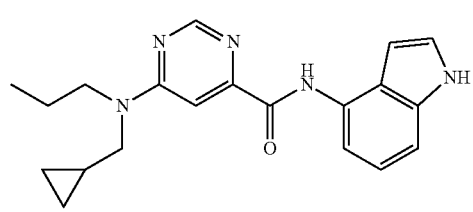
I-113
I-119
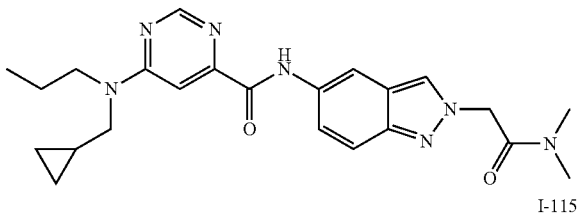
I-114
I-120
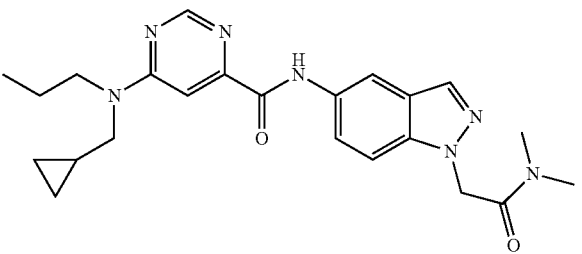
I-115
I-121
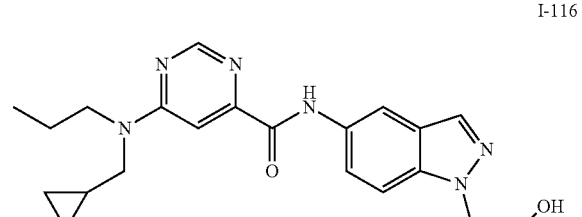
I-116
I-122
I-117
I-123

I-124

I-125
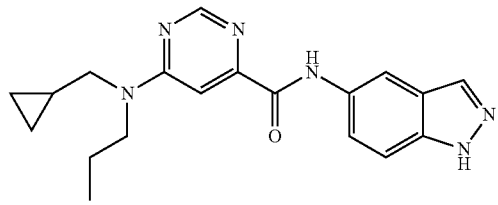
I-132
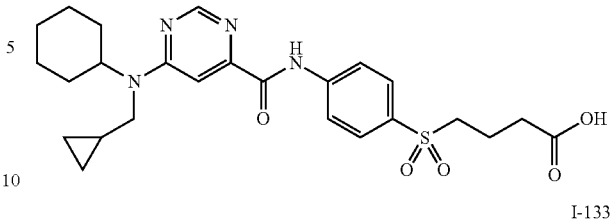
I-126
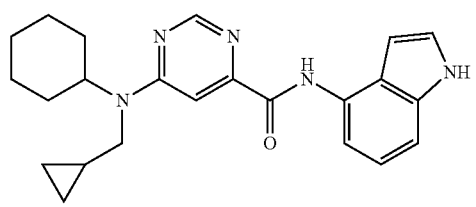
I-133
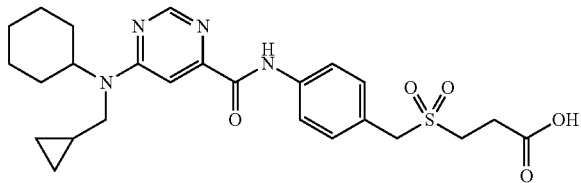
I-127
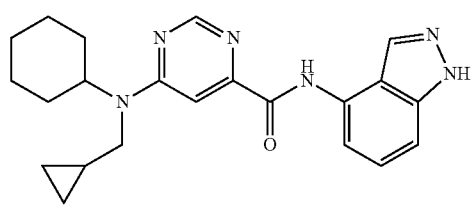
I-134
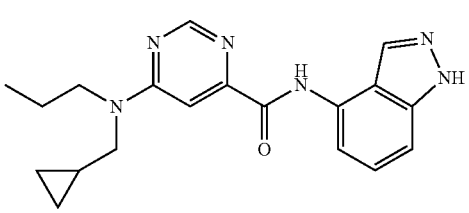
I-128
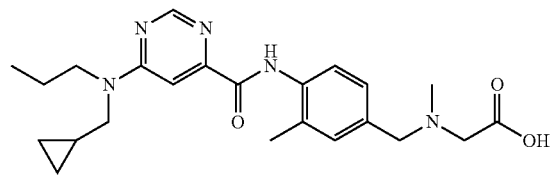
I-135
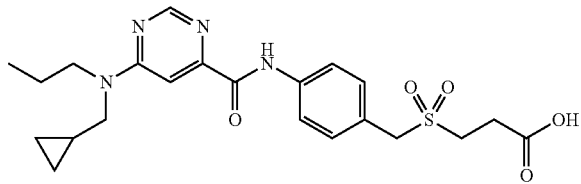
I-129
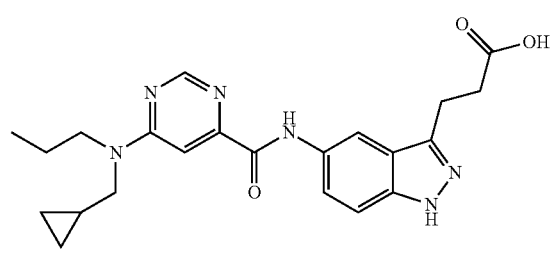
I-136
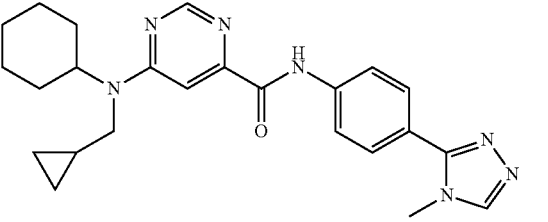
I-130
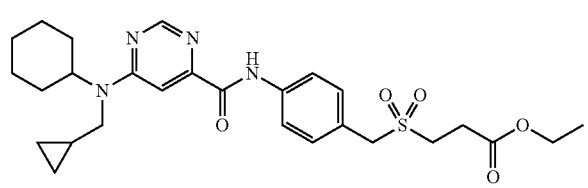
I-137
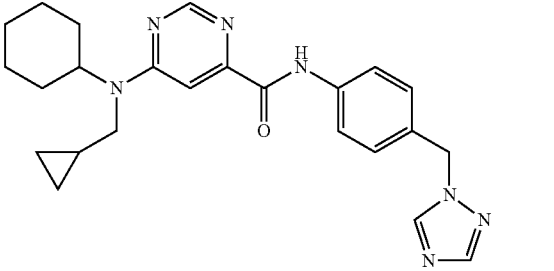
I-131
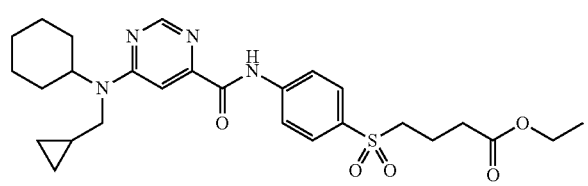
I-138
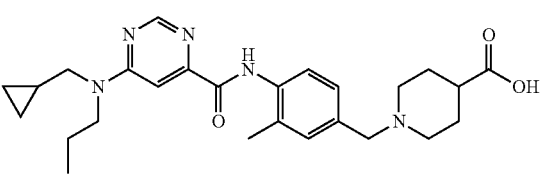

I-139
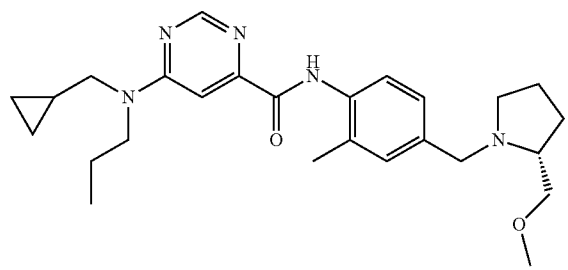
I-140
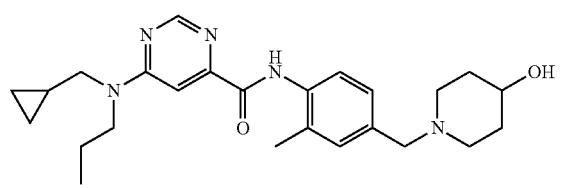
I-141
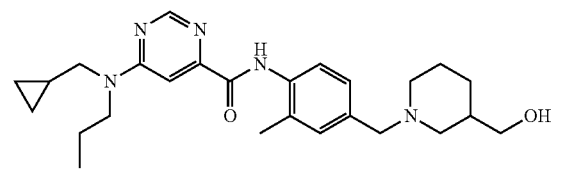
I-142
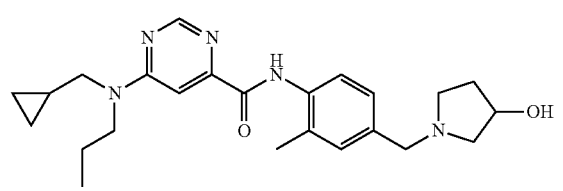
I-143
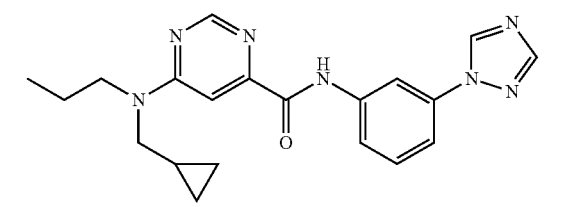
I-144
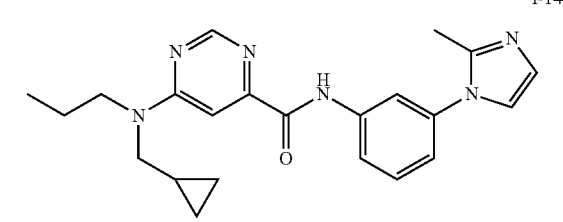
I-145
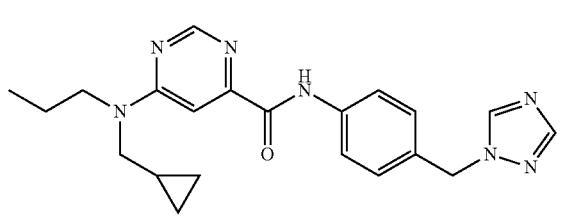
I-146
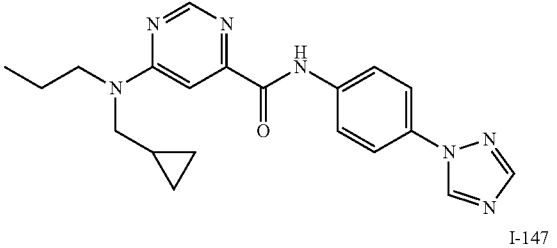
I-147
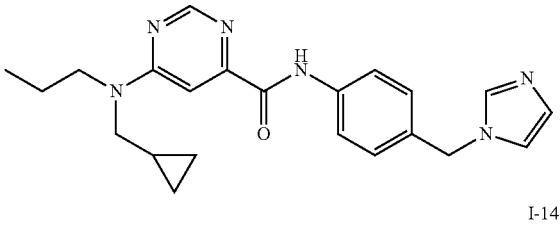
I-148
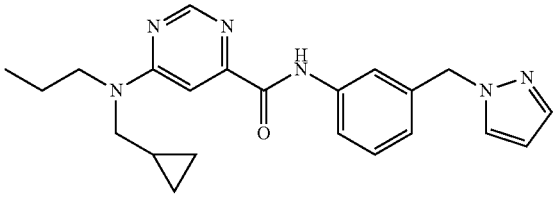
I-149
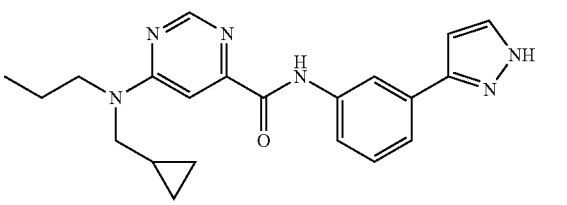
I-150
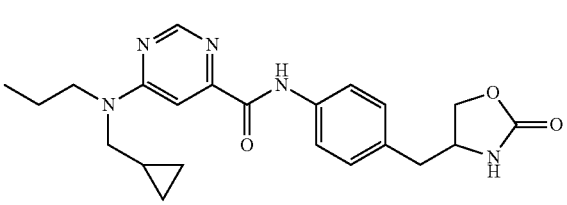
I-151
I-152
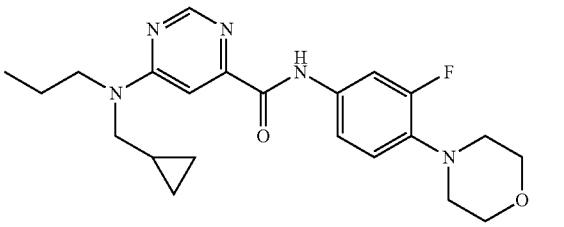

I-153
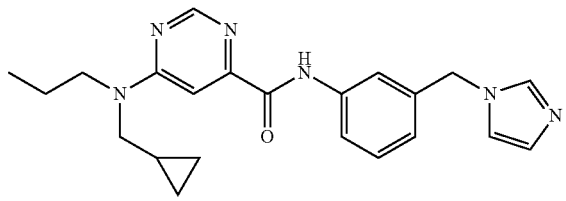
I-154
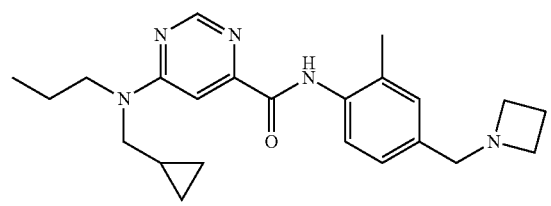
I-155
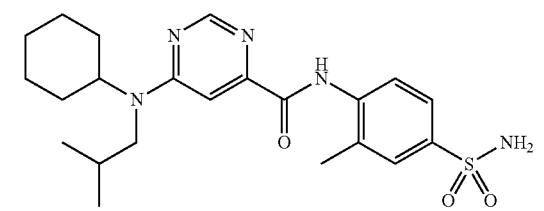
I-156
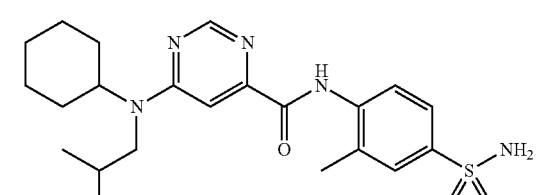
I-157
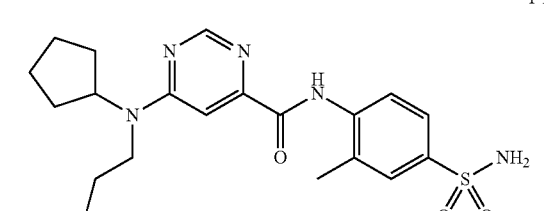
I-158
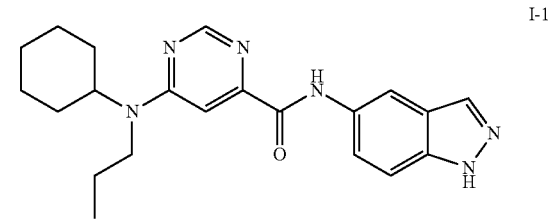
I-159
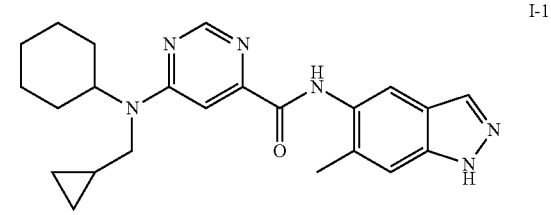
I-160
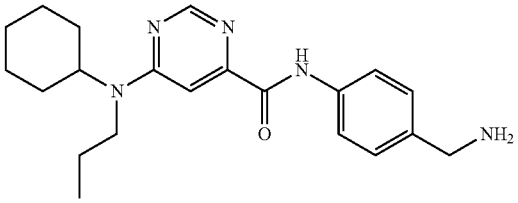
I-161
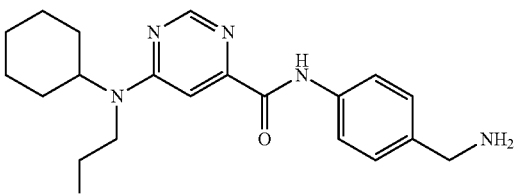
I-162
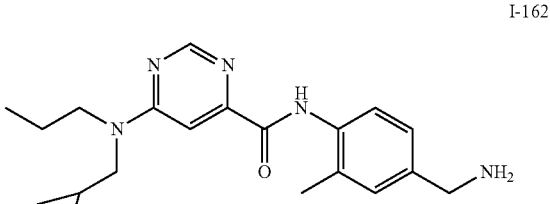
I-163
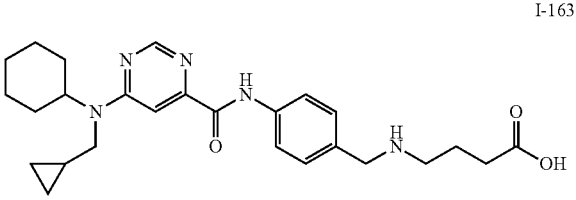
I-164
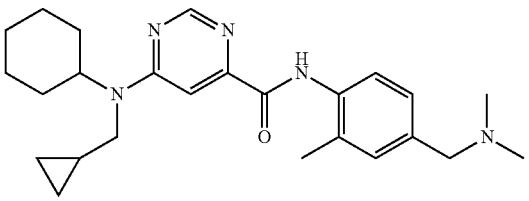
I-165
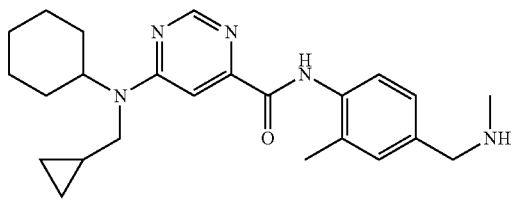
I-166
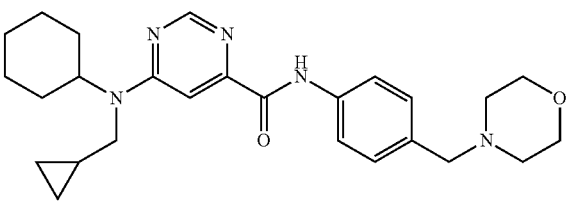

-continued
I-167
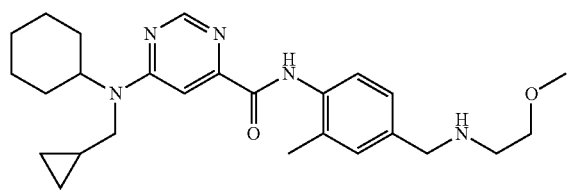
I-168
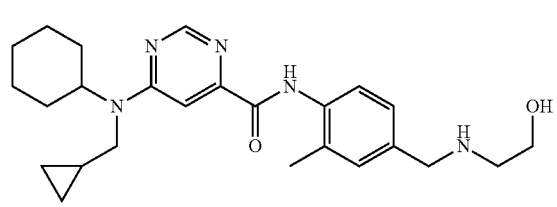
I-169
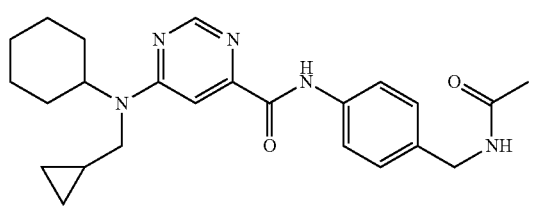
I-170
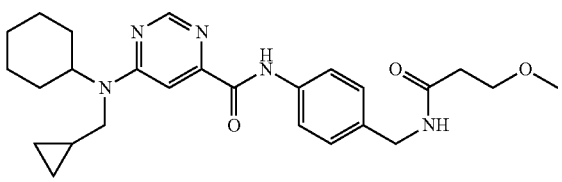
I-171
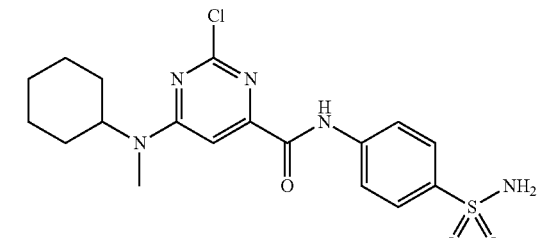
I-172
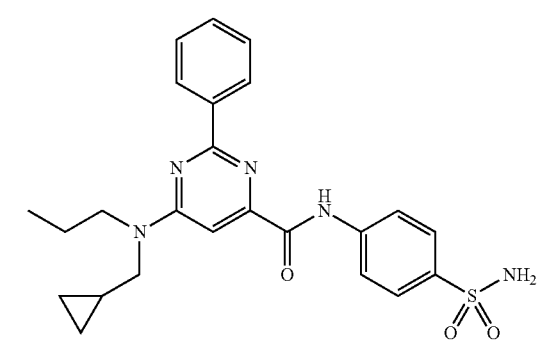
-continued
I-173
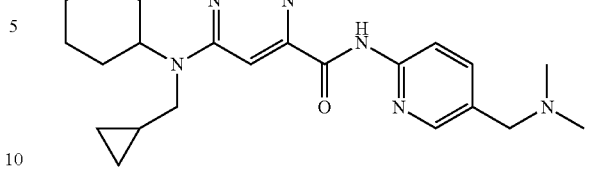
I-174
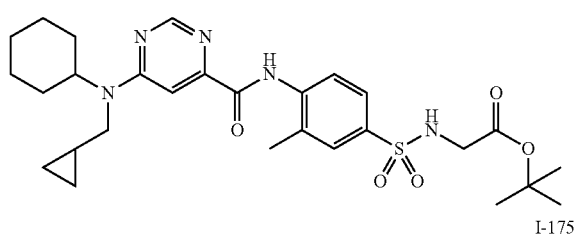
I-175
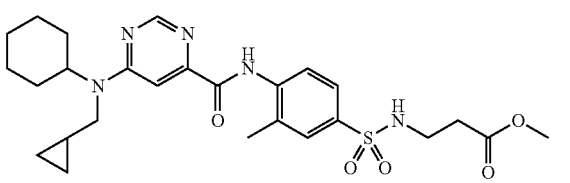
Intermediate 23
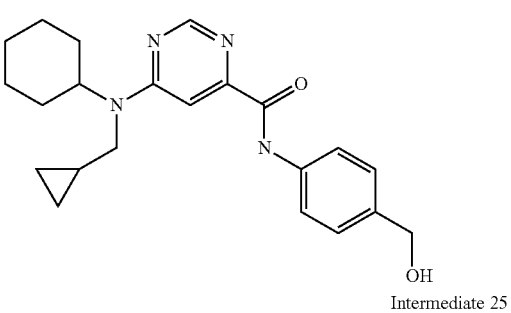
Intermediate 25
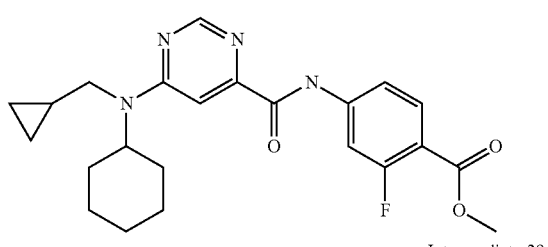
Intermediate 39
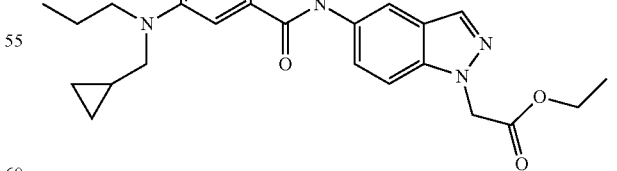
and pharmaceutically usable derivatives, solvates, salts and stereoisomers thereof, including mixtures thereof in all ratios.
For all radicals which occur more than once, such as, for example, R or $R^3$, their meanings are independent of one another.

Above and below, the radicals or parameters $R^a$, $R^b$, $R^1$, $R^2$, $R^3$, X, W, Q, R, A, Ar, Het and n have the meaning indicated under the formula I, unless expressly stated otherwise.

A denotes alkyl, is unbranched (linear) or branched, and has 1, 2, 3, 4, 5, 6, 7, 8, 9, 10, 11 or 12 carbon atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methyl-propyl, 1,1,2- or 1,2,2-trimethylpropyl, furthermore preferably, for example, trifluoromethyl. A very particularly preferably denotes alkyl having 1, 2, 3, 4, 5 or 6 carbon atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. A furthermore denotes $(CH_2)_nO(CH_2)_nOR^3$, $(CH_2)_nNR^3(CH_2)_2N(R^3)_2$, especially $(CH_2)_2$—O—$(CH_2)_2$ $OR^3$ or $(CH_2)_2NH(CH)_2N(R^3)_2$.

Alkyl denotes straight or branched carbon chain having 1, 2, 3, 4, 5, 6, 7, 8, 9, 10, 11 or 12 carbon atoms. Alkyl preferably denotes methyl, ethyl, n-propyl, isopropyl, n-butyl, isobutyl, tert-butyl.

Cycloalkyl denotes 3 to 8 membered cyclic alkyl optionally substituted with alkyl. Cycloalkyl preferably denotes cyclopropyl, cyclobutyl, cyclopentyl, cyclohexyl or cycloheptyl.

Alkylcycloalkyl denotes a $C_1$ to $C_4$ alkyl substituted with cycloalkyl. Alkylcycloalkyl preferably denotes methylcyclopropyl, methylcyclobutyl, methylcyclopentyl, methylcyclohexyl, ethylcyclopropyl, ethylcyclobutyl, ethylcyclopentyl, ethylcyclohexyl.

Cycloalkylalkylene preferably denotes cyclopropylmethylene, cyclobutylmethylene, cyclopentylmethylene, cyclohexylmethylene or cycloheptylmethylene.

Alkylene is preferably methylene, ethylene, propylene, butylene, pentylene or hexylene, furthermore branched alkylene.

$R^a$ is preferably A. $R^b$ is preferably cycloalkyl. Most preferably, $R^a$ is H or Alkylcycloalkyl, preferably

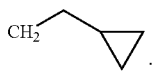

One of the groups $R^a$ and $R^b$ is preferably n-alkyl such as n-propyl, or cycloalkyl, especially cyclohexyl.

$R^3$ is preferably H.

Hal is preferably F, Cl or Br and especially Cl or Br.

X preferably denotes $NR^aR^b$ or $OR^b$. X is preferably one of the following groups:

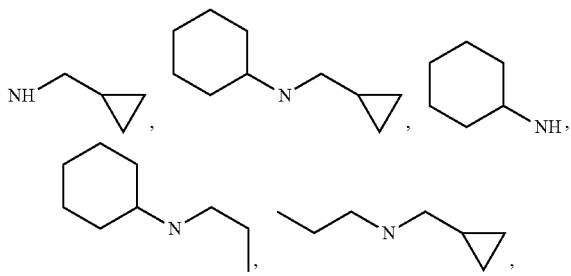

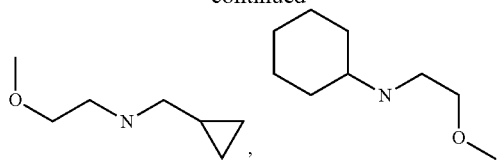

W is preferably CO.

Q is preferably $NR^3$. If Q is $NR^3$, $R^3$ in $NR^3$ is preferably H.

$R^1$ and $R^2$ are preferably H.

n is preferably 0, 1, 2, 3, 4 or 5 and more preferably 0, 1, 2, 3 or 4.

R preferably denotes Ar or Het.

An aromatic carbocyclic ring preferably denotes phenyl, naphthyl or biphenyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamido-phenyl, o-, m- or p-methoxyphenyl, o-, m- or p-ethoxyphenyl, o-, m- or p-ethoxycarbonyl-phenyl, o-, m- or p-(N,N-dimethylamino) phenyl, o-, m- or p-(N,N-dimethylaminocarbonyl)-phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o, m or pamino-sulfanyl-phenyl, o-, m- or p-phenoxyphenyl, further preferably 2,3-, 2,4-, 2,5-, 2,6-, 3,4- or 3,5-dimethylphenyl, 2,3-, 2,4-, 2,5-, 2,6-, 3,4- or 3,5-difluorophenyl, 2,3-, 2,4-, 2,5-, 2,6-, 3,4- or 3,5-dichloro-phenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N, N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acet-amidophenyl, 3-fluoro-4-methoxyphenyl, 3-amino-6-methylphenyl, 3-chloro-4-acetamido-phenyl or 2,5-dimethyl-4-chlorophenyl.

Ar preferably denotes, for example, phenyl which is unsubstituted or monosubstituted, disubstituted or trisubstituted by Hal, A, $OR^3$, $SO_2NHA$, —$[C(R^3)_2]_n$—Ar, —$[C(R^3)_2]_n$-Het, $SO_2A$, $COOR^3$ and/or CN. If Ar is phenyl, it is preferably substituted in para-position. Ar is preferably substituted by an aminosulfonyl- or a hydroxyl-group.

Ar particularly preferably denotes, for example, phenyl which is unsubstituted or monosubstituted or disubstituted by Hal, A, OA, OH, $SO_2A$, $SO_2NHA$, $SO_2NH_2$, $NHSO_2A$, $COOR^3$ and/or CN, such as, for example, 2-methylsulfonylphenyl, 2-aminosulfonylphenyl, phenoxyphenyl, 2-, 3- or 4-chlorophenyl, 3,4-dichlorophenyl, 4-methylphenyl, 4-bromophenyl, 3-fluoro-4-methoxyphenyl, 4-trifluoromethoxyphenyl, 4-ethoxyphenyl, 2-methoxyphenyl, 3-cyanophenyl, 4-ethoxycarbonylphenyl, 4-methoxycarbonylphenyl, 4-carboxyphenyl or 4-aminocarbonylphenyl, 4-hydroxyphenyl or 4-aminosulfonylphenyl.

Ar very particularly preferably denotes one of the following groups:
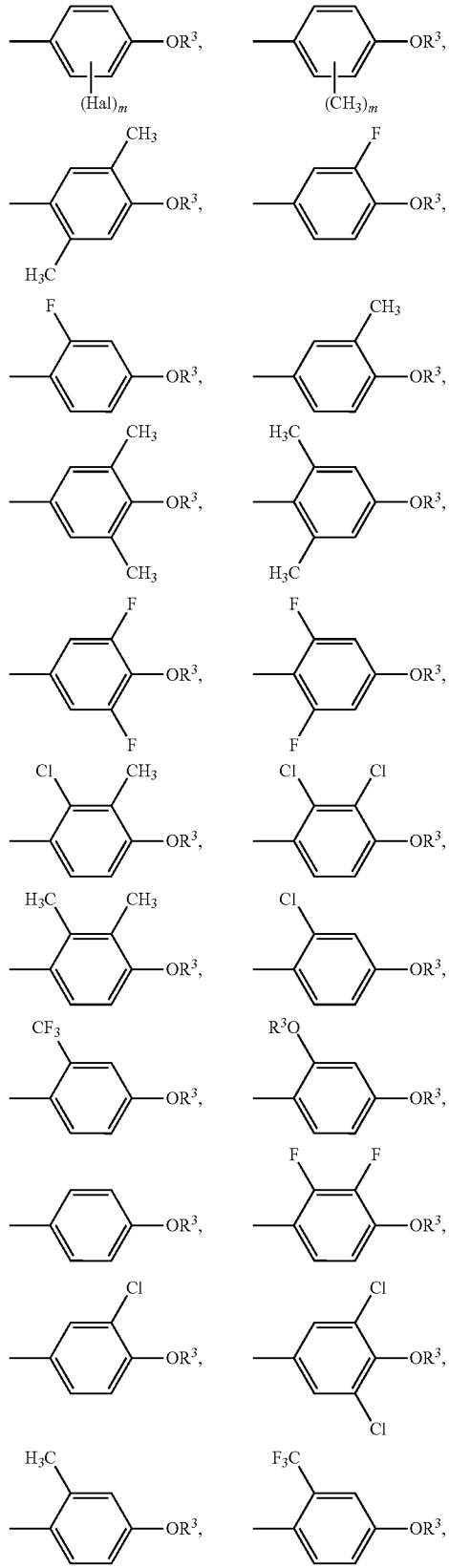
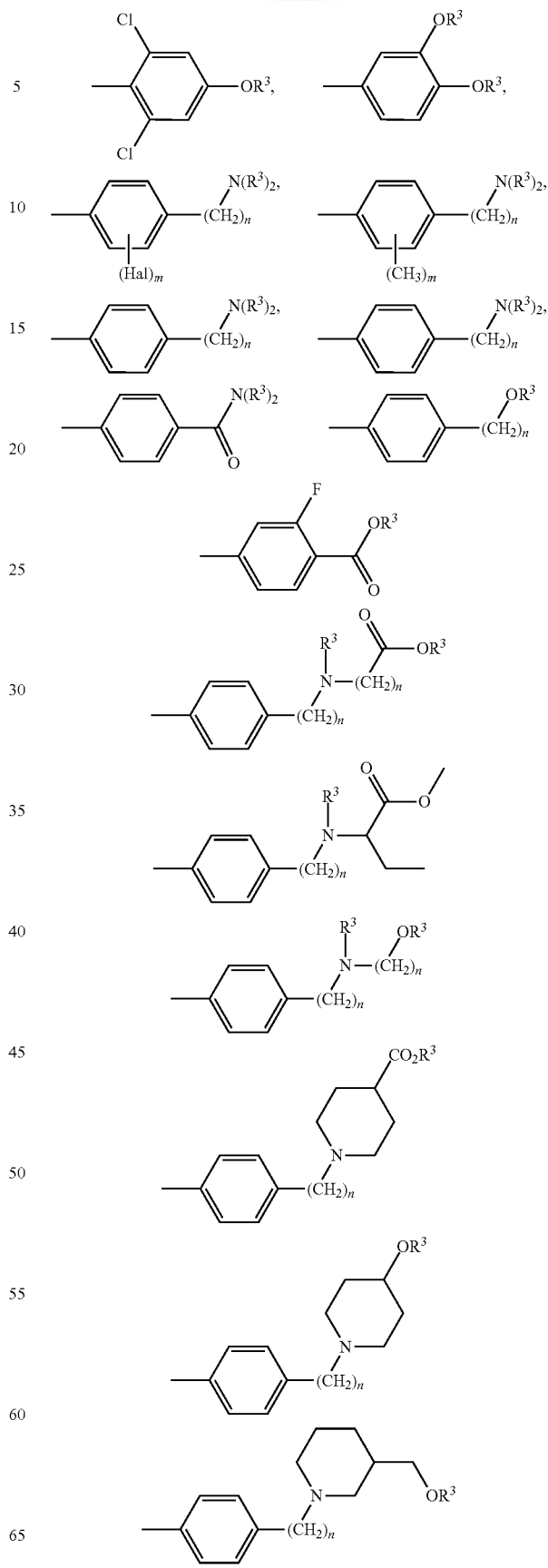

-continued
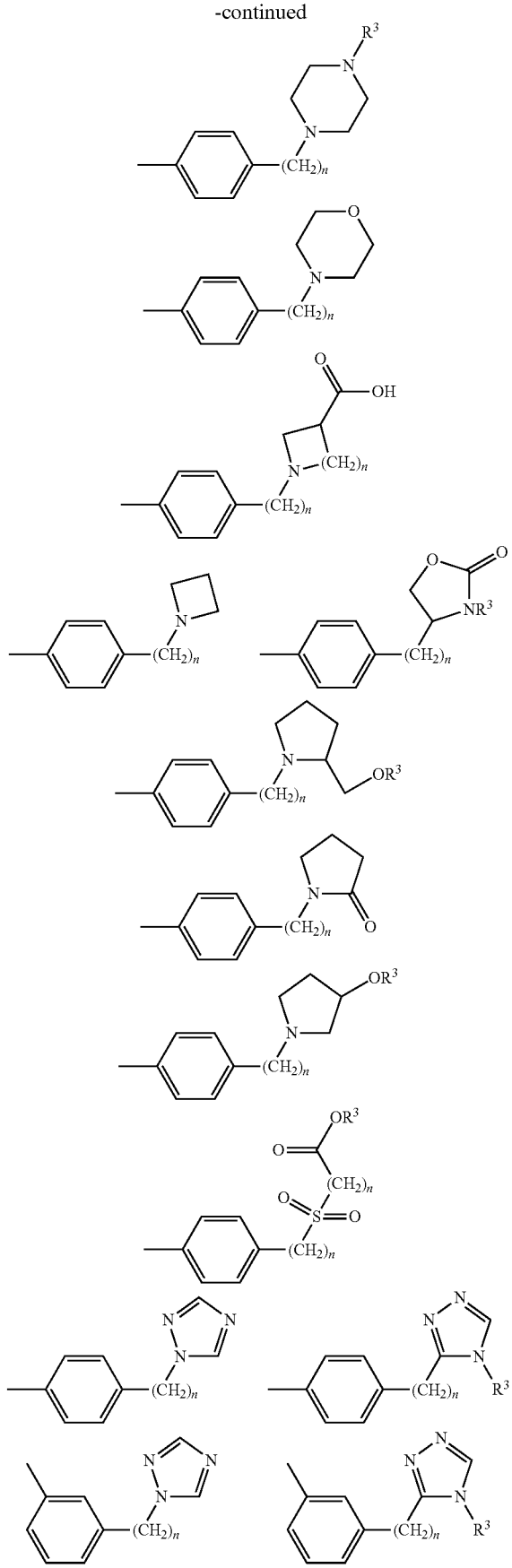
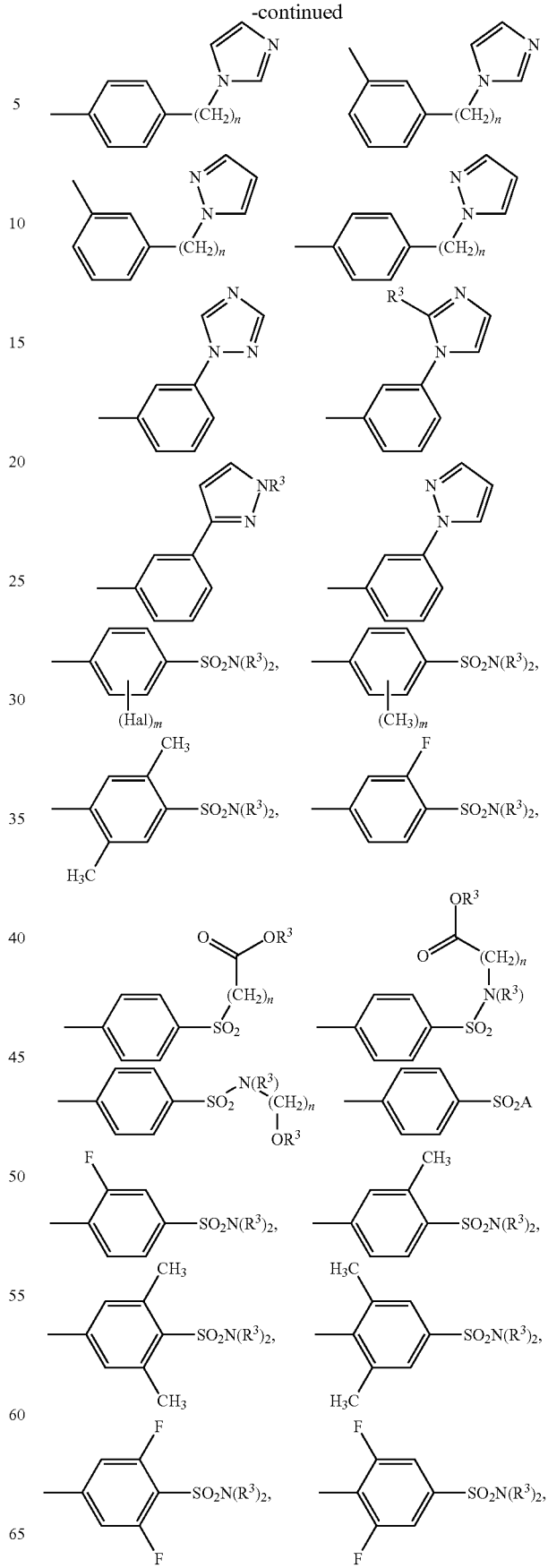

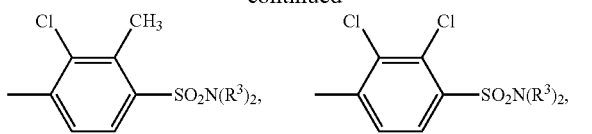
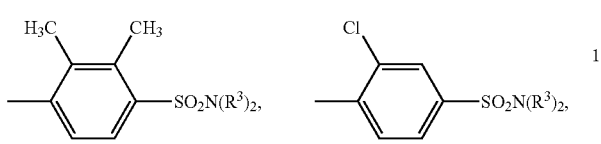
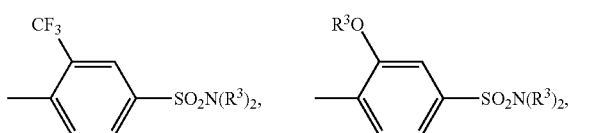
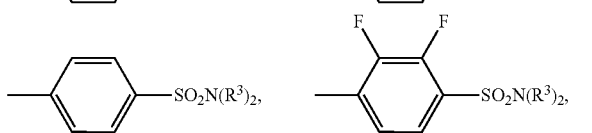
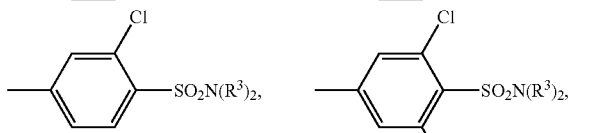
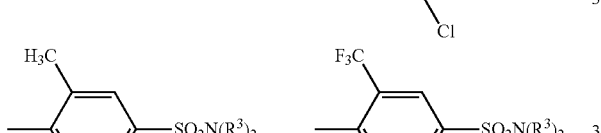
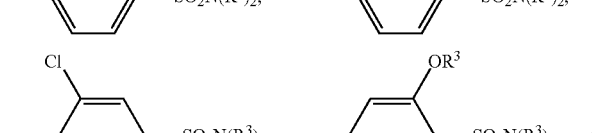
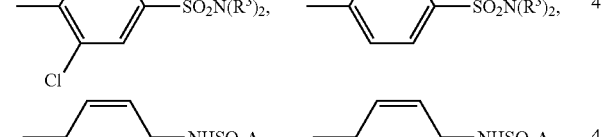
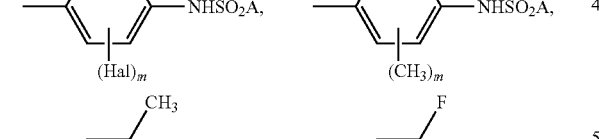
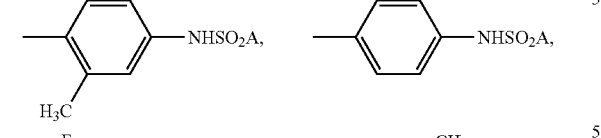
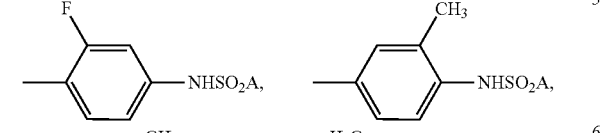
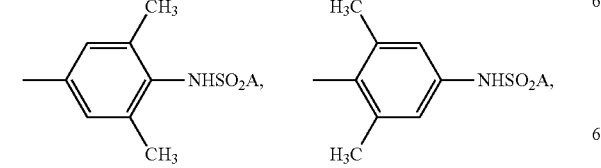
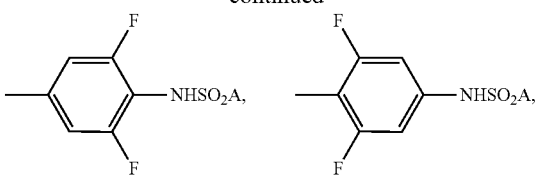
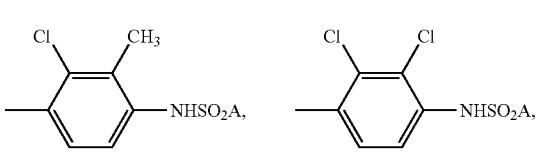
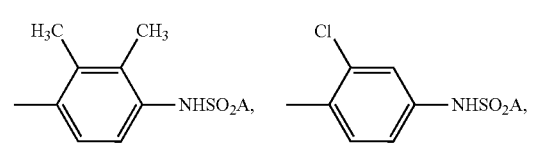
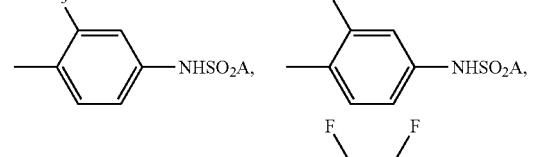
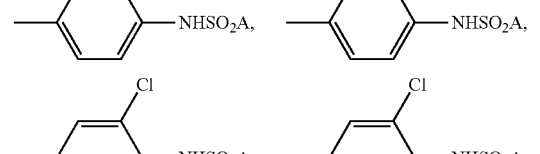
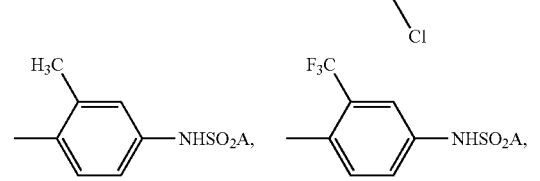
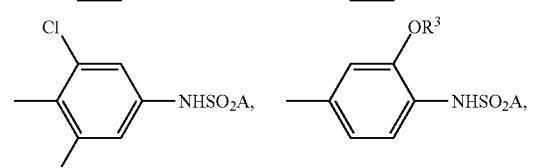
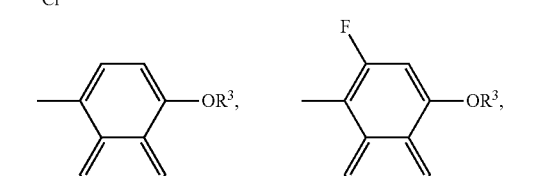
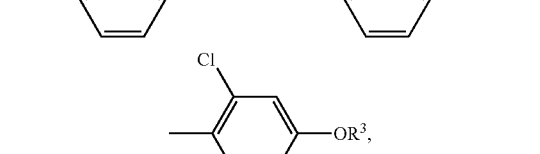
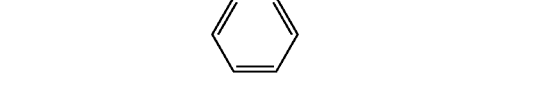

-continued wherein m is 1, 2, or 3, n is 0, 1, 2 or 3, $R^3$ is defined as above and preferably denotes H, and A is as defined above.

If X is Hal, it preferably denotes Br or Cl, particularly Cl.

Het is preferably a 6 to 14 membered ring system and denotes, notwithstanding further substitutions, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzo-dioxol-5-yl, 1,4-benzodioxane-6-yl, 2,1,3-benzothiadiazol-4- or -5-yl or 2,1,3-benzoxadiazol-5-yl.

The heterocyclic radicals may also be partially or fully hydrogenated.

Het can thus also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylene-dioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl or also 3,4-dihydro-2H-1,5-benzodioxepin-6- or -7-yl, furthermore preferably 2,3-dihydrobenzo-furanyl or 2,3-dihydro-2-oxofuranyl.

Het very particularly denotes one of the following groups:

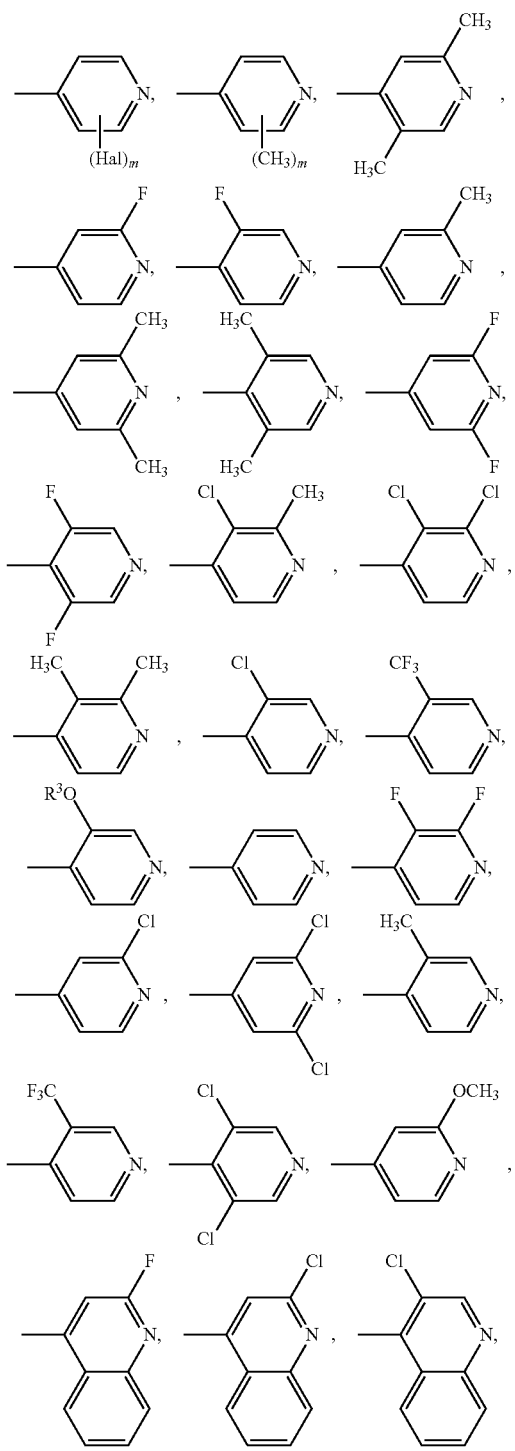

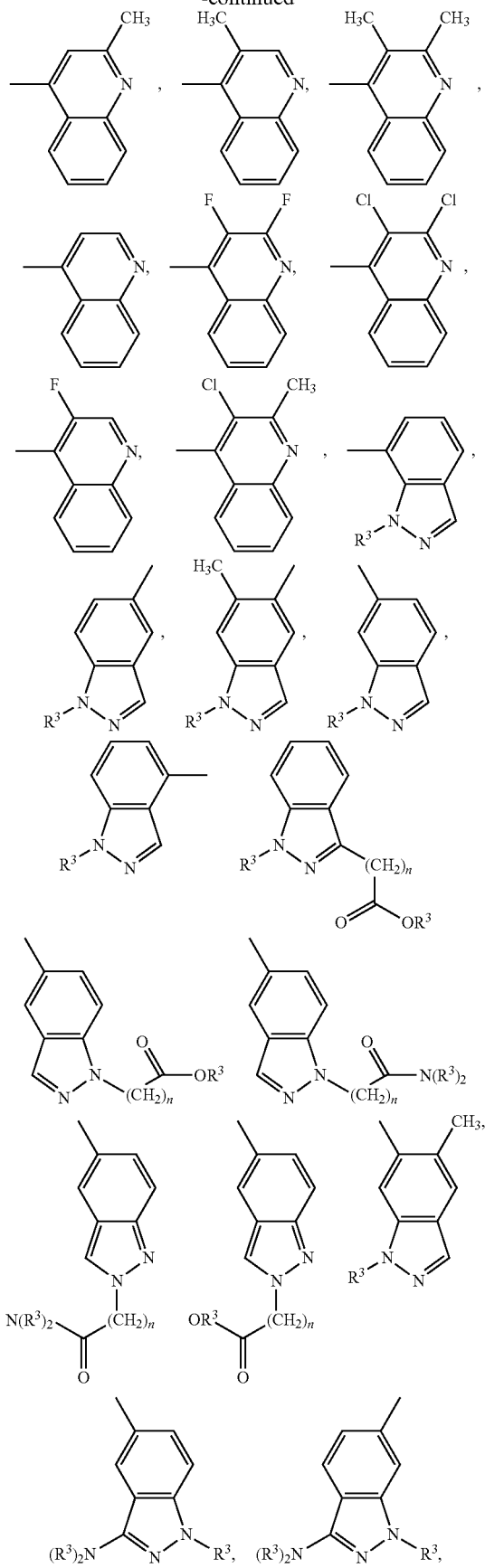
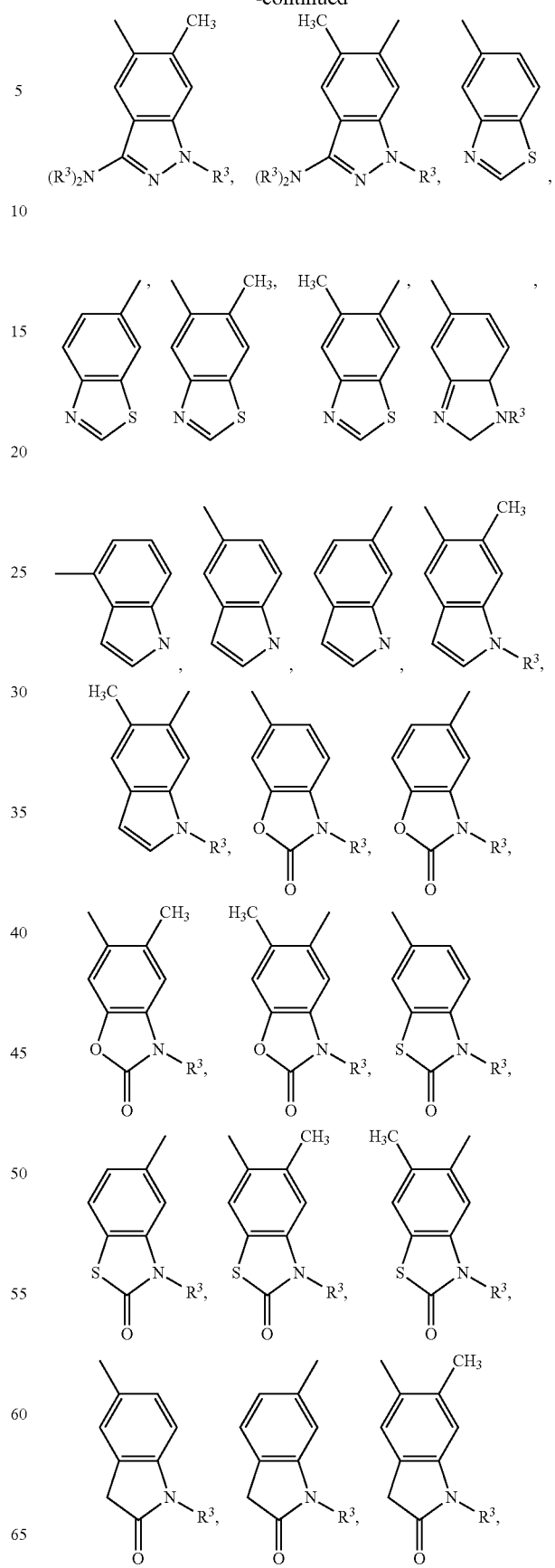

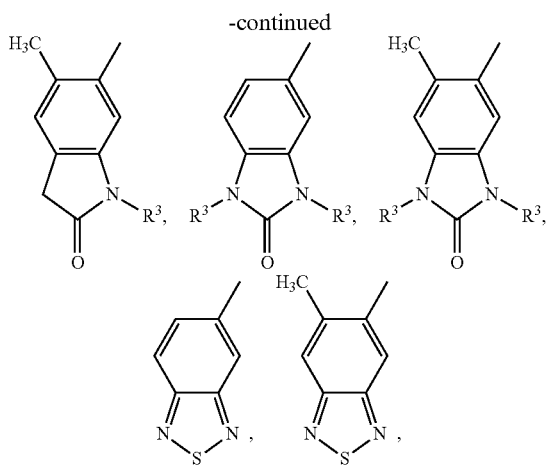

wherein m is 1, 2, or 3, n is 0, 1, 2 or 3 and $R^3$ is defined as above and preferably denotes H.

The compounds of the formula I can have one or more centres of chirality and can therefore occur in various stereoisomeric forms. The formula I covers all these forms.

Accordingly, the invention relates, in particular, to the use of those compounds of the formula (I) in which at least one of the said radicals has one of the preferred meanings indicated above. Some preferred groups of compounds can be expressed by the following sub-formulae Ia to Iq, which conform to the formula (I) and in which the radicals not designated in greater detail have the meaning indicated under the formula (I), but in which:

in Ia R denotes a monocyclic or bicyclic, aromatic carbocyclic or heterocyclic ring having 0 to 4 N, O and/or S atoms which is unsubstituted or monosubstituted or disubstituted by Hal, aminosulfonyl, methyl, hydroxyl, alkylsulfonyl, alkylaminosulfonyl, alkylsulfonylamino, $CF_3$, $OCF_3$, $SO_2NHA$, aminomethyl, hydroxyalkylaminosulfonyl, aminoalkylaminosulfonyl and/or $CONH_2$, wherein A is as defined above, in Ib R is substituted or unsubstituted phenyl, pyridyl, quinolin-4-yl, napthyl, preferably 4-aminosulfonyl-2-methyl-phenyl, 4-aminosulfonyl-phenyl, 4-hydroxy-phenyl, 4-hydroxy-2-methyl-phenyl, 2-fluoro-4-hydroxy-phenyl, 2-chloro-4-hydroxyphenyl, 4-hydroxy-naphtyl, quinolin-4-yl, 4-hydroxy-3-methyl-phenyl, 3-chloro-4-hydroxy-phenyl, 2,3-dimethyl-phenyl, 2,5-dimethyl-phenyl or 3-fluoro-4-hydroxy-phenyl, 4-(2-hydroxyethyl)aminosulfonyl-phenyl, 4-(2,3-dihydroxypropyl)aminosulfonyl-phenyl, 4-(2-methoxyethyl)aminosulfonyl-phenyl, 4-(ethylaminosulfonyl)-phenyl, 1H-indazol-5-yl, 6-methyl-1H-indazol-5-yl, 4-(aminomethyl)phenyl, 4-(aminocarbonyl)phenyl or 4-(2-hydroxyethyl)phenyl, in Id W denotes C=O or $SO_2$, in Ie Q denotes $NR^3$, in If $R^1$, $R^2$ denotes H, in Ig X denotes $NR^aR^b$ or $OR^b$, in Ih X is $NR^aR^b$, $R^a$ is hydrogen, alkyl or cycloalkyl, $R^b$ is cycloalkyl, R is selected from 4-aminosulfonyl-2-methyl-phenyl, 4-aminosulfonyl-phenyl, 4-(2-hydroxyethyl)aminosulfonyl-phenyl, 4-(2,3-dihydroxypropyl)aminosulfonyl-phenyl, 4-(2-methoxyethyl)aminosulfonyl-phenyl and 4-(ethylaminosulfonyl)-phenyl, W is CO,
Q is $NR^3$,
$R^1$, $R^2$ is H,
in Ii X is $NR^aR^b$,
$R^a$ is alkyl,
$R^b$ is cyclo alkyl or alkyl,
R is selected from 4-hydroxy-phenyl and 4-hydroxy-2-methyl-phenyl,
W is CO,
Q is $NR^3$,
$R^1$, $R^2$ are H,
in Ij X is O,
$R^b$ is cycloalkyl,
R is selected from 4-hydroxyphenyl and 4-hydroxy-2-methyl-phenyl,
W is CO,
Q is $NR^3$,
$R^1$, $R^2$ are H,
in Ik X is $NR^aR^b$,
$R^a$ is hydrogen or alkyl,
$R^b$ is alkyl or cycloalkyl,
R is selected from 1H-indazol-5-yl and 6-methyl-1H-indazol-5-yl,
W is CO,
Q is $NR^3$,
$R^1$, $R^2$ are H,
in Il X is $NR^aR^b$,
$R^a$ is alkyl,
$R^b$ is alkyl or cycloalkyl,
R is 4-(aminomethyl)phenyl,
W is CO,
Q is $NR^3$,
$R^1$, $R^2$ are H,
in Im X is $NR^aR^b$,
$R^a$ is hydrogen,
$R^b$ is cycloalkyl,
R is selected from 2-fluoro-4-hydroxy-phenyl, 2-chloro-4-hydroxyphenyl and 4-hydroxy-2-methyl-phenyl,
W is CO,
Q is $NR^3$,
$R^1$, $R^2$ are H,
in In X is $NR^aR^b$,
$R^a$ is hydrogen,
$R^b$ is alkyl,
R is 4-hydroxy-napthyl,
W is CO,
Q is $NR^3$,
$R^1$, $R^2$ are H,
in Io X is $NR^aR^b$,
$R^a$ is hydrogen or alkyl,
$R^b$ is alkyl,
R is selected from quinolin-4-yl and pyridine-4-yl,
W is CO,
Q is $NR^3$,
$R^1$, $R^2$ are H,
in Ip X is $NR^aR^b$,
$R^a$ is alkyl,
$R^b$ is alkyl or cycloalkyl,
R is 4-(aminocarbonyl)phenyl,
W is CO,
Q is $NR^3$,
$R^1$, $R^2$ are H,
in Iq X is $NR^aR^b$,
$R^a$ is hydrogen,
$R^b$ is alkyl, R is selected from 4-hydroxyphenyl, 4-hydroxy-3-methyl-phenyl, 3-chloro-4-hydroxy-phenyl, 2,3-dimethyl-phenyl, 2,5-dimethyl-phenyl, 3-fluoro-4-hydroxy-phenyl and 4-(2-hydroxyethyl)phenyl, W is CO, Q is $NR^3$, $R^1$, $R^2$ are H, and pharmaceutically usable derivatives, solvates, salts and stereoisomers thereof, including mixtures thereof in all ratios.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), under reaction conditions which are known and suitable for the said reactions. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, $3^{rd}$ Edition 1999.

Use can also be made here of variants which are known per se, but are not mentioned here in greater detail.

If desired, the starting materials can also be formed in situ so that they are not isolated from the reaction mixture, but instead are immediately converted further into the compounds of the formula I.

The starting compounds for the preparation of compounds of formula I are generally known. If they are novel, they can, however, be prepared by methods known per se.

The reactions are preferably carried out in an inert solvent. Examples of suitable inert solvents are hydrocarbons, such as hexane, petroleum ether, benzene, toluene or xylene; chlorinated hydrocarbons, such as trichloroethylene, 1,2-dichloro-ethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Pharmaceutical Salts and Other Forms

The said compounds of the formula (I) can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula (I) are for the most part prepared by conventional methods. If the compound of the formula I contains an acidic center, such as a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example sodium- or potassiumethoxide and sodium or potassiumpropoxide, alkalihydrides, such as sodium- or potassiumhydride; and various organic bases, such as piperidine, diethanolamine and N-methyl-glutamine, benzathine, choline, diethanolamine, ethylenediamine, meglumine, benethamine, diethylamine, piperazine and tromethamine. The aluminum salts of the compounds of the formula I are likewise included. In the case of certain compounds of the formula (I), which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoaryl-sulfonates, such as ethanesulfonate, toluenesulfonate and benzene-sulfonate, and other organic acids and corresponding salts thereof, such as acetate, trifluoro-acetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzene-sulfonate (besylate), bisulfate, bisulfite, bromide, butyrate, camphorate, camphor-sulfonate, caprylate, chloride, chlorobenzoate, citrate, cyclo-pentane-propionate, digluconate, dihydrogen-phosphate, dinitrobenzoate, dodecyl-sulfate, ethane-sulfonate, fumarate, galacterate (from mucic acid), galacturonate, glucoheptanoate, gluconate, glutamate, glycerophosphate, hemi-succinate, hemisulfate, heptanoate, hexanoate, hippurate, hydro-chloride, hydrobromide, hydroiodide, 2-hydroxy-ethane-sulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula (I) include aluminum, ammonium, calcium, copper, iron (III), iron(II), lithium, magne-sium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanol-amine, diethyl-amine, 2-diethyl-amino-ethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lidocaine, lysine, meglumine (N-methyl-D-glucamine), morpholine, piperazine, piperidine, polyamine resins, procaine, purines, theobromine, triethanol-amine, triethylamine, trimethylamine, tripropyl-amine and tris(hydroxy-methyl)-methylamine (tromethamine), but this is not intended to represent a restriction.

Compounds of the formula I of the present invention which contain basic nitrogen-containing groups can be quaternised using agents such as (C1-C4)-alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, do-decyl, lauryl, myristyl and stearyl chloride, bromide and iodide; and aryl-(C1-C4)alkyl halides, for example benzyl chloride and phenethyl bromide. Both water- and oil-soluble compounds of the formula I can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula (I) are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of the formula (I) are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula (I) contains more than one group which is capable of forming pharmaceutically acceptable salts of this type, the formula (I) also encompasses multiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula (I) can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of formula (I), in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function. These further medicaments, such as interferon beta, may be administered concomitantly or sequentially, e.g. by subcutaneous, intramuscular or oral routes.

These compositions can be used as medicaments in human and veterinary medicine.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I) and salts, solvates and physiologically functional derivatives thereof and the other active ingredients can also be administered in the form of liposome delivery systems, such as, for exam-ple, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range of 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

A therapeutically effective amount of a compound of the formula I and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a sphingosine 1-phosphate associated disorder, comprising administering to said subject an effective amount of a compound of formula I. The present invention preferably relates to a method, wherein the sphingosine 1-phosphate-1 associated disorder is an autoimmune disorder or condition associated with an overactive immune response.

The present invention furthermore relates to a method of treating a subject suffering from an immunoregulatory abnormality, comprising administering to said subject a compound of formula I in an amount that is effective for treating said immunoregulatory abnormality. The present invention preferably relates to a method wherein the immunoregulatory abnormality is an autoimmune or chronic inflammatory disease selected from the group consisting of: amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Preferred compounds of formula I exhibit a binding constant Ki for the binding to the $S1P_1$ receptor of less than about 5 μM, preferably less than about 1 μM and even more preferred less than about 0.1 μM.

In the following the present invention shall be illustrated by means of some examples, which are not construed to be viewed as limiting the scope of the invention.

EXAMPLES

General:

The HPLC data provided in the examples described below were obtained as followed.

HPLC columns: Xbridge™ $C_8$ column 50 mm×4.6 mm at a flow of 2 mL/min for conditions A and B.

Condition A: 8 min gradient from 0.1% TFA in $H_2O$ to 0.07% TFA in $CH_3CN$. Condition B: 8 min gradient from 95% $H_2O$ to 100% $CH_3CN$.

Phenomenex Luna 5 m C18 (2), 100 mm×4.6 mm at a flow of 2 mL/min for condition C.

Condition C: 8 min gradient from 95% (0.1% HCOOH in H2O) to 95% (0.1% HCOOH in $CH_3CN$).

Waters Xterra MS 5 m C18, 100 mm×4.6 mm at a flow of 2 mL/min for condition D.

Condition D: 8 min gradient from 95% (10 mM ammonium bicarbonatein H2O) to 95% $CH_3CN$.

UV detection (maxplot) for all conditions.

The MS data provided in the examples described below were obtained as followed: Mass spectrum: LC/MS Waters ZMD (ESI) or Micromass ZQ single quadrupole LC-MS (ESI or APCI).

The NMR data provided in the examples described below were obtained as followed: $^1$H-NMR: Bruker DPX-300 MHz or a Bruker DPX 400 MHz.

The microwave chemistry is performed on a single mode microwave reactor Emrys™ Optimiser from Personal Chemistry or on a Smith™ Creator from Personal Chemistry.

Preparative HPLC was performed on a mass directed autopurification Fractionlynx system from Waters. Column: Sunfire prep C18 OBD 19×100 mm; 5 microns. Mobile phase: 0.1% formic acid in water/0.1% formic acid in acetonitrile.

Intermediate 1 methyl 2-chloro-6-(cyclohexylamino)pyrimidine-4-carboxylate

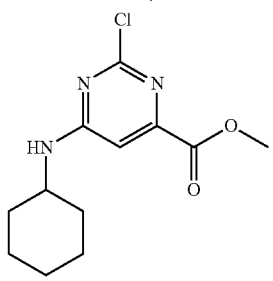

A cooled (0° C.) solution of methyl 2,4-dichloropyrimidine-6-carboxylate (Apollo, OR2558, 10.00 g; 48.31 mmol) in THF (300 mL) was treated with a solution of cyclohexylamine (Fluka, 5.53 mL; 48.3 mmol) and triethylamine (7.37 mL; 53.1 mmol) in THF (100 mL). The reaction mixture was stirred for 16 hours at RT. Water (50 mL) was poured into the reaction mixture which was extracted with EtOAc. The combined organic extracts were dried over magnesium sulfate, filtered and concentrated to obtain the crude product, which was purified by column chromatography (silica) eluting with cyclohexane containing increasing amounts of EtOAc. The title product was obtained as a white solid.

$^1$H NMR (300 MHz, DMSO-$d_6$) δ [ppm] 8.22 (1H, d, J=7.5 Hz), 7.05 (1H, s), 3.83 (1H, m), 1.88-1.53 (5H, m), 1.40-1.15 (5H, m). MS (ESI): 270.1. HPLC (Condition A): Rt 3.79 min (HPLC purity 99.5%).

Intermediate 2 methyl 2-chloro-6-(cyclopentylamino)pyrimidine-4-carboxylate

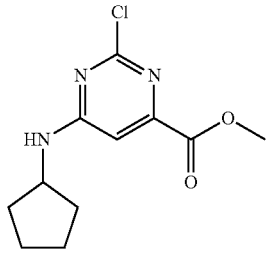 [SMILES: COC(=O)c1cc(NC2CCCC2)nc(Cl)n1]

A cooled (0° C.) solution of methyl 2,4-dichloropyrimidine-6-carboxylate (Apollo, OR2558, 4.50 g; 21.7 mmol) in anhydrous THF (200 mL) was treated with a solution of cyclopentylamine (Aldrich, 2.36 mL; 23.9 mmol) and triethylamine (3.03 mL; 21.7 mmol) in DCM (60 mL). The reaction mixture was stirred for 1 h30. The organic solvent was removed in vacuo and the crude was redissolved in EtOAc then washed with water and brine. The organic extracts were dried over magnesium sulfate, filtered and concentrated to obtain the crude product, which was purified by column chromatography (silica) eluting with cyclohexane containing increasing amounts of EtOAc. The title product was obtained as a white solid.

$^1$H NMR (300 MHz, DMSO-$d_6$) δ [ppm] 8.33 (1H, d, J=7.5 Hz), 7.04 (1H, s), 4.04 (1H, m), 3.82 (3H, s), 1.98-1.86 (2H, m), 1.72-1.37 (6H, m). MS (ESI$^+$): 256.1. HPLC (Condition A): Rt 3.41 min (HPLC purity 99.7%).

Intermediate 3 methyl 2-chloro-6-[(cyclohexylmethyl)amino]pyrimidine-4-carboxylate

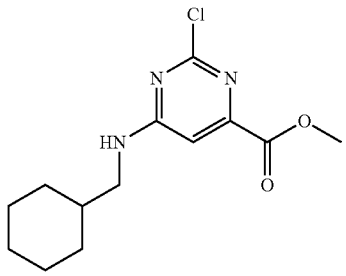 [SMILES: COC(=O)c1cc(NCC2CCCCC2)nc(Cl)n1]

A cooled (0° C.) solution of methyl 2,4-dichloropyrimidine-6-carboxylate (Apollo, OR2558, 2.62 g; 12.7 mmol) in anhydrous THF (95 mL) was treated with a solution of cyclohexanemethylamine (Aldrich, 1.68 mL; 12.66 mmol) and triethylamine (1.93 mL; 13.92 mmol) in THF (35 mL). The reaction mixture was stirred during 30 min. Water (50 mL) was poured into the reaction mixture, which was extracted with EtOAc. The combined organic extracts were dried over magnesium sulfate, filtered and concentrated, which was purified by column chromatography (silica) eluting with cyclohexane containing increasing amounts of EtOAc. The title product was obtained as a white solid.

$^1$H NMR (300 MHz, CDCl3) δ [ppm] 6.98 (1H, s), 5.62 and 5.15 (1H, bs), 3.95 (3H, s), 3.35 (1H, bs), 3.11 (1H, bs), 1.76-1.51 (6H, m), 1.26-1.13 (3H, m), 1.04-0.82 (2H, m). MS (ESI$^+$): 284.1. HPLC (Condition A): Rt 4.27 min (HPLC purity 99.6%).

Intermediate 4

6-(cyclohexylamino)pyrimidine-4-carboxylic Acid

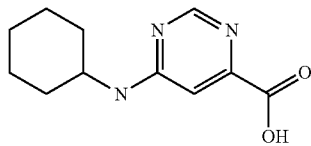 [SMILES: O=C(O)c1cc(NC2CCCCC2)ncn1]

A mixture of methyl 2-chloro-6-(cyclohexylamino)pyrimidine-4-carboxylate (Intermediate 1, 9.20 g; 34.1 mmol), triethylamine (14.3 mL; 102 mmol) and palladium on charcoal (750 mg) in EtOH (1 L) was stirred at RT under an atmosphere of hydrogen for 16 hours. The reaction mixture was filtered through celite and the solvent was evaporated in vacuo to give a mixture of methyl 6-(cyclohexylamino)pyrimidine-4-carboxylate and ethyl 6-(cyclohexylamino)pyrimidine-4-carboxylate. This crude was dissolved in a mixture of THF/EtOH/H$_2$O (3/2/1, 1 L) and treated with an aqueous lithium hydroxide solution (1N, 102 mmol). After 1 hour, the organic solvents were evaporated in vacuo and water was added. The aqueous layer was washed with DCM (200 mL), then acidified to pH 4 by addition of an HCl solution (1N). The aqueous layer was evaporated to reduce the volume by 30-50%. A white solid appeared and was filtered to afford the title compound as a white solid.

$^1$H NMR (300 MHz, DMSO-d$_6$) δ [ppm] 8.46 (1H, s), 8.19 (1H, d, J=7.5 Hz), 7.02 (1H, s), 3.86 (1H, m), 1.93-1.90 (2H, m), 1.73-1.69 (2H, m), 1.60-1.56 (2H, m), 1.37-1.14 (5H, m). MS (ESI$^+$): 222.1. HPLC (Condition A): Rt 1.71 min (HPLC purity 99.8%).

Intermediate 5

6-(cyclopentylamino)pyrimidine-4-carboxylic Acid

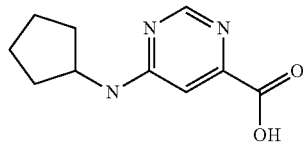 [SMILES: O=C(O)c1cc(NC2CCCC2)ncn1]

A mixture of methyl 2-chloro-6-[(cyclopentylmethyl)amino]pyrimidine-4-carboxylate (Intermediate 2, 2.00 g; 7.82 mmol; 1.00 eq.), palladium on charcoal (750 mg) and triethylamine (3.27 mL; 23.5 mmol) in EtOH (200 mL) was stirred under an atmosphere of hydrogen for 2 hours. After 2 hours the reaction mixture was filtered on celite and evaporated to give a mixture of methyl 6-(cyclopentylamino)pyrimidine-4-carboxylate and ethyl 6-(cyclopentylamino)pyrimidine-4-carboxylate. The crude mixture was dissolved in a mixture of THF/EtOH/H$_2$O (3/2/1, 120 mL) and treated with an aqueous solution of lithium hydroxide (1N, 23.5 mL, 23.5 mmol). The reaction mixture was stirred at RT for 60 minutes. Water was added (50 mL) and the aqueous layer was washed with DCM (30 mL). The aqueous layer was acidified to pH 5 by addition of an HCl solution (1N). The aqueous layer was evaporated in vacuo to reduce the volume by 30-50%. The resulting white solid was filtered to afford the title compound as a white solid.

$^1$H NMR (300 MHz, DMSO-d$_6$) δ [ppm] 8.48 (1H, s), 8.25 (1H, bs), 7.01 (1H, s), 4.29 (1H, m), 1.98-1.87 (2H, m), 1.73-1.44 (6H, m). MS (ESI$^+$): 208.1. HPLC (Condition A): Rt 1.34 min (HPLC purity 99.3%).

Intermediate 6

6-[(cyclohexylmethyl)amino]pyrimidine-4-carboxylic Acid

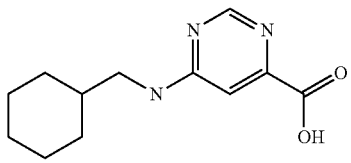 [SMILES: O=C(O)c1cc(NCC2CCCCC2)ncn1]

A mixture of methyl 2-chloro-6-[(cyclohexylmethyl)amino]pyrimidine-4-carboxylate (Intermediate 3, 2.25 g; 7.93 mmol), palladium on charcoal and triethylamine (3.32 mL; 23.8 mmol) in EtOH (400 mL) was stirred under an atmosphere of hydrogen. After 2 hours the reaction mixture was filtered on celite and evaporated to give a mixture of methyl 6-[(cyclohexylmethyl)amino]pyrimidine-4-carboxylate and ethyl 6-[(cyclohexylmethyl)amino]pyrimidine-4-carboxylate. The crude mixture was dissolved in a mixture of THF/EtOH/H2O (3/2/1, 84 mL) and treated with an aqueous solution of lithium hydroxide (1N, 16 mL, 16 mmol). The reaction mixture was stirred at RT for 60 minutes. Water was added (50 mL) and the aqueous layer was washed with chloroform. and the aqueous layer was washed with DCM (30 mL). The aqueous layer was acidified to pH 5 by addition of an HCl solution (1N). A precipitate was formed, which was filtered to afford the title compound.

$^1$H NMR (300 MHz, DMSO-d$_6$) δ [ppm] 8.52 (1H, s), 8.28 (1H, s), 7.09 (1H, s), 1.77-1.53 (7H, m), 1.25-1.14 (3H, m), 1.02-0.90 (3H, m). MS (ESI$^+$): 236.0. HPLC (Condition A): Rt 2.32 min (HPLC purity 98.8%).

Intermediate 7

6-chloro-N-(4-hydroxyphenyl)pyrimidine-4-carboxamide

Step 1-6-Chloropyrimidine-4-carbonyl Chloride

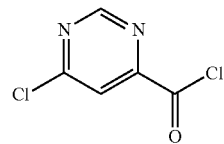

A stirred mixture of 6-hydroxypyrimidine-4-carboxylic acid (10.0 g, 71.4 mmol, prepared according to the method described by Daves, G. C.; Baiocchi, F.; Robins, R. K.; Cheng, C. C. in J. Org. Chem. 1961, 26, 2755-2763) and phosphorus pentachloride (58.0 g, 0.27 mol) was treated with phosphorus oxychloride (100 mL, 1.07 mol) and the resultant mixture was refluxed for 16 hours under nitrogen. The excess phosphorus oxychloride was distilled off and the residue was azeotroped three times with toluene and dried in vacuo. The solid product obtained was suspended in dry dichloromethane (100 mL), cooled (0° C.) and treated with dry DMF (2 mL) and oxalyl chloride (7.9 mL, 91 mmol). The resultant mixture was stirred at room temperature for 15 hours and evaporated in vacuo to afford 6-chloropyrimidine-4-carbonyl chloride as a brown liquid, which was used for the next step.

Step 2-6-chloro-N-(4-hydroxyphenyl)pyrimidine-4-carboxamide

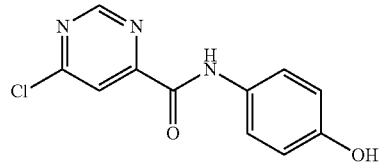 [SMILES: O=C(Nc1ccc(O)cc1)c1cc(Cl)ncn1]

A cooled (0° C.) solution of 4-amino phenol (Aldrich, 8.85 g, 82 mmol) and triethylamine (57 mL, 0.410 mol) in dry dichloromethane (100 mL) was treated with 6-chloropyrimidine-4-carbonyl chloride, obtained as described above (14.5 g, 82 mmol) and the resulting mixture was stirred at room temperature for 12 hours. The reaction mixture was concentrated in vacuo, diluted with water and extracted with EtOAc. The combined organic layers were dried on magnesium sulfate and evaporated in vacuo. The crude product was purified by column chromatography (silica) using as eluent petroleum ether/EtOAc to afford the title compound as a brown solid.

¹H NMR (DMSO-d₆, 400 MHz): δ 10.66 (1H, s), 9.39 (1H, s), 9.24 (1H, s), 8.17 (1H, s), 7.65-7.68 (2H, d, J=9.0 Hz), 6.74-6.77 (2H, d, J=9.0 Hz). MS (ESI⁻): 247.7. HPLC(Condition A): Rt 2.19 min (HPLC purity 96.0%). TLC:Chlorofrom/methanol (9/1): R_f-0.4.

Intermediate 8

6-Chloro-N-(4-hydroxy-2-methylphenyl)pyrimidine-4-carboxamide

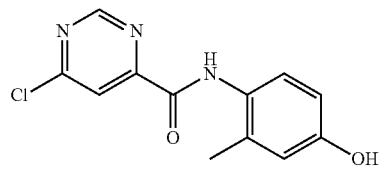 [SMILES: Cc1cc(O)ccc1NC(=O)c1cc(Cl)ncn1]

A cooled (0° C.) solution of 4-amino-m-cresol (Fluka, 4.17 g, 33.9 mmol) and triethylamine (23.6 mL, 0.170 mol) in dry dichloromethane (100 mL) was treated with 6-chloropyrimidine-4-carbonyl chloride, obtained as described above for Intermediate 7, step 1 (6.0 g, 34 mmol) and the resulting mixture was stirred at room temperature for 12 hours. The reaction mixture was concentrated in vacuo, diluted with water and extracted with EtOAc. The combined organic layers were dried on magnesium sulfate and evaporated in vacuo. The crude product was purified by column chromatography (silica) using as eluent petroleum ether/EtOAc to afford the title compound as yellow solid.

MS (ESI⁻): 247.7. HPLC (Condition A): Rt 2.19 min (HPLC purity 96.0%). ¹H NMR (DMSO-d₆, 400 MHz): δ 10.26 (1H, s), 9.33 (1H,s), 9.25 (1H, s), 8.17 (1H, s), 7.26 (1H, d, J=9.0 Hz), 6.67 (1H, s), 6.60 (1H, d, J=9.0 Hz), 2.15 (3H, s). MS (ESI⁻): 262.0. HPLC(Condition A): Rt 2.81 min (HPLC purity 96.5%).

TLC: Chlorofrom/methanol (9/1): R Chlorofrom/methanol (9/1): R_f-0.4.

Intermediate 9 methyl 2-chloro-6-[cyclohexylmethyl)amino]pyrimidine-4-carboxylate

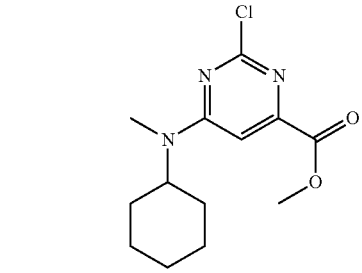 [SMILES: COC(=O)c1cc(N(C)C2CCCCC2)nc(Cl)n1]

A cooled (0° C.) solution of methyl 2,4-dichloropyrimidine-6-carboxylate (Apollo, OR2558, 25.00 g; 120 mmol) in THF (500 mL) was treated with a solution of n-methylcyclohexylamine (Aldrich, 15.7 ml; 121 mmol) and triethylamine (18.4 ml; 133 mmol) in THF (250 mL). The reaction mixture was stirred for 16 hours at RT. Water (250 mL) was poured into the reaction mixture which was extracted with EtOAc. The combined organic extracts were dried over magnesium sulfate, filtered and concentrated to obtain the crude product, which was purified by recrystallisation from MTBE. The title product was obtained as a beige solid (25.7 g, 75%).

¹H NMR (300 MHz, DMSO-d6) δ 7.28 and 7.08 (1H, s), 4.57 (1H, m), 3.85 (3H, s), 2.93 (3H, bs), 1.98-1.06 (10H, m). MS (ESI+): 284.1. HPLC (Condition A): Rt 4.35 min (HPLC purity 99.5%).

Intermediate 10

6-[cyclohexylmethyl)amino]pyrimidine-4-carboxylic Acid

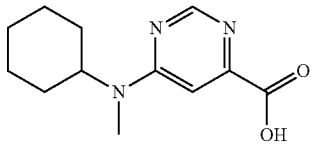 [SMILES: CN(c1cc(C(=O)O)ncn1)C1CCCCC1]

A mixture of methyl 2-chloro-6-[cyclohexyl(methyl) amino]pyrimidine-4-carboxylate (Intermediate 9, 10.00 g; 35.2 mmol), triethylamine (14.7 mL; 105 mmol) and palladium on charcoal (750 mg) in EtOH (1 L) was stirred at RT under an atmosphere of hydrogen for 16 hours. The reaction mixture was filtered through celite and the solvent was evaporated in vacuo to give a mixture of methyl 6-[cyclohexyl (methyl)amino]pyrimidine-4-carboxylate and ethyl 6-[cyclohexyl(methyl)amino]pyrimidine-4-carboxylate. This crude was dissolved in a mixture of THF/EtOH/H2O (3/2/1, 1 L) and treated with an aqueous lithium hydroxide solution (1N, 105 mL, 105 mmol). After 1 hour, the organic solvents were evaporated in vacuo and water (900) was added. The aqueous layer was washed with DCM (200 mL), then acidified to pH 4 by addition of a HCl solution (1N). The aqueous layer was evaporated to reduce the volume by 30-50%. A precipitate appeared and was filtered to afford the title compound as a white solid.

¹H NMR (300 MHz, DMSO-d6) δ 8.58 (1H, s), 7.15 (1H, s), 4.70 (1H, m), 3.01 (3H, s), 1.83-1.15 (10H, m). MS (ESI+): 235.8. HPLC (Condition A): Rt 2.03 min (HPLC purity 99.3%).

Intermediate 11 methyl 2-chloro-6-[cyclohexyhcyclopropylmethyl) amino]pyrimidine-4-carboxylate

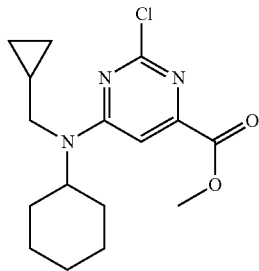 [SMILES: COC(=O)c1cc(N(CC2CC2)C2CCCCC2)nc(Cl)n1]

A cooled (0° C.) solution of methyl 2,4-dichloropyrimidine-6-carboxylate (Apollo, OR2558, 5.00 g; 24.1 mmol) in THF (50 mL) was treated with triethylamine (7.38 ml; 53.1 mmol) and cyclohexyl(cyclopropylmethyl)amine hydrochloride (Chembridge, 4.58 g; 24.1 mmol. The reaction mixture was stirred for 2 days at RT. The solvent was evaporated under reduced pressure, the remaining residue was partitioned between 100 ml of ethyl acetate and a saturated aqueous solution of NH4Cl (50 mL). The organic phase was washed with brine, dried over magnesium sulfate, filtered and concentrated to obtain the crude product, which was purified by column chromatography (silica) eluting with cyclohexane containing increasing amounts of EtOAc to give the title product as a yellow oil, which solidified upon standing (6.14 g, 78%).

¹H NMR (300 MHz, DMSO-d6) δ 7.20 (1H, s), 3.85 (3H, s), 4.5 (1H, bs), 3.30 (2H, m), 1.79-1.05 (11H, m), 0.49 (2H, s), 0.35 (2H, s). MS (ESI+): 325.9. HPLC (Condition A): Rt 5.07 min (HPLC purity 99.3%).

Intermediate 12 methyl 6-[cyclohexyl(cyclopropylmethyl)amino] pyrimidine-4-carboxylate

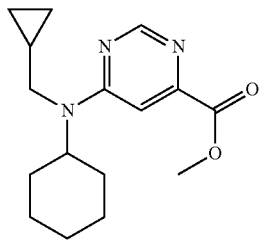 [SMILES: COC(=O)c1cc(N(CC2CC2)C2CCCCC2)ncn1]

A solution of methyl 2-chloro-6-[cyclohexyl(cyclopropylmethyl)amino]pyrimidine-4-carboxylate (Intermediate 11, 4.77 g; 14.7 mmol) in 150 ml of iPrOH was treated with 780 mg of palladium (10% on C). The suspension was degassed and a solution of ammonium formate (6.96 g; 110 mmol) in 20 ml of water was added. After stirring at RT for 45 minutes, the suspension was filtered on a pad of Celite, the remaining residue was twice rinsed with 50 ml of iPrOH and the combined filtrates were evaporated under reduced pressure. The remaining colorless residue was partitioned between 150 ml of MTBE and 150 ml of water. Both layers were separated. The organic phase was once washed with 100 ml of brine, dried over MgSO4 and concentrated under reduced pressure to give the title compound as colorless oil (4.14 g, 97%).

¹H NMR (300 MHz, DMSO-d6) δ 8.57 (1H, s), 7.21 (1H, s), 4.5 (1H, bs), 3.86 (3H, s), 3.35 (2H, m), 1.81-0.97 (11H, m), 0.50 (2H, s), 0.34 (2H, s). MS (ESI+): 290.3. HPLC (Condition A): Rt 2.91 min (HPLC purity 97.0%).

Intermediate 13

6-[cyclohexyl(cyclopropylmethyl)amino]pyrimidine-4-carboxylic Acid

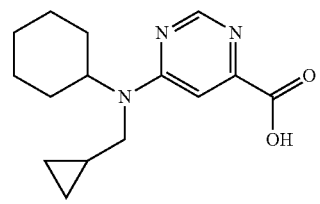 [SMILES: O=C(O)c1cc(N(CC2CC2)C2CCCCC2)ncn1]

A solution of methyl 6-[cyclohexyl(cyclopropylmethyl) amino]pyrimidine-4-carboxylate (Intermediate 12, 4.14 g; 14.3 mmol) in THF/EtOH/H2O (3/2/1, 120 ml) was treated with an aqueous solution of lithium hydroxide monohydrate (42.9 ml; 1.00 M; 42.9 mmol) at ambient temperature. After 1 hour, the organic solvents were evaporated in vacuo, the remaining aqueous layer was acidified with HCl (1 N) until pH=6 and extracted with DCM (4×50 ml). The combined organic layers were dried over MgSO₄ and evaporated to dryness to give the title compound as an off-white solid (3.64 g, 92.5%).

1H NMR (300 MHz, DMSO-d₆) δ 8.56 (1H, s), 7.19 (1H, s), 4.5 (1H, bs), 3.38 (2H, m), 1.80-0.96 (11H, m), 0.49 (2H, s), 0.39 (2H, s). MS (ESI−): 273.9. HPLC (Condition A): Rt 2.75 min (HPLC purity 99.4%).

Intermediate 14

4-amino-N-(2,3-dihydroxypropyl)benzenesulfonamide

Step 1-N-(2,3-dihydroxypropyl)-4-nitrobenzenesulfonamide

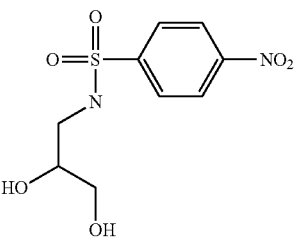 [SMILES: O=[N+]([O-])c1ccc(S(=O)(=O)NCC(O)CO)cc1]

A solution of 4-nitrobenzenesulfonyl chloride (Fluka, 1.00 g; 4.51 mmol) in DCM (20 mL) was treated with triethylamine (1.25 ml; 9.02 mmol) and 3-amino-1,2-propanediol (Aldrich, 518 µA; 6.77 mmol). After 2 hours, the organic solvents were evaporated in vacuo, the residue was taken up in EtOAc and extracted with a saturated NH$_4$Cl solution. The combined organic layers were dried over MgSO$_4$ and evaporated to dryness to give the title compound as a yellow solid.

1H NMR (300 MHz, DMSO-d6) δ 8.42 (2H, d, J=9.0 Hz), 8.05 (2H, d, J=9.0 Hz), 7.95 (1H, bs), 4.79 (1H, d, J=5.0 Hz), 4.55 (1H, bs), 3.44 (1H, m), 3.25 (2H, m), 2.95 (1H, dd, J=13.0 Hz, J=4.5 Hz), 2.67 (1H, dd, J=13.0 Hz, J=7.5 Hz). MS (ESI–): 275.1. HPLC (Condition A): Rt 1.62 min (HPLC purity 100.0%).

Step 2-4-amino-N-(2,3-dihydroxypropyl)benzenesulfonamide

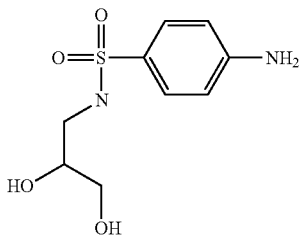

A solution of N-(2,3-dihydroxypropyl)-4-nitrobenzenesulfonamide (493 mg; 1.78 mmol) in MeOH (40 ml) was hydrogenated with an H-Cube flow hydrogenator (10% Pd/C cartridge (30 mm), 25° C., flow 1 mL/min, full H2 mode). The solvent was removed under reduced pressure to give the title compound as a colorless oil (388 mg, 88%).

$^1$H NMR (300 MHz, DMSO-d6) δ 7.40 (2H, d, J=9.0 Hz), 6.91 (1H, t, J=6.0 Hz), 6.60 (2H, d, J=9.0 Hz), 5.90 (2H, bs), 4.68 (1H, d, J=5.0 Hz), 4.49 (1H, t, J=5.5 Hz), 3.43 (1H, m), 3.25 (2H, t, J=5.5 Hz), 2.77 (1H, m), 2.54 (1H, m). MS (ESI+): 247.1.

Intermediate 15

4-amino-N-(2-methoxyethyl)benzenesulfonamide

Step 1-N-(2-methoxyethyl)-4-nitrobenzenesulfonamide

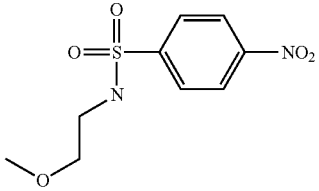 [SMILES: COCCNS(=O)(=O)c1ccc([N+](=O)[O-])cc1]

A solution of 4-nitrobenzenesulfonyl chloride (Fluka, 1.00 g; 4.51 mmol) in DCM (30 mL) was treated with 2-methoxyethylamine (Fluka, 1.9 ml; 22.6 mmol). After 2 hours, the organic solvents were evaporated in vacuo, the residue was taken up in EtOAc and extracted with a saturated NH$_4$Cl solution. The combined organic layers were dried over MgSO$_4$ and evaporated to dryness to give the title compound as a pale yellow solid (1.077 g, 92%).

$^1$H NMR (300 MHz, DMSO-d$_6$) δ 8.41 (2H, d, J=8.0 Hz), 8.15 (1H, s), 8.04 (2H, d, J=8.0 Hz), 3.30 (2H, m), 3.12 (3H, s), 2.99 (2H, t, J=5.5 Hz). MS (ESI$^-$): 258.8. HPLC (Condition A): Rt 2.65 min (HPLC purity 99.1%).

Step 2-4-amino-N-(2-methoxyethyl)benzenesulfonamide

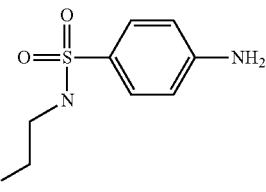

A solution of N-(2,3-dihydroxypropyl)-4-nitrobenzenesulfonamide (1.07 g; 4.23 mmol) in MeOH (100 ml) was hydrogenated with an H-Cube flow hydrogenator (10% Pd/C cartridge (30 mm), 25° C., flow 1 mL/min, full H$_2$ mode). The solvent was removed under reduced pressure to give the title compound as a colorless oil (1.00 g, quant).

$^1$H NMR (300 MHz, DMSO-d$_6$) δ 7.40 (2H, d, J=8.0 Hz), 7.17 (1H, t, J=6.0 Hz), 6.60 (2H, d, J=8.0 Hz), 5.92 (2H, bs), 3.27 (2H, t, J=6.0 Hz), 3.17 (3H, s), 2.79 (2H, t, J=6.0 Hz). MS (ESI$^-$): 229.1. HPLC (Condition A): Rt 1.21 min (HPLC purity 97.3%).

Intermediate 16

6-chloro-N-1H-indazol-5-ylpyrimidine-4-carboxamide

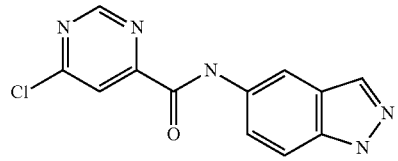 [SMILES: O=C(Nc1ccc2[nH]ncc2c1)c1cc(Cl)ncn1]

To a cooled (0° C.) solution of 6-chloropyrimidine-4-carbonyl chloride in DCM (60 mL), obtained as described above for Intermediate 7, step 1 (798 mg; 4.51 mmol) was added dropwise, during a period of 30 minutes, a solution of 5-aminoindazole (Aldrich, 500 mg; 3.76 mmol) and DIEA (1.29 ml; 7.51 mmol) in dry DMF (5 mL). At the end of addition the reaction mixture was concentrated in vacuo, diluted with water and extracted with EtOAc. A white precipitate separated from the organic phase. It was filtered and dried in vacuo to afford the title compound as a beige solid.

$^1$H NMR (300 MHz, DMSO-d$_6$) δ 13.09 (1H, s), 10.94 (1H, s), 9.29 (1H, d, J=1.0 Hz), 8.37 (1H, bs), 8.22 (1H, d, J=1.0 Hz), 8.09 (1H, t, J=1.0 Hz), 7.78 (1H, dd, J=9.0 Hz,

J=2.0 Hz), 7.55 (1H, d, J=9.0 Hz). MS (ESI⁻⁻): 272.1. HPLC (Condition A): Rt 2.51 min (HPLC purity 96.6%).

Intermediate 17

6-chloro-pyrimidine-4-carboxylic acid (2-methyl-4-sulfamoyl-phenyl)-amide

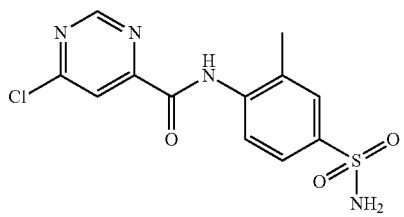 [SMILES: Cc1cc(S(N)(=O)=O)ccc1NC(=O)c1cc(Cl)ncn1]

A cooled (0° C.) solution of 6-chloropyrimidine-4-carbonyl chloride (4.56 g; 25.8 mmol) in DCM (80 ml) was treated dropwise over 30 minutes with a solution of 4-amino-3-methyl-benzenesulfonamide (4.00 g; 21.5 mmol) and DIEA (7.40 ml; 43.0 mmol) in anhydrous DMF (10 mL). At the end of addition the reaction mixture was concentrated under vacuum and the residue was taken up in EtOAc (200 mL). The organic phase was washed with water/brine (80 mL). A precipitate was formed, which was filtered and dried under vacuum to afford the crude product which was recrystallized from EtOH. The title product was obtained as a white solid.

¹H NMR (300 MHz, DMSO-d6) δ 10.65 (1H, br s), 9.31 (1H, d, J=1.1 Hz), 8.24 (1H, d, J=1.1 Hz), 7.85-7.68 (3H, m), 7.33 (2H, br s), 2.36 (3H, s). MS (ESI−): 325.1. HPLC (Condition A): Rt 2.73 min (HPLC purity 100.0%).

Intermediate 18

6-chloro-N-(2-methylphenyl)pyrimidine-4-carboxamide

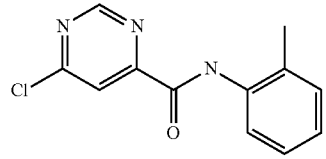 [SMILES: Cc1ccccc1NC(=O)c1cc(Cl)ncn1]

A cooled (0° C.) solution of 6-chloropyrimidine-4-carbonyl chloride (26.76 g; 151 mmol), obtained as described above for Intermediate 7 step 1, in anhydrous DCM (270 ml) was treated dropwise over 25 minutes with a solution of o-toluidine (13.6 ml; 126.0 mmol) and DIEA (43.4 ml; 252 mmol) in anhydrous DCM (100 mL). At the end of addition, the reaction mixture was washed with water then brine, dried over MgSO₄, filtered and dried under vacuum to afford the title compound used without further purification as a brown solid. ¹H NMR (300 MHz, DMSO-d6) δ 10.47 (1H, br s), 9.32 (1H, d, J=1.0 Hz), 8.25 (1H, d, J=1.0 Hz), 7.65-7.63 (1H, m), 7.34-7.19 (3H, m), 2.31 (3H, s). MS (ESI+): 248.0; MS (ESI−): 246.1. HPLC (Condition A): Rt 4.19 min (HPLC purity 96.0%).

Intermediate 19

6-[cyclohexyl(cyclopropylmethyl)amino]-N-(2-methylphenyl)pyrimidine-4-carboxamide

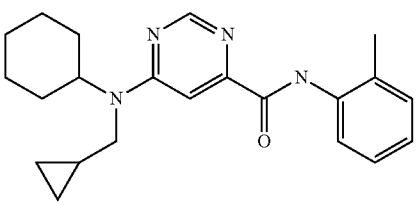 [SMILES: Cc1ccccc1NC(=O)c1cc(N(CC2CC2)C2CCCCC2)ncn1]

A solution of 6-chloro-N-(2-methylphenyl)pyrimidine-4-carboxamide (Intermediate 18; 3.00 g; 12.11 mmol) in EtOH (30 ml) was treated with DIEA (4.17 ml; 24.2 mmol) and cyclohexyl-cyclopropanemethyl-amine (Chembridge; 3.71 g; 24.2 mmol) and heated at 160° C. for 1 h. At the end of addition the reaction mixture was concentrated in vacuo, diluted with water and extracted with EtOAc. The combined organic layers were washed with NH4Cl, NaHCO3 and brine, dried on magnesium sulfate and evaporated in vacuo to afford the title compound as a brown solid, which was purified by precipitation from cyclohexane to afford the title compound as a beige solid.

¹H NMR (300 MHz, DMSO-d6) δ 10.22 (1H, br s), 8.69 (1H, d, J=0.9 Hz), 7.90 (1H, d, J=8.0 Hz), 7.37 (1H, d, J=1.1 Hz), 7.33-7.13 (3H, m), 2.34 (3H, s), 1.74-0.39 (18H, m). MS (ESI+): 365.3. HPLC (Condition A): Rt 4.82 min (HPLC purity 94.9%).

Intermediate 20

4-[({6-[cyclohexyl(cyclopropylmethyl)amino]pyrimidin-4-yl}carbonyl)amino]-3-methylbenzenesulfonyl Chloride

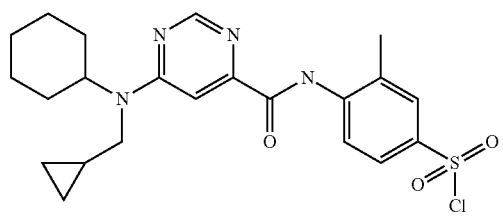 [SMILES: Cc1cc(S(=O)(=O)Cl)ccc1NC(=O)c1cc(N(CC2CC2)C2CCCCC2)ncn1]

A cooled (−78° C.) solution of 6-[cyclohexyl(cyclopropylmethyl)amino]-N-(2-methylphenyl)pyrimidine-4-carboxamide (Intermediate 19; 2.70 g; 7.41 mmol) in DCM (27 ml) was treated dropwise with a solution of chlorosulfonic acid (2.48 ml; 37.0 mmol) in DCM (2 mL). The reaction mixture was allowed to warm to RT, then it was stirred at RT for 16 hours. The solution was cooled again (−78° C.) and treated with a second aliquot of chlorosulfonic acid (0.99 ml; 14.8 mmol) and the reaction mixture was stirred at RT for 4 h. The mixture was cooled to 5° C. and a mixture of ice/water was carefully added. The resulting precipitate was filtered and dried under vacuum to give the title compound.

¹H NMR (300 MHz, DMSO-d6) δ 10.38 (1H, br s), 9.13 (1H, s), 7.98 (1H, s), 7.52-7.47 (3H, m), 2.24 (3H, s), 2.12-0.90 (18H, m). MS (ESI+): 463.3. HPLC (Condition A): Rt 4.01 min (HPLC purity 92.3%).

Intermediate 21

6-[(cyclopropylmethyl)(propyl)amino]pyrimidine-4-carboxylic Acid

Step 1: methyl 2-chloro-6-[(cyclopropylmethyl)(propyl)amino]pyrimidine-4-carboxylate

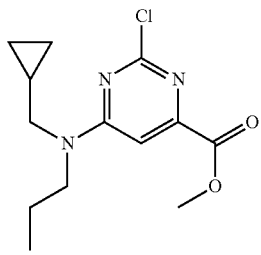 [SMILES: CCCN(CC1CC1)c1cc(C(=O)OC)nc(Cl)n1]

A cooled (0° C.) solution of methyl 2,4-dichloropyrimidine-6-carboxylate (Apollo, 10.00 g; 48.3 mmol) in dry THF (200 ml) was treated dropwise over 1 hour with a solution of N-(cyclopropylmethyl)propane-1-amine (6.92 ml; 48.3 mmol) and triethylamine (7.37 ml; 53.1 mmol) in THF (100 ml). The reaction mixture was stirred at room temperature for 18 hours. Water (200 mL) was poured into the reaction mixture, which was extracted with EtOAc. The combined organic extracts were dried over MgSO₄, filtered and concentrated under vacuum to afford the crude product, which was precipitated from MTBE (50 mL) to give the title compound as a beige solid.

MS (ESI+): 284.1. HPLC (Condition A): Rt 4.33 min (HPLC purity 97.4%).

Step 2: methyl 6-[(cyclopropylmethyl)(propyl)amino]pyrimidine-4-carboxylate

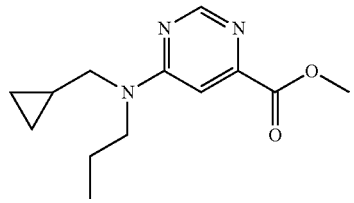 [SMILES: CCCN(CC1CC1)c1cc(C(=O)OC)ncn1]

A suspension of palladium on charcoal (1.2 g) in IPrOH (219 ml) was treated with a solution of (ammonium formate (12.16 g; 193 mmol) in 35 mL of water) followed by methyl 2-chloro-6-[(cyclopropylmethyl)(propyl)amino]pyrimidine-4-carboxylate (7.30 g; 25.7 mmol) and the mixture was stirred at room temperature for 1 h. The mixture was filtered through a pad of celite and rinsed with MeOH. Solvents were concentrated under vacuum. The crude was dissolved in DCM and washed with water and brine. The organic phase was dried over MgSO₄, filtered and concentrated under vacuum to afford the title compound as a yellow oil (5.24 g, 81.7%).

MS (ESI+): 250.2. HPLC (Condition A): Rt 2.26 min (HPLC purity 99.7%).

Step 3: 6-[(cyclopropylmethyl)(propyl)amino]pyrimidine-4-carboxylic acid

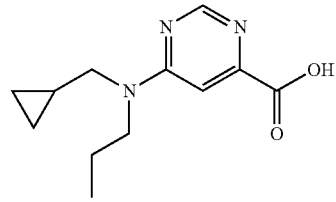 [SMILES: CCCN(CC1CC1)c1cc(C(=O)O)ncn1]

A solution of methyl 6-[(cyclopropylmethyl)(propyl)amino]pyrimidine-4-carboxylate (5.10 g; 20.5 mmol) in THF/EtOH/H₂O (3/2/1, total volume 400 mL) was treated with an aqueous solution (1N) LiOH (60 mL; 60 mmol). The reaction mixture was stirred at room temperature for 1 h. The solvents were concentrated under vacuum and then water (200 mL) was added. The aqueous layer was washed with DCM then acidified to pH 5 by addition of 1N HCl solution (60 mL). The aqueous layer was extracted with DCM (3 times) and the combined organic layers were dried over MgSO₄, filtered and concentrated under vacuum to give the title compound as a yellow solid (3.71 g, 77.1%).

¹H NMR (300MHz, DMSO-d6) δ 8.30 (1H, s), 6.89 (1H, s), 2.27-2.24 (4H, m), 1.41-1.29 (2H, m), 0.86 (1H, m), 0.65 (3H, t, J=7.5Hz), 0.25-0.23 (2H, m), 0.09-0.07 (2H, m). MS (ESI+): 236.2; MS (ESI−) 234.3. HPLC (Condition A): Rt 2.09 min (HPLC purity 100.0%).

Intermediate 22 tert-butyl (4-{[(6-chloropyrimidin-4-yl)carbonyl]amino}benzyl)carbamate

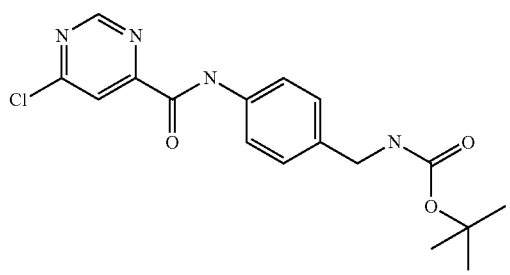 [SMILES: CC(C)(C)OC(=O)NCc1ccc(NC(=O)c2cc(Cl)ncn2)cc1]

To a cooled (0° C.) solution of 6-chloropyrimidine-4-carbonyl chloride in DCM (30 mL), obtained as described above for Intermediate 7, step 1 (1.43 g; 8.10 mmol) was added dropwise, during a period of 15 minutes, a solution of (4-amino-benzyl)-carbamic acid tert-butyl ester (Astatech, 1.50 g; 6.75 mmol) and DIEA (2.33 ml; 13.5 mmol) in DCM (5 mL). At the end of addition the reaction mixture was concentrated in vacuo, diluted with water and extracted with EtOAc. The resulting precipitate was filtered and dried under vacuum. The mother liquors were dried on MgSO₄, concentrated under vacuum to give a residue, which was precipitated from cyclohexane. The two solids were combined to give the title compound as a brown solid.

¹H NMR (300MHz, DMSO-d6) δ 10.85 (1H, br s), 9.27 (1H, d, J=1.0 Hz), 8.21 (1H, d, J=1.0 Hz), 7.81 (2H, d, J=8.5 Hz), 7.39-7.36 (1H, m), 7.24 (2H, d, J=8.5 Hz), 4.10 (2H, d, J=6.0 Hz), 1.39 (9H, s). MS (ESI−): 361.3. HPLC (Condition A): Rt 4.09 min (HPLC purity 98.9%).

Intermediate 23

6-[cyclohexyl(cyclopropylmethyl)amino]-N-[4-(hydroxymethyl)phenyl]pyrimidine-4-carboxamide

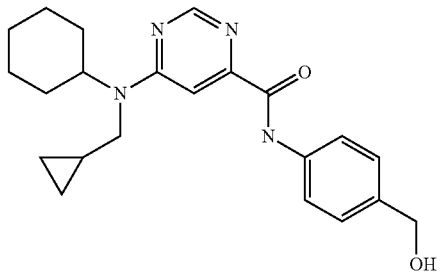 [SMILES: O=C(Nc1ccc(CO)cc1)c1cc(N(CC2CC2)C2CCCCC2)ncn1]

A solution of 6-(cyclohexyl-cyclopropylmethyl-amino)-pyrimidine-4-carboxylic acid (Intermediate 13, 1.00 g; 3.63 mmol) in dry DMF (100 ml) was treated with polymer-supported Mukaiyama reagent, prepared as described in "S. Crosignani et al. Org. Lett. 2004, 6(24), 4579-4582" (2987 mg; 6.54 mmol), 4-aminobenzyl alcohol (Fluka, 492 mg; 3.99 mmol) and triethylamine (1.52 ml; 10.9 mmol). The reaction mixture was then stirred at room temperature for 18 hours. DCM was added and the product was filtered through an SPE column (Isolute NH2, 10g) and the column washed with DCM. The mixture was concentrated then rediluted in EtOAc. The organic phase was washed 5 times with brine, dried over MgSO4 and the solvent removed under vacuum to give the title compound (990 mg, 72%).

¹H NMR (300MHz, DMSO-d6) δ [ppm] 10.55 (1H, s), 8.70 (1H, d, J=1.0 Hz), 8.80 (1H, s), 7.88 (2H, d, J=8.5 Hz), 7.37 (1H, d, J=1.0 Hz), 7.35 (2H, d, J=8.5 Hz), 5.19 (1H, t, J=5.5 Hz), 4.97 (1H, m), 4.51 (2H, d, J=5.5 Hz), 3.44 (2H, m), 2.10-1.28 (11H, m), 0.58-0.56 (2H, m), 0.45-0.40 (2H, m). MS (ESI+): 363.0. HPLC (Condition A): Rt 3.72 min (HPLC purity 88.9%).

Intermediate 24: 6-[cyclohexyl(cyclopropylmethyl)amino]-N-(4-formylphenyl)pyrimidine-4-carboxamide

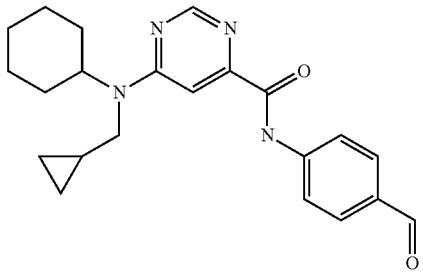 [SMILES: O=Cc1ccc(NC(=O)c2cc(N(CC3CC3)C3CCCCC3)ncn2)cc1]

A solution of 6-[cyclohexyl(cyclopropylmethyl)amino]-N-[4-(hydroxymethyl)phenyl]pyrimidine-4-carboxamide (Intermediate 23, 990 mg; 2.60 mmol) in DCM (100 ml) was treated with MnO₂ (2262 mg; 26.0 mmol) and the reaction mixture was stirred at room temperature for 18 hours the mixture was filtered through celite and the solvent was removed under vacuum affording the title compound as a yellow solid (912 mg; 79%), which was used without further purification for the following steps.

MS (ESI+): 379.0. HPLC (Condition A): Rt 4.45 min (HPLC purity 85.5%).

Intermediate 25 methyl 4-[({6-[cyclohexyl(cyclopropylmethyl)amino]pyrimidin-4-yl}carbonyl)amino]-2-fluorobenzoate

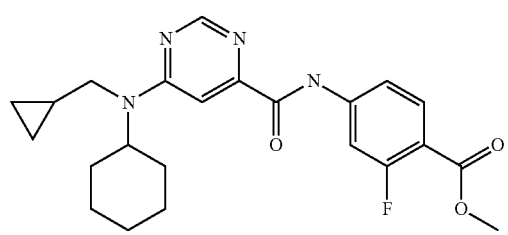 [SMILES: COC(=O)c1ccc(NC(=O)c2cc(N(CC3CC3)C3CCCCC3)ncn2)cc1F]

Following the general method as outlined in Example 1, starting from 6-(cyclohexyl-cyclopropylmethyl-amino)-pyrimidine-4-carboxylic acid (Intermediate 13) and 4-amino-2-fluoro-benzoic acid methyl ester (Bepharm), the title compound was obtained as a white solid after purification by column chromatography (silica) eluting with cyclohexane containing increasing amounts of EtOAc.

¹H NMR (300MHz, DMSO-d6) δ 11.06 (1H, s), 8.68 (1H, d, J=1.0 Hz), 7.99 (1H, d, J=13.0 Hz), 7.91-7.89 (2H, m), 7.33 (1H, d, J=1.0 Hz), 4.4 (1H, m), 3.84 (3H, s), 3.40 (2H, m), 1.84-1.15 (11H, m), 0.51-0.48 (2H, m), 0.37-0.33 (2H, m). MS (ESI+): 427.2.

Intermediate 26

N-(2-Methoxyethyl)cyclohexanamine

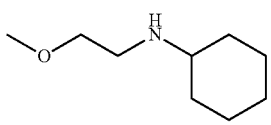

A solution of cyclohexanone (10 g, 0.10 mol) in Toluene (100 ml) was treated with 2-methoxy ethylamine (8.4 g, 0.11 mol) and refluxed at 110° C. for 3 h. The reaction mass was cooled and diluted with ethanol (50 ml) and sodium borohydride (5.8 g, 0.15 mol) was added in portions at 0° C. The reaction mass was stirred at RT for 12 h and concentrated under reduced pressure. The residue was dissolved in water (100 ml), extracted with DCM (2×100ml), dried over sodium sulphate and evaporated. The crude material was purified by column chromatography by using DCM and methanol (98:2) as eluent to afford the title compound as a pale yellow liquid.

¹H NMR (300MHz, DMSO-d6) δ 3.36 (2H, t), 3.33 (3H, s), 2.66 (2H, t), 2.35 (1H, m), 1.78 (2H, m), 1.66 (2H, d), 1.55 (H, d), 1.20 (3H, m), 0.98 (2H, m). MS (ESI+): 158.3.

Intermediate 27

N-Cyclopentyl-N-isobutylamine

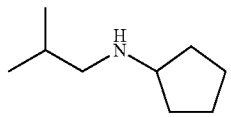

A mixture of cyclopentanone (10 g, 0.12 mol) and isobutyl amine (29.5 ml, 0.297 mol) was heated at 70° C. for 3 h under nitrogen. After cooling to 0° C., absolute ethanol (50 ml) was added to the reaction mixture, followed by sodium borohydride (6.59 g, 0.178 mol) in portions. The reaction mixture stirred at RT for 12 h, the solvent was removed under vacuum. The residue was taken up in MTBE and washed with water and brine. The organic layer was dried over $Na_2SO_4$, evaporated to dryness and the crude was purified by chromatography using silica gel (60-120 mesh), dichloromethane\methanol as eluent to afford of the titled compound as a yellow liquid.

¹H NMR (400MHz, CDCl3) d 2.97-3.01 (1H, m), 2.34-2.36 (2H, d), 1.81-1.82 (2H, m), 1.71-1.79 (3H, m), 1.62-1.69 (2H, m), 1.48-1.51 (3H, m), 0.99 (6H, d). MS (ESI+): 142.1.

Intermediate 28

(4-amino-3-methylphenyl)methanol

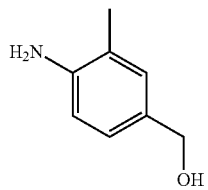

A solution of 3-methyl-4-nitrobenzyl alcohol (Aldrich; 2.000 g; 12.0 mmol) in MeOH (90 ml) is passed through the H-Cube flow hydrogenator fitted with a 10 mol % Pd/C catalyst cartridge (30×4 mm) heated to 25° C. with the full hydrogen option enabled. The flow rate is set at 1 mL/min. Solvent was removed to give the title compound (1.50 g, 91.4%) without further purification.

MS (ESI+): 138.1. HPLC (Condition A): Rt 1.41 min (HPLC purity 53.8%).

Intermediate 29

6-[(cyclopropylmethyl)(propyl)amino]-N-(4-(formyl-2-methylphenyl)pyrimidine-4-carboxamide

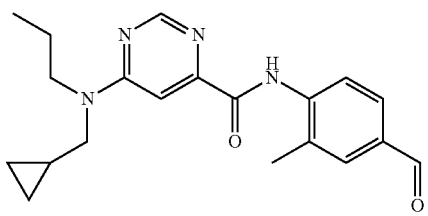 [SMILES: CCCN(CC1CC1)c1cc(C(=O)Nc2ccc(C=O)cc2C)ncn1]

A solution of 6-[(cyclopropylmethyl)(propyl)amino]-N-[4-(hydroxymethyl)-2-methylphenyl]pyrimidine-4-carboxamide (Example 85; 510 mg; 1.44 mmol) in DCM (80 ml) was treated with manganese(iv) oxide (1.250 g; 14.4 mmol) and the reaction was stirred at room temperature for 2 h. The reaction mixture was filtered over a pad of celite, rinsed with DCM and the filtrate was concentrated under vacuum to afford the title compound as a yellow solid (432 mg, 85.2%).

¹H NMR (300MHz, DMSO-d6) δ 10.44 (1H, br s), 9.95 (1H, s), 8.67 (1H, s), 8.32 (1H, d, J=8.9 Hz), 7.86 (2H, m), 7.31 (1H, br s), 3.57 (4H, br s), 2.45 (3H, s), 1.69-1.61 (2H, m), 1.10 (1H, br s), 0.94 (3H, m), 0.53-0.51 (2H, m), 0.37-0.36 (2H, m). MS (ESI+): 353.3;

MS (ESI−) 351.4. HPLC (Condition A): Rt 4.32 min (HPLC purity 100.0%).

Intermediate 30

4-{[(6-chloropyrimidin-4-yl)carbonyl]amino}-3-methylbenzenesulfonyl chloride

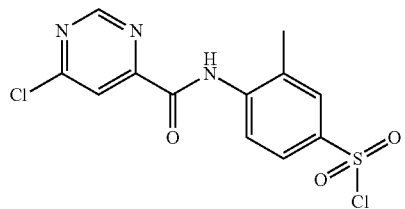 [SMILES: Cc1cc(S(=O)(=O)Cl)ccc1NC(=O)c1cc(Cl)ncn1]

A cooled (0° C.) solution of 6-chloro-N-(2-methylphenyl)pyrimidine-4-carboxamide (Intermediate 18; 14.00 g; 56.52 mmol) in DCM (280 ml) was treated dropwise with a solution of chlorosulfonic acid (37.8 ml; 565 mmol) in DCM (100 mL). The reaction mixture was allowed to warm from 0° C. to room temperature, then it was stirred at room temperature overnight. The mixture was cooled to 15° C., a mixture ice/water was added and it was stirred for a few minutes. Phases were separated and the organic layer was washed with cold water, brine, dried over $MgSO_4$, filtered and concentrated under vacuum to afford the title compound as a beige solid.

¹H NMR (300MHz, DMSO-d6) δ 10.48 (1H, br s), 9.31 (1H, d, J=1.0 Hz), 8.25 (1H, d, J=1.1 Hz), 7.61-7.57 (3H, m), 2.31 (3H, s). MS (ESI−): 344.1. HPLC (Condition A): Rt 4.76 min (HPLC purity 97.7%).

Intermediate 31 cyclohexyl 2,4-dichloropyrimidine-6-carboxylate

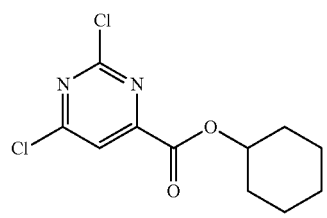 [SMILES: O=C(OC1CCCCC1)c1cc(Cl)nc(Cl)n1]

A cold (0° C.) solution of cyclohexanol (3.82 ml; 36.2 mmol) was treated with sodium hydride (869 mg; 36.2 mmol) in dry THF (100 ml) and stirred for 30 min at 0° C. It was slowly added to a cooled (0° C.) solution of methyl 2,4-dichloropyrimidine-6-carboxylate (Apollo, 10.00 g; 48.3 mmol) in dry THF (200 ml) and the resulting mixture was stirred for 24 h. The reaction mixture was concentrated under vacuum. The residue was taken up in EtOAc and the organic layer was washed with water, then brine, dried over MgSO$_4$, filtered off and concentrated under vacuum to afford a crude which was purified by flash chromatography eluting with cHex-EtOAc 8:2 to afford the title compound as a white solid.

$^1$H NMR (300MHz, DMSO-d6) δ 8.23 (1H, s), 5.01 (1H, m), 1.92 (2H, m), 1.77 (2H, m), 1.61-1.29 (6H, m). HPLC (Condition A): Rt 4.72 min (HPLC purity 98.5%).

Intermediate 32

6-(cyclohexyloxy)pyrimidine-4-carboxylic acid

Step 1: cyclohexyl 2-chloro-6-(cyclohexyloxy)pyrimidine-4-carboxylate

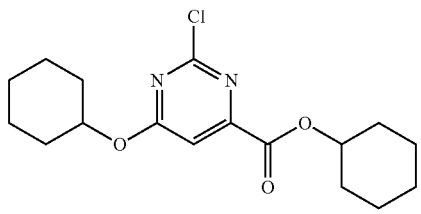 [SMILES: O=C(OC1CCCCC1)c1cc(OC2CCCCC2)nc(Cl)n1]

A cold (0° C.) solution of cyclohexanol (2.35 ml; 22.3 mmol) was treated with sodium hydride (534 mg; 22.3 mmol) in dry THF (25 ml) and stirred for 30 min at 0° C. It was slowly added to a cooled (0° C.) solution of cyclohexyl 2,6-dichloropyrimidine-4-carboxylate (Intermediate 31, 3.50 g; 12.72 mmol) in dry THF (70 ml) and the resulting mixture was stirred at 50° C. After 4 h the reaction was treated again with a solution cyclohexanol (0.34 ml; 3.18 mmol) and sodium hydride (76.3 mg; 3.18 mmol) in dry THF (3 mL) obtained as described above and it was stirred for an additional hour. The reaction mixture was concentrated under vacuum and the residue was taken up in EtOAc and the organic layer was washed with water, then brine, dried over MgSO$_4$, filtered off and concentrated under vacuum to afford the title compound (4.80 g, 99%) without further purification.

MS (ESI+): 338.9. HPLC (Condition A): Rt 6.04 min (HPLC purity 59.1%).

Step 2: cyclohexyl 6-(cyclohexyloxy)pyrimidine-4-carboxylate

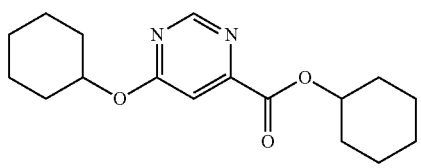 [SMILES: O=C(OC1CCCCC1)c1cc(OC2CCCCC2)ncn1]

A solution of ammonium formate was prepared by dissolving ammonium formate (13.40 g; 212 mmol) in water (30 ml). A suspension of palladium on calcium carbonate (754 mg; 0.71 mmol) in IPrOH (144 ml) and was treated with 7.5 mL of ammonium formate solution and with cyclohexyl 2-chloro-6-(cyclohexyloxy)pyrimidine-4-carboxylate (4.80 g; 14.2 mmol). After 10 min, a second aliquot of 7.5 mL of ammonium formate solution was added and the mixture was stirred at room temperature for 24 h. The mixture was filtered through a pad of celite and rinsed with MeOH. Solvents were concentrated under vacuum. The crude was dissolved in DCM and washed with water and brine. Organic phase was dried over MgSO$_4$, filtered off and concentrated under vacuum to afford the title compound as an orange solid without further purification.

MS (ESI+): 305.0. HPLC (Condition A): Rt 5.46 min (HPLC purity 95.0%).

Step 3: 6-(cyclohexyloxy)pyrimidine-4-carboxylic Acid

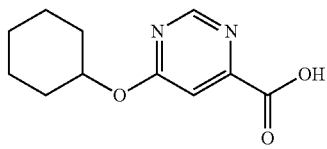 [SMILES: O=C(O)c1cc(OC2CCCCC2)ncn1]

A solution of cyclohexyl 6-(cyclohexyloxy)pyrimidine-4-carboxylate (2.00 g; 6.57 mmol) in THF/EtOH/H2O (3/2/1, total volume 200 mL) was treated with a 5N solution of sodium hydroxide (3.94 ml; 19.7 mmol). The reaction mixture was stirred at room temperature for 2 h. The mixture was concentrated under vacuum and then water was added. The aqueous layer was washed with DCM then acidified to pH 5 by addition of 1N HCl solution. The aqueous layer was washed with EtOAc (150 mL), then lyophilized and the obtained solid was washed with DCM. The suspension was filtered off and the filtrate was concentrated under vacuum to afford the title compound as a beige solid.

$^1$H NMR (300MHz, DMSO-d6) δ 6.34 (1H, d, J=5.2 Hz), 5.13 (1H, d, J=5.1 Hz), 2.77 (1H, m), 0.05 (10H, m). MS (ESI−): 220.8. HPLC (Condition A): Rt 2.94 min (HPLC purity 94.4%).

Intermediate 33 methyl 2-(4-(6-chloropyrimidine-4-carboxamido)-3-methylphenylsulfonamido)acetate

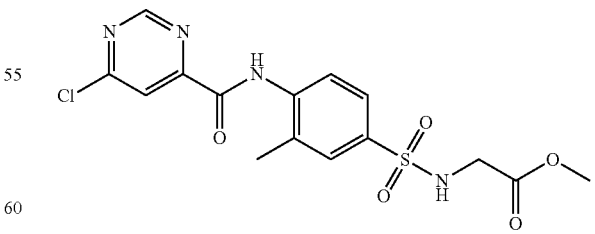

A solution of 4-(6-chloropyrimidine-4-carboxamido)-3-methylbenzene-1-sulfonyl chloride (Intermediate 30, 1.2g; 3.47 mmol) in THF (100ml) was treated with methyl 2-aminoacetate (540 mg; 4.34 mmol) and diisopropylamine (2 ml; 14.3 mmol). After stirring at RT for 18 hours the solvent was removed in vacuo and the residue redissolved in DCM and washed with water. The organic extracts were passed through a hydrophobic frit and the solvent removed in vacuo. The residue was purified by column chromatography (silica) eluting with petroleum ether containing increasing amounts of EtOAc. The title product was obtained as a white solid (1.05 g, 76%).

$^1$H NMR (400MHz, CDCl3) δ 10.03 (1H, s), 9.12 (1H, d, J=1.2 Hz), 8.58-8.51 (1H, m), 8.26 (1H, d, J=1.1 Hz), 7.82-7.73 (2H, m), 5.05 (1H, t, J=5.3 Hz), 3.81 (3H, d, J=5.3 Hz), 3.67 (3H, s), 2.50 (3H, s), 1.43 (1H, s).

Intermediate 34 tert-butyl 3-(4-(6-chloropyrimidine-4-carboxamido)-3-methylphenylsulfonamido)propanoate

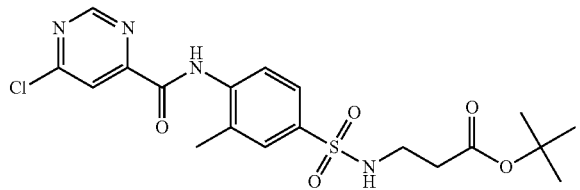 [SMILES: Cc1cc(S(=O)(=O)NCCC(=O)OC(C)(C)C)ccc1NC(=O)c1cc(Cl)ncn1]

A solution of 4-(6-chloropyrimidine-4-carboxamido)-3-methylbenzene-1-sulfonyl chloride (Intermediate 30, 1.2g; 3.47 mmol) in THF (100 ml) was treated with tert-butyl 3-aminopropanoate hydrochloride (800 mg; 4.4 mmol) and diisopropylamine (2 ml; 14.3 mmol). After stirring at RT for 18 hours the solvent was removed in vacuo and the residue redissolved in DCM and washed with water. The organic extracts were passed through a hydrophobic frit and the solvent removed in vacuo. The residue was purified by column chromatography (silica) eluting with petroleum ether containing increasing amounts of EtOAc. The title product was obtained as a white solid.

$^1$H NMR (400MHz, CDCl3) δ 10.03 (1H, s), 9.12 (1H, d, J=1.1 Hz), 8.54 (1H, d, J=8.5 Hz), 8.27 (1H, d, J=1.1 Hz), 7.82-7.76 (2H, m), 5.20 (1H, t, J=6.5 Hz), 3.16 (2H, app q, J=6.0 Hz), 2.50 (3H, s), 2.47 (3H, t, J=5.9 Hz), 1.43 (9H, s). MS (APCI-): 453. HPLC (Condition C): Rt 3.92 min (HPLC purity 99.5%).

Intermediate 35 ethyl 4-(4-(6-chloropyrimidine-4-carboxamido)-3-methylphenylsulfonamido)butanoate

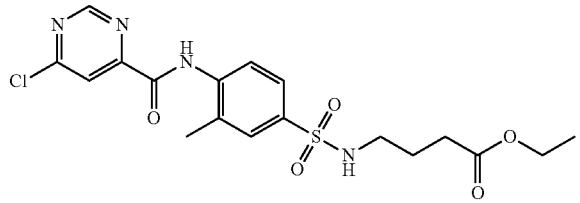 [SMILES: CCOC(=O)CCCNS(=O)(=O)c1ccc(NC(=O)c2cc(Cl)ncn2)c(C)c1]

A solution of 4-(6-chloropyrimidine-4-carboxamido)-3-methylbenzene-1-sulfonyl chloride (Intermediate 30, 1.2g; 3.47 mmol) in THF (100 ml) was treated with ethyl 4-aminobutanoate (720 mg; 4.34 mmol) and diisopropylamine (2 ml; 14.3 mmol). After stirring at RT for 18 hours the solvent was removed in vacuo and the residue redissolved in DCM and washed with water. The organic extracts were passed through a hydrophobic frit and the solvent removed in vacuo. The residue was purified by column chromatography (silica) eluting with petroleum ether containing increasing amounts of EtOAc. The title product was obtained as a white solid.

$^1$H NMR (400MHz, CDCl3) δ 10.03 (1H, s), 9.12 (1H, d, J=1.2 Hz), 8.53 (1H, d, J=8.48 Hz), 8.27 (1H, d, J=1.2 Hz), 7.79-7.74 (2H, m), 4.63 (1H, t, J=6.4 Hz), 4.12 (2H, q, J=7.0 Hz), 3.03 (2H, q, J=6.4 Hz), 2.49 (3H, s), 2.37 (2H, t, J=7.0 Hz), 1.82 (2H, qn, J=7.0 Hz), 1.25 (3H, t, J=7.0 Hz).

Intermediate 36 methyl 2-(4-(6-chloropyrimidine-4-carboxamido)-N,3-dimethylphenylsulfonamido)acetate

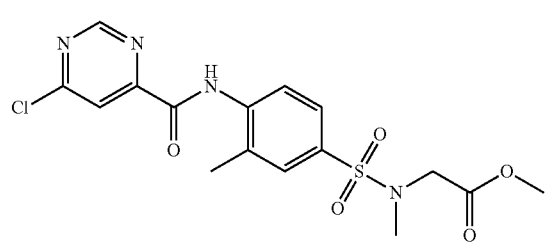 [SMILES: COC(=O)CN(C)S(=O)(=O)c1ccc(NC(=O)c2cc(Cl)ncn2)c(C)c1]

A solution of 4-(6-chloropyrimidine-4-carboxamido)-3-methylbenzene-1-sulfonyl chloride (Intermediate 30, 1.2g; 3.47 mmol) in THF (100 ml) was treated with methyl 2-(methylamino)acetate (666 mg; 4.77 mmol) and diisopropylamine (2 ml; 14.3 mmol). After stirring at RT for 18 hours the solvent was removed in vacuo and the residue redissolved in DCM and washed with water. The organic extracts were passed through a hydrophobic frit and the solvent removed in vacuo. The residue was purified by column chromatography (silica) eluting with petroleum ether containing increasing amounts of EtOAc. The title product was obtained as a white solid.

$^1$H NMR (400MHz, CDCl3) δ 10.03 (1H, s), 9.12 (1H, d, J=1.1 Hz), 8.55 (1H, d, J=8.6 Hz), 8.27 (1H, d, J=1.1 Hz), 7.77-7.71 (2H, m), 4.01 (2H, s), 3.69 (3H, s), 2.91 (3H, s), 2.50 (3H, s).

Intermediate 37

6-chloro-N-(2-methyl-4-(N-methylsulfamoyl)phenyl)pyrimidine-4-carboxamide

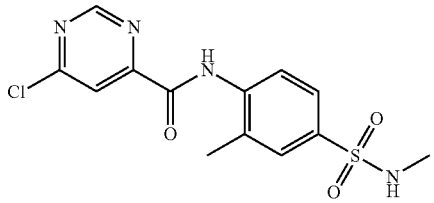 [SMILES: CNS(=O)(=O)c1ccc(NC(=O)c2cc(Cl)ncn2)c(C)c1]

A solution of 4-(6-chloropyrimidine-4-carboxamido)-3-methylbenzene-1-sulfonyl chloride (Intermediate 30, 400 mg; 1.15 mmol) in THF (20 ml) was treated with methylamine (0.7 ml, 2M in THF; 1.4 mmol) and diisopropylamine (0.4 ml; 2.9 mmol). After stirring at RT for 18 hours the solvent was removed in vacuo and the residue redissolved in DCM and washed with water. The organic extracts were passed through a hydrophobic frit and the solvent removed in vacuo. The residue was purified by column chromatography (silica) eluting with petroleum ether containing increasing amounts of EtOAc. The title product was obtained as a white solid.

¹H NMR (400MHz, CDCl3) δ 10.03 (1H, s), 9.12 (1H, d, J=1.1 Hz), 8.54 (1H, d, J=8.5 Hz), 8.27 (1H, d, J=1.1 Hz), 7.82-7.76 (2H, m), 4.26 (1H, q, J=5.4 Hz), 2.69 (3H, d, J=5.4 Hz), 2.50 (3H, s).

Intermediate 38

6-chloro-N-(4-(N-(2-methoxyethyl)sulfamoyl)-2-methylphenyl)pyrimidine-4-carboxamide

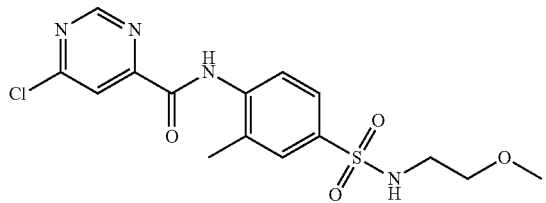 [SMILES: COCCNS(=O)(=O)c1ccc(NC(=O)c2cc(Cl)ncn2)c(C)c1]

A solution of 4-(6-chloropyrimidine-4-carboxamido)-3-methylbenzene-1-sulfonyl chloride (Intermediate 30, 400 mg; 1.15 mmol) in THF (20 ml) was treated with 2-methoxyethanamine (125 mL; 1.4 mmol) and diisopropylamine (0.4 ml; 2.9 mmol). After stirring at RT for 18 hours the solvent was removed in vacuo and the residue redissolved in DCM and washed with water. The organic extracts were passed through a hydrophobic frit and the solvent removed in vacuo. The residue was purified by column chromatography (silica) eluting with petroleum ether containing increasing amounts of EtOAc. The title product was obtained as a white solid.

¹H NMR (400MHz, CDCl3) δ 10.03 (1H, s), 9.12 (1H, s), 8.54 (1H, d, J=8.5 Hz), 8.27 (1H, s), 7.81-7.75 (2H, m), 4.81 (1H, t, J=6.0 Hz), 3.43 (2H, t, J=5.0 Hz), 3.29 (3H, s), 3.14 (2H, app q, J=5.3 Hz), 2.49 (3H, s).

Intermediate 39 ethyl 2-(5-(6-((cyclopropylmethyl)(propyl)amino)pyrimidine-4-carboxamido)-1H-indazol-1-yl)acetate

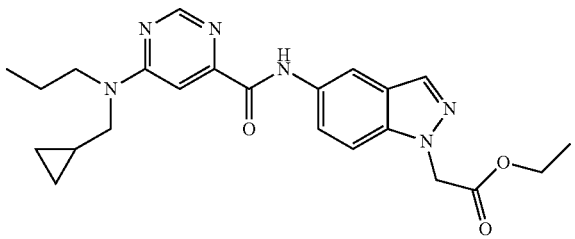 [SMILES: CCCN(CC1CC1)c1cc(C(=O)Nc2ccc3c(cnn3CC(=O)OCC)c2)ncn1]

A solution of 6-((cyclopropylmethyl)(propyl)amino)-N-(1H-indazol-5-yl)pyrimidine-4-carboxamide (Example 45, 350 mg; 1 mmol) in DMF (4 ml) was treated with potassium carbonate (140 mg; 1 mmol), and ethyl 2-bromoacetate (184 mg; 1.1 mmol). After stirring at RT for 18 hours the mixture was poured into water (20 ml) and stirred at RT for 30 minutes. The solid was removed by filtration and purified by column chromatography (silica) eluting with petroleum ether containing increasing amounts of EtOAc to give the title compound as an off-white solid, together with ethyl {5-[({6-[(cyclopropylmethyl)(propyl)amino]pyrimidin-4-yl}carbonyl)amino]-2H-indazol-2-yl}acetate (Example 120 below).

¹H NMR (400MHz, CDCl3) δ 10.07 (1H, s), 8.58 (1H, s), 8.36 (1H, s), 8.04 (1H, s), 7.64 (1H, dd, J=8.9, 2.02 Hz), 7.39 (1H, s), 7.34 (1H, d, J=8.9 Hz), 5.15 (2H, s), 4.22 (2H, q, J=7.1 Hz), 3.71-3.33 (4H, br m), 1.75-1.65 (2H, m), 1.25 (3H, t, J=7.1 Hz), 1.15-1.04 (1H, m), 0.97 (3H, t, J=7.0 Hz), 0.57 (2H, d, J=7.8 Hz), 0.35-0.29 (2H, m). MS (APCI+): 437. HPLC (Condition C): Rt 4.14 min (HPLC purity 95.8%).

Intermediate 40 ethyl 3-(4-nitrobenzylthio)propanoate

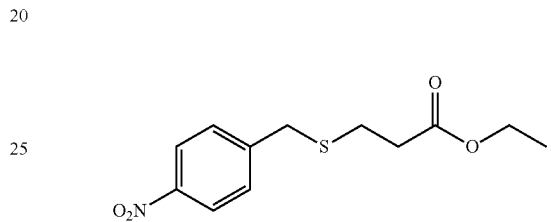

A mixture of 1-(bromomethyl)-4-nitrobenzene (Aldrich, 3.8 g; 17.6 mmol) in acetone (100 ml) was treated with potassium carbonate (2.22 g; 15.9 mmol) and ethyl 3-mercaptopropanoate (Aldrich, 2.14 g; 15.9 mmol). After stirring at RT for 18 hours the mixture filtered and the solid washed with acetone. The organic fractions were combined and the solvent removed in vacuo. The residue was purified by column chromatography (silica) eluting with petroleum ether containing increasing amounts of Et2O to give the title compound as an off-white solid (3.6 g, 84%).

¹H NMR (400MHz, CDCl3) δ 8.18 (2H, d, J=8.3 Hz), 7.51 (2H, d, J=8.3 Hz), 4.15 (2H, q, J=7.1 Hz), 3.82 (2H, s), 2.70 (2H, t, J=7.1 Hz), 2.57 (1H, t, J=7.1 Hz), 1.26 (3H, t, J=7.1 Hz).

Intermediate 41 ethyl 3-(4-nitrobenzylsulfonyl)propanoate

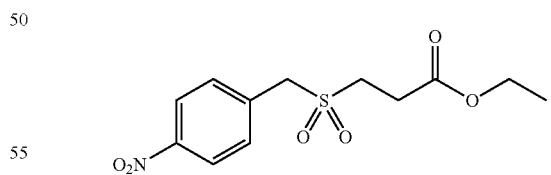

A solution of ethyl 3-(4-nitrobenzylthio)propanoate (Intermediate 40, 3.5 g; 13 mmol) in DCM (100 ml) was treated with mCPBA (7.0 g; 41 mmol). After stirring at RT for 72 hours the mixture was filtered and poured into saturated sodium bicarbonate solution. The layers were separated and the organic phase washed with saturated sodium bisulfate solution, saturated sodium bicarbonate solution and then passed through a hydrophobic frit. The solvent was removed in vacuo to give the title compound as an off-white solid (3.9 g, quant).

¹H NMR (400MHz, CDCl3) δ 8.28 (2H, d, J=8.4 Hz), 7.67 (2H, d, J=8.4 Hz), 4.40 (2H, s), 4.21 (2H, q, J=7.1 Hz), 3.26 (2H, t, J=7.1 Hz), 2.88 (2H, t, J=7.1 Hz), 1.29 (3H, t, J=7.1 Hz).

Intermediate 42 ethyl 3-(4-aminobenzylsulfonyl)propanoate

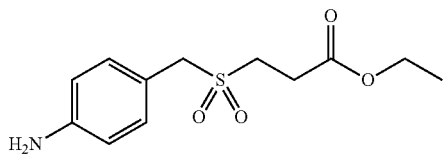 [SMILES: CCOC(=O)CCS(=O)(=O)Cc1ccc([N+](=O)[O-])cc1]

A solution of ethyl 3-(4-nitrobenzylsulfonyl)propanoate (Intermediate 41, 3.9 g; 12.9 mmol) in EtOAc (100 ml) and ethanol (200 ml) was treated with palladium (400 mg, 5% on C). The mixture was stirred under hydrogen for 5 hours, filtered and the solvent removed in vacuo to give the title compound as an off-white solid (3.5 g, quant).
¹H NMR (400MHz, CDCl3) δ 7.19 (2H, d, J=8.1 Hz), 6.68 (2H, d, J=8.1 Hz), 4.17 (2H, q, J=7.1 Hz), 4.16 (2H, s), 3.16 (2H, t, J=7.6 Hz), 2.77 (2H, t, J=7.6 Hz), 1.25 (3H, t, J=7.1 Hz).

Intermediate 43

3-iodo-5-nitro-1H-indazole

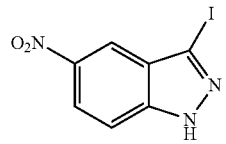 [SMILES: O=[N+]([O-])c1ccc2[nH]nc(I)c2c1]

A solution of 5-nitro-1H-indazole (Aldrich, 5.0 g; 30.7 mmol) in DMF (60 ml) was treated with iodine (15.6 g; 61.4 mmol) and potassium hydroxide (6.45 g; 115 mmol) at 65° C. After stirring at 65° C. for 1 hour the mixture was poured into saturated sodium metabisulfate solution (200 ml) and the solid removed by filtration, washed with water and dried to give the title compound as a light brown solid (8.9 g, quant).
¹H NMR (400MHz, CDCl3) δ 10.52 (1H, br s), 8.54 (1H, d, J=2.1 Hz), 8.36 (1H, dd, J=9.2, 2.1 Hz), 7.58 (1H, d, J=9.2 Hz).

Intermediate 44 tert-butyl 3-iodo-5-nitro-1H-indazole-1-carboxylate

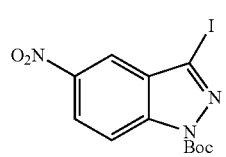 [SMILES: CC(C)(C)OC(=O)n1nc(I)c2cc([N+](=O)[O-])ccc21]

A solution of 3-iodo-5-nitro-1H-indazole (Intermediate 43, 5.0 g; 17.3 mmol) in MeCN (100 ml) was treated with DMAP (100 mg), triethylamine (2.65 ml; 19.0 mmol) and ditert-butyl dicarbonate (4.0 g; 18.3 mmol). After stirring at RT for 2 hours the solvent was removed in vacuo. The residue was partitioned between DCM and water and the mixture passed through a hydrophobic frit and the solvent removed in vacuo. The residue was triturated with petroleum ether to give the title compound as a light brown solid (5.2 g, 77%).
¹H NMR (400MHz, CDCl3) δ 8.48-8.44 (2H, m), 8.32-8.27 (1H, m), 1.74 (9H, s).

Intermediate 45 tert-butyl 5-amino-3-(3-methoxy-3-oxopropyl)-1H-indazole-1-carboxylate

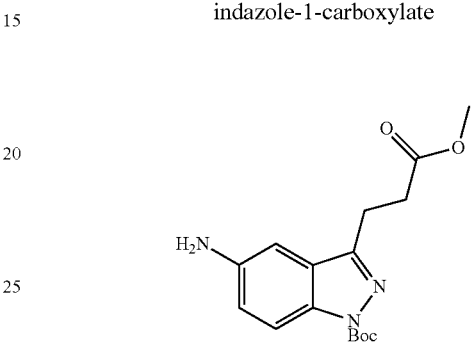

A solution of tert-butyl 3-iodo-5-nitro-1H-indazole-1-carboxylate (Intermediate 44, 4.6 g; 11.8 mmol) in DMF (76 ml) and water (12 ml) was treated with triethylamine (12 ml; 86 mmol), methyl acrylate (10.4 ml; 115 mmol) and tetrabutyl ammonium iodide (8.6 g; 23 mmol). The mixture was degassed and then dichlorobis(triphenylphosphine)palladium (II), (1.68 g; 2.4 mmol) was added. The mixture was heated to 50° C. for 18 hours and the volatile solvent removed in vacuo. The mixture was poured into water (600 ml) and extracted with EtOAc. The combined organic extracts were washed with water, dried over sodium sulfate, filtered and the solvent removed in vacuo. The residue was purified by column chromatography (silica) eluting with petroleum ether containing increasing amounts of EtOAc to give tert-butyl 3-(3-methoxy-3-oxoprop-1-enyl)-5-nitro-1H-indazole-1-carboxylate as a light brown solid (1.5 g, 37%). A solution of this residue (200 mg; 0.58 mmol) in methanol (100 ml) was treated with palladium (100mg, 5% on C). The mixture was stirred under hydrogen for 18 hours, filtered and the solvent removed in vacuo. The residue was purified by column chromatography (silica) eluting with petroleum ether containing increasing amounts of EtOAc to give the title compound as an off-white solid.
¹H NMR (400MHz, CDCl3) δ 7.85 (1H, d, J=8.75 Hz), 6.95-6.86 (2H, m), 3.72 (2H, br s), 3.70 (3H, s), 3.25-3.17 (2H, m), 2.93-2.84 (2H, m).

Intermediate 46 ethyl 4-(4-nitrophenylthio)butanoate

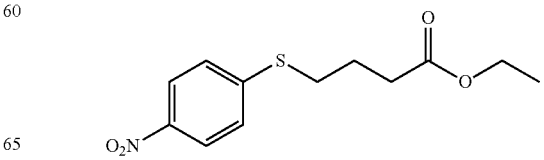

A solution of 4-nitrobenzenethiol (Aldrich, 2.5 g; 16.1 mmol) in acetone (110 ml) was treated with potassium carbonate (2.22 g; 16.1 mmol) and ethyl 4-bromobutanoate (Aldrich, 3.43 g; 17.6 mmol). After stirring at RT for 18 hours, the mixture was filtered and the solid washed with acetone. The organic fractions were combined and the solvent removed in vacuo. The residue was purified by column chromatography (silica) eluting with petroleum ether containing increasing amounts of Et2O to give the title compound as an off-white solid (4.0 g, 92%).

$^1$H NMR (400MHz, CDCl3) δ 8.13 (2H, d, J=8.8 Hz), 7.36 (2H, d, J=8.8 Hz), 4.16 (2H, q, J=7.1 Hz), 3.09 (2H, t, J=7.3 Hz), 2.49 (2H, t, J=7.0 Hz), 2.09-1.98 (2H, m), 1.27 (3H, t, J=7.1 Hz).

Intermediate 47 ethyl 4-(4-nitrophenylsulfonyl)butanoate

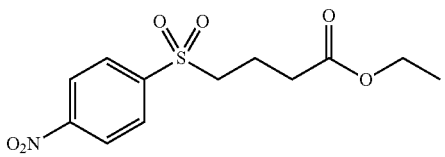 [SMILES: CCOC(=O)CCCS(=O)(=O)c1ccc([N+](=O)[O-])cc1]

A solution of ethyl 4-(4-nitrophenylthio)butanoate (Intermediate 46, 4.0 g; 14.9 mmol) in DCM (100 ml) was treated with mCPBA (8.0 g; 47 mmol). After stirring at RT for 72 hours the mixture was filtered and poured into saturated sodium bicarbonate solution. The layers were separated and the organic phase washed with saturated sodium bisulfate solution, saturated sodium bicarbonate solution and then passed through a hydrophobic frit. The solvent was removed in vacuo to give the title compound as an off-white solid (4.5 g, quant). $^1$H NMR (400MHz, CDCl3) δ 8.43 (2H, d, J=8.7 Hz), 8.13 (2H, d, J=8.7 Hz), 4.12 (2H, q, J=7.1 Hz), 3.29-3.22 (2H, m), 2.48 (2H, t, J=6.9 Hz), 2.10-1.99 (2H, m), 1.24 (3H, t, J=7.1 Hz).

Intermediate 48 ethyl 4-(4-aminophenylsulfonyl)butanoate

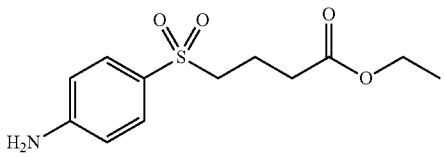

A solution of ethyl 4-(4-nitrophenylsulfonyl)butanoate (Intermediate 47, 4.5 g; 14.9 mmol) in ethanol (200 ml) was treated with palladium (450 mg, 5% on C). The mixture was stirred under hydrogen for 18 hours, filtered and the solvent removed in vacuo to give the title compound as an off-white solid (4.0 g, quant).

$^1$H NMR (400MHz, CDCl3) δ 7.65 (2H, d, J=8.6 Hz), 6.71 (2H, d, J=8.6 Hz), 4.36 (2H, br s), 4.11 (2H, q, J=7.1 Hz), 3.15-3.09 (2H, m), 2.43 (2H, t, J=7.2 Hz), 2.06-1.96 (2H, m), 1.23 (3H, t, J=7.1 Hz).

Example 1

6-(cyclohexylamino)-N-(4-hydroxy-2-methylphenyl) pyrimidine-4-carboxamide

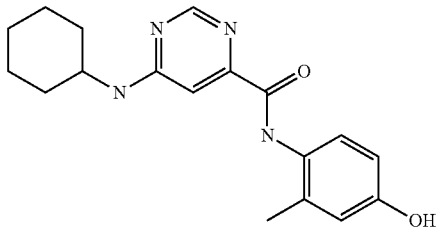 [SMILES: Cc1cc(O)ccc1NC(=O)c1cc(NC2CCCCC2)ncn1]

A mixture of 4-amino-m-cresol (Fluka, 40.00 mg; 0.32 mmol), 6-(cyclohexylamino)pyrimidine-4-carboxylic acid, Intermediate 4 (86.2 mg; 0.39 mmol) and triethylamine (136 μl; 0.97 mmol) in dry DMF (5.00 mL) was treated with polymer-supported Mukaiyama reagent (520 mg; 0.65 mmol) and stirred for 16 hours. DCM was added to the reaction mixture and the solution was filtered through a SPE-NH2 column (2 g). The DCM was evaporated in vacuo, the resulting solution was diluted with EtOAc, washed three times with brine, then the organic phase was dried over magnesium sulfate, filtered and evaporated in vacuo. The solid obtained was triturated in acetonitrile to afford the title compound as a yellow solid.

$^1$H NMR (300MHz, DMSO-d$_6$) δ [ppm] 9.88 (1H, s), 9.28 (1H, s), 8.50 (1H, s), 7.75 (1H, d, J=7.5 Hz), 7.46 (1H, d, J=8.5 Hz), 7.13 (1H, d, J=2.5 Hz), 6.64 (1H, d, J=2.5 Hz), 6.59 (1H, dd, J=8.5 Hz, J=2.5 Hz), 3.86 (1H, m), 2.15 (3H, s), 1.91-1.60 (5H, m), 1.34-1.15 (5H, m). MS (ESI$^+$): 327.1. HPLC (Condition A): Rt 2.69 min (HPLC purity 91.4%).

Example 2

6-[(cyclohexylmethyl)amino]-N-(4-hydroxyphenyl) pyrimidine-4-carboxamide

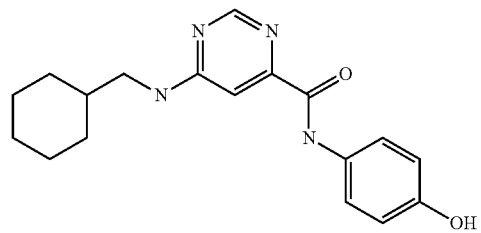 [SMILES: O=C(Nc1ccc(O)cc1)c1cc(NCC2CCCCC2)ncn1]

Following the general method as outlined in Example 1, starting from 6-[(cyclohexylmethyl)amino]pyrimidine-4-carboxylic acid (Intermediate 6) and 4-amino-phenol (Aldrich), the title compound was obtained as a white solid after trituration in EtOAc.

$^1$H NMR (300MHz, DMSO-d$_6$) δ [ppm] 10.21 (1H, s), 9.30 (1H, s), 8.51 (1H, s), 7.87 (1H, t, J=6.0 Hz), 7.62 (2H, d, J=9.0 Hz), 7.16 (1H, s), 6.71 (2H, d, J=9.0 Hz), 3.21 (2H, m), 2.77-1.46 (6H, m), 1.25-1.06 (3H, m), 1.01-0.85 (2H, m). MS (ESI⁺): 327.1. HPLC (Condition A): Rt 3.04 min (HPLC purity 96.6%).

Example 3

6-(cyclopentylamino)-N-(4-hydroxyphenyl)pyrimidine-4-carboxamide

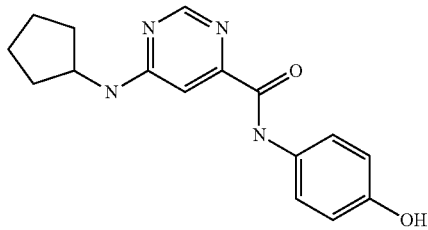 [SMILES: O=C(Nc1ccc(O)cc1)c1cc(NC2CCCC2)ncn1]

Following the general method as outlined in Example 1, starting from 6-[(cyclopentyl)amino]pyrimidine-4-carboxylic acid (Intermediate 5) and 4-aminophenol (Aldrich), the title compound was obtained as a yellow solid after trituration in acetonitrile. $^1$H NMR (300MHz, DMSO-$d_6$) δ [ppm] 10.22 (1H, s), 9.32 (1H, s), 8.52 (1H, s), 7.85 (1H, d, J=7.0 Hz), 7.62 (2H, d, J=9.0 Hz), 7.13 (1H, s), 6.72 (2H, d, J=9.0 Hz), 4.28 (1H, m), 1.94 (2H, m), 1.74-1.40 (6H, m). MS (ESI⁺): 299.1. HPLC (Condition A): Rt 2.17 min (HPLC purity 96.6%).

Example 4

6-(cyclohexylamino)-N-(4-hydroxy-3-methylphenyl)pyrimidine-4-carboxamide

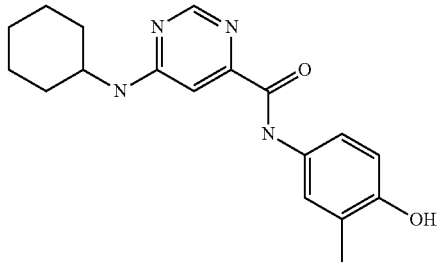 [SMILES: Cc1cc(NC(=O)c2cc(NC3CCCCC3)ncn2)ccc1O]

Following the general method as outlined in Example 1, starting from 6-(cyclohexylamino)pyrimidine-4-carboxylic acid (Intermediate 4) and 4-amino-o-cresol (Aldrich), the title compound was obtained as a brown solid.

$^1$H NMR (300MHz, CDCl₃) δ [ppm] 9.70 (1H, s), 8.45 (s, 1H), 7.45 (1H, d, J=2.5 Hz), 7.37 (1H, dd, J=9.0 Hz, J=2.5 Hz), 7.13 (1H, s), 6.72 (1H, d, J=9.0 Hz), 5.21 (2H, bs), 2.2 (3H, s), 1.94 (1H, m), 1.74-1.56 (4H, m), 1.38-1.12 (6H, m). MS (ESI⁺): 327.1. HPLC (Condition A): Rt 2.79 min (HPLC purity 84.1%).

Example 5

6-(cyclohexylamino)-N-(4-hydroxy-1-naphthyl)pyrimidine-4-carboxamide

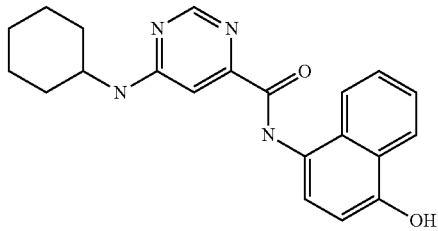 [SMILES: O=C(Nc1ccc(O)c2ccccc12)c1cc(NC2CCCCC2)ncn1]

Following the general method as outlined in Example 1, starting from 6-(cyclohexylamino)pyrimidine-4-carboxylic acid (Intermediate 4) and 4-amino-1-naphtol (Aldrich), the title compound was obtained as a grey solid.

$^1$H NMR (300MHz, DMSO-$d_6$) δ [ppm] 10.43 (1H, s), 10.21 (1H, s), 8.57 (1H, s), 8.16 (1H, s), 7.92 (2H, d, J=9.0 Hz), 7.56-7.46 (3H, m), 7.16 (1H, s), 6.87 (1H, d, J=8.5 Hz), 3.89 (1H, m), 1.98-1.57 (5H, m), 1.36-1.16 (5H, m). MS (ESI⁺): 363.1. HPLC (Condition A): Rt 3.18 min (HPLC purity 86.8%).

Example 6

N-(3-chloro-4-hydroxyphenyl)-6-(cyclohexylamino)pyrimidine-4-carboxamide

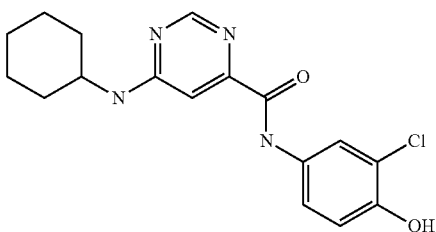

Following the general method as outlined in Example 1, starting from 6-(cyclohexylamino)pyrimidine-4-carboxylic acid (Intermediate 4) and 4-amino-2-chlorophenol (Aldrich), the title compound was obtained as a white solid after trituration in dichloromethane.

$^1$H NMR (300MHz, DMSO-$d_6$) δ [ppm] 10.40 (1H, s), 10.05 (1H, s), 8.51 (1H, s), 7.96 (1H, d, J=2.5 Hz), 7.77 (1H, d, J=7.5 Hz), 7.58 (1H, dd, J=8.5 Hz, J=2.5 Hz), 7.13 (1H, s), 6.91 (1H, d, J=8.5 Hz), 3.86 (1H, m), 1.91-1.60 (5H, m), 1.34-1.19 (5H, m). MS (ESI⁺): 347.1. HPLC (Condition A): Rt 2.95 min (HPLC purity 92.9%).

Example 7

6-(cyclohexylamino)-N-(2-fluoro-4-hydroxyphenyl)pyrimidine-4-carboxamide

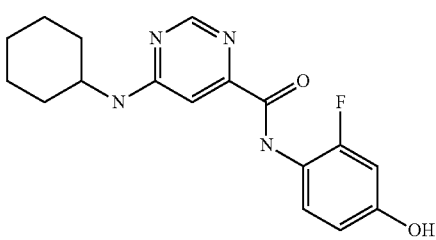

Following the general method as outlined in Example 1, starting from 6-(cyclohexylamino)pyrimidine-4-carboxylic acid (Intermediate 4) and 4-amino-3-fluorophenol (Apollo), the title compound was obtained as a white solid after trituration in dichloromethane.

$^1$H NMR (300MHz, DMSO-$d_6$) δ [ppm] 10.01 (1H, s), 9.87 (1H, s), 8.51 (1H, s), 7.79 (1H, d, J=8.0 Hz), 7.72 (1H, t, J=9.0 Hz), 7.13 (1H, s), 6.67 (1H, dd, J=12.5 Hz, J=2.5 Hz), 6.61 (1H, dd, J=9.0 Hz, J=2.5 Hz), 3.86 (1H, m), 1.91-1.56 (5H, m), 1.34-1.15 (5H, m). MS (ESI⁺): 331.1. HPLC (Condition A): Rt 2.86 min (HPLC purity 96.9%).

Example 8

N-(2-chloro-4-hydroxyphenyl)-6-(cyclohexylamino)pyrimidine-4-carboxamide

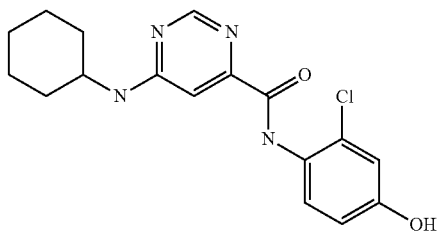 [SMILES: O=C(Nc1ccc(O)cc1F)c1cc(NC2CCCCC2)ncn1]

Following the general method as outlined in Example 1, starting from 6-(cyclohexylamino)pyrimidine-4-carboxylic acid (Intermediate 4) and 4-amino-3-chlorophenol (Chontech), the title compound was obtained as a white solid after trituration in dichloromethane.

MS (ESI): 347.1. HPLC (Condition A): Rt 3.41 min (HPLC purity 96.2%).

Example 9

6-(cyclohexylamino)-N-(4-hydroxy-2,3-dimethylphenyl)pyrimidine-4-carboxamide

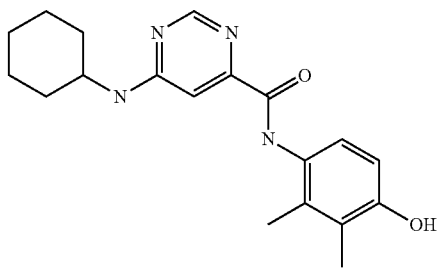 [SMILES: Cc1c(O)ccc(NC(=O)c2cc(NC3CCCCC3)ncn2)c1C]

Following the general method as outlined in Example 1, starting from 6-(cyclohexylamino)pyrimidine-4-carboxylic acid (Intermediate 4) and 4-amino-2,3-xylenol (TCI), the title compound was obtained as a white solid after trituration in dichloromethane. $^1$H NMR (300MHz, DMSO-$d_6$) δ [ppm] 9.91 (1H, s), 9.20 (1H, s), 8.50 (1H, s), 7.73 (1H, d, J=8.0 Hz), 7.18 (1H, d, J=8.5 Hz), 7.12 (1H, s), 6.65 (1H, d, J=8.5 Hz), 3.87 (1H, m), 2.07 (3H, s), 2.06 (3H, s), 1.91-1.61 (5H, m), 1.56-1.15 (5H, m). MS (ESI): 341.1. HPLC (Condition A): Rt 3.02 min (HPLC purity 77.8%).

Example 10

6-(cyclohexylamino)-N-(4-hydroxy-2,5-DIMETHYLPHENYL)pyrimidine-4-carboxamide

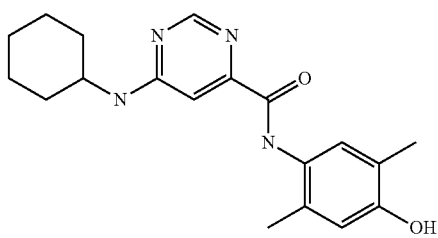 [SMILES: Cc1cc(NC(=O)c2cc(NC3CCCCC3)ncn2)c(C)cc1O]

Following the general method as outlined in Example 1, starting from 6-(cyclohexylamino)pyrimidine-4-carboxylic acid (Intermediate 4) and 4-amino-2,5-dimethylphenol (Aldrich), the title compound was obtained as a white solid yield after purification by column chromatography (silica) eluting with cyclohexane containing increasing amounts of EtOAc.
$^1$H NMR (300MHz, DMSO-$d_6$) δ [ppm] 9.83 (1H, s), 9.16 (1H, s), 8.50 (1H, s), 7.75 (1H, d, J=7.5 Hz), 7.39 (1H, s), 7.12 (1H, s), 6.63 (1H, s), 3.86 (1H, m), 2.11 (3H, s), 2.09 (3H, s), 1.91-1.60 (5H, m), 1.56-1.15 (5H, m). MS (ESI$^+$): 341.1. HPLC (Condition A): Rt 2.91 min (HPLC purity 89.7%).

Example 11

6-(cyclohexylamino)-N-(3,5-dichloro-4-hydroxyphenyl)pyrimidine-4-carboxamide

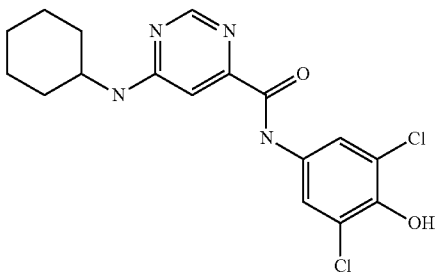 [SMILES: O=C(Nc1cc(Cl)c(O)c(Cl)c1)c1cc(NC2CCCCC2)ncn1]

Following the general method as outlined in Example 1, starting from 6-(cyclohexylamino)pyrimidine-4-carboxylic acid (Intermediate 4) and 4-amino-2,6-dichlorophenol (ABCR), the title compound was obtained as a yellow solid after purification by column chromatography (silica) eluting with cyclohexane containing increasing amounts of EtOAc.
MS (ESI$^+$): 381.0. HPLC (Condition A): Rt 3.30 min (HPLC purity 79.3%).

Example 12

6-(cyclohexylamino)-N-pyridin-4-ylpyrimidine-4-carboxamide

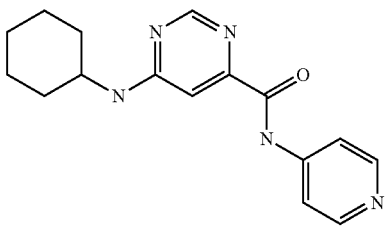 [SMILES: O=C(Nc1ccncc1)c1cc(NC2CCCCC2)ncn1]

Following the general method as outlined in Example 1, starting from 6-(cyclohexylamino)pyrimidine-4-carboxylic acid (Intermediate 4) and 4-aminopyridine (Aldrich), the title compound was obtained as a yellow solid after purification by column chromatography (silica) eluting with cyclohexane containing increasing amounts of EtOAc. $^1$H NMR (300MHz, DMSO-$d_6$) δ [ppm] 10.82 (1H, s), 8.56 (1H, s), 8.47 (1H, d, J=5.0 Hz), 7.89 (2H, d, J=5.0 Hz), 7.84 (1H, d, J=9.0 Hz), 7.16 (1H, s), 3.88 (1H, m), 1.91-1.57 (5H, m), 1.39-1.16 (5H, m). MS (ESI): 298.0. HPLC (Condition A): Rt 2.12 min (HPLC purity 99.4%).

Example 13

6-(cyclohexylamino)-N-{4-[(methylsulfonyl)amino]phenyl}pyrimidine-4-carboxamide

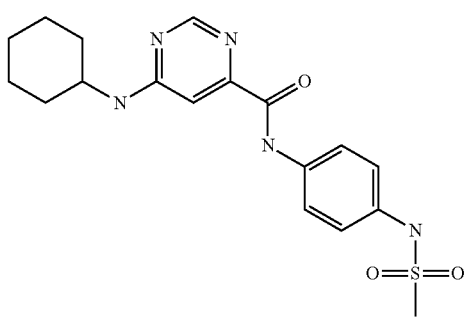 [SMILES: CS(=O)(=O)Nc1ccc(NC(=O)c2cc(NC3CCCCC3)ncn2)cc1]

Following the general method as outlined in Example 1, starting from 6-(cyclohexylamino)pyrimidine-4-carboxylic acid (Intermediate 4) and N-(4-aminophenyl)methanesulfonamide (prepared according to the method described by Lee et al. in Bioorg. Med. Chem. Lett. 2005, 15, 4136-4142), the title compound was obtained as a white solid after trituration in dichloromethane.

$^1$H NMR (300MHz, DMSO-$d_6$) δ [ppm] 10.44 (1H, s), 9.62 (1H, s), 8.53 (1H, s), 7.81 (2H, d, J=9.0 Hz), 7.77 (1H, s), 7.17 (2H, d, J=9.0 Hz), 7.14 (1H, s), 3.86 (1H, m), 2.94 (3H, s), 1.90-1.57 (5H, m), 1.34-1.11 (5H, m). MS (ESI$^+$): 390.0. HPLC (Condition A): Rt 2.66 min (HPLC purity 93.0%).

Example 14

6-(cyclohexylamino)-N-(3-fluoro-4-hydroxyphenyl)pyrimidine-4-carboxamide

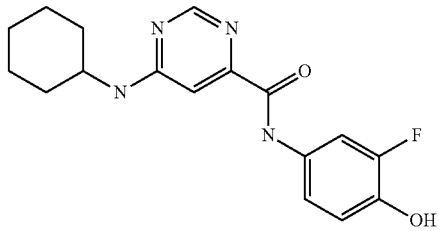 [SMILES: O=C(Nc1ccc(O)c(F)c1)c1cc(NC2CCCCC2)ncn1]

Following the general method as outlined in Example 1, starting from 6-(cyclohexylamino)pyrimidine-4-carboxylic acid (Intermediate 4) and 4-amino-2-chlorophenol (prepared according to the method described by Aymes, D. J.; Paris, M. R. in Bull. Soc. Chim. Fr. 1980, 3-4, 175-178), the title compound was obtained as a colorless oil after purification by column chromatography (silica) eluting with cyclohexane containing increasing amounts of EtOAc.

MS (ESI$^+$): 331.1. HPLC (Condition A): Rt 2.69 min (HPLC purity 98.9%).

Example 15

6-(cyclohexylamino)-N-[4-hydroxy-2-(trifluoromethyl)phenyl]pyrimidine-4-carboxamide

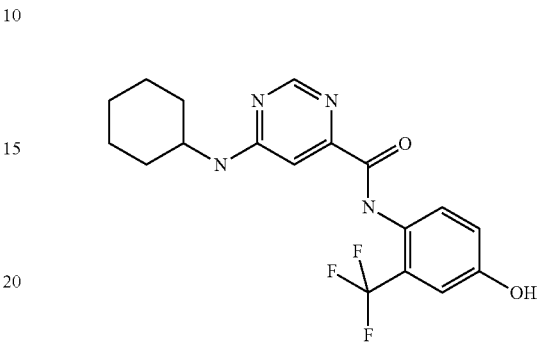

Following the general method as outlined in Example 1, starting from 6-(cyclohexylamino)pyrimidine-4-carboxylic acid (Intermediate 4) and 4-amino-3-(trifluoromethyl)phenol (prepared according to the method described by Filler, R.; Novar, H. J. in Org. Chem. 1961, 26, 2707-2710"), the title compound was obtained as a white solid after purification by column chromatography (silica) eluting with cyclohexane containing increasing amounts of EtOAc.

$^1$H NMR (300MHz, DMSO-$d_6$) δ [ppm] 10.11 (1H, s), 9.87 (1H, s), 8.51 (1H, s), 7.82 (1H, d, J=7.5 Hz), 7.80 (1H, d, J=9.0 Hz), 7.15 (1H, s), 7.15-7.05 (2H, m), 3.88 (1H, m), 2.06-1.56 (5H, m), 1.34-1.15 (5H, m). MS (ESI$^+$): 381.1. HPLC (Condition A): Rt 3.60 min (HPLC purity 94.7%).

Example 16

6-(cyclohexylamino)-N-quinolin-4-ylpyrimidine-4-carboxamide

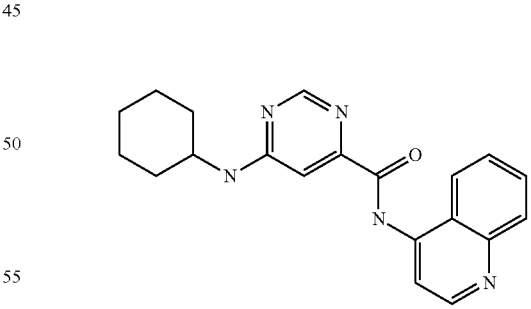

Following the general method as outlined in Example 1, starting from 6-(cyclohexylamino)pyrimidine-4-carboxylic acid (Intermediate 4) and 4-aminoquinoline (Tyger), the title compound was obtained as a red solid after trituration in methanol.

$^1$H NMR (300MHz, DMSO-$d_6$) δ [ppm] 11.07 (1H, s), 8.87 (1H, d, J=5.0 Hz), 8.63 (1H, s), 8.22 (1H, d, J=5.0 Hz), 8.04 (2H, d, J=8.0 Hz), 7.92 (1H, d, J=8.0 Hz), 7.80 (1H, t, J=8.0 Hz), 7.70 (1H, t, J=8.0 Hz), 7.23 (1H, s), 3.90 (1H, m), 1.98-1.55 (5H, m), 1.40-1.13 (5H, m). MS (ESI⁺): 348.1. HPLC (Condition A): Rt 2.99 min (HPLC purity 92.8%).

Example 17

N-[4-(aminosulfonyl)phenyl]-6-(cyclohexylamino)pyrimidine-4-carboxamide

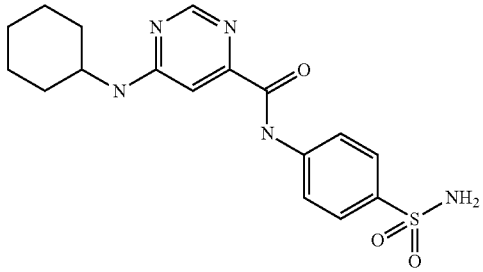 [SMILES: NS(=O)(=O)c1ccc(NC(=O)c2cc(NC3CCCCC3)ncn2)cc1]

Following the general method as outlined in Example 1, starting from 6-(cyclohexylamino)pyrimidine-4-carboxylic acid (Intermediate 4) and sulfanilamide (Acros), the title compound was obtained as a white solid after trituration in methanol.

¹H NMR (300MHz, DMSO-d₆) δ [ppm] 10.72 (1H, bs), 9.31 (1H, s), 8.52 (1H, s), 8.01 (2H, d, J=9.0 Hz), 7.80 (1H, d, J=7.5 Hz), 7.74 (2H, d, J=9.0 Hz), 7.24 (2H, bs), 3.83 (1H, m), 1.94-1.84 (2H, m), 1.75-1.63 (2H, m), 1.60-1.50 (1H, m), 1.35-1.11 (5H, m). MS (ESI⁺): 376.0. HPLC (Condition A): Rt 2.59 min (HPLC purity 99.5%).

Example 18

N-[4-(aminosulfonyl)-2-methylphenyl]-6-(cyclohexylamino)pyrimidine-4-carboxamide

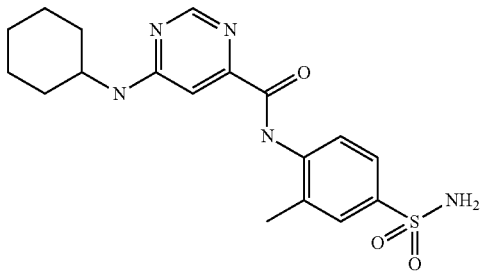

Following the general method as outlined in Example 1, starting from 6-(cyclohexylamino)pyrimidine-4-carboxylic acid (Intermediate 4) and 4-amino-3-methyl-benzenesulfonamide (Biofocus), the title compound was obtained as a white solid after trituration in methanol.

¹H NMR (300MHz, DMSO-d₆) δ [ppm] 10.22 (1H, bs), 8.48 (1H, s), 8.03 (1H, d, J=8.5 Hz), 7.78 (1H, d, J=7.5 Hz), 7.65-7.58 (2H, m), 7.20 (2H, bs), 7.10 (1H, s), 3.80 (1H, m), 2.29 (3H, s), 1.87-1.77 (2H, m), 1.69-1.60 (2H, m), 1.55-1.47 (1H, m), 1.31-1.06 (5H, m). MS (ESI⁺): 390.0. HPLC (Condition A): Rt 2.97 min (HPLC purity 95.3%).

Example 19

6-[cyclohexyl(methyl)amino]-N-(4-hydroxyphenyl)pyrimidine-4-carboxamide

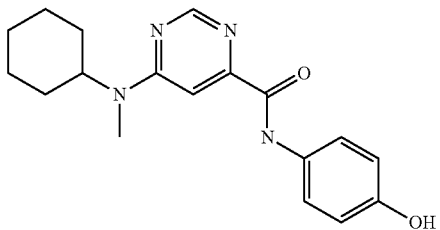 [SMILES: CN(c1cc(C(=O)Nc2ccc(O)cc2)ncn1)C1CCCCC1]

A solution of 6-chloro-N-(4-hydroxy-2-methylphenyl)pyrimidine-4-carboxamide, Intermediate 7 (75.0 mg; 0.30 mmol) in THF (4 mL) was treated with triethylamine (42 μl; 0.30 mmol) and N-methylcyclohexylamine (Aldrich, 43 μl; 0.33 mmol). The reaction mixture was stirred for 24 h. The solvents were removed in vacuo, then the crude product was purified by column chromatography (silica), eluting with cyclohexane containing an increasing amount of EtOAc. The title compound was obtained as a yellow solid.

¹H NMR (300MHz, DMSO-d₆) δ [ppm] 10.29 (1H, s), 9.31 (1H, s), 8.59 (1H, s), 7.65 (2H, d, J=9.0 Hz), 7.20 (1H, s), 6.72 (2H, d, J=9.0 Hz), 4.75 (1H, m), 2.95 (3H, s), 1.90-1.54 (5H, m), 1.34-1.11 (5H, m). MS (ESI⁺): 327.4. HPLC (Condition A): Rt 2.86 min (HPLC purity 92.6%).

Example 20

N-(4-hydroxyphenyl)-6-[(2-methylphenyl)amino]pyrimidine-4-carboxamide

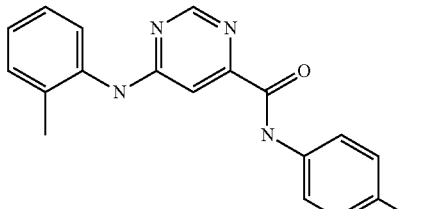

A solution of 6-chloro-N-(4-hydroxy-2-methylphenyl)pyrimidine-4-carboxamide, Intermediate 7 (50.0 mg; 0.20 mmol) in ethanol (3 mL) was treated with N-ethyldiisopropylamine (69 μl; 0.4 mmol) and o-toluidine (Fluka, 21.5 μl; 0.20 mmol). The reaction mixture was heated at 160° C. for 3 hours under microwave irradiation. The solvents were removed in vacuo, EtOAc was added and the organic phase was washed with a citric acid solution, dried over magnesium sulfate then evaporated in vacuo. The crude product was purified by column chromatography (silica), eluting with cyclohexane containing an increasing amount of EtOAc. The title compound was obtained as a yellow solid.

¹H NMR (300MHz, DMSO-d₆) δ [ppm] 10.32 (1H, s), 9.42 (1H, s), 9.31 (1H, s), 8.61 (1H, s), 7.63 (2H, d, J=9.0 Hz), 7.44 (1H, d, J=8.0 Hz), 7.31-7.17 (4H, m), 6.73 (2H, d, J=9.0

Hz), 2.21 (3H, s). MS (ESI+): 321.0. HPLC (Condition A): Rt 2.82 min (HPLC purity 62.9%).

Example 21

6-[cyclohexyl(methyl)amino]-N-(4-hydroxy-2-methylphenyl)pyrimidine-4-carboxamide

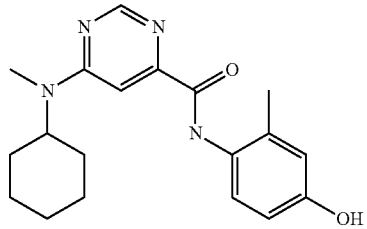 [SMILES: Cc1cc(O)ccc1NC(=O)c1cc(N(C)C2CCCCC2)ncn1]

Following the general method as outlined in Example 20, starting from 6-chloro-N-(4-hydroxy-2-methylphenyl)pyrimidine-4-carboxamide (Intermediate 8) and N-methylcyclohexylamine (Aldrich), the title compound was obtained as a yellow solid after purification by column chromatography (silica) eluting with cyclohexane containing increasing amounts of EtOAc.

$^1$H NMR (300MHz, DMSO-$d_6$) δ [ppm] 9.95 (1H, s), 9.31 (1H, s), 8.59 (1H, s), 7.44 (1H, d, J=8.5 Hz), 7.20 (1H, s), 6.66 (1H, d, J=2.5 Hz), 6.59 (1H, dd, J=8.5 Hz, J=2.5 Hz), 2.95 (3H, s), 2.16 (3H, s), 1.87-1.77 (2H, m), 1.60-1.11 (9H, m). MS (ESI+): 341.1. HPLC (Condition A): Rt 3.04 min (HPLC purity 96.6%).

Example 22

6-(dipropylamino)-N-(4-hydroxyphenyl)pyrimidine-4-carboxamide

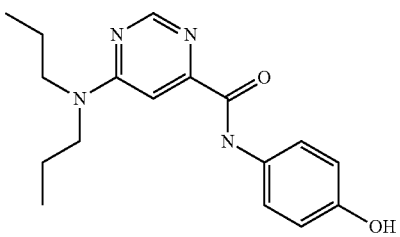 [SMILES: CCCN(CCC)c1cc(C(=O)Nc2ccc(O)cc2)ncn1]

Following the general method as outlined in Example 20, starting from 6-chloro-N-(4-hydroxy-2-methylphenyl)pyrimidine-4-carboxamide (Intermediate 7) and dipropylamine (Aldrich), the title compound was obtained as a brown solid.

$^1$H NMR (300MHz, DMSO-$d_6$) δ [ppm] 10.29 (1H, s), 9.31 (1H, s), 8.58 (1H, s), 7.64 (2H, d, J=9.0 Hz), 7.16 (1H, s), 6.72 (2H, d, J=9.0 Hz), 3.50 (4H, m), 1.57 (4H, m), 0.89 (6H, t, J=7.0 Hz). MS (ESI+): 315.1. HPLC (Condition A): Rt 2.71 min (HPLC purity 78.6%).

Example 23

6-(cycloheptylamino)-N-(4-HYDROXY-2-methylphenyl)pyrimidine-4-carboxamide

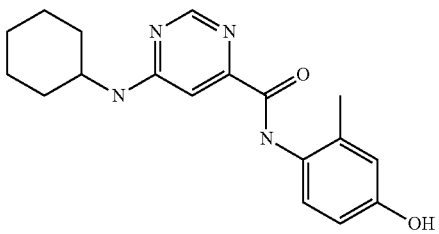 [SMILES: Cc1cc(O)ccc1NC(=O)c1cc(NC2CCCCC2)ncn1]

Following the general method as outlined in Example 20, starting from 6-chloro-N-(4-hydroxy-2-methylphenyl)pyrimidine-4-carboxamide (Intermediate 8) and cycloheptylamine (Aldrich), the title compound was obtained as a beige solid after purification by column chromatography (silica) eluting with cyclohexane containing increasing amounts of EtOAc.

$^1$H NMR (300MHz, DMSO-$d_6$) δ [ppm] 9.88 (1H, s), 9.29 (1H, s), 8.51 (1H, s), 7.78 (1H, d, J=7.5 Hz), 7.45 (1H, d, J=8.5 Hz), 7.13 (1H, s), 6.64 (1H, d, J=2.5 Hz), 6.59 (1H, dd, J=8.5 Hz, J=2.5 Hz), 4.06 (1H, m), 2.15 (3H, s), 1.94-1.85 (2H, m), 1.67-1.42 (10H, m).

MS (ESI+): 341.1. HPLC (Condition A): Rt 3.00 min (HPLC purity 99.5%).

Example 24

N-(4-hydroxy-2-methylphenyl)-6-[(2-methylcyclohexyl)amino]pyrimidine-4-carboxamide

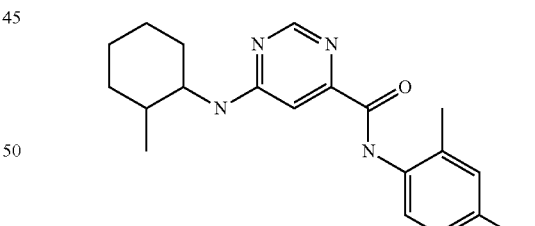

Following the general method as outlined in Example 20, starting from 6-chloro-N-(4-hydroxy-2-methylphenyl)pyrimidine-4-carboxamide (Intermediate 8) and 2-methylcyclohexylamine (Aldrich), the title compound was obtained as a white solid after purification by column chromatography (silica) eluting with cyclohexane containing increasing amounts of EtOAc.

$^1$H NMR (300MHz, DMSO-$d_6$) δ [ppm] 9.87 (1H, s), 9.29 (1H, s), 8.48 (1H, s), 7.71 (1H, d, J=8.5 Hz), 7.46 (1H, d, J=8.5 Hz), 7.12 (1H, s), 6.64 (1H, d, J=2.5 Hz), 6.60 (1H, dd, J=8.5 Hz, J=2.5 Hz), 3.65 (1H, m), 2.15 (3H, s), 1.90 (1H, m), 1.79-1.58 (3H, m), 1.42-1.02 (5H, m), 0.86 (3H, d, J=6.5 Hz).

MS (ESI+): 341.1. HPLC (Condition A): Rt 2.96 min (HPLC purity 99.8%).

Example 25

6-[cyclohexyl(ethyl)amino]-N-(4-hydroxy-2-methylphenyl)pyrimidine-4-carboxamide

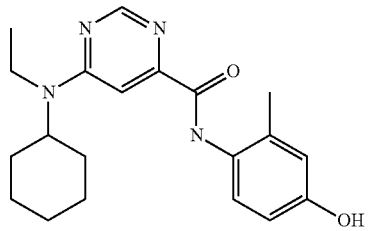 [SMILES: CCN(c1cc(C(=O)Nc2ccc(O)cc2C)ncn1)C1CCCCC1]

Following the general method as outlined in Example 20, starting from 6-chloro-N-(4-hydroxy-2-methylphenyl)pyrimidine-4-carboxamide (Intermediate 8) and N-ethylcyclohexylamine (Aldrich), the title compound was obtained as a yellow solid after purification by column chromatography (silica) eluting with cyclohexane containing increasing amounts of EtOAc.

$^1$H NMR (300MHz, DMSO-d$_6$) δ [ppm] 9.88 (1H, s), 9.26 (1H, s), 8.53 (1H, s), 7.39 (1H, d, J=8.5 Hz), 7.1 (1H, s), 6.59 (1H, d, J=2.5 Hz), 6.53 (1H, dd, J=8.5 Hz, J=2.5 Hz), 3.43 (1H, m), 2.09 (3H, s), 1.74-1.70 (2H, m), 1.58-1.47 (6H, m), 1.32-1.28 (2H, m), 1.11-1.01 (5H, m). MS (ESI+): 355.1. HPLC (Condition A): Rt 3.24 min (HPLC purity 97.6%).

Example 26

6-(cyclohexyloxy)-N-(4-hydroxyphenyl)pyrimidine-4-carboxamide

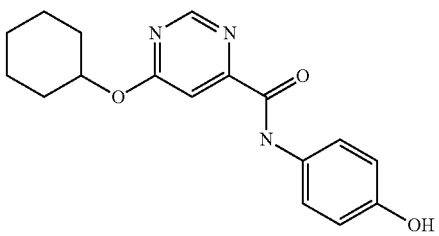

Cyclohexanol (Fluka, 4.00 mL; 37.8 mmol) was treated with sodium hydride (35.0 mg; 0.80 mmol) and stirred during 10 minutes. Tetrahydrofuran (3 mL) was added, followed by 6-chloro-N-(4-hydroxy-2-methylphenyl)pyrimidine-4-carboxamide, Intermediate 7 (50.0 mg; 0.20 mmol). After 2 hours the solvents were removed in vacuo, the crude was redissolved in EtOAc. The organic phase was washed with sat. ammonium chloride and brine, dried over magnesium sulfate, filtered and evaporated in vacuo to give a residue, which was purified by column chromatography (silica) eluting with cyclohexane containing increasing amounts of EtOAc. The title compound was obtained as a white solid.

$^1$H NMR (300MHz, DMSO-d$_6$) δ [ppm] 10.44 (1H, s), 9.35 (1H, s), 8.94 (1H, s), 7.64 (2H, d, J=9.0 Hz), 7.34 (1H, s), 6.73 (2H, d, J=9.0 Hz), 5.15 (1H, m), 2.03-1.93 (2H, m), 1.79-1.68 (2H, m), 1.59-1.12 (6H, m). MS (ESI−): 312.0. HPLC (Condition A): Rt 4.18 min (HPLC purity 93.3%).

Example 27

6-(cyclohexylamino)-N-{2-methoxy-4-[(methylsulfonyl)amino]phenyl}pyrimidine-4-carboxamide

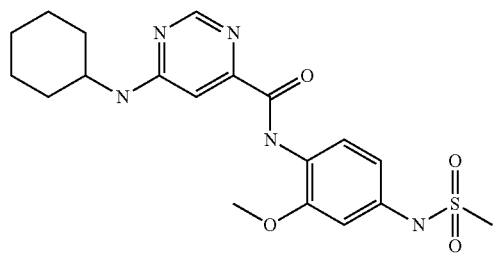 [SMILES: COc1cc(NS(C)(=O)=O)ccc1NC(=O)c1cc(NC2CCCCC2)ncn1]

Following the general method as outlined in Example 1, starting from 6-(cyclohexylamino)pyrimidine-4-carboxylic acid (Intermediate 4) and N-(4-amino-3-methoxyphenyl)methanesulfonamide (Kaironkem), the title compound was obtained as a white solid after trituration in DCM.

$^1$H NMR (300MHz, DMSO-d$_6$) δ 10.27 (1H, s), 9.67 (1H, s), 8.53 (1H, s), 8.32 (1H, d, J=8.5 Hz), 7.85 (1H, d, J=7.5 Hz), 7.17 (1H, s), 6.96 (1H, d, J=2.0 Hz), 6.84 (1H, dd, J=8.5 Hz, J=2.0 Hz), 3.89 (3H, s), 3.88 (1H, m), 2.98 (3H, s), 1.91-1.58 (5H, m), 1.39-1.16 (5H, m). MS (ESI+): 419.9. HPLC (Condition A): Rt 3.43 min (HPLC purity 99.2%).

Example 28

6-(cyclohexylamino)-N-1H-indazol-5-ylpyrimidine-4-carboxamide

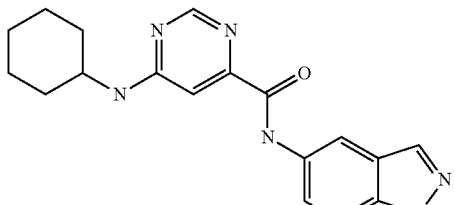

Following the general method as outlined in Example 1, starting from 6-(cyclohexylamino)pyrimidine-4-carboxylic acid (Intermediate 4) and 5-aminoindazole (Aldrich), the title compound was obtained as a pink solid after trituration in DCM.

$^1$H NMR (300MHz, DMSO-d$_6$) δ 13.03 (1H, s), 10.48 (1H, s), 8.55 (1H, s), 8.36 (1H, s), 8.06 (1H, s), 7.79 (1H, d, J=7.5 Hz), 7.73 (1H, dd, J=9.0 Hz, J=2.0 Hz), 7.51 (1H, d, J=9.0 Hz), 7.19 (1H, s), 3.89 (1H, m), 1.90 (2H, m), 1.75-1.52 (3H, m), 1.39-1.21 (5H, m). MS (ESI⁺): 337.0. HPLC (Condition A): Rt 2.49 min (HPLC purity 97.1%).

Example 29

N-[4-(aminosulfonyl)-2-methylphenyl]-6-[cyclohexyl(methyl)amino]pyrimidine-4-carboxamide

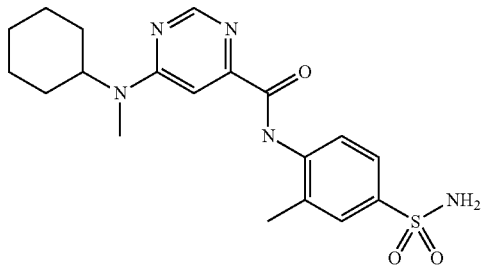 [SMILES: Cc1cc(S(N)(=O)=O)ccc1NC(=O)c1cc(N(C)C2CCCCC2)ncn1]

Following the general method as outlined in Example 1, starting from 6-[cyclohexyl(methyl)amino]pyrimidine-4-carboxylic acid (Intermediate 10) and 4-amino-3-methyl-benzenesulfonamide (Biofine), the title compound was obtained as a white solid after purification by preparative HPLC.

¹H NMR (300MHz, DMSO-d₆) δ 10.37 (1H, s), 8.65 (1H, d, J=2.0 Hz), 8.08 (1H, d, J=8.5 Hz), 7.73-7.68 (2H, m), 7.29-7.23 (3H, m), 4.5 (1H, bs), 2.99 (3H, s), 2.38 (3H, s), 1.90-1.13 (11H, m). MS (ESI⁺): 404.0. HPLC (Condition A): Rt 3.44 min (HPLC purity 99.2%).

Example 30

N-[4-(aminosulfonyl)phenyl]-6-[cyclohexyl(methyl)amino]pyrimidine-4-carboxamide

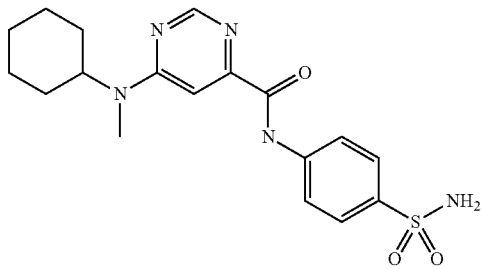 [SMILES: CN(c1cc(C(=O)Nc2ccc(S(N)(=O)=O)cc2)ncn1)C1CCCCC1]

Following the general method as outlined in Example 1, starting from 6-[cyclohexyl(methyl)amino]pyrimidine-4-carboxylic acid (Intermediate 10) and 4-amino-benzenesulfonamide (Acros), the title compound was obtained as a pale brown solid after purification by preparative HPLC.

MS (ESI⁺): 390.0. HPLC (Condition A): Rt 2.91 min (HPLC purity 99.7%).

Example 31

6-[cyclohexyl(methyl)amino]-N-{4-[(ethylamino)sulfonyl]phenyl}pyrimidine-4-carboxamide

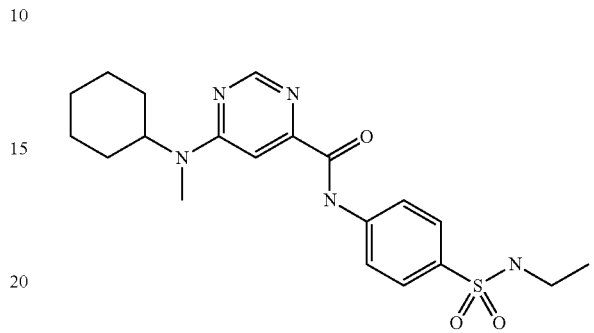

Following the general method as outlined in Example 1, starting from 6-[cyclohexyl(methyl)amino]pyrimidine-4-carboxylic acid (Intermediate 10) and 4-amino-N-ethyl-benzenesulfonamide (Oakwood), the title compound was obtained as a white solid after trituration in methanol.

¹H NMR (300MHz, DMSO-d₆) δ 10.89 (1H, s), 8.66 (1H, s), 8.10 (2H, d, J=9.0 Hz), 7.77 (2H, d, J=9.0 Hz), 7.46 (1H, bs), 7.25 (1H, bs), 4.5 (1H, bs), 2.98 (3H, s), 2.78 (2H, q, J=7.5 Hz), 1.86-1.10 (10H, m), 0.97 (3H, t, J=7.5 Hz). MS (ESI⁺): 418.1. HPLC (Condition A): Rt 3.54 min (HPLC purity 99.4%).

Example 32

N-(4-hydroxy-2-methylphenyl)-6-[methyl(4-methylcyclohexyl)amino]pyrimidine-4-carboxamide

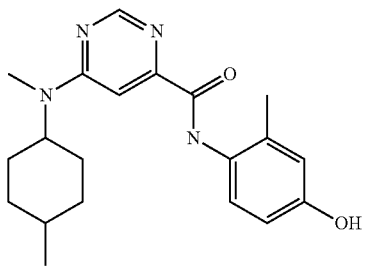 [SMILES: Cc1cc(O)ccc1NC(=O)c1cc(N(C)C2CCC(C)CC2)ncn1]

Following the general method as outlined in Example 20, starting from 6-chloro-N-(4-hydroxy-2-methylphenyl)pyrimidine-4-carboxamide (Intermediate 8) and N,4-dimethylcyclohexanamine (Enamine), the title compound was obtained as a mixture of cis-trans stereoisomers, as a yellow solid after purification by column chromatography (silica) eluting with cyclohexane containing increasing amounts of EtOAc.

MS (ESI+): 355.0. HPLC (Condition A): Rt 3.37 min (HPLC purity 90.5%).

Example 33

6-[cyclohexyl(cyclopropylmethyl)amino]-N-(4-hydroxy-2-methylphenyl)pyrimidine-4-carboxamide

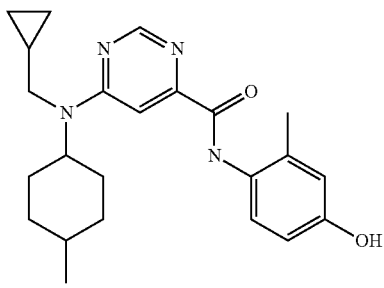 [SMILES: Cc1cc(O)ccc1NC(=O)c1cc(N(CC2CC2)C2CCC(C)CC2)ncn1]

Following the general method as outlined in Example 20, starting from 6-chloro-N-(4-hydroxy-2-methylphenyl)pyrimidine-4-carboxamide (Intermediate 8) and cyclohexylcyclopropanemethylamine (Chembridge), the title compound was obtained as a yellow solid after purification by column chromatography (silica) eluting with cyclohexane containing increasing amounts of EtOAc.

$^1$H NMR (300MHz, DMSO-$d_6$) δ 9.96 (1H, s), 9.30 (1H, s), 8.62 (1H, d, J=2.0 Hz), 7.47 (1H, d, J=8.5 Hz), 7.29 (1H, d, J=2.0 Hz), 6.66 (1H, d, J=2.5 Hz), 6.61 (1H, dd, J=8.5 Hz, J=2.5 Hz), 4.5 (1H, bs), 3.40 (2H, m), 2.18 (3H, s), 1.83-0.99 (11H, m), 0.51 (2H, m), 0.36 (2H, m). MS (ESI+): 381.0. HPLC (Condition A): Rt 3.87 min (HPLC purity 95.8%).

Example 34

6-(cyclohexyloxy)-N-(4-hydroxy-2-methylphenyl)pyrimidine-4-carboxamide

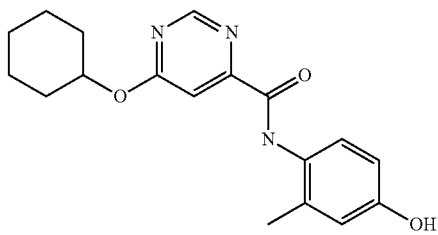

Following the general method as outlined in Example 26, starting from 6-chloro-N-(4-hydroxy-2-methylphenyl)pyrimidine-4-carboxamide (Intermediate 8) and cyclohexanol (Fluka), the title compound was obtained as a yellow solid after purification by preparative HPLC.

MS (ESI+): 328.0. HPLC (Condition A): Rt 4.34 min (HPLC purity 97.1%).

Example 35

6-[cyclohexyl(methyl)amino]-N-1H-indazol-5-ylpyrimidine-4-carboxamide

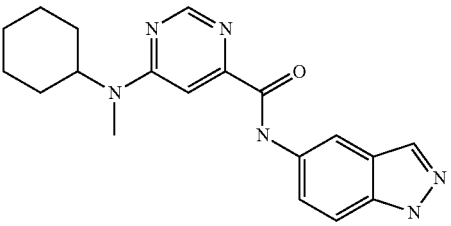 [SMILES: CN(c1cc(C(=O)Nc2ccc3[nH]ncc3c2)ncn1)C1CCCCC1]

Following the general method as outlined in Example 1, starting from 6-[cyclohexyl(methyl)amino]pyrimidine-4-carboxylic acid (Intermediate 10) and 5-aminoindazole (Aldrich), the title compound was obtained as a white solid after purification by column chromatography (silica) eluting with cyclohexane containing increasing amounts of EtOAc.

$^1$H NMR (300MHz, DMSO-$d_6$) δ 10.04 (1H, s), 10.56 (1H, s), 8.64 (1H, d, J=1.0 Hz), 8.36 (1H, d, J=2.0 Hz), 8.07 (1H, s), 7.75 (1H, dd, J=9.0 Hz, J=2.0 Hz), 7.53 (1H, d, J=9.0 Hz), 7.26 (1H, m), 4.5 (1H, bs), 2.99 (3H, s), 1.83-1.14 (10H, m). MS (ESI+): 351.2. HPLC (Condition A): Rt 2.74 min (HPLC purity 99.3%).

Example 36

6-(2-butoxy)-N-(4-hydroxy-2-methylphenyl)pyrimidine-4-carboxamide

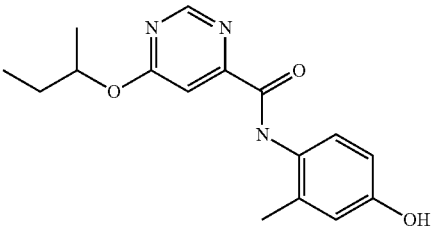 [SMILES: CCC(C)Oc1cc(C(=O)Nc2ccc(O)cc2C)ncn1]

Following the general method as outlined in Example 26, starting from 6-chloro-N-(4-hydroxy-2-methylphenyl)pyrimidine-4-carboxamide (Intermediate 8) and 2-butanol (Fluka), the title compound was obtained as a yellow solid after purification by column chromatography (silica) eluting with cyclohexane containing increasing amounts of EtOAc.

$^1$H NMR (300MHz, DMSO-$d_6$) δ 10.06 (1H, s), 9.34 (1H, s), 8.93 (1H, d, J=1.0 Hz), 7.36 (1H, d, J=8.5 Hz), 7.34 (1H, d, J=1.0 Hz), 6.66 (1H, d, J=2.5 Hz), 6.65 (1H, d, J=8.5 Hz, J=2.5 Hz), 5.26 (1H, sextet, J=6.5 Hz), 2.16 (3H, s), 1.70

(2H, m), 1.32 (3H, d, J=6.5 Hz), 0.92 (3H, d, J=7.5 Hz). MS (ESI⁺): 302.1. HPLC (Condition A): Rt 3.94 min (HPLC purity 96.0%).

Example 37

6-[cyclohexyl(methyl)amino]-N-(4-{[(2-hydroxyethyl)amino]sulfonyl}phenyl)pyrimidine-4-carboxamide

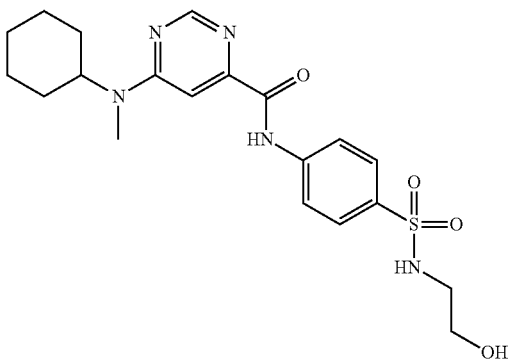 [SMILES: CN(c1cc(C(=O)Nc2ccc(S(=O)(=O)NCCO)cc2)ncn1)C1CCCCC1]

Following the general method as outlined in Example 1, starting from 6-[cyclohexyl(methyl)amino]pyrimidine-4-carboxylic acid (Intermediate 10) and 4-amino-N-(2-hydroxyethyl)benzenesulfonamide (prepared according to the method described by R. N. Misra et al. in Bioorg. Med. Chem. Lett. 2004, 14, 2973-2977), the title compound was obtained as a white solid after purification by column chromatography (silica) eluting with cyclohexane containing increasing amounts of EtOAc.

¹H NMR (300MHz, DMSO-$d_6$) δ 10.89 (1H, s), 8.65 (1H, d, J=1.0 Hz), 8.10 (2H, d, J=9.0 Hz), 7.77 (2H, d, J=9.0 Hz), 7.52 (1H, bs), 7.26 (1H, bs), 4.69 (1H, bs), 4.1 (1H, bs), 3.36 (2H, m), 2.98 (3H, s), 2.78 (2H, d, J=6.5 Hz), 1.82-1.10 (10H, m). MS (ESI⁺): 434.3. HPLC (Condition A): Rt 2.94 min (HPLC purity 98.8%).

Example 38

N-[4-(aminosulfonyl)-2-methylphenyl]-6-[cyclohexyl(cyclopropylmethyl)amino]pyrimidine-4-carboxamide

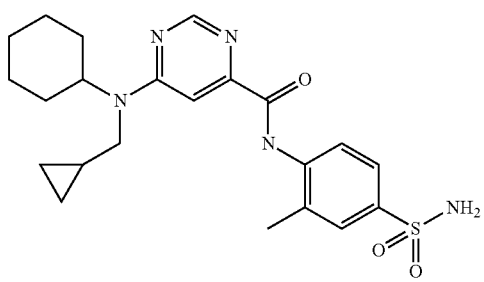 [SMILES: Cc1cc(S(N)(=O)=O)ccc1NC(=O)c1cc(N(CC2CC2)C2CCCCC2)ncn1]

Following the general method as outlined in Example 1, starting from 6-[cyclohexyl(cyclopropylmethyl)amino]pyrimidine-4-carboxylic acid (Intermediate 13) and 4-amino-3-methyl-benzenesulfonamide (Biofine), the title compound was obtained as an off-white solid after trituration in methanol.

¹H NMR (300MHz, DMSO-$d_6$) δ 10.37 (1H, s), 8.69 (1H, d, J=2.5 Hz), 8.08 (1H, d, J=8.5 Hz), 7.73-7.65 (2H, m), 7.35 (1H, s), 7.31 (2H, s), 3.40 (1H, m), 3.17 (2H, d, J=7.0 Hz), 2.38 (3H, s), 1.83-0.85 (11H, m), 0.51 (2H, m), 0.36 (2H, m). MS (ESI⁺): 444.0. HPLC (Condition A): Rt 4.26 min (HPLC purity 96.1%).

Example 39

6-[cyclohexyl(methyl)amino]-N-(6-methyl-1H-indazol-5-yl)pyrimidine-4-carboxamide

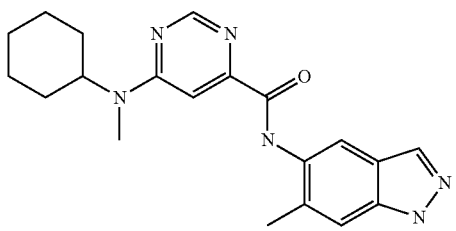 [SMILES: Cc1cc2[nH]ncc2cc1NC(=O)c1cc(N(C)C2CCCCC2)ncn1]

Following the general method as outlined in Example 1, starting from 6-[cyclohexyl(methyl)amino]pyrimidine-4-carboxylic acid (Intermediate 10) and 5-amino-6-methylindazole (Bionet), the title compound was obtained as a beige solid after trituration in DCM.

¹H NMR (300MHz, DMSO-$d_6$) δ 12.81 (1H, s), 10.08 (1H, s), 8.49 (1H, d, J=1.0 Hz), 8.01 (1H, s), 7.88 (1H, s), 7.29 (1H, s), 7.10 (1H, bs), 4.5 (1H, bs), 2.83 (3H, s), 2.26 (3H, s), 1.70-1.00 (10H, m). MS (ESI⁺): 365.1. HPLC (Condition A): Rt 3.05 min (HPLC purity 96.9%).

Example 40

6-[cyclohexyl(methyl)amino]-N-(4-{[(2,3-dihydroxypropyl)amino]sulfonyl}phenyl)pyrimidine-4-carboxamide

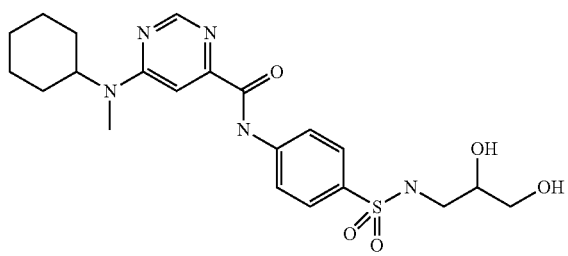 [SMILES: CN(c1cc(C(=O)Nc2ccc(S(=O)(=O)NCC(O)CO)cc2)ncn1)C1CCCCC1]

Following the general method as outlined in Example 1, starting from 6-[cyclohexyl(methyl)amino]pyrimidine-4-carboxylic acid (Intermediate 10) and 4-amino-N-(2,3-dihydroxypropyl)benzenesulfonamide (Intermediate 14), the title compound was obtained as a white solid after trituration in DCM.

¹H NMR (300MHz, DMSO-$d_6$) δ 10.97 (1H, s), 8.66 (1H, d, J=1.0 Hz), 8.10 (2H, d, J=9.0 Hz), 7.78 (2H, d, J=9.0 Hz), 7.41 (1H, bs), 7.25 (1H, bs), 4.76 (1H, d, J=5.0 Hz), 4.53 (1H, t, J=5.0 Hz), 4.0 (1H, bs), 3.45 (1H, m), 3.26 (2H, m), 2.98

(3H, s), 2.85 (1H, m), 2.59 (1H, m), 1.83-1.14 (10H, m). MS (ESI+): 464.3. HPLC (Condition A): Rt 2.75 min (HPLC purity 93.6%).

Example 41

6-[cyclohexyl(methyl)amino]-N-(2-oxo-2,3-dihydro-1H-indol-5-yl)pyrimidine-4-carboxamide

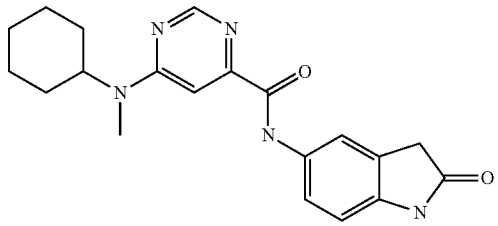 [SMILES: CN(c1cc(C(=O)Nc2ccc3c(c2)CC(=O)N3)ncn1)C1CCCCC1]

Following the general method as outlined in Example 1, starting from 6-[cyclohexyl(methyl)amino]pyrimidine-4-carboxylic acid (Intermediate 10) and 4-aminooxindole (Apollo), the title compound was obtained as a white solid after trituration in DCM.

$^1$H NMR (300MHz, DMSO-$d_6$) δ 10.42 (1H, s), 10.36 (1H, s), 8.62 (1H, d, J=1.0 Hz), 7.77 (1H, s), 7.65 (1H, d, J=8.5 Hz, J=2.0 Hz), 7.21 (1H, bs), 6.79 (1H, d, J=8.5 Hz), 4.7 (1H, bs), 3.49 (2H, s), 2.97 (3H, s), 1.87-1.09 (10H, m). MS (ESI+): 366.3. HPLC (Condition A): Rt 2.40 min (HPLC purity 98.9%).

Example 42

6-[cyclohexyl(methyl)amino-N-(4-{[(2-methoxyethyl)amino]sulfonyl]phenyl}pyrimidine-4-carboxamide

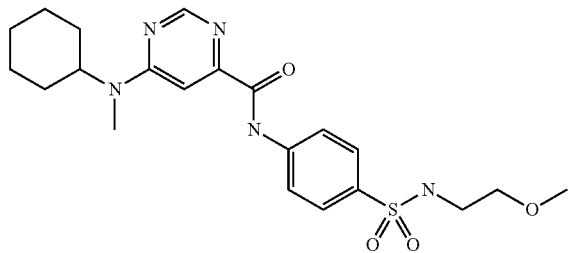 [SMILES: COCCNS(=O)(=O)c1ccc(NC(=O)c2cc(N(C)C3CCCCC3)ncn2)cc1]

Following the general method as outlined in Example 1, starting from 6-[cyclohexyl(methyl)amino]pyrimidine-4-carboxylic acid (Intermediate 10) and 4-amino-N-(2-methoxyethyl)benzenesulfonamide (Intermediate 15), the title compound was obtained as a white solid after purification by column chromatography (silica) eluting with cyclohexane containing increasing amounts of EtOAc.

$^1$H NMR (300MHz, DMSO-$d_6$) δ 10.89 (1H, s), 8.65 (1H, d, J=1.0 Hz), 8.10 (2H, m), 7.77 (2H, m), 7.64 (1H, bs), 7.25 (1H, bs), 4.80 (1H, bs), 3.30 (2H, t, J=6.0 Hz), 3.17 (3H, s), 2.98 (3H, s), 2.90 (2H, t, J=6.0 Hz), 1.83-1.14 (10H, m). MS (ESI+): 448.3. HPLC (Condition A): Rt 2.92 min (HPLC purity 99.3%).

Example 43

6-[cyclohexyl(methyl)amino]-N-quinolin-4-ylpyrimidine-4-carboxamide

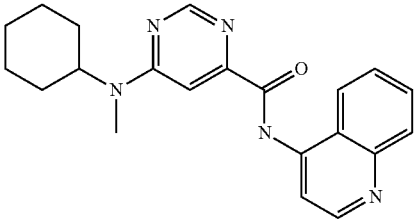 [SMILES: CN(c1cc(C(=O)Nc2ccnc3ccccc23)ncn1)C1CCCCC1]

Following the general method as outlined in Example 1, starting from 6-[cyclohexyl(methyl)amino]pyrimidine-4-carboxylic acid (Intermediate 10) and 4-aminoquinoline (Tyger), the title compound was obtained as an off-white solid after purification by column chromatography (silica) eluting with cyclohexane containing increasing amounts of EtOAc.

$^1$H NMR (300MHz, DMSO-$d_6$) δ 11.19 (1H, s), 8.90 (1H, d, J=5.0 Hz), 8.73 (1H, d, J=1.0 Hz), 8.24 (1H, d, J=5.0 Hz), 8.07 (2H, m), 7.83 (1H, m), 7.73 (1H, m), 7.32 (1H, bs), 4.5 (1H, bs), 3.01 (3H, s), 1.85-1.10 (10H, m). MS (ESI+): 362.2. HPLC (Condition A): Rt 3.40 min (HPLC purity 98.8%).

Example 44

6-[cyclohexyl(cyclopropylmethyl)amino]-N-1H-indazol-5-ylpyrimidine-4-carboxamide

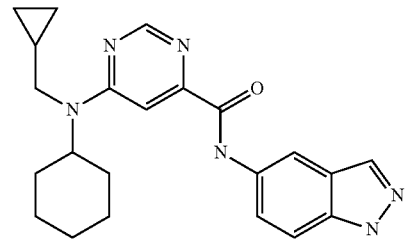 [SMILES: O=C(Nc1ccc2[nH]ncc2c1)c1cc(N(CC2CC2)C2CCCCC2)ncn1]

Following the general method as outlined in Example 20, starting from 6-chloro-N-1H-indazol-5-ylpyrimidine-4-carboxamide (Intermediate 16) and cyclohexylcyclopropanemethylamine (Chembridge), the title compound was obtained as a pale yellow foam.

$^1$H NMR (300MHz, DMSO-$d_6$) δ 13.11 (1H, s), 10.64 (1H, s), 8.73 (1H, d, J=1.0 Hz), 8.42 (1H, s), 8.13 (1H, s), 7.82 (1H, dd, J=9.0 Hz, J=2.0 Hz), 7.58 (1H, d, J=9.0 Hz), 7.40 (1H, s), 4.5 (1H, bs), 3.47 (2H, m), 1.96-1.05 (11H, m), 0.59 (2H, m), 0.43 (2H, m). MS (ESI+): 391.0. HPLC (Condition A): Rt 3.18 min (HPLC purity 95.8%).

Example 45

6-[(cyclopropylmethyl)(propyl)amino]-N-1H-indazol-5-ylpyrimidine-4-carboxamide

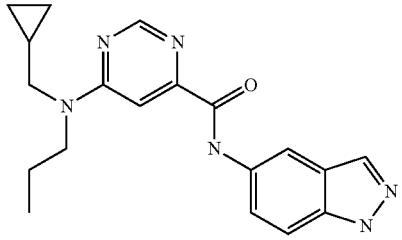 [SMILES: CCCN(CC1CC1)c1cc(C(=O)Nc2ccc3[nH]ncc3c2)ncn1]

Following the general method as outlined in Example 20, starting from 6-chloro-N-1H-indazol-5-ylpyrimidine-4-carboxamide (Intermediate 16) and n-propylcyclopropanemethylamine (Aldrich), the title compound was obtained as a beige foam in 89% yield.

$^1$H NMR (300MHz, DMSO-d$_6$) δ 13.05 (1H, s), 10.56 (1H, s), 8.64 (1H, J=1.0 Hz), 8.36 (1H, J=1.0 Hz), 8.06 (1H, s), 7.76 (1H, dd, J=9.0 Hz, J=2.0 Hz), 7.52 (1H, d, J=9.0 Hz), 7.28 (1H, s), 3.54 (4H, m), 1.64 (2H, m), 1.09 (1H, m), 0.91 (3H, t, J=7.0 Hz), 0.50 (2H, m), 0.34 (2H, m). MS (ESI+): 351.0. HPLC (Condition A): Rt 2.91 min (HPLC purity 95.5%).

Example 46

6-[cyclohexyl(cyclopropylmethyl)amino]-N-quinolin-4-ylpyrimidine-4-carboxamide

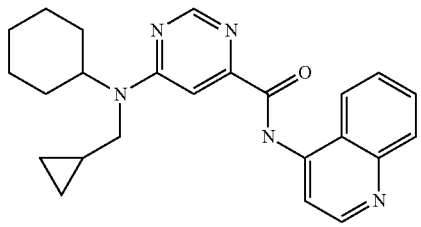 [SMILES: O=C(Nc1ccnc2ccccc12)c1cc(N(CC2CC2)C2CCCCC2)ncn1]

Following the general method as outlined in Example 1, starting from 6-[cyclohexyl(cyclopropylmethyl)amino]pyrimidine-4-carboxylic acid (Intermediate 13) and 4-aminoquinoline (Tyger), the title compound was obtained as a white solid after purification by column chromatography (silica) eluting with cyclohexane containing increasing amounts of EtOAc.

$^1$H NMR (300MHz, DMSO-d$_6$) δ 11.15 (1H, s), 8.91 (1H, d, J=5.0 Hz), 8.75 (1H, d, J=1.0 Hz), 8.24 (1H, d, J=5.0 Hz), 8.10-8.05 (2H, m), 7.84 (1H, m), 7.73 (1H, m), 7.40 (1H, d, J=1.0 Hz), 4.5 (1H, bs), 3.45 (2H, m), 1.84-1.00 (11H, m), 0.54 (2H, m), 0.39 (2H, m). MS (ESI+): 402.4. HPLC (Condition A): Rt 4.25 min (HPLC purity 99.5%).

Example 47

6-[cyclohexyl(cyclopropylmethyl)amino]-N-(6-methyl-1H-indazol-5-yl)pyrimidine-4-carboxamide

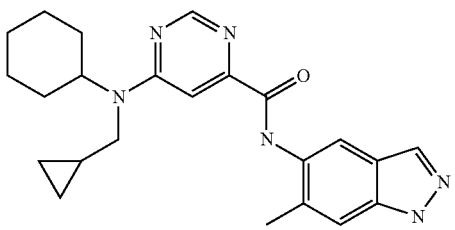 [SMILES: Cc1cc2[nH]ncc2cc1NC(=O)c1cc(N(CC2CC2)C2CCCCC2)ncn1]

Following the general method as outlined in Example 1, starting from 6-[cyclohexyl(cyclopropylmethyl)amino]pyrimidine-4-carboxylic acid (Intermediate 13) and 5-amino-6-methylindazole (Bionet), the title compound was obtained as an off-white solid after purification by column chromatography (silica) eluting with cyclohexane containing increasing amounts of EtOAc.

$^1$H NMR (300MHz, DMSO-d$_6$) δ 12.96 (1H, s), 10.22 (1H, s), 8.66 (1H, d, J=1.0 Hz), 8.17 (1H, s), 8.02 (1H, s), 7.44 (1H, s), 7.34 (1H, d, J=1.0 Hz), 4.5 (1H, bs), 3.42 (2H, m), 2.41 (3H, s), 1.84-1.01 (11H, m), 0.52 (2H, m), 0.37 (2H, m). MS (ESI+): 405.4. HPLC (Condition A): Rt 4.48 min (HPLC purity 98.4%).

Example 48

N-[4-(aminomethyl)phenyl]-6-[cyclohexyl(cyclopropylmethyl)amino]-pyrimidine-4-carboxamide, dihydrochloride Step 1-tert-butyl {4-[({6-[cyclohexyl(cyclopropylmethyl)amino]-pyrimidin-4-yl}carbonyl)amino]benzyl}carbamate

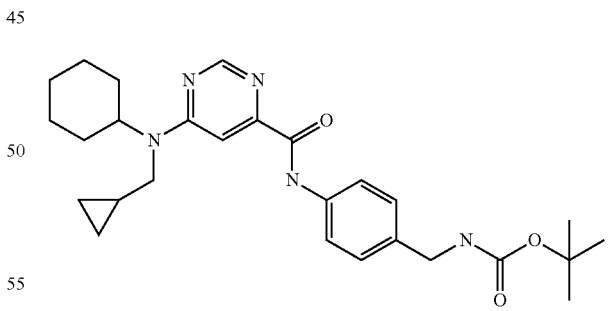

Following the general method as outlined in Example 1, starting from 6-[cyclohexyl(cyclopropylmethyl)amino]pyrimidine-4-carboxylic acid (Intermediate 13) and tert-butyl (4-amino-benzyl)-carbamate (Astatech), the title compound was obtained as a white foam in 82% yield after purification by column chromatography (silica) eluting with cyclohexane containing increasing amounts of EtOAc.

$^1$H NMR (300MHz, DMSO-d$_6$) δ 10.50 (1H, s), 8.65 (1H, d, J=1.0 Hz), 7.81 (2H, d, J=8.5 Hz), 7.37 (1H, t, J=6.0 Hz), 7.32 (1H, d, J=1.0 Hz), 7.22 (2H, d, J=8.5 Hz), 4.5 (1H, bs), 4.09 (2H, d, J=6.0 Hz), 3.40 (2H, m), 1.83-1.15 (11H, m), 1.40 (9H, s), 0.52 (2H, m), 0.37 (2H, m). MS (ESI⁺): 480.1. HPLC (Condition A): Rt 4.59 min (HPLC purity 94.2%).

Step 2-N-[4-(aminomethyl)phenyl]-6-[cyclohexyl(cyclopropylmethyl)amino]pyrimidine-4-carboxamide, dihydrochloride

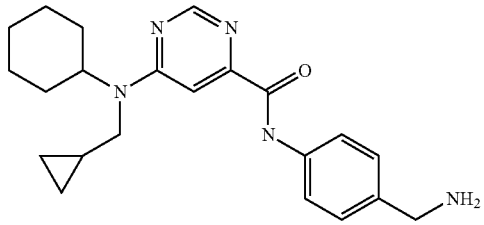 [SMILES: NCc1ccc(NC(=O)c2cc(N(CC3CC3)C3CCCCC3)ncn2)cc1]

A solution of tert-butyl {-4-[({6-[cyclohexyl(cyclopropylmethyl)amino]pyrimidin-4-yl}carbonyl)amino]benzyl}carbamate (175.00 mg; 0.36 mmol) in dioxane (2 mL) was treated with a solution of hydrogen chloride in dioxane (1.82 ml; 4.00 M; 7.30 mmol). The resulting solution was stirred for 2 h, then the solvents were evaporated under reduced pressure to give the title compound as a pale yellow solid (163.1 mg, 99%).

¹H NMR (300MHz, DMSO-d₆) δ 11.2 (1H, bs), 8.72 (1H, s), 8.38 (3H, bs), 7.96 (2H, d, J=8.5 Hz), 7.50 (2H, d, J=8.5 Hz), 6.2 (1H, bs), 4.5 (1H, bs), 4.00 (2H, q, J=5.5 Hz), 3.52 (2H, m), 1.82-1.05 (11H, m), 0.52 (2H, m), 0.41 (2H, m). MS (ESI⁺): 352.4. HPLC (Condition A): Rt 3.04 min (HPLC purity 100.0%).

Example 49

6-[cyclohexyl(cyclopropylmethyl)amino]-N-pyridin-4-ylpyrimidine-4-carboxamide

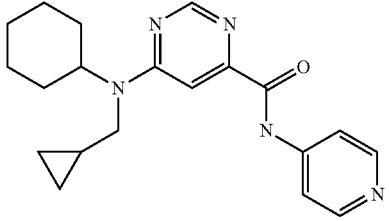 [SMILES: O=C(Nc1ccncc1)c1cc(N(CC2CC2)C2CCCCC2)ncn1]

Following the general method as outlined in Example 1, starting from 6-[cyclohexyhcyclopropylmethyl)amino]pyrimidine-4-carboxylic acid (Intermediate 13) and 4-aminopyridine (Tyger), the title compound was obtained as a white solid after purification by column chromatography (silica) eluting with cyclohexane containing increasing amounts of EtOAc.

¹H NMR (300MHz, DMSO-d₆) δ 10.92 (1H, s), 8.68 (1H, d, J=1.0 Hz), 8.49 (2H, m), 7.91 (2H, m), 7.32 (1H, d, J=1.0 Hz), 4.5 (1H, bs), 3.40 (2H, m), 1.82-1.00 (11H, m), 0.51 (2H, m), 0.37 (2H, m). MS (ESI⁺): 402.4. HPLC (Condition A): Rt 3.34 min (HPLC purity 100.0%).

Example 50

N-[4-(aminocarbonyl)phenyl]-6-[cyclohexyl(cyclopropylmethyl)amino]pyrimidine-4-carboxamide

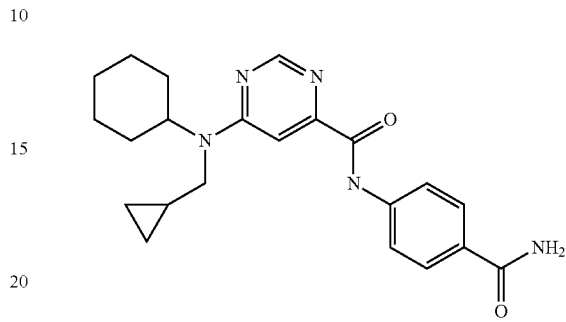

Following the general method as outlined in Example 1, starting from 6-[cyclohexyhcyclopropylmethyl)amino]pyrimidine-4-carboxylic acid (Intermediate 13) and 4-aminobenzamide (Aldrich), the title compound was obtained as a brown solid in 85% yield after trituration in DCM.

¹H NMR (300MHz, DMSO-d₆) δ 10.75 (1H, s), 8.67 (1H, d, J=1.0 Hz), 7.98 (2H, d, J=9.0 Hz), 7.90 (1H, bs), 7.87 (2H, d, J=9.0 Hz), 7.33 (1H, d, J=1.0 Hz), 7.31 (1H, bs), 4.5 (1H, bs), 3.40 (2H, m), 1.83-0.98 (11H, m), 0.52 (2H, m), 0.36 (2H, m). MS (ESI⁺): 394.4. HPLC (Condition A): Rt 3.79 min (HPLC purity 93.2%).

Example 51

6-[cyclohexyl(cyclopropylmethyl)amino]-N-(4-{[(2,3-dihydroxypropyl)amino]sulfonyl}phenyl)pyrimidine-4-carboxamide

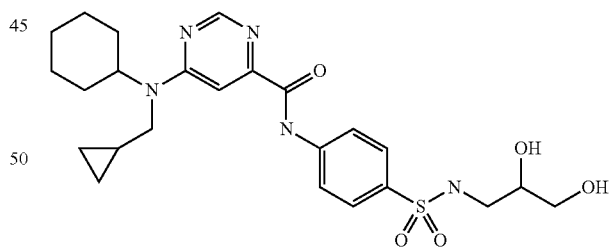

Following the general method as outlined in Example 1, starting from 6-[cyclohexyl(cyclopropylmethyl)amino]pyrimidine-4-carboxylic acid (Intermediate 13) and 4-amino-N-(2,3-dihydroxypropyl)benzenesulfonamide (Intermediate 15), the title compound was obtained as a brown solid after purification by column chromatography (silica) eluting with cyclohexane containing increasing amounts of EtOAc.

¹H NMR (300MHz, DMSO-d₆) δ 10.91 (1H, s), 8.68 (1H, d, J=1.0 Hz), 8.10 (2H, d, J=9.0 Hz), 7.78 (2H, d, J=9.0 Hz), 7.42 (1H, bs), 7.33 (1H, bs), 4.77 (1H, d, J=5.0 Hz), 4.8 (1H, bs), 4.54 (1H, m), 3.44 (2H, m), 3.27 (2H, m), 3.17 (1H, d, J=5.5 Hz) 2.86 (1H, m), 2.58 (1H, m), 1.83-0.99 (11H, m), 0.52 (2H, m), 03.8 (2H, m). MS (ESI⁺): 504.4. HPLC (Condition A): Rt 3.62 min (HPLC purity 100.0%).

Example 52

6-(cyclohexylamino)-N-(4-hydroxyphenyl)pyrimidine-4-carboxamide

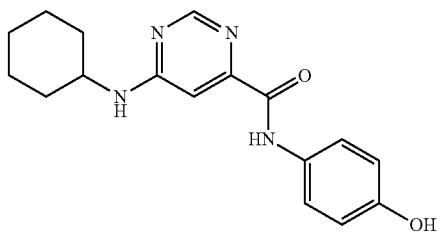 [SMILES: O=C(Nc1ccc(O)cc1)c1cc(NC2CCCCC2)ncn1]

Following the general method as outlined in Example 1, starting from 6-(cyclohexylamino)pyrimidine-4-carboxylic acid (Intermediate 4) and 4-aminophenol (Aldrich), the title compound was obtained as a slightly yellow solid.

¹H NMR (300MHz, DMSO-d₆) δ 10.26 (1H, s), 9.35 (1H, s), 8.56 (1H, s), 7.80 (1H, d, J=6.0 Hz), 7.67 (2H, d, J=9.0 Hz), 7.18 (1H, s), 6.76 (2H, d, J=9.0 Hz), 3.91 (1H, m), 1.94 (2H, m), 1.80-1.60 (3H, m), 1.45-1.18 (5H, m). MS (ESI): 313.1. HPLC (Condition A): Rt 2.49 min (HPLC purity 95.4%).

Example 53

6-(cyclohexylamino)-N-[4-(2-hydroxy-ethyl)-phenyl]pyrimidine-4-carboxamide

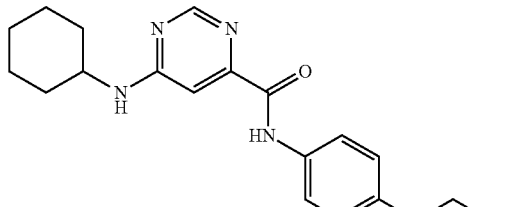

Following the general method as outlined in Example 1, starting from 6-(cyclohexylamino)pyrimidine-4-carboxylic acid (Intermediate 4) and 2-(4-aminophenyl)ethanol (Fluka), the title compound was obtained as a white solid after trituration in acetonitrile.

¹H NMR (300MHz, DMSO-d₆) δ 10.41 (1H, s), 8.58 (1H, s), 7.83 (1H, d, J=6.0 Hz), 7.78 (2H, d, J=9.0 Hz), 7.21 (3H, m), 4.67 (1H, d, J=6.0 Hz), 3.92 (1H, m), 3.63 (2H, m), 2.73 (2H, d, J=6.0 Hz), 1.94 (2H, m), 1.80-1.55 (3H, m), 1.45-1.17 (5H, m). MS (ESI⁺): 341.1. HPLC (Condition A): Rt 2.61 min (HPLC purity 94.1%).

Example 54

N-[4-(aminosulfonyl)-2-methylphenyl]-6-[cyclohexyl(propyl)amino]pyrimidine-4-carboxamide

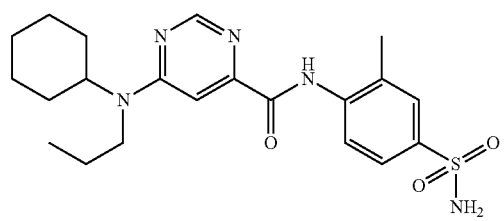 [SMILES: CCCN(c1cc(C(=O)Nc2ccc(S(N)(=O)=O)cc2C)ncn1)C1CCCCC1]

Following the general method as outlined in Example 20, starting from 6-chloro-pyrimidine-4-carboxylic acid (2-methyl-4-sulfamoyl-phenyl)-amide (Intermediate 17) and cyclohexylpropylamine (Chembridge), the title compound was obtained as a beige solid in 82% yield.

¹H NMR (300MHz, DMSO-d6) δ [ppm] 10.36 (1H, bs), 8.66 (1H, s), 8.08 (1H, d, J=8.5 Hz), 7.73-7.68 (2H, m), 7.30 (2H, bs), 7.17 (1H, bs), 4.80 (1H, m), 2.38 (3H, s), 1.85-1.10 (14H, m), 0.94 (3H, t, J=6.5 Hz). MS (ESI+): 431.9. HPLC (Condition A): Rt 4.19 min (HPLC purity 97.6%).

Example 55

N-[4-(aminosulfonyl)-2-methylphenyl]-6-[cyclohexyl(2-methoxyethyl)amino]pyrimidine-4-carboxamide

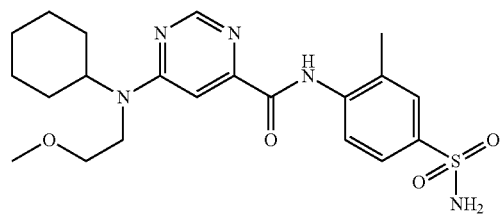 [SMILES: COCCN(c1cc(C(=O)Nc2ccc(S(N)(=O)=O)cc2C)ncn1)C1CCCCC1]

Following the general method as outlined in Example 20, starting from 6-chloro-pyrimidine-4-carboxylic acid (2-methyl-4-sulfamoyl-phenyl)-amide (Intermediate 17) and cyclohexyl-(2-methoxy-ethyl)-amine (Intermediate 26), the title compound was obtained as a white solid in 82% yield.

¹H NMR (300MHz, DMSO-d6) δ [ppm] 10.37 (1H, bs), 8.68 (1H, s), 8.09 (1H, d, J=8.5 Hz), 7.74-7.68 (2H, m), 7.35

(1H, bs), 7.30 (2H, bs), 4.71 (1H, m), 3.65 (2H, m), 3.49 (2H, t, J=6.5 Hz), 3.26 (3H, s), 2.38 (3H, s), 1.89-1.11 (10H, m). MS (ESI+): 448.0. HPLC (Condition A): Rt 3.88 min (HPLC purity 97.3%).

Example 56

N-[4-(aminosulfonyl)-2-methylphenyl]-6-[(cyclopropylmethyl)(propyl)amino]pyrimidine-4-carboxamide

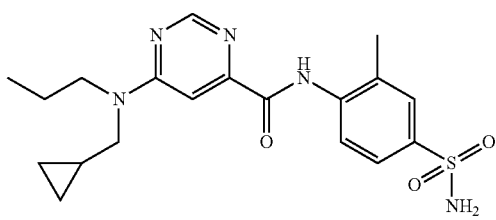 [SMILES: CCCN(CC1CC1)c1cc(C(=O)Nc2ccc(S(N)(=O)=O)cc2C)ncn1]

Following the general method as outlined in Example 20, starting from 6-chloro-pyrimidine-4-carboxylic acid (2-methyl-4-sulfamoyl-phenyl)-amide (Intermediate 17) and propylcyclopropanemethylamine (Aldrich), the title compound was obtained as an off-white solid in 86% yield.

$^1$H NMR (300MHz, DMSO-d6) δ [ppm] 10.36 (1H, bs), 8.63 (1H, s), 8.07 (1H, d, J=8.5 Hz), 7.72 (1H, d, J=2.0 Hz), 7.68 (1H, dd, J=8.5 Hz, J=2.0 Hz), 7.29 (3H, bs), 3.54 (4H, bs), 2.37 (3H, s), 1.61 (2H, sextet, J=7.0 Hz), 1.07 (1H, bs), 0.90 (3H, t, J=7.0 Hz), 0.48 (2H, m), 0.33 (2H, m). MS (ESI+): 403.9. HPLC (Condition A): Rt 3.57 min (HPLC purity 99.4%).

Example 57

N-[4-(aminosulfonyl)-2-methylphenyl]-6-(dipropylamino)pyrimidine-4-carboxamide

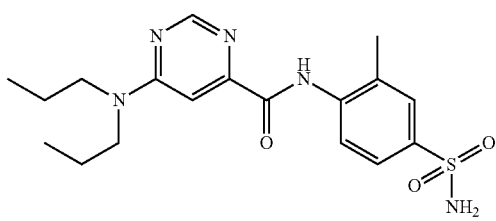 [SMILES: CCCN(CCC)c1cc(C(=O)Nc2ccc(S(N)(=O)=O)cc2C)ncn1]

Following the general method as outlined in Example 20, starting from 6-chloro-pyrimidine-4-carboxylic acid (2-methyl-4-sulfamoyl-phenyl)-amide (Intermediate 17) and dipropylamine (Aldrich), the title compound was obtained as a white solid in 87% yield.

$^1$H NMR (300MHz, DMSO-d6) δ [ppm] 10.36 (1H, bs), 8.64 (1H, d, J=1.0 Hz), 8.08 (1H, d, J=8.5 Hz), 7.73 (1H, d, J=2.0 Hz), 7.69 (1H, dd, J=8.5 Hz, J=2.0 Hz), 7.30 (2H, bs), 7.23 (1H, d, J=1.0 Hz), 3.53 (4H, bs), 2.38 (3H, s), 1.60 (4H, sextet, J=7.0 Hz), 0.91 (6H, t, J=7.0 Hz). MS (ESI+): 392.3. HPLC (Condition A): Rt 3.40 min (HPLC purity 98.2%).

Example 58

N-[4-(aminosulfonyl)-2-methylphenyl]-6-[cyclopentyl(isobutyl)amino]pyrimidine-4-carboxamide

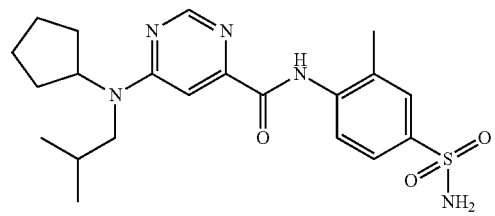 [SMILES: Cc1cc(S(N)(=O)=O)ccc1NC(=O)c1cc(N(CC(C)C)C2CCCC2)ncn1]

Following the general method as outlined in Example 20, starting from 6-chloro-pyrimidine-4-carboxylic acid (2-methyl-4-sulfamoyl-phenyl)-amide (Intermediate 17) and cyclopentyl-isobutyl-amine (Intermediate 27), the title compound was obtained as a white solid in 80% yield.

$^1$H NMR (300MHz, DMSO-d6) δ [ppm] 10.36 (1H, bs), 8.66 (1H, d, J=1.0 Hz), 8.08 (1H, d, J=8.5 Hz), 7.73 (1H, d, J=2.0 Hz), 7.69 (1H, dd, J=8.5 Hz, J=2.0 Hz), 7.33 (2H, bs), 7.30 (1H, bs), 4.57 (1H, m), 3.37 (2H, d, J=7.0 Hz), 2.38 (3H, s), 2.10-1.58 (9H, m), 0.90 (6H, d, J=6.5 Hz). MS (ESI+): 432.3. HPLC (Condition A): Rt 4.22 min (HPLC purity 99.9%).

Example 59

N-[4-(aminosulfonyl)-2-methylphenyl]-6-[bis(2-methoxyethyl)amino]pyrimidine-4-carboxamide

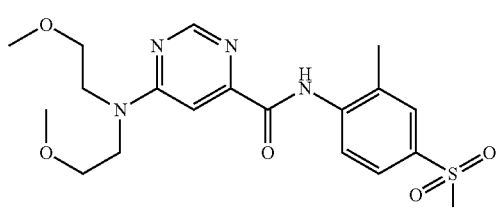

Following the general method as outlined in Example 20, starting from 6-chloro-pyrimidine-4-carboxylic acid (2-methyl-4-sulfamoyl-phenyl)-amide (Intermediate 17) and bis(2-methoxyethyl)amine (Aldrich), the title compound was obtained as a white solid in 84% yield.

$^1$H NMR (300MHz, DMSO-d6) δ [ppm] 10.37 (1H, bs), 8.65 (1H, d, J=1.0 Hz), 8.07 (1H, d, J=8.5 Hz), 7.73 (1H, d, J=2.0 Hz), 7.69 (1H, dd, J=8.5 Hz, J=2.0 Hz), 7.38 (1H, d, J=1.0 Hz), 7.31 (2H, m), 3.84 (2H, m), 3.76 (2H, m), 3.55

(4H, t, J=5.5 Hz), 3.26 (6H, s), 2.38 (3H, s). MS (ESI+): 424.3. HPLC (Condition A): Rt 2.19 min (HPLC purity 99.9%).

Example 60

N-[4-(aminosulfonyl)-2-methylphenyl]-6-[isopropyl (propyl)amino]pyrimidine-4-carboxamide

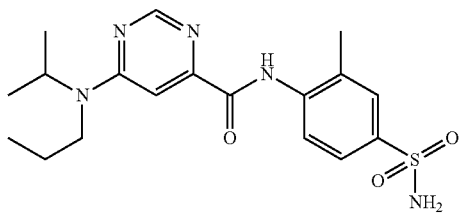 [SMILES: CCCN(c1cc(C(=O)Nc2ccc(S(N)(=O)=O)cc2C)ncn1)C(C)C]

Following the general method as outlined in Example 20, starting from 6-chloro-pyrimidine-4-carboxylic acid (2-methyl-4-sulfamoyl-phenyl)-amide (Intermediate 17) and propyl-isopropylamine (Matrix), the title compound was obtained as a white solid.

$^1$H NMR (300MHz, DMSO-d6) δ [ppm] 10.37 (1H, bs), 8.66 (1H, d, J=1.0 Hz), 8.08 (1H, d, J=8.5 Hz), 7.73 (1H, d, J=2.0 Hz), 7.69 (1H, dd, J=8.5 Hz, J=2.0 Hz), 7.30 (2H, bs), 7.21 (1H, bs), 5.10 (1H, m), 3.35 (2H, bs), 2.38 (3H, s), 1.57 (2H, sextet, J=7.0 Hz), 1.21 (6H, d, J=6.5 Hz), 0.95 (3H, t, J=7.0 Hz). MS (ESI+): 392.2. HPLC (Condition A): Rt 3.24 min (HPLC purity 98.5%).

Example 61

N-({4-[({6-[cyclohexyl(cyclopropylmethyl)amino] pyrimidin-4-yl}carbonyl)amino]-3-methylphenyl}sulfonyl)glycine

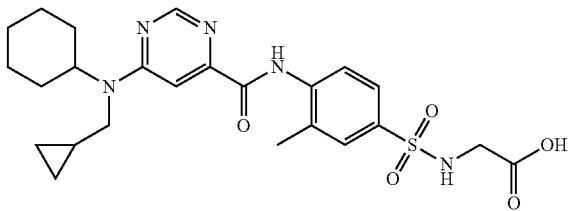 [SMILES: Cc1cc(S(=O)(=O)NCC(=O)O)ccc1NC(=O)c1cc(N(CC2CC2)C2CCCCC2)ncn1]

A solution of methyl 2-(4-(6-chloropyrimidine-4-carboxamido)-3-methylphenylsulfonamido)acetate (Intermediate 33, 123 mg; 0.31 mmol) and diisopropylamine (105.5 mL; 0.61 mmol) in ethanol (4 ml) was treated with N-(cyclopropylmethyl)cyclohexanamine (56.6 mg; 0.4 mmol). The mixture was heated to 160° C. in a microwave for 1 hour and the solvent removed in vacuo. The residue was purified by column chromatography (silica) eluting with petroleum ether containing increasing amounts of EtOAc to give a mixture of methyl 2-(4-(6-(cyclohexyl(cyclopropylmethyl)amino)pyrimidine-4-carboxamido)-3-methylphenylsulfonamido)acetate and ethyl 2-(4-(6-(cyclohexyl(cyclopropylmethyl)amino)pyrimidine-4-carboxamido)-3-methylphenylsulfonamido)acetate which was used directly without any further purification. The residue was redissolved in methanol (10 ml) and tetrahydrofuran (10 ml) and treated with 5 N NaOH solution (1 ml). After stirring at RT for 5 hours the solvent was removed in vacuo. The residue was redissolved in water (10 ml) and acidified with conc. HCl. The aqueous phase was extracted with EtOAc and the organic extracts passed through a hydrophobic frit and the solvent removed in vacuo. The residue was triturated with petroleum ether to yield the title compound as a white solid (136 mg, 87%).

$^1$H NMR (400MHz, CDCl3) δ 10.31 (1H, s), 8.55 (1H, d, J=1.1 Hz), 8.51 (1H, d, J=8.5 Hz,), 7.78-7.72 (2H, m), 7.42 (1H, s), 5.11 (1H, br s), 3.85 (2H, d, J=3.7 Hz), 3.47-3.30 (2H, br m), 2.48 (3H, s), 1.93-1.81 (4H, m), 1.79-1.68 (1H, m), 1.61-1.39 (4H, m), 1.28-1.12 (2H, m), 1.11-0.96 (1H, m), 0.63-0.53 (2H, m), 0.40-0.33 (2H, m). MS (APCI+): 502. HPLC (Condition C): Rt 4.41 min (HPLC purity 92.0%).

Example 62

N-({4-[({6-[cyclohexyl(cyclopropylmethyl)amino] pyrimidin-4-yl}carbonyl)amino]-3-methylphenyl}sulfonyl)-beta-alanine

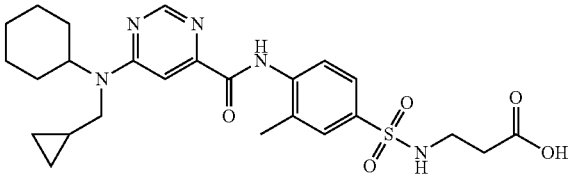 [SMILES: Cc1cc(S(=O)(=O)NCCC(=O)O)ccc1NC(=O)c1cc(N(CC2CC2)C2CCCCC2)ncn1]

A solution of tert-butyl 3-(4-(6-chloropyrimidine-4-carboxamido)-3-methylphenylsulfonamido)propanoate (Intermediate 34, 140 mg; 0.31 mmol) and diisopropylamine (105.5 mL; 0.61 mmol) in ethanol (4 ml) was treated with N-(cyclopropylmethyl)cyclohexanamine (56.6 mg, 0.4 mmol). The mixture was heated to 160° C. in a microwave for 1 hour and the solvent reduced to one tenth of the volume in vacuo. The solid formed was triturated with water and the residue purified by column chromatography (silica) eluting with petroleum ether containing increasing amounts of EtOAc to give tert-butyl 3-(4-(6-(cyclohexyl(cyclopropylmethyl)amino)pyrimidine-4-carboxamido)-3-methylphenylsulfonamido)propanoate which was used directly without any further purification. The residue was redissolved in DCM (4.5 ml) and treated with TFA (0.5 ml). After stirring at RT for 2 hours the solvent was removed in vacuo to give the title compound as an off-white solid.

$^1$H NMR (400MHz, CDCl3) δ 10.58 (1H, s), 8.61 (1H, s), 8.35 (1H, br s), 7.74 (2H, s), 7.52 (1H, s), 5.63 (1H, s), 3.67-3.28 (2H, m), 3.31-3.12 (2H, m), 2.61 (2H, s), 2.48 (3H, s), 1.98-1.67 (5H, m), 1.66-1.37 (5H, m), 1.30-1.11 (1H, m) 1.12-0.94 (1H, m), 0.69-0.50 (2H, m), 0.44-0.30 (2H, m). MS (APCI+): 516. HPLC (Condition C): Rt 4.38 min (HPLC purity 97.3%).

Example 63

4-[({4-[({6-[cyclohexyl(cyclopropylmethyl)amino] pyrimidin-4-yl}carbonyl)amino]-3-methylphenyl}sulfonyl)amino]butanoic acid

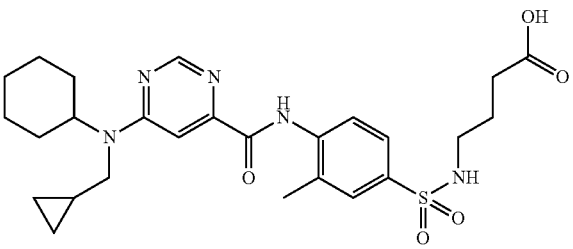 [SMILES: Cc1cc(S(=O)(=O)NCCCC(=O)O)ccc1NC(=O)c1cc(N(CC2CC2)C2CCCCC2)ncn1]

A solution of ethyl 4-(4-(6-chloropyrimidine-4-carboxamido)-3-methylphenylsulfonamido)butanoate (Intermediate 35, 123 mg; 0.31 mmol) and diisopropylamine (105.5 mL; 0.61 mmol) in ethanol (4 ml) was treated with N-(cyclopropylmethyl)cyclohexanamine (56.6 mg, 0.4 mmol). The mixture was heated to 160° C. in a microwave for 1 hour and the solvent removed in vacuo. The residue purified by column chromatography (silica) eluting with petroleum ether containing increasing amounts of EtOAc to give ethyl 4-(4-(6-(cyclohexyl(cyclopropylmethyl)amino)pyrimidine-4-carboxamido)-3-methylphenylsulfonamido)butanoate which was used directly without any further purification. The residue was dissolved in methanol (10 ml) and THF (10 ml) and treated with 5 N NaOH solution (1 ml). After stirring at RT for 5 hours the solvent was removed in vacuo. The residue was redissolved in water (10 ml) and acidified with concentrated HCl. The aqueous phase was extracted with EtOAc and the organic extracts passed through a hydrophobic frit and the solvent removed in vacuo. The residue was triturated with petroleum ether to yield the title compound as a white solid (120 mg, 73%).

$^1$H NMR (400MHz, CDCl3) δ 10.52 (1H, s), 8.60 (1H, s), 8.33 (1H, br s), 7.78-7.72 (2H, m), 7.50 (1H, s), 4.85 (1H, t, J=6.3 Hz), 3.43 (2H, br s), 3.04 (2H, app q, J=6.5 Hz), 2.47 (3H, s), 2.43-2.35 (2H, m), 1.93-1.70 (7H, m), 1.63-1.39 (5H, m), 1.29-1.25 (1H, m), 1.11-0.98 (1H, br m), 0.66-0.54 (2H, br m), 0.42-0.36 (2H, br m). MS (APCI+): 530. HPLC (Condition C): Rt 4.38 min (HPLC purity 90.3%).

Example 64

6-[cyclohexyl(cyclopropylmethyl)amino]-N-{4-[(dimethylamino)sulfonyl]-2-methylphenyl}pyrimidine-4-carboxamide

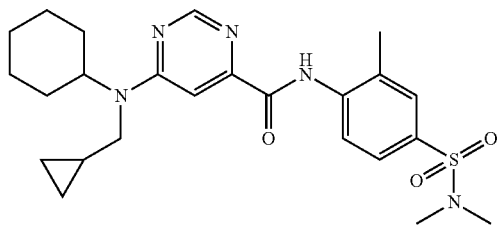 [SMILES: Cc1cc(S(=O)(=O)N(C)C)ccc1NC(=O)c1cc(N(CC2CC2)C2CCCCC2)ncn1]

A solution of 4-[({6-[cyclohexyl(cyclopropylmethyl)amino]pyrimidin-4-yl}carbonyl)amino]-3-methylbenzenesulfonyl chloride (Intermediate 20, 50 mg; 0.11 mmol) in THF (5 ml) was treated with polymer-supported-diisopropylethylamine (60.7 mg; 0.22 mmol) and dimethylamine (8 μl; 0.13 mmol, Aldrich) and the reaction mixture was stirred at room temperature for three hours. The resin was filtered and the solvents were evaporated to give a residue, which was purified by column chromatography (silica) using as eluent petroleum ether/EtOAc to afford the title compound as a yellow oil.

MS (ESI$^+$): 472.4. HPLC (Condition A): Rt 3.34 min (HPLC purity 98.9%).

Example 65

N-[4-(aminosulfonyl)-2-methylphenyl]-6-(cyclohexyloxy)pyrimidine-4-carboxamide

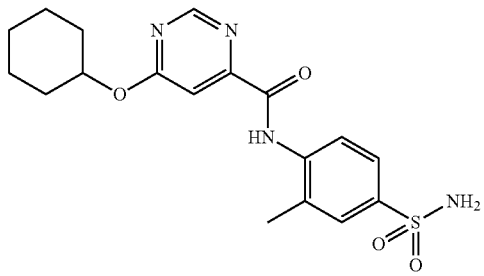 [SMILES: Cc1cc(S(N)(=O)=O)ccc1NC(=O)c1cc(OC2CCCCC2)ncn1]

Following the general method as outlined in Example 1, starting 6-(cyclohexyloxy)pyrimidine-4-carboxylic acid (Intermediate 32) and 4-amino-3-methylbenzenesulfonamide (Biofine), the title compound was obtained as a white solid.

MS (ESI+): 391.3. HPLC (Condition A): Rt 3.90 min (HPLC purity 99.8%).

Example 66

6-[cyclohexyl(2-methoxyethyl)amino]-N-1H-indazol-5-ylpyrimidine-4-carboxamide

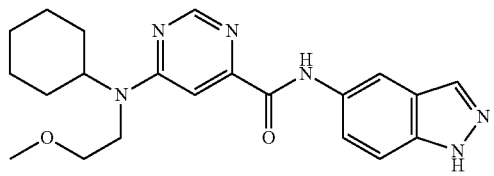 [SMILES: COCCN(c1cc(C(=O)Nc2ccc3[nH]ncc3c2)ncn1)C1CCCCC1]

Following the general method as outlined in Example 20, starting from 6-chloro-pyrimidine-4-carboxylic acid (1H-indazol-5-yl)-amide (Intermediate 16) and cyclohexyl-(2-methoxy-ethyl)-amine (Intermediate 26), the title compound was obtained as a yellow solid.

$^1$H NMR (300MHz, DMSO-d6) δ [ppm] 13.05 (1H, bs), 10.57 (1H, bs), 8.67 (1H, s), 8.36 (1H, d, J=1.5 Hz), 8.06 (1H, s), 7.76 (1H, dd, J=9.0 Hz, J=1.5 Hz), 7.52 (1H, d, J=9.0 Hz), 7.34 (1H, s), 5.76 (1H, m), 3.65 (2H, m), 3.49 (2H, t, J=6.5 Hz), 3.30 (3H, s), 1.83-1.11 (10H, m). MS (ESI$^+$): 395.3. HPLC (Condition A): Rt 3.09 min (HPLC purity 90.8%).

Example 67

N-1H-indazol-5-yl-6-[isopropyl(propyl)amino]pyrimidine-4-carboxamide

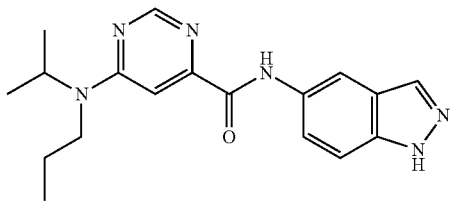 [SMILES: CCCN(c1cc(C(=O)Nc2ccc3[nH]ncc3c2)ncn1)C(C)C]

Following the general method as outlined in Example 20, starting from 6-chloro-pyrimidine-4-carboxylic acid (1H-indazol-5-yl)-amide (Intermediate 16) and propyl-isopropylamine (Matrix), the title compound was obtained as a white solid.

$^1$H NMR (300MHz, DMSO-d6) δ [ppm] 13.05 (1H, bs), 10.62 (1H, s), 8.65 (1H, d, J=1.0 Hz), 8.36 (1H, d, J=1.5 Hz), 8.06 (1H, s), 7.76 (1H, dd, J=9.0 Hz, J=1.5 Hz), 7.52 (1H, d, J=9.0 Hz), 7.21 (1H, bs), 5.1 (1H, m), 3.35 (2H, m), 1.59 (2H, m), 1.21 (6H, d, J=6.5 Hz), 0.95 (3H, t, J=7.0 Hz). MS (ESI+): 339.3. HPLC (Condition A): Rt 2.29 min (HPLC purity 100%).

Example 68

6-(dipropylamino)-N-1H-indazol-5-ylpyrimidine-4-carboxamide

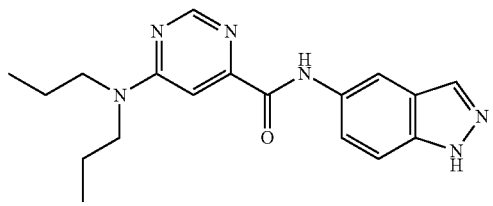 [SMILES: CCCN(CCC)c1cc(C(=O)Nc2ccc3[nH]ncc3c2)ncn1]

Following the general method as outlined in Example 20, starting from 6-chloro-pyrimidine-4-carboxylic acid (1h-indazol-5-yl)-amide (Intermediate 16) and dipropylamine (Aldrich), the title compound was obtained as a white solid.

$^1$H NMR (300MHz, DMSO-d6) δ [ppm] 13.05 (1H, bs), 10.55 (1H, s), 8.63 (1H, d, J=1.0 Hz), 8.35 (1H, d, J=1.5 Hz), 8.06 (1H, s), 7.75 (1H, dd, J=9.0 Hz, J=2.0 Hz), 7.52 (1H, d, J=9.0 Hz), 7.22 (1H, d, J=1.0 Hz), 3.5 (4H, m), 1.60 (4H, sextet, J=7.0 Hz), 0.91 (6H, d, J=7.0 Hz). MS (ESI+): 339.3. HPLC (Condition A): Rt 2.85 min (HPLC purity 99.6%).

Example 69

6-[cyclopentyl(isobutyl)amino]-N-1H-indazol-5-ylpyrimidine-4-carboxamide

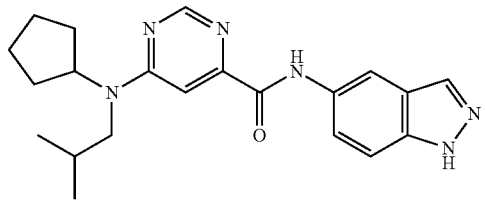 [SMILES: CC(C)CN(c1cc(C(=O)Nc2ccc3[nH]ncc3c2)ncn1)C1CCCC1]

Following the general method as outlined in Example 20, starting from 6-chloro-pyrimidine-4-carboxylic acid (1H-indazol-5-yl)-amide (Intermediate 16) and cyclopentyl-isobutyl-amine (Intermediate 27), the title compound was obtained as a white solid in 78% yield.

$^1$H NMR (300MHz, DMSO-d6) δ [ppm] 13.05 (1H, bs), 10.57 (1H, bs), 8.65 (1H, s), 8.36 (1H, d, J=1.5 Hz), 8.06 (1H, s), 7.76 (1H, dd, J=9.0 Hz, J=2.0 Hz), 7.52 (1H, d, J=9.0 Hz), 7.32 (1H, s), 4.55 (1H, m), 3.36 (2H, m), 2.10-1.60 (9H, m), 0.91 (6H, d, J=6.5 Hz). MS (ESI+): 379.3. HPLC (Condition A): Rt 3.76 min (HPLC purity 99.5%).

Example 70

6-[bis(2-methoxyethyl)amino]-N-1H-indazol-5-ylpyrimidine-4-carboxamide

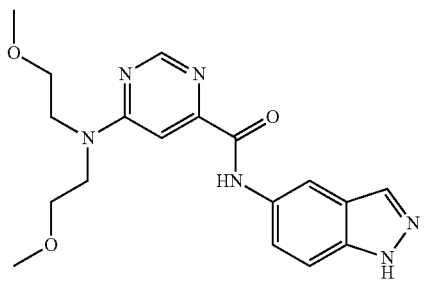 [SMILES: COCCN(CCOC)c1cc(C(=O)Nc2ccc3[nH]ncc3c2)ncn1]

Following the general method as outlined in Example 20, starting from 6-chloro-pyrimidine-4-carboxylic acid (1H-indazol-5-yl)-amide (Intermediate 16) and bis(2-methoxyethyl)amine (Aldrich), the title compound was obtained as a white solid.

$^1$H NMR (300MHz, DMSO-d6) δ [ppm] 13.06 (1H, bs), 10.57 (1H, s), 8.64 (1H, d, J=1.0 Hz), 8.35 (1H, d, J=1.5 Hz), 8.07 (1H, s), 7.75 (1H, dd, J=9.0 Hz, J=2.0 Hz), 7.52 (1H, d, J=9.0 Hz), 7.36 (1H, d, J=1.0 Hz), 3.8 (4H, m), 3.56 (4H, t, J=5.5 Hz), 3.27 (6H, s). MS (ESI+): 371.4. HPLC (Condition A): Rt 2.02 min (HPLC purity 98.0%).

Example 71

6-[(cyclopropylmethyl)(propyl)amino]-N-(6-methyl-1H-indazol-5-yl)pyrimidine-4-carboxamide

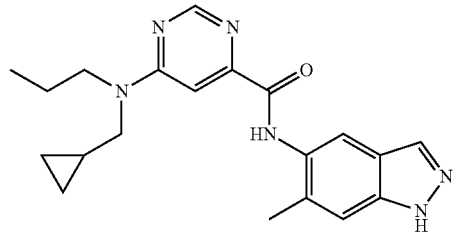 [SMILES: CCCN(CC1CC1)c1cc(C(=O)Nc2cc3cn[nH]c3cc2C)ncn1]

Following the general method as outlined in Example 1, starting from 6-[(cyclopropylmethyl)(propyl)amino]pyrimidine-4-carboxylic acid (Intermediate 21) and 6-methyl-1H-indazol-5-yl-amine (Bionet), the title compound was obtained as a pale brown solid.

$^1$H NMR (300MHz, DMSO-d6) δ [ppm] 12.96 (1H, bs), 10.22 (1H, s), 8.63 (1H, d, J=1.0 Hz), 8.16 (1H, s), 8.02 (1H, s), 7.44 (1H, s), 7.52 (1H, d, J=9.0 Hz), 7.28 (1H, bs), 3.5 (4H, m), 2.41 (3H, s), 1.62 (2H, sextet, J=8.0 Hz), 1.10 (1H, m), 0.91 (3H, t, J=7.0 Hz), 0.51-0.48 (2H, m), 0.37-0.33 (2H, m). MS (ESI+): 365.4. HPLC (Condition A): Rt 3.10 min (HPLC purity 98.5%).

Example 72

N-[4-(aminomethyl)phenyl]-6-(dipropylamino)pyrimidine-4-carboxamide hydrochloride Step 1-tert-butyl[4-({[6-(dipropylamino)pyrimidin-4-yl]carbonyl}amino)benzyl]carbamate

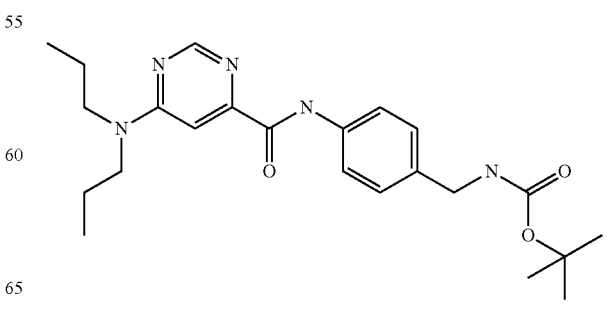

A solution of tert-butyl (4-{[(6-chloropyrimidin-4-yl)carbonyl]amino}benzyl)carbamate (Intermediate 22, 70 mg; 0.19 mmol) in EtOH (7 ml) was treated with dipropylamine (40 µl; 0.29 mmol) and triethylamine (54 µl; 0.39 mmol). The mixture was heated in a sealed microwave tube and irradiated at 100 °C. during 2h30. The solvent was removed under vacuum and the residue redissolved in EtOAc. The organic layer was washed twice with a 10% citric acid solution and with brine, dried over MgSO4, filtered and the solvent removed under vacuum to give the title compound (175 mg, quant.).

MS (ESI+): 428.3. HPLC (Condition A): Rt 3.96 min (HPLC purity 96.1%).

Step 2-N-[4-(aminomethyl)phenyl]-6-(dipropylamino)pyrimidine-4-carboxamide hydrochloride

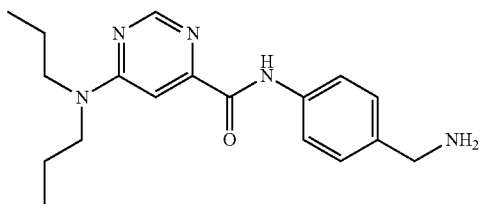 [SMILES: CCCN(CCC)c1cc(C(=O)Nc2ccc(CN)cc2)ncn1]

A solution of tert-butyl[4-({[6-(dipropylamino)pyrimidin-4-yl]carbonyl}amino)benzyl]carbamate (83.0 mg; 0.19 mmol) in acetonitrile (5 ml) was treated with a solution of hydrogen chloride in dioxane (4M, 730 µl; 2.9 mmol). After 30 minutes the precipitate was filtered and washed with acetonitrile to give the title compound as a beige solid.

¹H NMR (300MHz, DMSO-d6) δ [ppm] 11.26 (1H, bs), 8.69 (1H, s), 8.37 (2H, bs), 7.96 (2H, d, J=8.5 Hz), 7.77 (1H, bs), 7.49 (2H, d, J=8.5 Hz), 5.88 (1H, bs), 4.00 (2H, m), 3.63 (4H, bs), 1.62 (4H, m), 0.92 (6H, m). MS (ESI+): 328.4. HPLC (Condition A): Rt 2.24 min (HPLC purity 98.2%).

Example 73 tert-butyl N-{4-[({6-[cyclohexyl(cyclopropylmethyl)amino]pyrimidin-4-yl}carbonyl)amino]benzyl}glycinate

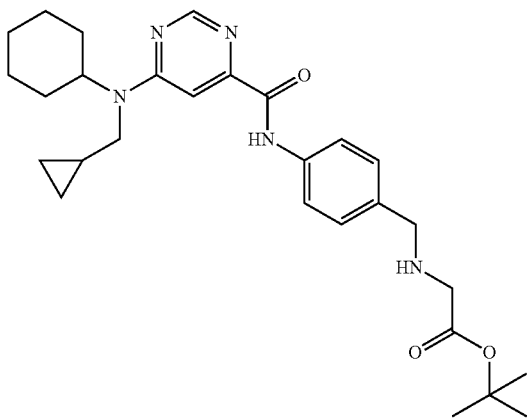 [SMILES: CC(C)(C)OC(=O)CNCc1ccc(NC(=O)c2cc(N(CC3CC3)C3CCCCC3)ncn2)cc1]

A solution of 6-[cyclohexyl(cyclopropylmethyl)amino]-N-(4-formylphenyl)pyrimidine-4-carboxamide (Intermediate 24, 80 mg; 0.18 mmol) in DCM (8 ml) was treated with Glycine tert-butyl ester hydrochloride (Sachem, 60.6 mg; 0.36 mmol) and triethylamine (50 µl; 0.36 mmol). After 2 minutes sodium triacetoxyborohydride (96 mg; 0.45 mmol) and acetic acid (2 µl; 0.04 mmol) were added and the reaction was stirred at room temperature for 20 hours. The solvent was removed under vacuum and the residue was redissolved in EtOAc. The organic phase was washed twice with an aqueous solution (1N) of NaOH and once with brine, dried (MgSO4) and the solvent removed under vacuum to afford the title compound as a colorless oil (62.7 mg, 70%) after purification by column chromatography (silica) eluting with cyclohexane containing increasing amounts of EtOAc.

MS (ESI+): 494.5. HPLC (Condition A): Rt 3.80 min (HPLC purity 99.1%).

Example 74

Methyl 2-({4-[({6-[cyclohexyl(cyclopropylmethyl)amino]pyrimidin-4-yl}carbonyl)amino]benzyl}amino)butanoate

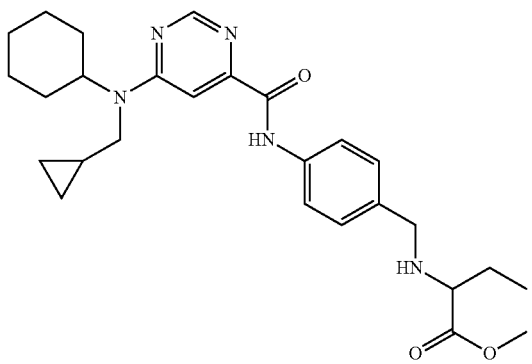 [SMILES: CCC(NCc1ccc(NC(=O)c2cc(N(CC3CC3)C3CCCCC3)ncn2)cc1)C(=O)OC]

Following the general method as outlined in Example 73, starting from 6-[cyclohexyl(cyclopropylmethyl)amino]-N-(4-formylphenyl)pyrimidine-4-carboxamide (Intermediate 24; 80.00 mg; 0.18 mmol) and 2-amino-butyric acid methyl ester hydrochloride (Sigma, 55 mg; 0.36 mmol), the title compound was obtained as a colorless oil after purification by column chromatography (silica) eluting with cyclohexane containing increasing amounts of EtOAc.

MS (ESI+): 480.4. HPLC (Condition A): Rt 3.38 min (HPLC purity 98.7%).

Example 75 tert-butyl N-{4-[({6-[cyclohexyl(cyclopropylmethyl)amino]pyrimidin-4-yl}carbonyl)amino]benzyl}-N-methylglycinate

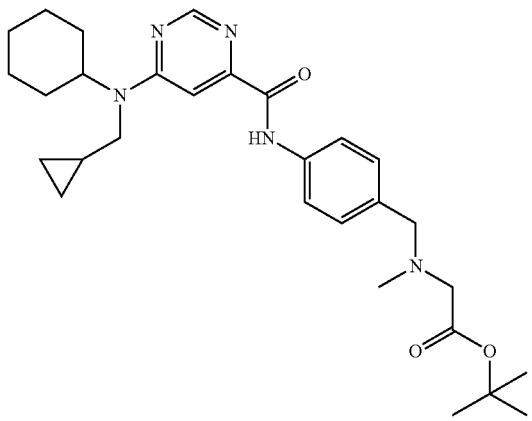 [SMILES: CN(CC(=O)OC(C)(C)C)Cc1ccc(NC(=O)c2cc(N(CC3CC3)C3CCCCC3)ncn2)cc1]

Following the general method as outlined in Example 73, starting from 6-[cyclohexyl(cyclopropylmethyl)amino]-N-(4-formylphenyl)pyrimidine-4-carboxamide (Intermediate 24) and sarcosine tert-butyl ester hydrochloride (Aldrich), the title compound was obtained as a yellow oil in 74% yield after purification by column chromatography (silica) eluting with cyclohexane containing increasing amounts of EtOAc.

MS (ESI+): 508.5. HPLC (Condition A): Rt 3.76 min (HPLC purity 99.7%).

Example 76

Methyl N-{4-[({6-[cyclohexyl(cyclopropylmethyl)amino]pyrimidin-4-yl}carbonyl)amino]benzyl}-beta-alaninate

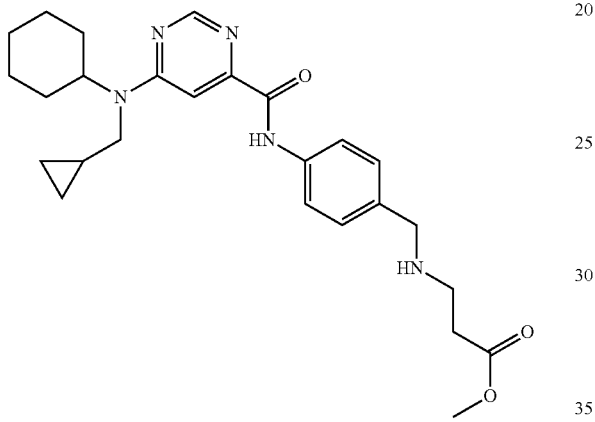

Following the general method as outlined in Example 73, starting from 6-[cyclohexyl(cyclopropylmethyl)amino]-N-(4-formylphenyl)pyrimidine-4-carboxamide (Intermediate 24) and beta-alanine methyl ester hydrochloride (Fluka), the title compound was obtained as a white solid after purification by column chromatography (silica) eluting with cyclohexane containing increasing amounts of EtOAc.

MS (ESI+): 466.5. HPLC (Condition A): Rt 3.35 min (HPLC purity 99.1%).

Example 77

6-[cyclohexyl(cyclopropylmethyl)amino]-N-{4-[(dimethylamino)methyl]phenyl}pyrimidine-4-carboxamide

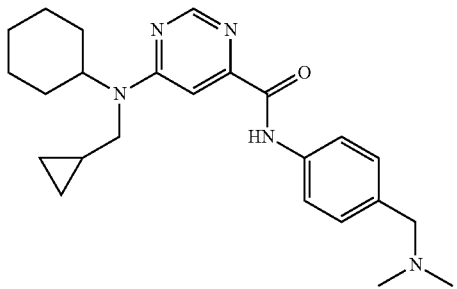 [SMILES: CN(C)Cc1ccc(NC(=O)c2cc(N(CC3CC3)C3CCCCC3)ncn2)cc1]

Following the general method as outlined in Example 73, starting from 6-[cyclohexyl(cyclopropylmethyl)amino]-N-(4-formylphenyl)pyrimidine-4-carboxamide (Intermediate 24) and dimethylamine, the title compound was obtained as a colorless oil after purification by column chromatography (silica) eluting with cyclohexane containing increasing amounts of EtOAc.

$^1$H NMR (300MHz, DMSO-d6) δ [ppm] 10.51 (1H, s), 8.65 (1H, s), 7.82 (2H, d, J=8.5 Hz), 7.32 (1H, s), 7.26 (2H, d, J=8.5 Hz), 4.5 (1H, m), 3.35 (2H, s), 2.13 (6H, s), 1.84-1.15 (11H, m), 0.54-0.51 (2H, m), 0.40-0.36 (2H, m). MS (ESI$^+$): 408.5. HPLC (Condition A): Rt 3.22 min (HPLC purity 99.5%).

Example 78

6-[cyclohexyl(cyclopropylmethyl)amino]-N-[4-(piperazin-1-ylmethyl)phenyl]pyrimidine-4-carboxamide Step 1-tert-butyl 4-{4-[({6-[cyclohexyl(cyclopropylmethyl)amino]pyrimidin-4-yl}carbonyl)amino]benzyl}piperazine-1-carboxylate

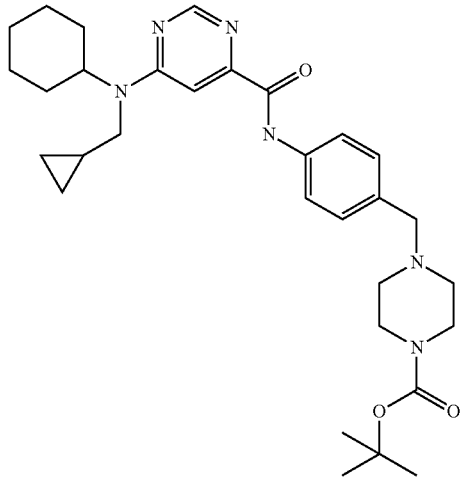 [SMILES: CC(C)(C)OC(=O)N1CCN(Cc2ccc(NC(=O)c3cc(N(CC4CC4)C4CCCCC4)ncn3)cc2)CC1]

Following the general method as outlined in Example 73, starting from 6-[cyclohexyl(cyclopropylmethyl)amino]-N-(4-formylphenyl)pyrimidine-4-carboxamide (Intermediate 24) and 1-boc-piperazine (Fluka), the title compound was obtained as a white solid after purification by column chromatography (silica) eluting with cyclohexane containing increasing amounts of EtOAc.

MS (ESI+): 549.6. HPLC (Condition A): Rt 3.88 min (HPLC purity 98.6%).

Step 2-6-[cyclohexyl(cyclopropylmethyl)amino]-N-[4-(piperazin-1-ylmethyl)phenyl]pyrimidine-4-carboxamide ditrifluoroacetate

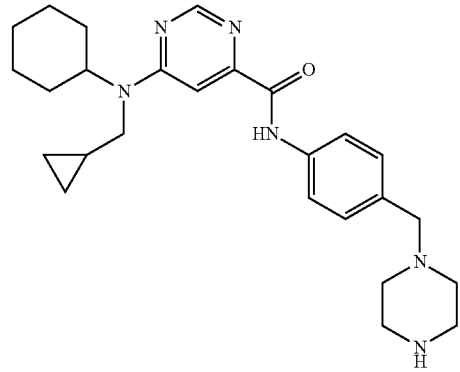 [SMILES: O=C(Nc1ccc(CN2CCNCC2)cc1)c1cc(N(CC2CC2)C2CCCCC2)ncn1]

A solution of tert-butyl 4-{4-[({6-[cyclohexyl(cyclopropylmethyl)amino]pyrimidin-4-yl}carbonyl)amino]benzyl}piperazine-1-carboxylate (60.00 mg; 0.11 mmol) in DCM (5 mL) was treated with trifluoroacetic acid (500 µl; 6.53 mmol) and the reaction mixture was stirred for 18 hours. The solvents were evaporated to give the title compound as a yellow solid (73 mg, 99%).

¹H NMR (300MHz, DMSO-d6) δ [ppm] 10.47 (1H, s), 8.68 (2H, bs), 8.44 (1H, d, J=1.0 Hz), 7.73 (2H, d, J=8.5 Hz), 7.21 (2H, d, J=8.5 Hz), 7.10 (1H, d, J=1.0 Hz), 5.5 (1H, s), 3.86 (1H, bs), 3.0 (4H, bs), 2.8 (4H, bs), 1.67-0.92 (11H, m), 0.54-0.51 (2H, m), 0.40-0.36 (2H, m). MS (ESI+): 449.5. HPLC (Condition A): Rt 2.86 min (HPLC purity 98.1%).

Example 79

N-{4-[({6-[cyclohexyl(cyclopropylmethyl)amino]pyrimidin-4-yl}carbonyl)amino]benzyl}glycine trifluoroacetate

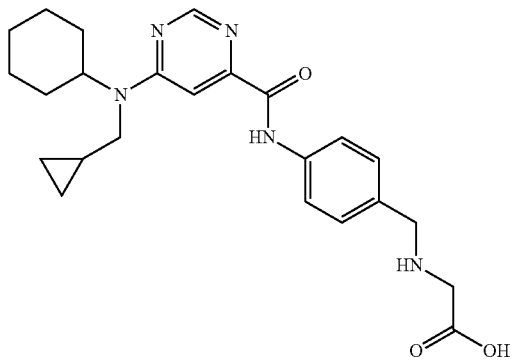 [SMILES: O=C(O)CNCc1ccc(NC(=O)c2cc(N(CC3CC3)C3CCCCC3)ncn2)cc1]

A solution of tert-butyl N-{4-[({6-[cyclohexyl(cyclopropylmethyl)amino]pyrimidin-4-yl}carbonyl)amino]benzyl}glycinate (Example 73; 60 mg; 0.12 mmol) in DCM (5 ml) was treated with trifluoroacetic acid (200 µl; 2.61 mmol) and the reaction mixture was stirred at room temperature for 24 hours. The solvents were removed to give the title compound as a yellow oil in 77% yield.

¹H NMR (300MHz, DMSO-d6) δ [ppm] 10.70 (1H, s), 9.28 (2H, bs), 8.67 (1H, J=1.0 Hz), 7.95 (2H, d, J=8.5 Hz), 7.47 (2H, d, J=8.5 Hz), 7.34 (1H, d, J=1.0 Hz), 4.14 (2H, bs), 3.86 (2H, bs), 1.84-1.15 (11H, m), 0.58-0.56 (2H, m), 0.45-0.40 (2H, m). MS (ESI⁺): 438.4. HPLC (Condition A): Rt 3.02 min (HPLC purity 96.6%).

Example 80

2-({4-[({6-[cyclohexyl(cyclopropylmethyl)amino]pyrimidin-4-yl}carbonyl)amino]benzyl}amino)butanoic Acid

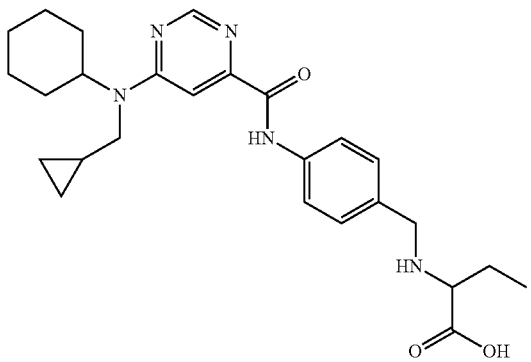 [SMILES: CCC(NCc1ccc(NC(=O)c2cc(N(CC3CC3)C3CCCCC3)ncn2)cc1)C(=O)O]

A solution of methyl 2-({4-[({6-[cyclohexyl(cyclopropylmethyl)amino]pyrimidin-4-yl}carbonyl)amino]benzyl}amino)butanoate (Example 74, 50 mg; 0.10 mmol) in a mixture of MeOH (2 ml) and THF (2 ml) was treated with an aqueous solution (5 N) of sodium hydroxide (300µl; 1.5 mmol) and the reaction mixture was stirred at room temperature for 24 hours. The mixture was acidified with HCl 1N until pH 4. The precipitate was filtered and dried under vacuum to give the title compound as a white solid.

¹H NMR (300MHz, DMSO-d6) δ [ppm] 10.56 (1H, s), 8.66 (1H, s), 7.87 (2H, d, J=8.5 Hz), 7.39 (2H, d, J=8.5 Hz), 7.33 (1H, s), 4.5 (1H, m), 3.93 (1H, d, J=13.5 Hz), 3.81 (1H, d, J=13.5 Hz), 3.12 (2H, m), 1.83-1.01 (14H, m), 0.89 (3H, t, J=7.5 Hz), 0.54-0.51 (2H, m), 0.40-0.36 (2H, m). MS (ESI+): 466.4. HPLC (Condition A): Rt 3.14 min (HPLC purity 99.8%).

Example 81

N-{4-[({6-[cyclohexyl(cyclopropylmethyl)amino]pyrimidin-4-yl}carbonyl)amino]benzyl}-N-methylglycine trifluoroacetate

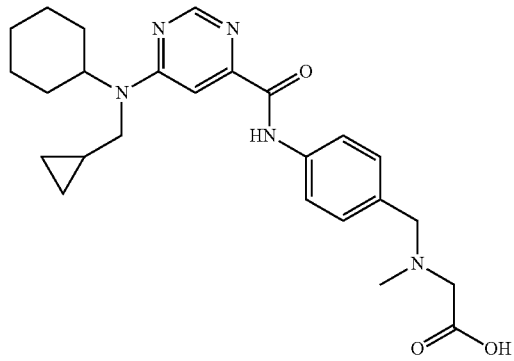 [SMILES: CN(CC(=O)O)Cc1ccc(NC(=O)c2cc(N(CC3CC3)C3CCCCC3)ncn2)cc1]

Following the general method as outlined in Example 79, starting from tert-butyl N-{4-[({6-[cyclohexyl(cyclopropylmethyl)amino]pyrimidin-4-yl}carbonyl)amino]benzyl}-N-methylglycinate (Example 75), the title compound was obtained as a yellow oil.

¹H NMR (300MHz, DMSO-d6) δ [ppm] 10.76 (1H, s), 8.69 (1H, s), 8.00 (2H, d, J=8.5 Hz), 7.51 (2H, d, J=8.5 Hz), 7.36 (1H, s), 4.32 (2H, bs), 4.07 (2H, bs), 3.42 (2H, m), 2.77 (3H, s), 1.84-1.11 (12H, m), 0.54-0.51 (2H, m), 0.40-0.36 (2H, m). MS (ESI+): 452.5. HPLC (Condition A): Rt 3.08 min (HPLC purity 99.4%).

Example 82

N-{4-[({6-[cyclohexyl(cyclopropylmethyl)amino]pyrimidin-4-yl}carbonyl)amino]benzyl}-beta-alanine

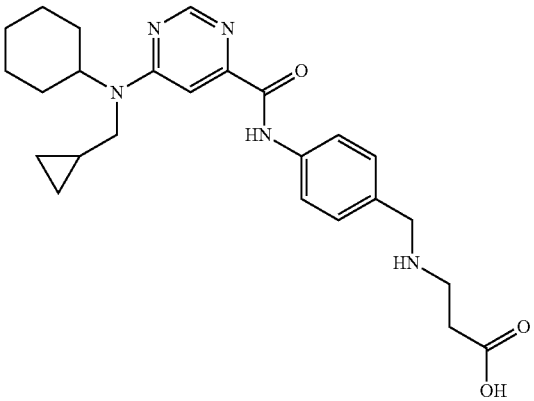 [SMILES: O=C(O)CCNCc1ccc(NC(=O)c2cc(N(CC3CC3)C3CCCCC3)ncn2)cc1]

Following the general method as outlined in Example 80, starting from methyl N-{4-[({6-[cyclohexyl(cyclopropylmethyl)amino]pyrimidin-4-yl}carbonyl)amino]benzyl}-beta-alaninate (Example 76), the title compound was obtained as a pale yellow solid in 82% yield.

MS (ESI+): 452.4. HPLC (Condition A): Rt 3.12 min (HPLC purity 89.0%).

Example 83

Methyl N-{4-[({6-[cyclohexyl(cyclopropylmethyl)amino]pyrimidin-4-yl}carbonyl)amino]benzyl}-2-methylalaninate

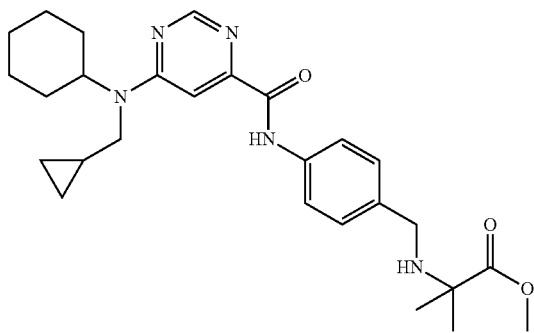 [SMILES: COC(=O)C(C)(C)NCc1ccc(NC(=O)c2cc(N(CC3CC3)C3CCCCC3)ncn2)cc1]

Following the general method as outlined in Example 73, starting from 6-[cyclohexyl(cyclopropylmethyl)amino]-N-(4-formylphenyl)pyrimidine-4-carboxamide (Intermediate 24) and 2-aminoisobutyric acid methyl ester hydrochloride (Sigma), the title compound was obtained as a colorless oil after purification by column chromatography (silica) eluting with cyclohexane containing increasing amounts of EtOAc.

MS (ESI+): 480.5. HPLC (Condition A): Rt 3.34 min (HPLC purity 95.4%).

Example 84

1-{4-[({6-[cyclohexyl(cyclopropylmethyl)amino]pyrimidin-4-yl}carbonyl)amino]benzyl}azetidine-3-carboxylic acid

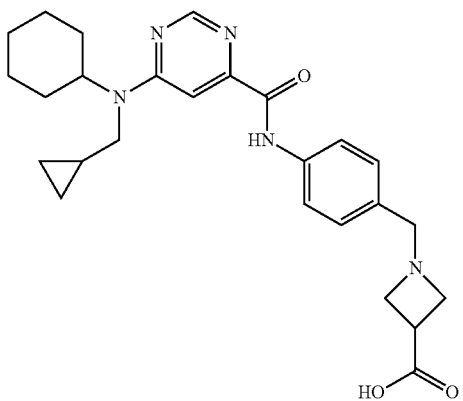 [SMILES: O=C(Nc1ccc(CN2CC(C(=O)O)C2)cc1)c1cc(N(CC2CC2)C2CCCCC2)ncn1]

Following the general method as outlined in Example 73, starting from 6-[cyclohexyl(cyclopropylmethyl)amino]-N-(4-formylphenyl)pyrimidine-4-carboxamide (Intermediate 24) and azetidine-3-carboxylic acid (Apollo), the title compound was obtained as a yellow solid after precipitation from DCM/MeOH.

$^1$H NMR (300MHz, DMSO-d6) δ [ppm] 10.50 (1H, s), 8.65 (1H, s), 7.81 (2H, d, J=8.5 Hz), 7.32 (1H, s), 7.24 (2H, d, J=8.5 Hz), 4.4 (1H, m), 3.50 (2H, bs), 3.34-3.32 (2H, m), 3.17-3.13 (3H, m), 1.87-1.15 (11H, m), 0.54-0.51 (2H, m), 0.40-0.36 (2H, m). MS (ESI+): 464.5. HPLC (Condition A): Rt 3.20 min (HPLC purity 98.6%).

Example 85

6-[(cyclopropylmethyl)(propyl)amino]-N-[4-(hydroxymethyl)-2-methylphenyl]pyrimidine-4-carboxamide

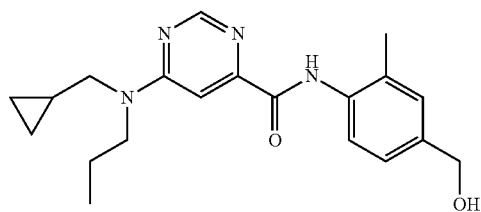 [SMILES: CCCN(CC1CC1)c1cc(C(=O)Nc2ccc(CO)cc2C)ncn1]

Following the general method as outlined in Example 1, starting from 6-[(cyclopropylmethyl)(propyl)amino]pyrimidine-4-carboxylic acid (Intermediate 21) and (4-amino-3-methylphenyl)methanol (Intermediate 28), the title compound was obtained as a white solid after purification by column chromatography (silica) eluting with cyclohexane containing increasing amounts of EtOAc.

$^1$H NMR (300MHz, DMSO-d6) δ [ppm] 10.15 (1H, s), 8.62 (1H, s), 7.77 (1H, d, J=8.0 Hz), 7.26-7.15 (3H, m), 5.15 (1H, t, J=5.5 Hz), 4.45 (2H, d, J=5.5 Hz), 3.5 (4H, m), 2.28 (3H, s), 1.62 (2H, sextet, J=7.5 Hz), 1.14 (1H, m), 0.90 (3H, t, J=7.0 Hz), 0.51-0.48 (2H, m), 0.37-0.33 (2H, m). MS (ESI+): 355.3. HPLC (Condition A): Rt 3.06 min (HPLC purity 100%).

Example 86 tert-butyl N-({4-[({6-[cyclohexyl(cyclopropylmethyl)amino]pyrimidin-4-yl}carbonyl)amino]-3-methylphenyl}sulfonyl)-beta-alaninate

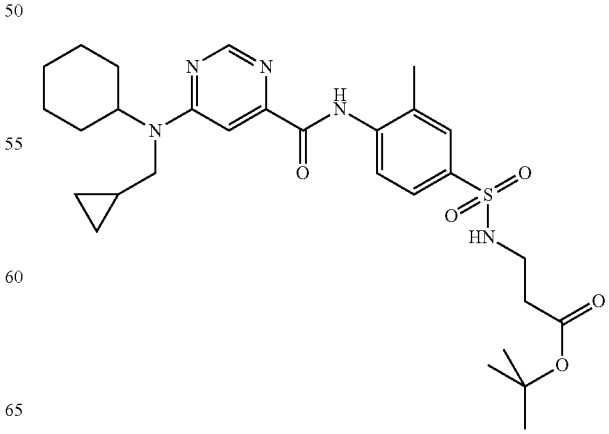

A solution of 4-[({6-[cyclohexyl(cyclopropylmethyl)amino]pyrimidin-4-yl}carbonyl)amino]-3-methylbenzenesulfonyl chloride (Intermediate 20, 100 mg; 0.22 mmol) in anhydrous THF (10 ml) was treated with beta-alanine tert-butyl ester hydrochloride (Bachem, 43 mg; 0.24 mmol) and triethylamine (60 µl; 0.43 mmol). After stirring for 4 hours, the precipitate was filtered and purified by column chromatography (silica) eluting with cyclohexane containing increasing amounts of EtOAc, to give the title compound as a yellow solid.

MS (ESI+): 572.5. HPLC (Condition A): Rt 3.91 min (HPLC purity 100%).

Example 87

N-1H-indazol-5-yl-6-[isopropyl(2-methoxyethyl)amino]pyrimidine-4-carboxamide

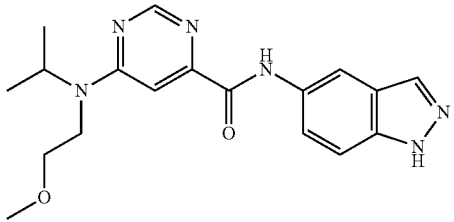 [SMILES: COCCN(c1cc(C(=O)Nc2ccc3[nH]ncc3c2)ncn1)C(C)C]

Following the general method as outlined in Example 20, starting from 6-chloro-pyrimidine-4-carboxylic acid (1H-indazol-5-yl)-amide (Intermediate 16) and N-(2-methoxyethyl)isopropylamine (ABCR), the title compound was obtained as a yellow solid after purification by column chromatography (silica) eluting with cyclohexane containing increasing amounts of EtOAc.

$^1$H NMR (300MHz, DMSO-d6) δ [ppm] 13.05 (1H, bs), 10.57 (1H, bs), 8.67 (1H, d, J=1.0 Hz), 8.36 (1H, d, J=1.5 Hz), 8.06 (1H, s), 7.76 (1H, dd, J=9.0 Hz, J=1.5 Hz), 7.52 (1H, d, J=9.0 Hz), 7.35 (1H, s), 4.9 (1H, m), 3.62 (2H, m), 3.51 (2H, m), 3.33 (3H, s), 1.21 (6H, d, J=6.5 Hz). MS (ESI+): 355.3. HPLC (Condition A): Rt 2.42 min (HPLC purity 97.4%).

Example 88

N-[4-(aminomethyl)phenyl]-6-[(cyclopropylmethyl)(propyl)amino]pyrimidine-4-carboxamide

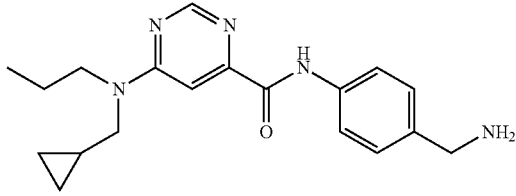 [SMILES: CCCN(CC1CC1)c1cc(C(=O)Nc2ccc(CN)cc2)ncn1]

Following the general method as outlined in Example 72 (Steps 1 and 2), starting from tert-butyl (4-{[(6-chloropyrimidin-4-yl)carbonyl]amino}benzyl)carbamate (Intermediate 22) and N-propylcyclopropanemethylamine (Aldrich), the title compound was obtained as a beige solid after purification by column chromatography (silica) eluting with cyclohexane containing increasing amounts of EtOAc.

$^1$H NMR (300MHz, DMSO-d6) δ [ppm] 11.24 (1H, bs), 8.70 (1H, s), 8.39 (3H, bs), 7.97 (2H, d, J=8.5 Hz), 7.81 (1H, bs), 7.51 (2H, d, J=8.5 Hz), 4.00 (2H, q, J=5.5 Hz), 3.72-3.61 (4H, m), 1.65 (2H, sextet, J=7.5 Hz), 1.14 (1H, m), 0.94 (3H, m), 0.51-0.48 (2H, m), 0.37-0.33 (2H, m). MS (ESI+): 340.4. HPLC (Condition A): Rt 2.39 min (HPLC purity 98.9%).

Example 89

N-[4-(aminomethyl)phenyl]-6-[(cyclopropylmethyl)(2-methoxyethyl)amino]pyrimidine-4-carboxamide hydrochloride

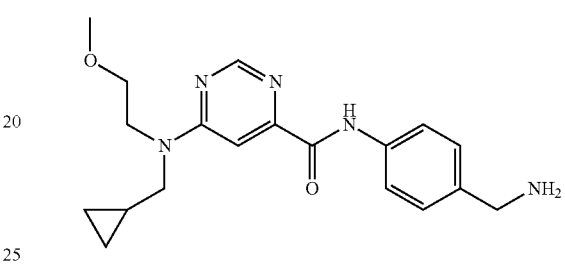

Following the general method as outlined in Example 72 (Steps 1 and 2), starting from tert-butyl (4-{[(6-chloropyrimidin-4-yl)carbonyl]amino}benzyl)carbamate (Intermediate 22) and N-(cyclopropylmethyl)-2-methoxyethanamine, the title compound was obtained as a pale yellow solid after purification by column chromatography (silica) eluting with cyclohexane containing increasing amounts of EtOAc.

MS (ESI+): 356.3. HPLC (Condition A): Rt 1.99 min (HPLC purity 98.5%).

Example 90

6-[(cyclopropylmethyl)(2-methoxyethyl)amino]-N-1H-indazol-5-ylpyrimidine-4-carboxamide

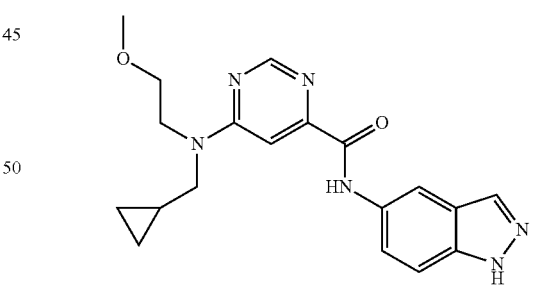

Following the general method as outlined in Example 20, starting from 6-chloro-pyrimidine-4-carboxylic acid (1H-indazol-5-yl)-amide (Intermediate 16) and N-(cyclopropylmethyl)-2-methoxyethanamine, the title compound was obtained as a beige solid after purification by column chromatography (silica) eluting with cyclohexane containing increasing amounts of EtOAc.

$^1$H NMR (300MHz, DMSO-d6) δ [ppm] 13.04 (1H, s), 10.56 (1H, s), 8.64 (1H, s), 8.35 (1H, d, J=1.0 Hz), 8.06 (1H, s), 7.74 (1H, d, J=8.5 Hz), 7.52 (1H, d, J=8.5 Hz), 7.34 (1H, d, J=1.0 Hz), 3.80 (2H, bs), 3.58-3.49 (3H, m), 3.26 (3H, s), 1.09 (1H, m), 0.51-0.48 (2H, m), 0.37-0.33 (2H, m). MS (ESI+): 367.4. HPLC (Condition A): Rt 2.48 min (HPLC purity 99.8%).

Example 91

6-[(cyclopropylmethyl)(propyl)amino]-N-(1,2,3,4-tetrahydroisoquinolin-6-yl)pyrimidine-4-carboxamide hydrochloride

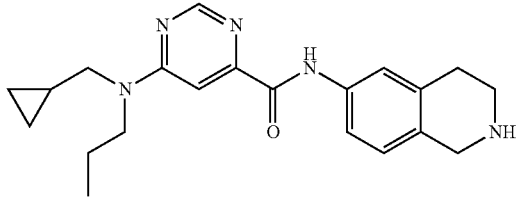 [SMILES: CCCN(CC1CC1)c1cc(C(=O)Nc2ccc3c(c2)CCNC3)ncn1]

Following the general method as outlined in Example 48 (steps 1 and 2), starting from 6-[(cyclopropylmethyl)propylamino]pyrimidine-4-carboxylic acid (Intermediate 21) and 6-amino-2-N-Boc-1,2,3,4-tetrahydro-isoquinoline (ABCR), the title compound was obtained as a pale yellow solid.

$^1$H NMR (300MHz, DMSO-d6) δ [ppm] 10.96 (1H, bs), 9.34 (2H, bs), 8.67 (1H, s), 7.78 (1H, s), 7.74 (1H, d, J=8.5 Hz), 7.60 (1H, bs), 7.22 (1H, d, J=8.5 Hz), 4.6 (2H, m), 3.63-3.57 (4H, m), 3.36 (2H, m), 2.97 (2H, t, J=7.5 Hz), 1.63 (2H, sextet, J=7.5 Hz), 1.11 (1H, m), 0.91 (3H, m), 0.51-0.48 (2H, m), 0.37-0.33 (2H, m). MS (ESI+): 366.3. HPLC (Condition A): Rt 2.48 min (HPLC purity 100%).

Example 92

6-[(cyclopropylmethyl)(propyl)amino]-N-(1,2,3,4-tetrahydroisoquinolin-7-yl)pyrimidine-4-carboxamide hydrochloride

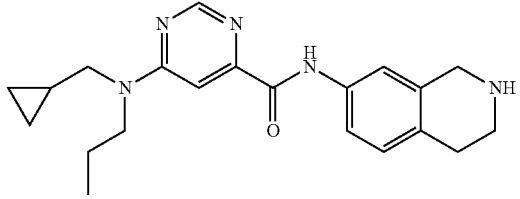 [SMILES: CCCN(CC1CC1)c1cc(C(=O)Nc2ccc3c(c2)CNCC3)ncn1]

Following the general method as outlined in Example 48 (steps 1 and 2), starting from 6-[(cyclopropylmethyl)(propyl)amino]pyrimidine-4-carboxylic acid (Intermediate 21) and 7-amino-2-N-Boc-1,2,3,4-tetrahydro-isoquinoline (JW-Pharmlab), the title compound was obtained as a pale yellow solid.

$^1$H NMR (300MHz, DMSO-d6) δ [ppm] 10.94 (1H, bs), 9.33 (2H, bs), 8.67 (1H, s), 7.79 (1H, s), 7.74 (1H, d, J=8.5 Hz), 7.58 (1H, bs), 7.22 (1H, d, J=8.5 Hz), 4.22 (2H, m), 3.63-3.57 (4H, m), 3.36 (2H, m), 3.00 (2H, t, J=7.5 Hz), 1.62 (2H, sextet, J=7.5 Hz), 1.11 (1H, m), 0.91 (3H, m), 0.51-0.48 (2H, m), 0.37-0.33 (2H, m). MS (ESI+): 366.3. HPLC (Condition A): Rt 2.45 min (HPLC purity 100%).

Example 93

6-[(cyclopropylmethyl)(propyl)amino]-N-[2-methyl-4-(morpholin-4-ylmethyl)phenyl]pyrimidine-4-carboxamide

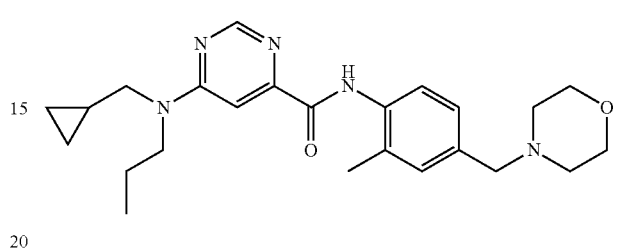

A solution of 6-((cyclopropylmethyl)(propyl)amino)-N-(4-formyl-2-methylphenyl)pyrimidine-4-carboxamide (Intermediate 29, 80 mg; 0.23 mmol) in DCM was treated with morpholine (40 mL; 0.46 mmol) followed by polymer supported triacetoxy borohydride (150 mg). After stirring for 15 hours the mixture was filtered and washed with water. The organic fraction was passed through a hydrophobic frit and the solvent removed in vacuo. The residue was purified by column chromatography (silica) eluting with petroleum ether containing increasing amounts of EtOAc to give the title compound as an off-white solid (90 mg, 92%).

$^1$H NMR (400MHz, CDCl3) δ 10.04 (1H, br s), 8.57 (1H, d, J=1.1 Hz), 8.21 (1H, d, J=8.1 Hz), 7.37 (1H, br s), 7.24-7.17 (2H, m), 3.74-3.69 (4H, m), 3.53 (4H, br s), 3.46 (2H, s), 2.49-2.42 (4H, m), 2.40 (3H, s), 1.76-1.63 (2H, m), 1.16-1.04 (1H, m), 0.96 (3H, t, J=7.4 Hz), 0.61-0.52 (2H, m), 0.35-0.29 (2H, m). MS (APCI−): 422. HPLC (Condition D): Rt 4.34 min (HPLC purity 98.4%).

Example 94

6-[(cyclopropylmethyl)(propyl)amino]-N-{4-[(dimethylamino)methyl]-2-methylphenyl}pyrimidine-4-carboxamide

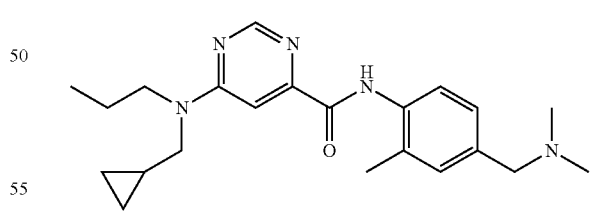

A solution of 6-((cyclopropylmethyl)(propyl)amino)-N-(4-formyl-2-methylphenyl)pyrimidine-4-carboxamide (Intermediate 29, 100 mg; 0.28 mmol) in DCM (5 ml) was treated with dimethylamine (Aldrich, 0.25 ml, 2M in THF; 0.5 mmol) followed by polymer supported triacetoxy borohydride (150 mg). After stirring for 18 hours the mixture was filtered and the solvent removed in vacuo. The residue was purified by column chromatography (silica) eluting with petroleum ether containing increasing amounts of EtOAc to give the title compound as an off-white solid.

¹H NMR (400MHz, CDCl3) δ 10.04 (1H, brs), 8.57 (1H, s), 8.21 (1H, d, J=8.4 Hz), 7.37 (1H, s), 7.21-7.14 (2H, m), 3.69-3.41 (4H, br m), 3.38 (2H, s), 2.40 (3H, s), 2.25 (6H, s), 1.75-1.62 (2H, m), 1.16-1.02 (1H, m), 0.96 (3H, t, J=7.4 Hz), 0.62-0.51 (2H, m), 0.34-0.27 (2H, m). MS (APCI+): 382. HPLC (Condition C): Rt 2.57 min (HPLC purity 98.9%).

Example 95

6-[(cyclopropylmethyl)(propyl)amino]-N-(4-{[(2-methoxyethyl)amino]methyl}-2-methylphenyl)pyrimidine-4-carboxamide

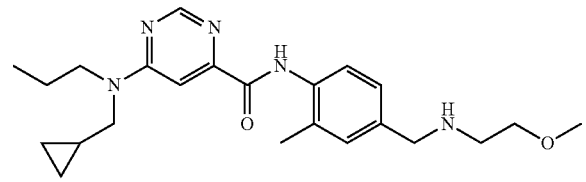 [SMILES: CCCN(CC1CC1)c1cc(C(=O)Nc2ccc(CNCCOC)cc2C)ncn1]

A solution of 6-((cyclopropylmethyl)(propyl)amino)-N-(4-formyl-2-methylphenyl)pyrimidine-4-carboxamide (Intermediate 29, 100 mg; 0.28 mmol) in DCM (5 ml) was treated with 2-methoxyethanamine (Aldrich, 112.7 mg; 0.42 mmol) followed by polymer supported triacetoxy borohydride (150 mg). After stirring for 15 hours the mixture was filtered and the solvent removed in vacuo. The residue was purified by column chromatography (silica) eluting with petroleum ether containing increasing amounts of EtOAc to give the title compound as an off-white solid.

¹H NMR (400MHz, CDCl3) δ 10.03 (1H, br s), 8.57 (1H, d, J=1.1 Hz), 8.20 (1H, d, J=8.6 Hz), 7.37 (1H, s), 7.24-7.18 (2H, m), 3.78 (2H, s), 3.66-3.40 (4H, m), 3.52 (2H, t, J=5.2 Hz), 3.36 (3H, s), 2.81 (2H, t, J=5.2 Hz), 2.40 (3H, s), 1.74-1.64 (2H, m), 1.15-1.04 (1H, m), 0.96 (3H, t, J=7.38 Hz), 0.61-0.52 (2H, m), 0.34-0.27 (2H, m). MS (APCI+): 412. HPLC (Condition C): Rt 2.59 min (HPLC purity 97.4%).

Example 96

6-[(cyclopropylmethyl)(propyl)amino]-N-(4-{[(2-hydroxyethyl)(methyl)amino]methyl}-2-methylphenyl)pyrimidine-4-carboxamide

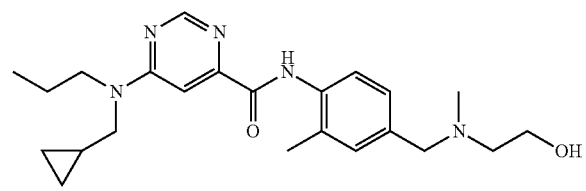 [SMILES: CCCN(CC1CC1)c1cc(C(=O)Nc2ccc(CN(C)CCO)cc2C)ncn1]

A solution of 6-((cyclopropylmethyl)(propyl)amino)-N-(4-formyl-2-methylphenyl)pyrimidine-4-carboxamide (Intermediate 29, 100 mg; 0.28 mmol) in DCM (5 ml) was treated with 2-(methylamino)ethanol (Aldrich, 112.7 mg; 0.42 mmol) followed by polymer supported triacetoxy borohydride (150 mg). After stirring for 15 hours the mixture was filtered and the solvent removed in vacuo. The residue was purified by column chromatography (silica) eluting with petroleum ether containing increasing amounts of EtOAc to give the title compound as an off-white solid.

¹H NMR (400MHz, CDCl3) δ 10.05 (1H, brs), 8.57 (1H, d, J=1.1 Hz), 8.22 (1H, d, J=8.1 Hz), 7.37 (1H, s), 7.18 (2H, m), 3.64 (2H, t, J=5.4 Hz), 3.63-3.39 (4H, br m), 3.53 (2H, s), 2.61 (2H, t, J=5.4 Hz), 2.40 (3H, s), 2.23 (3H, s), 1.75-1.62 (2H, m), 1.14-1.05 (1H, m), 0.97 (3H, t, J=7.4 Hz), 0.62-0.51 (2H, m), 0.35-0.28 (2H, m). MS (APCI+): 412. HPLC (Condition C): Rt 2.53 min (HPLC purity 99.9%).

Example 97

N-{4-[({6-[(cyclopropylmethyl)(propyl)amino]pyrimidin-4-yl}carbonyl)amino]-3-methylbenzyl}-beta-alanine

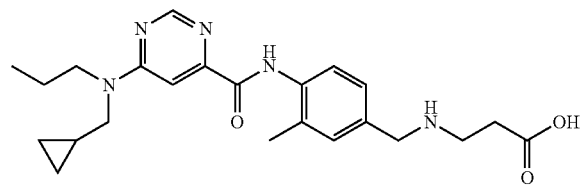 [SMILES: CCCN(CC1CC1)c1cc(C(=O)Nc2ccc(CNCCC(=O)O)cc2C)ncn1]

A solution of 6-((cyclopropylmethyl)(propyl)amino)-N-(4-formyl-2-methylphenyl)pyrimidine-4-carboxamide (Intermediate 29, 100 mg; 0.28 mmol) in DCM (5 ml) was treated with tert-butyl 3-aminopropanoate hydrochloride (Bachem, 227.1 mg; 1.24 mmol) and polymer supported carbonate (150 mg) followed by polymer supported triacetoxy borohydride (150 mg). After stirring for 18 hours the mixture was filtered and the solvent removed in vacuo. The residue was purified by column chromatography (silica) eluting with petroleum ether containing increasing amounts of EtOAc to give tert-butyl 34446-((cyclopropylmethyl)(propyl)amino) pyrimidine-4-carboxamido)-3-methylbenzylamino)propanoate which was used directly without any further purification. The residue was taken up into DCM (4.5 ml) and TFA (0.5 ml) added. After stirring at RT for 2 hours the solvent was removed in vacuo. The residue was taken up into dilute HCl and precipitated by basification to pH 3-4. The solid was removed by filtration, washed with water and dried to give the title compound as a white solid.

¹H NMR (400MHz, DMSO-d6) δ 10.26 (1H, s), 8.66 (1H, s), 7.91 (1H, d, J=8.1 Hz), 7.45-7.26 (3H, m), 4.02 (2H, s), 3.71-3.15 (5H, br m), 3.06-2.97 (2H, m), 2.63-2.53 (2H, m), 2.35 (3H, s), 1.73-1.59 (2H, m), 1.20-1.04 (1H, m), 1.00-0.88 (3H, m), 0.60-0.47 (2H, m), 0.42-0.33 (2H, m). MS (APCI+): 426. HPLC (Condition C): Rt 2.58 min (HPLC purity 94.6%).

Example 98

6-[(cyclopropylmethyl)(propyl)amino]-N-{2-methyl-4-[(2-oxopyrrolidin-1-yl)methyl]phenyl}pyrimidine-4-carboxamide

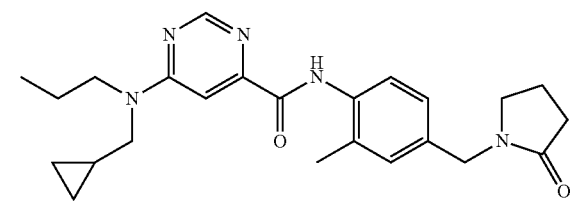 [SMILES: CCCN(CC1CC1)c1cc(C(=O)Nc2ccc(CN3CCCC3=O)cc2C)ncn1]

A solution of 6-((cyclopropylmethyl)(propyl)amino)-N-(4-formyl-2-methylphenyl)pyrimidine-4-carboxamide (Intermediate 29, 100 mg; 0.28 mmol) in DCM (5 ml) was treated with tert-butyl 4-aminobutanoate hydrochloride (Bachem, 244.6 mg; 1.25 mmol) and polymer supported carbonate (150 mg) followed by polymer supported triacetoxy borohydride (150 mg). After stirring for 18 hours the mixture was filtered and the solvent removed in vacuo. The residue was purified by column chromatography (silica) eluting with petroleum ether containing increasing amounts of EtOAc to give the title compound as a white solid (85 mg, 70%).

$^1$H NMR (400MHz, CDCl3) δ 10.06 (1H, br s), 8.57 (1H, s), 8.22 (1H, d, J=8.1 Hz), 7.36 (1H, s), 7.16-7.09 (2H, m), 4.41 (2H, s), 3.62-3.42 (4H, br m), 3.27 (2H, t, J=7.1 Hz), 2.45 (2H, t, J=8.11 Hz), 2.39 (3H, s), 2.04-1.95 (2H, m), 1.73-1.64 (2H, m), 1.15-1.04 (1H, m), 0.96 (3H, t, J=7.3 Hz), 0.60-0.52 (2H, m), 0.35-0.29 (2H, m). MS (APCI+): 422. HPLC (Condition C): Rt 4.11 min (HPLC purity 98.4%).

Example 99

N-({4-[({6-[(cyclopropylmethyl)(propyl)amino]pyrimidin-4-yl}carbonyl)amino]-3-methylphenyl}sulfonyl)-beta-alanine

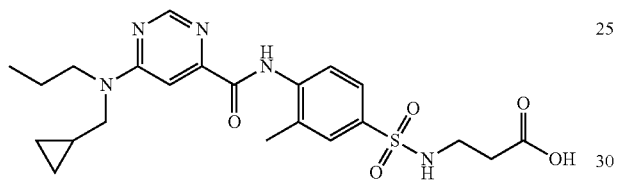

A solution of tert-butyl 3-(4-(6-chloropyrimidine-4-carboxamido)-3-methylphenylsulfonamido)propanoate (Intermediate 34, 140 mg; 0.31 mmol) and diisopropylamine (105.5 mL; 0.61 mmol) in ethanol (4 ml) was treated with N-(cyclopropylmethyl)propan-1-amine (45.3 mg; 0.4 mmol). The mixture was heated to 160° C. in a microwave for 1 hour and then filtered and the solvent removed in vacuo. The residue was purified by column chromatography (silica) eluting with petroleum ether containing increasing amounts of EtOAc to give tert-butyl 3-(4-(6-((cyclopropylmethyl)(propyl)amino)pyrimidine-4-carboxamido)-3-methylphenylsulfonamido)propanoate which was used directly without any further purification. The residue was redissolved in DCM (4.5 ml) and treated with TFA (0.5 ml). After stirring at RT for 2 hours the solvent was removed in vacuo to give the title compound as an off-white solid.

$^1$H NMR (400MHz, CDCl3) δ 10.33 (1H, s), 8.59-8.50 (2H, m), 7.80-7.70 (2H, m), 7.35 (1H, s), 5.71 (1H, br s), 3.73-3.33 (4H, br m), 3.22 (2H, br s), 2.61 (2H, s), 2.47 (3H, s), 1.76-1.62 (2H, m), 1.14-1.03 (1H, m), 0.97 (3H, t, J=7.0 Hz), 0.63-0.52 (2H, m), 0.37-0.27 (2H, m). MS (APCI+): 476. HPLC (Condition C): Rt 3.89 min (HPLC purity 99.0%).

Example 100

N-{4-[({6-[(cyclopropylmethyl)(propyl)amino]pyrimidin-4-yl}carbonyl)amino]-3-methylbenzyl}glycine

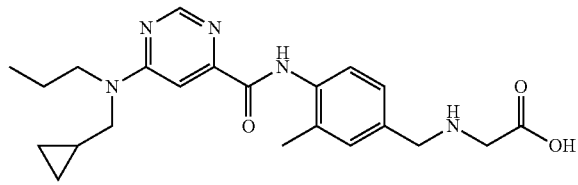 [SMILES: CCCN(CC1CC1)c1cc(C(=O)Nc2ccc(CNCC(=O)O)cc2C)ncn1]

A solution of 6-((cyclopropylmethyl)(propyl)amino)-N-(4-formyl-2-methylphenyl)pyrimidine-4-carboxamide (Intermediate 29, 100 mg; 0.28 mmol) in DCM (5 ml) was treated with tert-butyl 2-aminoacetate (164 mg; 1.25 mmol) followed by polymer supported triacetoxy borohydride (150 mg). After stirring for 18 hours the mixture was filtered and the solvent removed in vacuo. The residue was purified by column chromatography (silica) eluting with petroleum ether containing increasing amounts of EtOAc to give tert-butyl 3-(4-(6-((cyclopropylmethyl)(propyl)amino)pyrimidine-4-carboxamido)-3-methylbenzylamino)propanoate which was used directly without any further purification. The residue was taken up into DCM (4.5 ml) and TFA (0.5 ml) added. After stirring at RT for 2 hours the solvent was removed in vacuo. The residue was taken up into dilute HCl and precipitated by basification to pH 3-4. The solid was removed by filtration, washed with water and dried to give the title compound as a white solid.

$^1$H NMR (400MHz, DMSO-d6) δ 10.22 (1H, s), 8.65 (1H, s), 7.87 (1H, d, J=8.2 Hz), 7.37-7.26 (3H, m), 3.94 (2H, s), 3.74-3.17 (4H, br m), 3.14 (2H, s), 2.32 (3H, s), 1.68-1.60 (2H, m), 1.25 (1H, br s), 0.93 (3H, t), 0.58-0.46 (2H, m), 0.39-0.31 (2H, m). MS (APCI+): 412. HPLC (Condition C): Rt 2.75 min (HPLC purity 93.9%).

Example 101

N-({4-[({6-[cyclohexyl(cyclopropylmethyl)amino]pyrimidin-4-yl}carbonyl)amino]-3-methylphenyl}sulfonyl)-N-methyl glycine

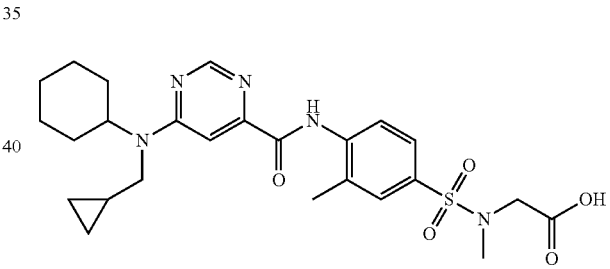

A solution of methyl 2-(4-(6-chloropyrimidine-4-carboxamido)-N,3-dimethylphenylsulfonamido)acetate (Intermediate 36, 123 mg; 0.30 mmol) and diisopropylamine (105.5 mL; 0.61 mmol) in methanol (4 ml) was treated with N-(cyclopropylmethyl)cyclohexanamine (45.3 mg; 0.37 mmol). The mixture was heated to 160° C. in a microwave for 1 hour and then the solvent removed in vacuo. The residue was purified by column chromatography (silica) eluting with petroleum ether containing increasing amounts of EtOAc to give methyl 2-(4-(6-(cyclohexyl(cyclopropylmethyl)amino)pyrimidine-4-carboxamido)-N,3-dimethylphenylsulfonamido)acetate which was used directly without any further purification. The residue was redissolved in methanol (10 ml) and THF (10 ml) and treated with 5 N NaOH (1 ml). After stirring at RT for 5 hours the solvent was removed in vacuo. The residue was redissolved in water (10 ml) and acidified with concentrated HCl. The aqueous phase was extracted with EtOAc and the organic extracts passed through a hydrophobic frit and the solvent removed in vacuo. The residue was triturated with petroleum ether to yield the title compound as a white solid.

¹H NMR (400MHz, CDCl3) δ 10.38 (1H, s), 8.59 (1H, s), 8.54 (1H, d, J=8.6 Hz), 7.74-7.68 (2H, m), 7.44 (1H, s), 4.01 (2H, s), 3.52-3.30 (2H, br m), 2.92 (3H, s), 2.49 (3H, s), 1.94-1.77 (4H, m), 1.77-1.73 (1H, m), 1.54-1.41 (4H, m), 1.29-1.13 (2H, m), 1.11-0.96 (1H, m) 0.64-0.54 (2H, m), 0.41-0.35 (2H, m). MS (APCI+): 516. HPLC (Condition C): Rt 4.59 min (HPLC purity 97.1%).

Example 102

N-({4-[({6-[(cyclopropylmethyl)(propyl)amino]pyrimidin-4-yl}carbonyl)amino]-3-methylphenyl}sulfonyl)-N-methylglycine

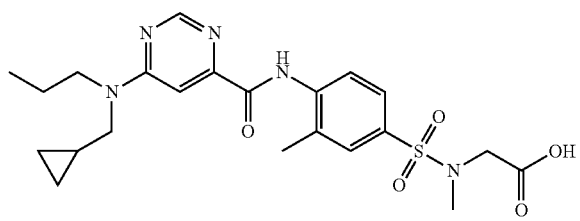 [SMILES: CCCN(CC1CC1)c1cc(C(=O)Nc2ccc(S(=O)(=O)N(C)CC(=O)O)cc2C)ncn1]

A solution of methyl 2-(4-(6-chloropyrimidine-4-carboxamido)-N,3-dimethylphenylsulfonamido)acetate (Intermediate 36, 123 mg; 0.30 mmol) and diisopropylamine (105.5 mL; 0.61 mmol) in methanol (4 ml) was treated with N-(cyclopropylmethyl)propan-1-amine (45.3 mg; 0.4 mmol). The mixture was heated to 160° C. in a microwave for 1 hour and then the solvent removed in vacuo. The residue was purified by column chromatography (silica) eluting with petroleum ether containing increasing amounts of EtOAc to give methyl 2-(4-(6-((cyclopropylmethyl)(propyl)amino)pyrimidine-4-carboxamido)-N,3-dimethylphenylsulfonamido)acetate which was used directly without any further purification. The residue was redissolved in methanol (10 ml) and THF (10 ml) and treated with 5 N NaOH (1 ml). After stirring at RT for 5 hours the solvent was removed in vacuo. The residue was redissolved in water (10 ml) and acidified with conc. HCl. The aqueous phase was extracted with EtOAc and the organic extracts passed through a hydrophobic frit and the solvent removed in vacuo. The residue was triturated with petroleum ether to yield the title compound as an off-white solid.

¹H NMR (400MHz, CDCl3) δ 10.34 (1H, s), 8.59-8.51 (2H, m), 7.76-7.66 (2H, m), 7.35 (1H, s), 4.02 (2H, s), 3.70-3.39 (4H, br m), 2.92 (3H, s), 2.49 (3H, s), 1.74-1.64 (2H, m), 1.15-1.04 (1H, m), 0.97 (3H, t, J=7.33 Hz), 0.63-0.52 (2H, m), 0.35-0.29 (2H, m). MS (APCI+): 476. HPLC (Condition C): Rt 4.13 min (HPLC purity 97.1%).

Example 103

N-({4-[({6-[(cyclopropylmethyl)(propyl)amino]pyrimidin-4-yl}carbonyl)amino]-3-METHYLPHENYL}sulfonyl)glycine

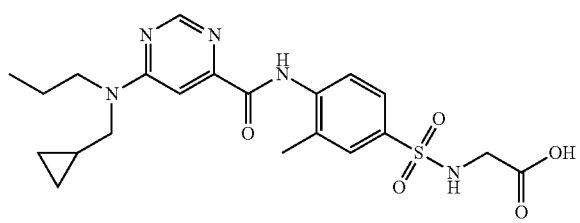 [SMILES: CCCN(CC1CC1)c1cc(C(=O)Nc2ccc(S(=O)(=O)NCC(=O)O)cc2C)ncn1]

A solution of methyl 2-(4-(6-chloropyrimidine-4-carboxamido)-3-methylphenylsulfonamido)acetate (Intermediate 33, 123 mg; 0.31 mmol) and diisopropylamine (105.5 mL; 0.61 mmol) in ethanol (4 ml) was treated with N-(cyclopropylmethyl)propan-1-amine (45.3 mg; 0.4 mmol). The mixture was heated to 160° C. in a microwave for 1 hour and the solvent removed in vacuo. The residue was purified by column chromatography (silica) eluting with petroleum ether containing increasing amounts of EtOAc to give a mixture of methyl 2-(4-(6-((cyclopropylmethyl)(propyl)amino)pyrimidine-4-carboxamido)-3-methylphenylsulfonamido)acetate and ethyl 2-(4-(6-((cyclopropylmethyl)(propyl)amino)pyrimidine-4-carboxamido)-3-methylphenylsulfonamido)acetate which was used directly without any further purification. The residue was redissolved in methanol (10 ml) and tetrahydrofuran (10 ml) and treated with 5 N NaOH solution (1 ml). After stirring at RT for 5 hours the solvent was removed in vacuo. The residue was redissolved in water (10 ml) and acidified with conc. HCl. The aqueous phase was extracted with EtOAc and the organic extracts passed through a hydrophobic frit and the solvent removed in vacuo. The residue was triturated with petroleum ether to yield the title compound as a white solid.

¹H NMR (400MHz, CDCl3) δ 10.28 (1H, s), 8.52-8.43 (2H, m), 7.79-7.69 (2H, m), 7.36-7.30 (1H, m), 5.41-5.22 (1H, br s), 3.87-3.78 (2H, m), 3.71-3.61 (2H, br m), 3.26-2.81 (2H, br m) 2.46 (3H, s), 1.73-1.64 (2H, m), 1.13-1.03 (1H, m) 0.96 (3H, t, J=7.30 Hz), 0.63-0.52 (2H, m), 0.35-0.29 (2H, m). MS (APCI+): 502. HPLC (Condition C): Rt 4.41 min (HPLC purity 92.0%).

Example 104

N-{4-[({6-[(cyclopropylmethyl)(propyl)amino]pyrimidin-4-yl}carbonyl)amino]-3-methylbenzyl}alanine

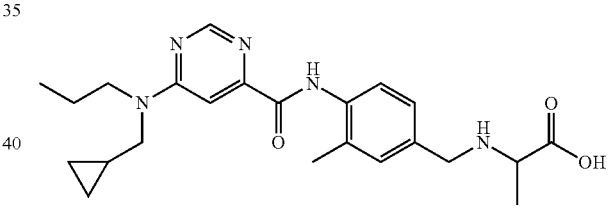

A solution of 6-((cyclopropylmethyl)(propyl)amino)-N-(4-formyl-2-methylphenyl)pyrimidine-4-carboxamide (Intermediate 29, 100 mg; 0.28 mmol) in DCM (5 ml) was treated with tert-butyl 2-aminopropanoate hydrochloride (227.1 mg; 1.24 mmol) and polymer supported carbonate (150 mg) followed by polymer supported triacetoxy borohydride (150 mg). After stirring for 18 hours the mixture was filtered and the solvent removed in vacuo. The residue was purified by column chromatography (silica) eluting with petroleum ether containing increasing amounts of EtOAc to give tert-butyl 24446-((cyclopropylmethyl)(propyl)amino) pyrimidine-4-carboxamido)-3-methylbenzylamino)propanoate which was used directly without any further purification. The residue was taken up into DCM (4.5 ml) and TFA (0.5 ml) added. After stirring at RT for 2 hours the solvent was removed in vacuo. The residue was taken up into dilute HCl and precipitated by basification to pH 3-4. The solid was removed by filtration, washed with water and dried to give the title compound as a white solid (85 mg, 71%).

¹H NMR (400MHz, DMSO-d6) δ 10.23 (1H, s), 8.66 (1H, s), 7.88 (1H, d, J=8.2 Hz), 7.39-7.28 (3H, m), 3.97 (1H, d, J=13.0 Hz), 3.88 (1H, d, J=13.0 Hz), 3.70-3.44 (4H, m), 3.23-3.14 (1H, m) 2.33 (3H, s), 1.73-1.59 (2H, m), 1.30 (3H, d, J=6.9 Hz), 1.19-1.06 (1H, m), 1.00-0.90 (3H, m), 0.58-0.49 (2H, m) 0.41-0.34 (2H, m). MS (APCI+): 426. HPLC (Condition C): Rt 2.74 min (HPLC purity 99.5%).

Example 105

6-[cyclohexyl(cyclopropylmethyl)amino]-N-{2-methyl-4-[(methylamino)sulfonyl]phenyl}pyrimidine-4-carboxamide

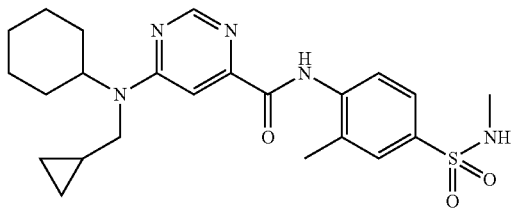 [SMILES: CNS(=O)(=O)c1ccc(NC(=O)c2cc(N(CC3CC3)C3CCCCC3)ncn2)c(C)c1]

A solution of 6-chloro-N-(2-methyl-4-(N-methylsulfamoyl)phenyl)pyrimidine-4-carboxamide (Intermediate 37, 80 mg; 0.235 mmol) and diisopropylamine (82 mL; 0.47 mmol) in ethanol (2.5 ml) was treated with N-(cyclopropylmethyl)cyclohexanamine (49.1 mg; 0.29 mmol). The mixture was heated to 160° C. in a microwave for 1 hour and then filtered. The solid was washed with a 1:1 mixture of water:ethanol and allowed to dry to give the title compound as a white solid (75 mg, 70%).

$^1$H NMR (400MHz, CDCl3) δ 10.35 (1H, s), 8.62-8.58 (2H, m,), 7.80-7.72 (2H, m), 7.43 (1H, s), 4.27 (1H, q, J=5.4 Hz), 3.39 (2H, br s), 2.68 (3H, d, J=5.4 Hz), 2.49 (3H, s), 1.93-1.78 (4H, m), 1.74 (1H, d, J=13.5 Hz), 1.57-1.38 (5H, m), 1.28-1.11 (1H, m), 1.11-1.00 (1H, m), 0.59 (2H, br d, J=7.9 Hz), 0.40-0.33 (2H, m). MS (APCI+): 458. HPLC (Condition C): Rt 4.70 min (HPLC purity 97.7%).

Example 106

6-[(cyclopropylmethyl)(propyl)amino]-N-(4-{[(2-methoxyethyl)amino]sulfonyl}-2-methylphenyl)pyrimidine-4-carboxamide

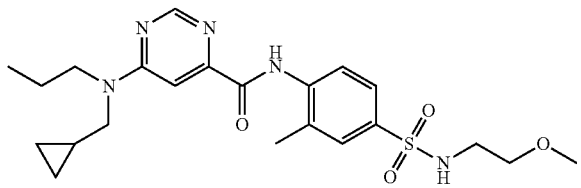 [SMILES: CCCN(CC1CC1)c1cc(C(=O)Nc2ccc(S(=O)(=O)NCCOC)cc2C)ncn1]

A solution of 6-chloro-N-(4-(N-(2-methoxyethyl)sulfamoyl)-2-methylphenyl)pyrimidine-4-carboxamide (Intermediate 38, 100 mg; 0.26 mmol) and diisopropylamine (91 mL; 0.52 mmol) in ethanol (2.5 ml) was treated with N-(cyclopropylmethyl)propan-1-amine (0.7 ml, 0.33 mmol). The mixture was heated to 160° C. in a microwave for 1 hour and the solvent removed in vacuo. The residue was purified by column chromatography (silica) eluting with petroleum ether containing increasing amounts of EtOAc to give the title compound as a white solid.

$^1$H NMR (400MHz, CDCl3) δ 10.34 (1H, s), 8.60-8.57 (2H, m), 7.79-7.73 (2H, m), 7.35 (1H, br s), 4.77 (1H, t, J=6.0 Hz), 3.54 (4H, br s), 3.42 (2H, t, J=5.1 Hz), 3.28 (3H, s), 3.16-3.10 (2H, m), 2.48 (3H, s), 1.75-1.65 (2H, m), 1.15-1.04 (1H, br m), 1.01-0.93 (3H, m), 0.58 (2H, br d, J=7.8 Hz), 0.35-0.29 (2H, m). MS (APCI+): 462. HPLC (Condition C): Rt 4.27 min (HPLC purity 99.1%).

Example 107

6-[cyclohexyl(cyclopropylmethyl)amino]-N-(4-{[(2-methoxyethyl)amino]sulfonyl}-2-methylphenyl)pyrimidine-4-carboxamide

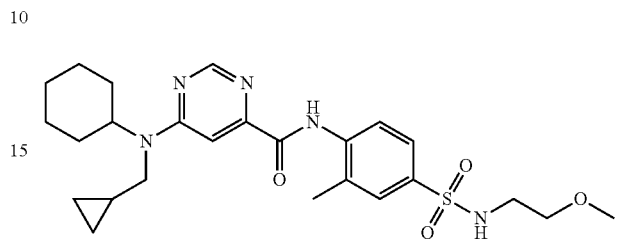

A solution of 6-chloro-N-(4-(N-(2-methoxyethyl)sulfamoyl)-2-methylphenyl)pyrimidine-4-carboxamide (Intermediate 38, 100 mg; 0.26 mmol) and diisopropylamine (91 mL; 0.52 mmol) in ethanol (2.5 ml) was treated with N-(cyclopropylmethyl)cyclohexanamine (54.4 mg; 0.33 mmol). The mixture was heated to 160° C. in a microwave for 1 hour and the solvent removed in vacuo. The residue was purified by column chromatography (silica) eluting with petroleum ether containing increasing amounts of EtOAc to give the title compound as a white solid (110 mg, 84%).

$^1$H NMR (400MHz, CDCl3) δ 10.35 (1H, s), 8.61-8.56 (2H, m), 7.78-7.71 (2H, m), 7.43 (1H, s), 4.76 (1H, t, J=6.0 Hz), 3.45-3.39 (4H, m), 3.28 (3H, s), 3.16-2.93 (2H, m), 2.49 (3H, s), 1.94-1.78 (4H, m), 1.74 (1H, d, J=13.5 Hz), 1.61-1.23 (5H, m), 1.24-1.11 (1H, m), 1.10-0.98 (1H, br m), 0.65-0.51 (2H, m), 0.38-0.33 (2H, m). MS (APCI+): 502. HPLC (Condition C): Rt 4.74 min (HPLC purity 99.2%).

Example 108

4-[({4-[({6-[(cyclopropylmethyl)(propyl)amino]pyrimidin-4-yl}carbonyl)amino]-3-methylphenyl}sulfonyl)amino]butanoic acid

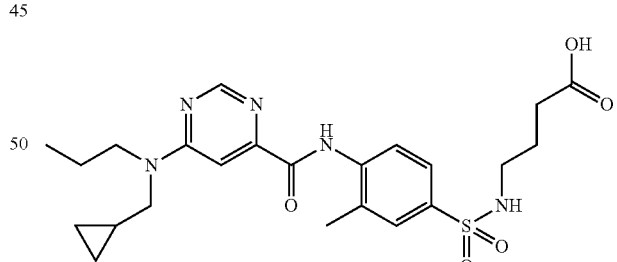

A solution of ethyl 4-(4-(6-chloropyrimidine-4-carboxamido)-3-methylphenylsulfonamido)butanoate (Intermediate 35, 123 mg; 0.31 mmol) and diisopropylamine (105.5 mL; 0.61 mmol) in ethanol (4 ml) was treated with N-(cyclopropylmethyl)propan-1-amine (45.3 mg; 0.4 mmol). The mixture was heated to 160° C. in a microwave for 1 hour and the solvent removed in vacuo. The residue purified by column chromatography (silica) eluting with petroleum ether containing increasing amounts of EtOAc to give ethyl 4-(4-(6-((cyclopropylmethyl)(propyl)amino)pyrimidine-4-carboxamido)-3-methylphenylsulfonamido)butanoate which was used directly without any further purification. The residue was dissolved in methanol (10 ml) and THF (10 ml) and treated with 5 N NaOH solution (1 ml). After stirring at RT for 5 hours the solvent was removed in vacuo. The residue was redissolved in water (10 ml) and acidified with conc. HCl. The aqueous phase was extracted with EtOAc and the organic extracts passed through a hydrophobic frit and the solvent removed in vacuo. The residue was triturated with petroleum ether to yield the title compound as a white solid.

$^1$H NMR (400MHz, CDCl3) δ 10.34 (1H, s), 8.58 (1H, s), 8.48 (1H, d, J=8.5 Hz), 7.78-7.72 (2H, m), 7.37 (1H, br s), 4.78 (1H, t, J=6.3 Hz), 3.54 (4H, br s), 3.05 (2H, app q, J=6.5 Hz), 2.47 (3H, s), 2.41 (2H, t, J=6.9 Hz), 1.87-1.77 (2H, m), 1.75-1.65 (2H, m), 1.14-1.04 (1H, m), 1.01-0.93 (3H, m), 0.58 (2H, br d, J=7.8 Hz), 0.36-0.29 (2H, m). MS (APCI+): 490. HPLC (Condition C): Rt 3.90 min (HPLC purity 98.9%).

Example 109

6-[(cyclopropylmethyl)(propyl)amino]-N-{2-methyl-4-[(methylamino)sulfonyl]phenyl}pyrimidine-4-carboxamide

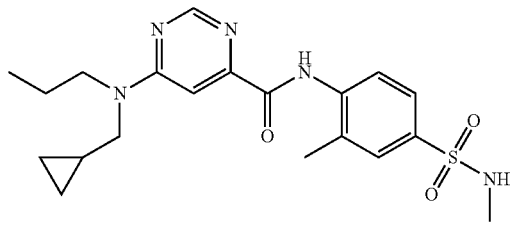 [SMILES: CCCN(CC1CC1)c1cc(C(=O)Nc2ccc(S(=O)(=O)NC)cc2C)ncn1]

A solution of 6-chloro-N-(2-methyl-4-(N-methylsulfamoyl)phenyl)pyrimidine-4-carboxamide (Intermediate 37, 80 mg; 0.235 mmol) and diisopropylamine (82 mL; 0.47 mmol) in ethanol (2.5 ml) was treated with N-(cyclopropylmethyl)propan-1-amine (0.7 ml; 0.29 mmol). The mixture was heated to 160° C. in a microwave for 1 hour and the solvent removed in vacuo. The residue purified by column chromatography (silica) eluting with petroleum ether containing increasing amounts of EtOAc to give the title compound as a white solid.

$^1$H NMR (400MHz, CDCl3) δ 10.35 (1H, s), 8.62-8.55 (2H, m), 7.79-7.73 (2H, m), 7.36 (1H, s), 4.38 (1H, q, J=5.4 Hz), 3.80-3.29 (4H, br m), 2.68 (3H, d, J=5.4 Hz), 2.49 (3H, s), 1.76-1.64 (2H, m), 1.16-1.03 (1H, m), 0.98 (3H, t, J=7.4 Hz), 0.58 (2H, br d, J=7.8 Hz), 0.36-0.29 (2H, m). MS (APCI+): 418. HPLC (Condition C): Rt 4.22 min (HPLC purity 98.5%).

Example 110

6-[(cyclopropylmethyl)(propyl)amino]-N-[4-(methylsulfonyl)phenyl]pyrimidine-4-carboxamide

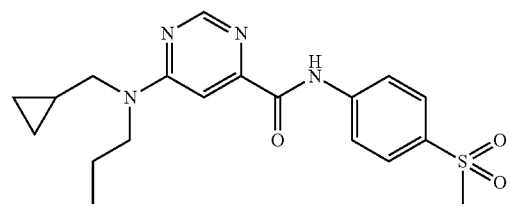 [SMILES: CCCN(CC1CC1)c1cc(C(=O)Nc2ccc(S(C)(=O)=O)cc2)ncn1]

Following the general method as outlined in Example 1, starting from 6-[cyclopropylmethyl)(propyl)amino]pyrimidine-4-carboxylic acid (Intermediate 21) and 4-(methylsulfonyl)aniline (Enamine), the title compound was obtained as a white solid after purification by column chromatography (silica) eluting with cyclohexane containing increasing amounts of EtOAc.

$^1$H NMR (300MHz, DMSO-d6) δ 10.97 (1H, s), 8.66 (1H, d, J=1.0 Hz), 8.17 (2H, d, J=9.0 Hz), 7.91 (2H, d, J=9.0 Hz), 7.28 (1H, bs), 3.5 (4H, bs), 3.20 (3H, s), 1.62 (2H, sextet, J=7.5 Hz), 1.09 (1H, m), 0.91 (3H, t, J=7.5 Hz), 0.51-0.48 (2H, m), 0.37-0.33 (2H, m). MS (ESI+): 389.2. HPLC (Condition A): Rt 3.93 min (HPLC purity 99.1%).

Example 111

6-[(cyclopropylmethyl)(propyl)amino]-N-{2-methyl-4-[(methylamino)methyl]phenyl}pyrimidine-4-carboxamide

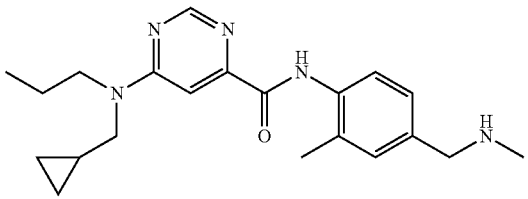 [SMILES: CCCN(CC1CC1)c1cc(C(=O)Nc2ccc(CNC)cc2C)ncn1]

A solution of 6-((cyclopropylmethyl)(propyl)amino)-N-(4-formyl-2-methylphenyl)pyrimidine-4-carboxamide (Intermediate 29, 100 mg; 0.28 mmol) in DCM (5 ml) was treated with methylamine (0.25 ml, 2M in THF; 0.5 mmol) followed by polymer supported triacetoxy borohydride (150 mg). After stirring for 15 hours a further portion of methylamine (1 ml, 2M in THF; 2 mmol) was added. After stirring for a further 24 hours the mixture was filtered and the solvent removed in vacuo. The residue was purified by column chromatography (silica) eluting with petroleum ether containing increasing amounts of EtOAc to give the title compound as an off-white solid.

$^1$H NMR (400MHz, CDCl3) δ 10.04 (1H, s), 8.57 (1H, s), 8.21 (1H, d, J=8.8 Hz), 7.37 (1H, s), 7.23-7.18 (2H, m), 3.72 (2H, s), 3.66-3.39 (4H, br m), 2.47 (3H, s), 2.40 (3H, s), 1.73-1.65 (2H, m), 1.15-1.03 (1H, m) 0.96 (3H, t, J=7.4 Hz), 0.56 (2H, br d, J=7.7 Hz), 0.33-0.28 (2H, m). MS (APCI+): 368. HPLC (Condition C): Rt 2.50 min (HPLC purity 99.7%).

Example 112

6-[cyclohexyl(cyclopropylmethyl)amino]-N-[4-(methylsulfonyl)phenyl]pyrimidine-4-carboxamide

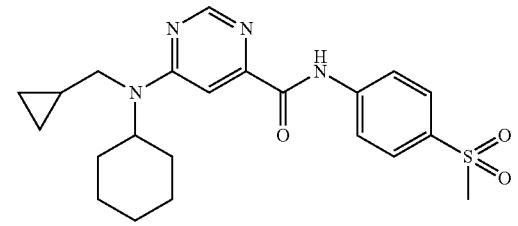 [SMILES: CS(=O)(=O)c1ccc(NC(=O)c2cc(N(CC3CC3)C3CCCCC3)ncn2)cc1]

Following the general method as outlined in Example 1, starting from 6-(cyclohexyl-cyclopropylmethyl-amino)-pyrimidine-4-carboxylic acid (Intermediate 13) and 4-(methylsulfonyl)aniline (Enamine), the title compound was obtained as a white solid after purification by column chromatography (silica) eluting with cyclohexane containing increasing amounts of EtOAc.

$^1$H NMR (300MHz, DMSO-d6) δ 10.98 (1H, s), 8.68 (1H, d, J=1.0 Hz), 8.17 (2H, d, J=9.0 Hz), 7.91 (2H, d, J=9.0 Hz), 7.34 (1H, d, J=1.0 Hz), 4.4 (1H, m), 3.40 (2H, m), 3.20 (3H, s), 1.83-1.15 (11H, m), 0.51-0.48 (2H, m), 0.37-0.33 (2H, m). MS (ESI+): 429.0. HPLC (Condition A): Rt 4.22 min (HPLC purity 97.8%).

Example 113

6-[(cyclopropylmethyl)(propyl)amino]-N-1H-indol-4-ylpyrimidine-4-carboxamide

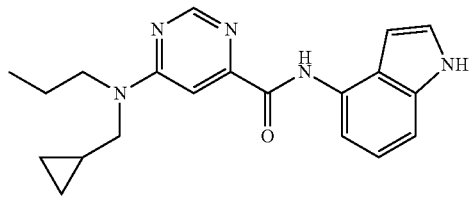 [SMILES: CCCN(CC1CC1)c1cc(C(=O)Nc2cccc3[nH]ccc23)ncn1]

A cooled (0° C.) solution of 6-((cyclopropylmethyl)(propyl)amino)pyrimidine-4-carboxylic acid (Intermediate 21, 0.23 g; 0.98 mmol) in DCM (5 ml) was treated with DMF (1 drop of a 10% solution in DCM) followed by (COCl)2 (0.1 ml; 1.15 mmol). After stirring at 0° C. for 30 minutes, the mixture was treated with 1H-indol-4-amine (Aldrich, 146 mg; 1.1 mmol) and diisopropylamine (0.5 ml; 2.9 mmol). After stirring overnight, water was added and the layers separated. The organic phase was passed through a hydrophobic frit and the solvent removed in vacuo. The residue was purified by column chromatography (silica) eluting with petroleum ether containing increasing amounts of Et2O to give the title compound as an off-white solid.

$^1$H NMR (400MHz, CDCl3) δ 10.40 (1H, s), 8.62 (1H, s), 8.28 (1H, br s), 8.13-8.08 (1H, m), 7.42 (1H, s), 7.28-7.19 (3H, m), 6.77-6.70 (1H, m), 3.71-3.35 (4H, br m), 1.77-1.63 (2H, m), 1.16-1.04 (1H, m), 0.97 (3H, t, J=7.33 Hz), 0.62-0.51 (2H, m), 0.35-0.29 (2H, m). MS (APCI+): 350. HPLC (Condition D): Rt 4.04 min (HPLC purity 98.6%).

Example 114

6-[(cyclopropylmethyl)(propyl)amino]-N-{2-[2-(dimethylamino)-2-oxoethyl]-2H-indazol-5-yl}pyrimidine-4-carboxamide

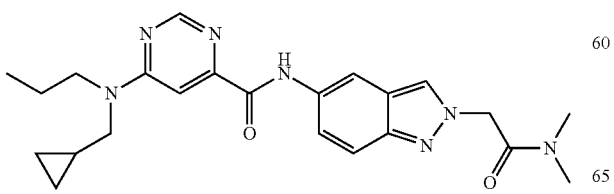

A solution of 6-((cyclopropylmethyl)(propyl)amino)-N-(1H-indazol-5-yl)pyrimidine-4-carboxamide (Example 45, 350 mg; 1 mmol) in DMF (4 ml) was treated with potassium carbonate (140 mg; 1 mmol), potassium iodide (1 mg) and 2-chloro-N,N-dimethylacetamide (140 mg; 1.15 mmol). After stirring at RT for 72 hours the mixture was poured in water (20 ml) and stirred at RT for 1 hour. The solid was removed by filtration, washed with water and dried. The residue was purified by column chromatography (silica) eluting with petroleum ether containing increasing amounts of EtOAc to give the title compound as an off-white solid, together with 6-[(cyclopropylmethyl)(propyl)amino]-N-{1-[2-(dimethylamino)-2-oxoethyl]-1H-indazol-5-yl}pyrimidine-4-carboxamide (Example 115 below).

$^1$H NMR (400MHz, CDCl3) δ 9.99 (1H, s), 8.58 (1H, s), 8.42 (1H, s), 8.05 (1H, s), 7.68 (1H, d, J=9.2 Hz), 7.40-7.30 (2H, m), 5.26 (2H, s), 3.72-3.36 (4H, br m), 3.13 (3H, s), 3.01 (3H, s), 1.75-1.65 (2H, m), 1.16-1.03 (1H, m), 1.01-0.93 (3H, m), 0.64-0.49 (2H, m0), 0.35-0.29 (2H, m). MS (APCI+): 436. HPLC (Condition C): Rt 3.38 min (HPLC purity 93.6%).

Example 115

6-[(cyclopropylmethyl)(propyl)amino]-N-{1-[2-(dimethylamino)-2-oxoethyl]-1H-indazol-5-yl}pyrimidine-4-carboxamide

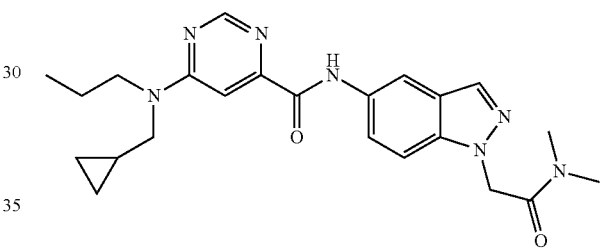

The title compound was isolated from the reaction described above for the synthesis of 6-[(cyclopropylmethyl)(propyl)amino]-N-{2-[2-(dimethylamino)-2-oxoethyl]-2H-indazol-5-yl}pyrimidine-4-carboxamide (Example 114 above).

$^1$H NMR (400MHz, CDCl3) δ 10.03 (1H, s), 8.58 (1H, s), 8.36 (1H, s), 8.02 (1H, s), 7.58 (1H, dd, J=8.9, 2.0 Hz), 7.46 (1H, d, J=8.9 Hz), 7.38 (1H, s), 5.23 (2H, s), 3.80-3.30 (4H, br m), 3.09 (3H, s), 2.97 (3H, s), 1.76-1.63 (2H, m), 1.16-1.04 (1H, m), 1.01-0.93 (3H, m), 0.57 (2H, d, J=7.7 Hz), 0.35-0.29 (2H, m). MS (APCI+): 436. HPLC (Condition C): Rt 3.50 min (HPLC purity 97.9%).

Example 116

{5-[({6-[(cyclopropylmethyl)(propyl)amino]pyrimidin-4-yl}carbonyl)amino]-1H-indazol-1-YL}acetic Acid

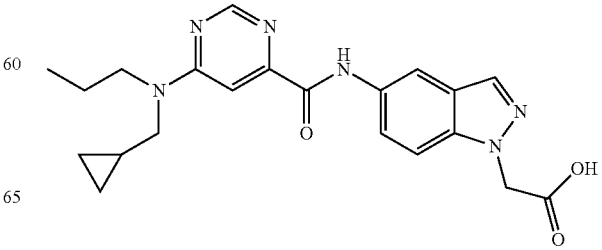

A solution of ethyl 2-(5-(6-((cyclopropylmethyl)(propyl)amino)pyrimidine-4-carboxamido)-1H-indazol-1-yl)acetate (Intermediate 39, 106 mg; 0.24 mmol) in ethanol (10 ml) was treated with 10% NaOH solution (5 ml). After stirring at RT for 2 hours the solvent was reduced in vacuo to one quarter of its original volume and water (20 ml) added. The mixture was acidified with dilute HCl and DCM (50 ml) added. After stirring at RT for 30 minutes the mixture was filtered through a hydrophobic frit and the solvent removed in vacuo. The solid formed was washed with water and dried to give the title compound as a pale yellow solid.

¹H NMR (400MHz, DMSO-d6) δ 10.74 (1H, s), 8.71 (1H, s), 8.37 (1H, s), 8.13 (1H, s), 7.81 (1H, dd, J=9.0, 1.9 Hz), 7.68 (1H, d, J=9.0 Hz), 7.43 (1H, br s), 5.29 (2H, s), 3.94-3.34 (4H, br m), 1.70-1.64 (2H, m), 1.20-1.09 (1H, m), 1.01-0.90 (3H, m), 0.60-0.49 (2H, m), 0.43-0.37 (2H, m). MS (APCI+): 409. HPLC (Condition C): Rt 3.54 min (HPLC purity 93.4%).

Example 117

N-[1-(2-amino-2-oxoethyl)-1H-indazol-5-yl]-6-[(cyclopropylmethyl)(propyl)amino]pyrimidine-4-carboxamide

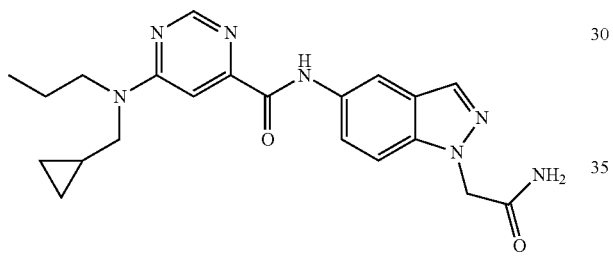

A solution of 6-((cyclopropylmethyl)(propyl)amino)-N-(1H-indazol-5-yl)pyrimidine-4-carboxamide (Example 45, 350 mg; 1 mmol) in DMF (4 ml) was treated with potassium carbonate (140 mg; 1 mmol), potassium iodide (1 mg) and 2-bromoacetamide (160 mg; 1.16 mmol). After stirring at RT for 72 hours the mixture was poured in water (20 ml) and stirred at RT for 1 hour. The solid was removed by filtration, washed with water and dried. The residue was purified by column chromatography (silica) eluting with EtOAc containing increasing amounts of MeOH to give the title compound as an off-white solid, together with N-[2-(2-amino-2-oxoethyl)-2H-indazol-5-yl]-6-[(cyclopropylmethyl)(propyl)amino]pyrimidine-4-carboxamide (Example 118 below).

¹H NMR (400MHz, CDCl3) δ 10.09 (1H, s), 8.58 (1H, d, J=1.1 Hz), 8.43 (1H, d, J=1.9 Hz), 8.11 (1H, d, J=0.9 Hz), 7.63 (1H, dd, J=9.0, 1.96 Hz), 7.43 (1H, d, J=8.95 Hz), 7.38 (1H, br s), 5.82 (1H, s), 5.44 (1H, s), 5.06 (2H, s), 3.68-3.36 (4H, br m), 1.76-1.63 (2H, m), 1.16-1.04 (1H, m), 0.98 (3H, t, J=7.36 Hz), 0.63-0.52 (2H, m), 0.36-0.30 (2H, m). MS (APCI+): 408. HPLC (Condition C): Rt 3.21 min (HPLC purity 98.5%).

Example 118

N-[2-(2-amino-2-oxoethyl)-2H-indazol-5-yl]-6-[(cyclopropylmethyl)(propyl)amino]pyrimidine-4-carboxamide

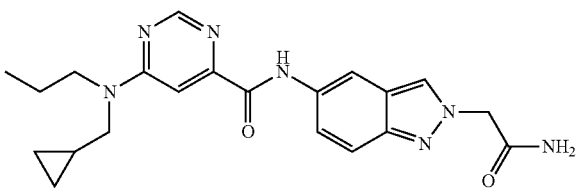 [SMILES: CCCN(CC1CC1)c1cc(C(=O)Nc2ccc3nn(CC(N)=O)cc3c2)ncn1]

The title compound was isolated from the reaction described above for the synthesis of N-[1-(2-amino-2-oxoethyl)-1H-indazol-5-yl]-6-[(cyclopropylmethyl)(propyl)amino]pyrimidine-4-carboxamide (Example 117 above).

¹H NMR (400MHz, CDCl3) δ 10.04 (1H, s), 8.58 (1H, s), 8.47 (1H, d, J=1.9 Hz), 8.02 (1H, s), 7.72 (1H, d, J=9.2 Hz), 7.41-7.35 (2H, m), 6.53 (1H, br s), 5.47 (1H, br s), 5.10 (2H, s), 3.69-3.38 (4H, br m), 1.74-1.66 (2H, m), 1.15-1.05 (1H, m), 0.98 (3H, t, J=7.3 Hz), 0.57 (2H, br d, J=7.8 Hz), 0.35-0.30 (2H, m). MS (APCI+): 408. HPLC (Condition C): Rt 3.15 min (HPLC purity 99.4%).

Example 119

ETHYL 3-({-4-[({6-[(cyclopropylmethyl)(propyl)amino]pyrimidin-4-yl}carbonyl)amino]benzyl}sulfonyl)propanoate

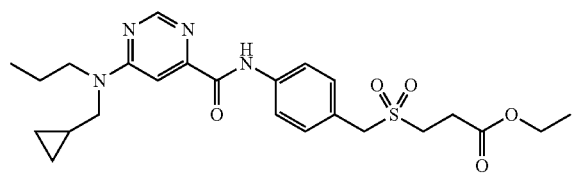 [SMILES: CCCN(CC1CC1)c1cc(C(=O)Nc2ccc(CS(=O)(=O)CCC(=O)OCC)cc2)ncn1]

A cooled (0° C.) solution of 6-((cyclopropylmethyl)(propyl)amino)pyrimidine-4-carboxylic acid (Intermediate 21, 0.2 g; 0.85 mmol) in DCM (5 ml) was treated with triethylamine (0.13 ml; 0.93 mmol) and methyl chloroformate (0.085 ml; 1.1 mmol). After stirring at 0° C. for 30 minutes, ethyl 3-(4-aminobenzylsulfonyl)propanoate (Intermediate 42, 230 mg; 0.85 mmol) was added. After stirring at 0° C. for 5 minutes and RT for 1 hour water was added and the mixture passed through a hydrophobic frit. The solvent was removed in vacuo and the residue purified by column chromatography (silica) eluting with petroleum ether containing increasing amounts of EtOAc to give the title compound as a white solid.

¹H NMR (400MHz, CDCl3) δ 10.06 (1H, s), 8.57 (1H, s), 7.83 (2H, d, J=8.3 Hz), 7.46 (2H, d, J=8.3 Hz), 7.35 (1H, br s), 4.28 (2H, s), 4.22-4.12 (2H, m), 3.76-3.30 (4H, m), 3.20 (2H, t, J=7.5 Hz), 2.81 (2H, t, J=7.5 Hz), 1.74-1.64 (2H, m), 1.27 (3H, t, J=7.1 Hz), 1.15-1.04 (1H, m), 0.97 (3H, t, J=7.3 Hz), 0.57 (2H, br d, J=7.8 Hz), 0.35-0.29 (2H, m). MS (APCI+): 489. HPLC (Condition C): Rt 4.07 min (HPLC purity 99.0%).

Example 120

Ethyl {5-[({6-[(cyclopropylmethyl)(propyl)amino]pyrimidin-4-yl}carbonyl)amino]-2H-indazol-2-yl}acetate

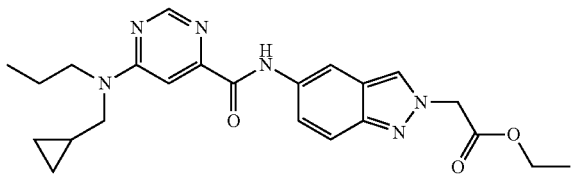 [SMILES: CCCN(CC1CC1)c1cc(C(=O)Nc2ccc3nn(CC(=O)OCC)cc3c2)ncn1]

The title compound was isolated from the reaction described above for the synthesis of ethyl 2-(5-(6-((cyclopropylmethyl)(propyl)amino)pyrimidine-4-carboxamido)-1H-indazol-1-yl)acetate (Intermediate 39 above).

$^1$H NMR (400MHz, CDCl3) δ 10.00 (1H, s), 8.58 (1H, s), 8.46 (1H, d, J=2.0 Hz), 8.00 (1H, s), 7.70 (1H, d, J=9.2 Hz), 7.38 (1H, s), 7.33 (1H, dd, J=9.2, 2.0 Hz), 5.19 (2H, s), 4.27 (2H, q, J=7.1 Hz), 3.68-3.36 (4H, br m), 1.75-1.65 (2H, m), 1.29 (3H, t, J=7.1 Hz), 1.15-1.05 (1H, m), 0.97 (3H, t, J=7.3 Hz), 0.61-0.52 (2H, m), 0.35-0.30 (2H, m). MS (APCI+): 437. HPLC (Condition C): Rt 4.00 min (HPLC purity 96.7%).

Example 121

{5-[({6-[(cyclopropylmethyl)(propyl)amino]pyrimidin-4-yl}carbonyl)amino]-2H-indazol-2-yl}acetic Acid

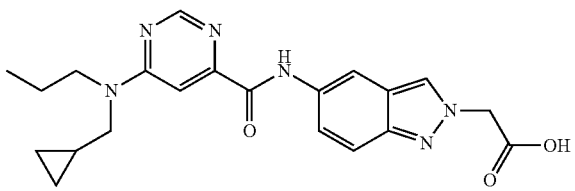 [SMILES: CCCN(CC1CC1)c1cc(C(=O)Nc2ccc3nn(CC(=O)O)cc3c2)ncn1]

A solution of ethyl {5-[({6-[(cyclopropylmethyl)(propyl)amino]pyrimidin-4-yl}carbonyl)amino]-2H-indazol-2-yl}acetate (Example 120, 90 mg; 0.20 mmol) in ethanol (10 ml) was treated with 10% NaOH solution (5 ml). After stirring at RT for 2 hours the solvent was reduced in vacuo to one quarter of its original volume and water (20 ml) added. The mixture was acidified with dilute HCl and the solid removed by filtration, washed with water and dried to give the title compound as a yellow solid.

$^1$H NMR (400MHz, CDCl3) δ 10.05 (1H, s), 8.58 (1H, s), 8.46 (1H, s), 8.01 (1H, s), 7.72 (1H, d, J=9.2 Hz), 7.42 (1H, dd, J=9.2, 2.0 Hz), 7.37 (1H, br s) 5.24 (2H, s), 3.71-3.37 (4H, m), 1.77-1.62 (2H, m), 1.16-1.05 (1H, m), 0.97 (3H, t, J=7.3 Hz), 0.58 (2H, br d, J=7.7 Hz), 0.33 (2H, d, J=5.14 Hz). MS (APCI+): 409. HPLC (Condition C): Rt 3.49 min (HPLC purity 91.6%).

Example 122

4-[({6-[cyclohexyl(cyclopropylmethyl)amino]pyrimidin-4-yl}carbonyl)amino]-2-fluorobenzoic Acid

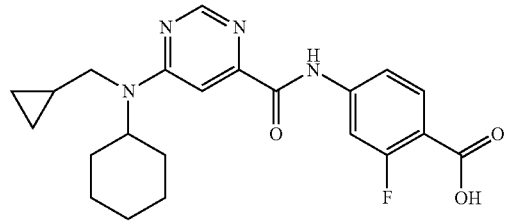 [SMILES: O=C(Nc1ccc(C(=O)O)c(F)c1)c1cc(N(CC2CC2)C2CCCCC2)ncn1]

A solution of methyl 4-[({6-[cyclohexyl(cyclopropylmethyl)amino]pyrimidin-4-yl}carbonyl)amino]-2-fluorobenzoate (Intermediate 25, 85 mg; 0.20 mmol) in THF (5 ml) and MeOH (5 ml) was treated with an aqueous solution (5 M) of sodium hydroxide (198 μl; 0.99 mmol). After stirring for 40 hours, HCl 1 N was added until pH 3, then the solution was concentrated under vacuum, EtOAc was added and the organic layer was washed with brine, dried (MgSO$_4$) and removed under vacuum to afford an oily residue which was purified by preparative HPLC to give the title compound as an amorphous white solid.

$^1$H NMR (300MHz, DMSO-d6) δ 10.89 (1H, s), 8.67 (1H, d, J=1.0 Hz), 7.89-7.75 (3H, m), 7.33 (1H, d, J=1.0 Hz), 4.6 (1H, m), 3.40 (2H, m), 1.84-1.05 (11H, m), 0.51-0.48 (2H, m), 0.37-0.33 (2H, m). MS (ESI+): 413.2. HPLC (Condition A): Rt 4.08 min (HPLC purity 100%).

Example 123

Methyl 3-{5-[({6-[(cyclopropylmethyl)(propyl)amino]pyrimidin-4-yl}carbonyl)amino]-1H-indazol-3-yl}propanoate

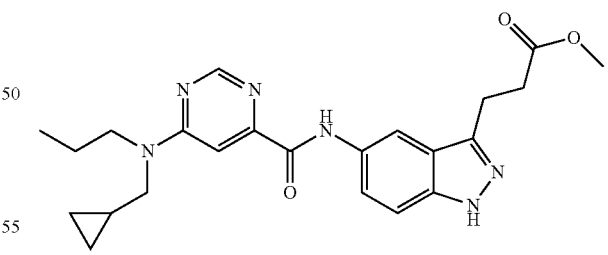

A solution of 6-((cyclopropylmethyl)(propyl)amino)pyrimidine-4-carboxylic acid (Intermediate 21, 31 mg; 0.13 mmol) in DCM (5 ml) was treated with tert-butyl 5-amino-3-(3-methoxy-3-oxopropyl)-1H-indazole-1-carboxylate (Intermediate 45, 35 mg; 0.11 mmol) and polymer-supported Mukaiyama reagent (300mg). After stirring at RT for 3 hours the mixture was filtered and washed with water. The organic phase was passed through a hydrophobic frit and the solvent removed in vacuo. The residue was purified by column chromatography (silica) eluting with petroleum ether containing increasing amounts of EtOAc to give tert-butyl 5-(6-((cyclopropylmethyl)(propyl)amino)pyrimidine-4-carboxamido)-3-(3-methoxy-3-oxopropyl)-1H-indazole-1-carboxylate.

The intermediate was redissolved in DCM (2 ml) and treated with TFA (1 ml) and water (1 drop). After stirring at RT for 3 hours the solvent was removed in vacuo. The residue was partitioned between DCM and saturated sodium bicarbonate solution. The separated organic phase was passed through a hydrophobic frit and the solvent removed in vacuo. The residue was purified by column chromatography (silica) eluting with petroleum ether containing increasing amounts of EtOAc to give the title compound as an off-white solid.

$^1$H NMR (400MHz, CDCl3) δ 10.06 (1H, s), 9.76 (1H, s), 8.58 (1H, s), 8.37 (1H, d, J=1.9 Hz), 7.57 (1H, dd, J=8.9, 1.9 Hz), 7.43 (1H, d, J=8.9 Hz), 7.39 (1H, br s), 3.71 (3H, s), 3.63-3.43 (4H, m), 3.32 (2H, t, J=7.6 Hz), 2.90 (2H, t, J=7.6 Hz), 1.75-1.65 (2H, m), 1.15-1.06 (1H, m), 0.97 (3H, t, J=7.4 Hz), 0.61-0.53 (2H, m), 0.35-0.29 (2H, m). MS (APCI+): 437. HPLC (Condition C): Rt 3.83 min (HPLC purity 98.7%).

Example 124

4-({4-[({6-[(cyclopropylmethyl)(propyl)amino]pyrimidin-4-yl}carbonyl)amino]phenyl}sulfonyl)butanoic Acid

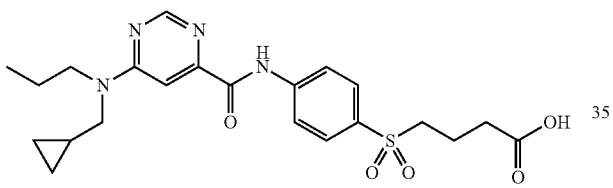

A cooled (0° C.) solution of 6-((cyclopropylmethyl)(propyl)amino)pyrimidine-4- carboxylic acid (Intermediate 21, 100 mg; 0.43 mmol) in DCM (5 ml) was treated with triethylamine (0.1 ml; 0.72 mmol) and methyl chloroformate (0.060 ml; 0.78 mmol). After stirring at 0° C. for 30 minutes, ethyl 4-(4-aminophenylsulfonyl)butanoate (Intermediate 48, 125 mg; 0.46 mmol) was added. After stirring at 0° C. for 5 minutes and RT for 1 hour water was added and the mixture passed through a hydrophobic frit. The solvent was removed in vacuo and the residue purified by column chromatography (silica) eluting with petroleum ether containing increasing amounts of EtOAc to give ethyl (4-(6-((cyclopropvlmethvl)(propyl)amino)pyrimidine-4-carboxamido)phenylsulfonyl)butanoate. The intermediate was redissolved in ethanol (3 ml) and treated with 10% sodium hydroxide solution (2 ml). After stirring at RT for 18 hours the mixture was acidified to pH 3 with dilute HCl and EtOAc added. The organic phase was removed in vacuo and the aqueous phase extracted with EtOAc. The combined organic extracts were passed through a hydrophobic frit and the solvent removed in vacuo. The residue was triturated with diisopropyl ether and allowed to dry to give the title compound as an off-white solid.

$^1$H NMR (400MHz, CDCl3) δ 10.27 (1H, s), 8.57 (1H, s), 7.98 (2H, d, J=8.7 Hz), 7.92 (2H, d, J=8.7 Hz), 7.35 (1H, br s), 3.71-3.37 (4H, br m), 3.20 (2H, t, J=7.6 Hz), 2.54 (2H, t, J=7.0 Hz), 2.11-2.01 (2H, m), 1.74-1.64 (2H, m), 1.16-1.04 (1H, m), 0.97 (3H, t, J=7.3 Hz), 0.58 (2H, br d, J=7.7 Hz), 0.35-0.29 (2H, m). MS (APCI+): 461. HPLC (Condition C): Rt 3.68 min (HPLC purity 92.0%).

Example 125

N-1H-benzimidazol-5-yl-6-[(cyclopropylmethyl)(propyl)amino]pyrimidine-4-carboxamide

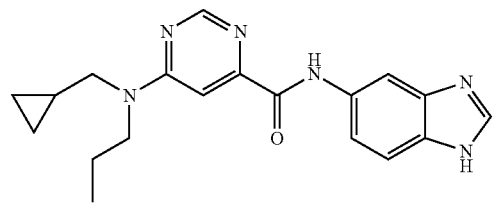 [SMILES: CCCN(CC1CC1)c1cc(C(=O)Nc2ccc3[nH]cnc3c2)ncn1]

Following the general method as outlined in Example 1, starting from 6-(cyclopropylmethyl-propyl-amino)-pyrimidine-4-carboxylic acid (Intermediate 21) and 5-aminobenzimidazole (ABCR), the title compound was obtained as a white solid after purification by preparative HPLC.

$^1$H NMR (300MHz, DMSO-d6) δ 12.46 (1H, s), 10.54 (1H, s), 8.64 (1H, d, J=1.0 Hz), 8.28 (1H, s), 8.19 (1H, s), 7.58 (2H, s), 7.28 (1H, bs), 3.5 (4H, bs), 1.62 (2H, sextet, J=7.5 Hz), 1.09 (1H, m), 0.92 (3H, t, J=7.5 Hz), 0.51-0.48 (2H, m), 0.37-0.33 (2H, m). MS (ESI+): 351.2. HPLC (Condition A): Rt 2.48 min (HPLC purity 100%).

Example 126

6-[cyclohexyl(cyclopropylmethyl)amino]-N-1H-INDOL-4-ylpyrimidine-4-carboxamide

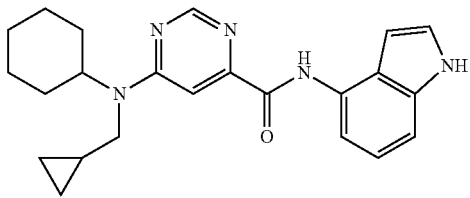 [SMILES: O=C(Nc1cccc2[nH]ccc12)c1cc(N(CC2CC2)C2CCCCC2)ncn1]

A solution of 6-(cyclohexyl(cyclopropylmethyl)amino)pyrimidine-4-carboxylic acid (Intermediate 13, 110 mg; 0.40 mmol) in DCM was treated with polymer-supported Mukaiyama reagent (1.1 g) followed by 1H-indol-4-amine (Aldrich, 58.2 mg; 0.44 mmol). After stirring at RT for 72 hours the mixture was filtered and washed with saturated sodium bicarbonate solution. The organic phase was passed through a hydrophobic frit and the solvent removed in vacuo. The residue was purified by column chromatography (silica) eluting with petroleum ether containing increasing amounts of EtOAc to give the title compound as a white solid (120 mg, 77%).

$^1$H NMR (400MHz, DMSO-d6) δ 11.33 (1H, s), 10.39 (1H, s), 8.72 (1H, s), 7.85 (1H, d, J=7.6 Hz), 7.44-7.40 (2H, m), 7.29 (1H, d, J=8.1 Hz), 7.15 (1H, t, J=7.9 Hz), 6.54 (1H, s), 3.52-3.40 (2H, m), 1.93-1.70 (4H, m), 1.73-1.54 (3H, m), 1.52-1.37 (2H, m), 1.28-1.15 (2H, m), 1.13-0.99 (1H, m), 0.62-0.51 (2H, m), 0.45-0.39 (2H, m). MS (APCI+): 390. HPLC (Condition C): Rt 4.80 min (HPLC purity 99.1%).

Example 127

6-[cyclohexyl(cyclopropylmethyl)amino]-N-1H-indazol-4-ylpyrimidine-4-carboxamide

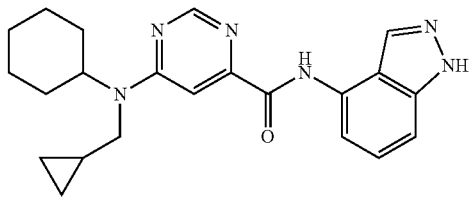

A solution of 6-(cyclohexyl(cyclopropylmethyl)amino) pyrimidine-4-carboxylic acid (Intermediate 13, 110 mg; 0.40 mmol) in DCM was treated with polymer-supported Mukaiyama reagent (1.1 g) followed by 1H-indazol-4-amine (Key Organics, 58.6 mg; 0.44 mmol). After stirring at RT for 72 hours the mixture was filtered and washed with saturated sodium bicarbonate solution. The organic phase was passed through a hydrophobic frit and the solvent removed in vacuo. The residue was purified by column chromatography (silica) eluting with petroleum ether containing increasing amounts of EtOAc to give the title compound as a white solid.
$^1$H NMR (400MHz, DMSO-d6) δ 10.49 (1H, s), 10.23 (1H, s), 8.65 (1H, s), 8.31 (1H, s), 8.04 (1H, d, J=8.0 Hz), 7.49 (1H, s), 7.43 (1H, t, J=8.0 Hz), 7.31 (1H, d, J=8.0 Hz), 3.56-3.25 (2H, br s), 1.94-1.80 (4H, m), 1.74 (1H, d, J=13.4 Hz), 1.63-1.37 (5H, m), 1.29-1.09 (1H, m), 1.12-1.00 (1H, m), 0.59 (2H, br d, J=7.8 Hz), 0.41-0.34 (2H, m). MS (APCI+): 391. HPLC (Condition C): Rt 4.50 min (HPLC purity 98.3%).

Example 128

N-{4-[({6-[(cyclopropylmethyl)(propyl)amino]pyrimidin-4-yl}carbonyl)amino]-3-Methylbenzyl}-N-methylglycine

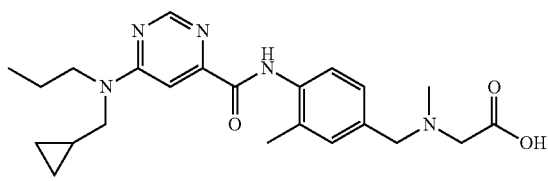 [SMILES: CCCN(CC1CC1)c1cc(C(=O)Nc2ccc(CN(C)CC(=O)O)cc2C)ncn1]

A solution of 6-((cyclopropylmethyl)(propyl)amino)-N-(4-formyl-2-methylphenyl)pyrimidine-4-carboxamide (Intermediate 29, 100 mg; 0.28 mmol) in DCM (5 ml) was treated with tert-butyl 2-(methylamino)acetate hydrochloride (227.1 mg; 1.24 mmol) and polymer supported carbonate (150 mg) followed by polymer supported triacetoxy borohydride (150 mg). After stirring for 18 hours the mixture was filtered and the solvent removed in vacuo. The residue was purified by column chromatography (silica) eluting with petroleum ether containing increasing amounts of EtOAc to give tert-butyl 2-((4-(6-((cyclopropylmethyl)(propyl)amino) pyrimidine-4-carboxamido)-3-methylbenzyl)(methyl) amino)acetate which was used directly without any further purification. The residue was taken up into DCM (4.5 ml) and TFA (0.5 ml) added. After stirring at RT for 2 hours the solvent was removed in vacuo. The residue was taken up into dilute HCl and precipitated by basification to pH 3-4. The solid was removed by filtration, washed with water and dried to give the title compound as a white solid.
$^1$H NMR (400MHz, DMSO-d6) δ 10.20 (1H, s), 8.66 (1H, s), 7.94-7.82 (1H, m), 7.38-7.17 (3H, m), 3.77 (2H, s), 3.71-3.37 (4H, m), 3.30 (2H, s), 2.39 (3H, s), 2.33 (3H, s), 1.73-1.59 (2H, m), 1.19-1.04 (1H, m), 1.02-0.88 (3H, m), 0.60-0.47 (2H, m), 0.43-0.32 (2H, m). MS (APCI+): 426. HPLC (Condition C): Rt 2.84 min (HPLC purity 91.3%).

Example 129

3-{54({6-[(cyclopropylmethyl)(propyl)amino]pyrimidin-4-yl}carbonyl)amino-1H-indazol-3-yl}propanoic Acid

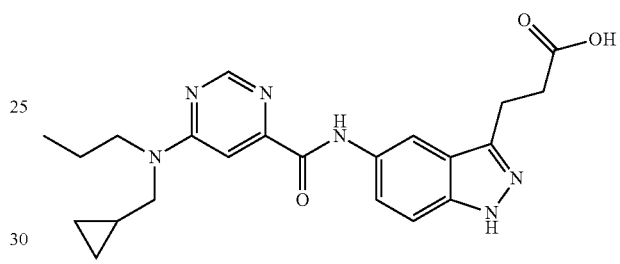

A solution of methyl 3-{5-[({6-[(cyclopropylmethyl)(propyl)amino]pyrimidin-4-yl}carbonyl)amino]-1H-indazol-3-yl}propanoate (Example 123, 20 mg; 0.05 mmol) in ethanol (1 ml) was treated with 10% sodium hydroxide solution (1 ml). After stirring at RT for 2 hours the mixture was acidified to pH 3 with dilute HCl and extracted with EtOAc. The combined organic extracts were passed through a hydrophobic frit and the solvent removed in vacuo. The residue was purified by column chromatography (silica) eluting with EtOAc containing increasing amounts of MeOH to give the title compound as a white solid.
$^1$H NMR (400MHz, CDCl3) δ 10.03 (1H, s), 8.56 (1H, s), 8.36 (1H, s), 7.50-7.30 (3H, m), 6.62 (1H, br s), 3.68-3.37 (4H, br m), 3.32 (2H, s), 2.89 (2H, s), 1.74-1.64 (2H, m), 1.15-1.03 (1H, m), 0.96 (3H, t, J=7.31 Hz), 0.57 (2H, br d, J=7.70 Hz), 0.34-0.29 (2H, m). Note: OH not observed. MS (APCI−): 421. HPLC (Condition C): Rt 3.33 min (HPLC purity 97.8%).

Example 130

Ethyl 3-({-4-[({6-[cyclohexyl(cyclopropylmethyl) amino]pyrimidin-4-yl}carbonyl)amino] benzyl}sulfonyl)propanoate

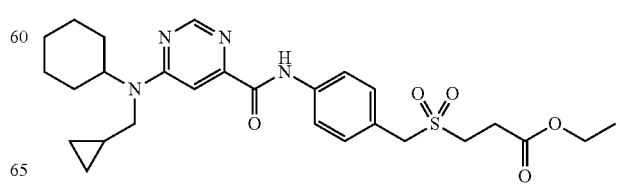

A cooled (0° C.) solution of 6-(cyclohexyl(cyclopropylmethyl)amino)pyrimidine-4-carboxylic acid (Intermediate 13, 130 mg; 0.47 mmol) in DCM was treated with diisopropylamine (90 mL; 0.52 mmol) and methyl chloroformate (40 mL; 0.52 mmol). After stirring at 0° C. for 15 minutes, ethyl 3-(4-aminobenzylsulfonyl)propanoate (Intermediate 42, 130 mg; 0.48 mmol) was added. After stirring at 0° C. for 30 minutes and RT for 1 hour, saturated sodium bicarbonate solution was added and the mixture stirred for 15 minutes. DCM was added and the layers separated. The organic extract was filtered through a hydrophobic frit and the solvent removed in vacuo. The residue was purified by column chromatography (silica) eluting with petroleum ether containing increasing amounts of EtOAc to give the title compound as an off-white solid.

$^1$H NMR (400MHz, CDCl3) δ 10.06 (1H, s), 8.58 (1H, s), 7.83 (2H, d, J=8.2 Hz), 7.49-7.41 (3H, m), 4.27 (2H, s), 4.18 (2H, q, J=7.1 Hz), 3.48-3.29 (2H, m), 3.20 (2H, t, J=7.5 Hz), 2.80 (2H, t, J=7.5 Hz), 1.92-1.78 (4H, m), 1.78-1.67 (1H, m), 1.61-1.37 (5H, m), 1.27 (3H, t, J=7.1 Hz), 1.22-1.11 (1H, m), 1.10-0.97 (1H, m,) 0.65-0.51 (2H, m), 0.39-0.32 (2H, m). MS (APCI+): 529. HPLC (Condition C): Rt 4.52 min (HPLC purity 98.8%).

Example 131

Ethyl 4-({4-[({6-[cyclohexyl(cyclopropylmethyl)amino]pyrimidin-4-yl}carbonyl)amino]phenyl}sulfonyl)butanoate

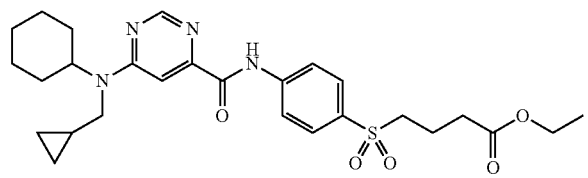 [SMILES: CCOC(=O)CCCS(=O)(=O)c1ccc(NC(=O)c2cc(N(CC3CC3)C3CCCCC3)ncn2)cc1]

A cooled (0° C.) solution of 6-(cyclohexyl(cyclopropylmethyl)amino)pyrimidine-4-carboxylic acid (Intermediate 13, 130 mg; 0.47 mmol) in DCM was treated with diisopropylamine (90 mL; 0.52 mmol) and methyl chloroformate (40 mL; 0.52 mmol). After stirring at 0° C. for 15 minutes, ethyl 4-(4-aminophenylsulfonyl)butanoate (Intermediate 48, 130 mg; 0.48 mmol) was added. After stirring at 0° C. for 30 minutes and RT for 1 hour, saturated sodium bicarbonate solution was added and the mixture stirred for 15 minutes. DCM was added and the layers separated. The organic extract was filtered through a hydrophobic frit and the solvent removed in vacuo. The residue was purified by column chromatography (silica) eluting with petroleum ether containing increasing amounts of EtOAc to give the title compound as a white solid.

$^1$H NMR (400MHz, CDCl3) δ 10.27 (1H, s), 8.59 (1H, s), 7.98 (2H, d, J=8.7 Hz), 7.92 (2H, d, J=8.7 Hz), 7.43 (1H, s), 4.11 (2H, q, J=7.1 Hz), 3.49-3.29 (2H, br m), 3.22-3.16 (2H, m), 2.45 (2H, t, J=7.1 Hz), 2.09-1.98 (2H, m), 1.93-1.78 (4H, m), 1.78-1.68 (1H, m), 1.54-1.37 (5H, m), 1.23 (3H, t, J=7.14 Hz), 1.21-1.12 (1H, m), 1.11-0.96 (1H, m), 0.65-0.52 (2H, m), 0.41-0.33 (2H, m). MS (APCI+): 529. HPLC (Condition C): Rt 4.66 min (HPLC purity 96.3%).

Example 132

4-({4-[({6-[cyclohexyl(cyclopropylmethyl)amino]pyrimidin-4-yl}carbonyl)amino]phenyl}sulfonyl)butanoic acid

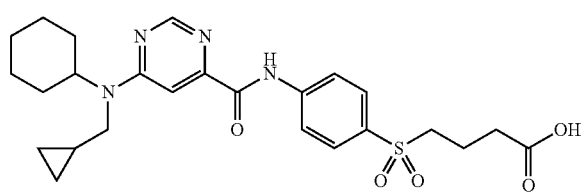 [SMILES: O=C(O)CCCS(=O)(=O)c1ccc(NC(=O)c2cc(N(CC3CC3)C3CCCCC3)ncn2)cc1]

A solution of ethyl 4-({4-[({6-[cyclohexyl(cyclopropylmethyl)amino]pyrimidin-4-yl}carbonyl)amino]phenyl}sulfonyl)butanoate (Example 131, 80 mg; 0.16 mmol) in THF (5 ml) was treated with 10% sodium hydroxide solution (20 ml). After stirring for 45 minutes the mixture was cooled to 0° C. and acidified with concentrated HCl. The mixture was extracted with EtOAc and the combined organic extracts washed with water, passed through a hydrophobic frit and the solvent removed in vacuo. The residue was purified by column chromatography (silica) eluting with DCM containing increasing amounts of methanol to give the title compound as a white solid (65 mg, 81%).

$^1$H NMR (400MHz, CDCl3) δ 10.28 (1H, s), 8.58 (1H, s), 7.98 (2H, d, J=8.5 Hz), 7.92 (2H, d, J=8.5 Hz), 7.42 (1H, s), 3.51-3.30 (2H, br s) 3.20 (2H, t, J=7.6 Hz), 2.54 (2H, t, J=7.0 Hz), 2.11-2.00 (2H, m), 1.93-1.78 (5H, m), 1.74 (1H, d, J=13.7 Hz), 1.57-1.37 (4H, m), 1.26-1.12 (1H, m), 1.04 (1H, s), 0.59 (2H, br s), 0.40-0.34 (2H, m). (APCI+): 501. HPLC (Condition C): Rt 4.18 min (HPLC purity 98.9%).

Example 133

3-({4-[({6-[cyclohexyl(cyclopropylmethyl)amino]pyrimidin-4-yl}carbonyl)amino]benzyl}sulfonyl)propanoic Acid

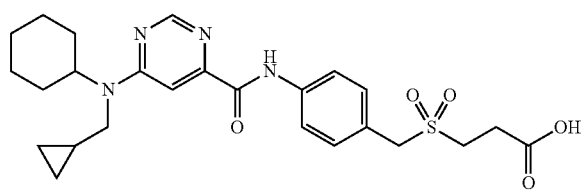 [SMILES: O=C(O)CCS(=O)(=O)Cc1ccc(NC(=O)c2cc(N(CC3CC3)C3CCCCC3)ncn2)cc1]

A solution of ethyl 3-({4-[({6-[cyclohexyl(cyclopropylmethyl)amino]pyrimidin-4-yl}carbonyl)amino]benzyl}sulfonyl)propanoate (Example 130, 130 mg; 0.25 mmol) in THF (5 ml) was treated with concentrated HCl (4 ml). After stirring at RT for 24 hours and 45° C. for 24 hours, the solvent was reduced in vacuo to half the volume and the mixture extracted with EtOAc. The combined organic extracts were washed with water, passed through a hydrophobic frit and the solvent removed in vacuo. The residue was purified by column chromatography (silica) eluting with DCM containing increasing amounts of methanol to give the title compound as a white solid (75 mg, 77%).

$^1$H NMR (400 MHz, DMSO-d6) δ 10.66 (1H, s), 8.70 (1H, s), 7.95 (2H, d, J=8.1 Hz), 7.43 (2H, d, J=8.1 Hz), 7.37 (1H, s), 4.54 (2H, s), 3.49-3.26 (4H, m), 2.69 (2H, t, J=7.4 Hz), 1.91-1.71 (4H, m), 1.72-1.53 (3H, m), 1.52-1.34 (2H, m), 1.30-1.16 (1H, m), 1.12-0.97 (1H, m), 0.62-0.50 (2H, m), 0.44-0.37 (2H, m). MS (APCI+): 501. HPLC (Condition C): Rt 4.08 min (HPLC purity 98.4%).

Example 134

6-[(cyclopropylmethyl)(propyl)amino]-N-1H-indazol-4-ylpyrimidine-4-carboxamide

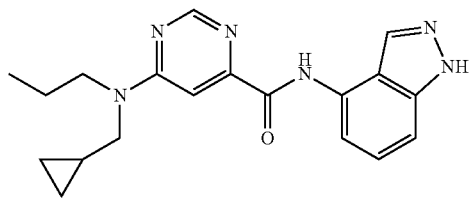 [SMILES: CCCN(CC1CC1)c1cc(C(=O)Nc2cccc3[nH]ncc23)ncn1]

A solution of 6-((cyclopropylmethyl)(propyl)amino)pyrimidine-4-carboxylic acid (Intermediate 21, 230 mg; 0.98 mmol) in DCM (5 ml) was treated with polymer-supported Mukaiyama reagent (400 mg) and triethylamine (0.41 ml; 2.9 mmol) followed by 1H-indazol-4-amine (Key Organics, 150 mg; 1.12 mmol). After stirring at RT for 72 hours the mixture was filtered and washed with saturated sodium bicarbonate solution. The organic phase was passed through a hydrophobic frit and the solvent removed in vacuo. The residue was purified by column chromatography (silica) eluting with petroleum ether containing increasing amounts of EtOAc to give the title compound as a white solid.

$^1$H NMR (400 MHz, CDCl3) δ 10.48 (1H, s), 10.20 (1H, s), 8.64 (1H, s), 8.30 (1H, s), 8.03 (1H, d, J=7.6 Hz), 7.47-7.39 (2H, m), 7.31 (1H, d, J=8.4 Hz), 3.73-3.37 (4H, br m), 1.77-1.65 (2H, m), 1.16-1.05 (1H, m), 0.98 (3H, t, J=7.4 Hz), 0.58 (2H, br d, J=7.7 Hz), 0.36-0.29 (2H, m). MS (APCI+): 351. HPLC (Condition C): Rt 3.88 min (HPLC purity 93.5%).

Example 135

3-({4-[({6-[(cyclopropylmethyl)(propyl)amino]pyrimidin-4-yl}carbonyl)amino]benzyl}sulfonyl)propanoic Acid

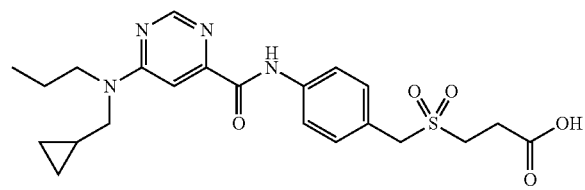 [SMILES: CCCN(CC1CC1)c1cc(C(=O)Nc2ccc(CS(=O)(=O)CCC(=O)O)cc2)ncn1]

A solution of ethyl 3-({4-[({6-[(cyclopropylmethyl)(propyl)amino]pyrimidin-4-yl}carbonyl)amino]benzyl}sulfonyl)propanoate (Example 119, 120 mg, 0.25 mmol) in THF (5 ml) was treated with concentrated HCl (2 ml). After stirring at RT for 48 hours a further portion of concentrated HCl (5 ml) was added. After stirring for a further 72 hours, the solvent was reduced in vacuo to half the volume and the mixture extracted with EtOAc. The combined organic extracts were washed with water, passed through a hydrophobic frit and the solvent removed in vacuo. The residue was purified by column chromatography (silica) eluting with DCM containing increasing amounts of methanol to give the title compound as a white solid (90 mg, 78%).

$^1$H NMR (400 MHz, CDCl3) δ 12.62 (1H, br s), 10.66 (1H, s), 8.67 (1H, s), 7.95 (2H, d, J=8.3 Hz), 7.43 (2H, d, J=8.3 Hz), 7.30 (1H, s), 4.54 (2H, s), 3.75-3.42 (4H, br m), 3.30 (2H, t, J=7.5 Hz), 2.73-2.64 (2H, m), 1.72-1.59 (2H, m), 1.18-1.07 (1H, m), 1.01-0.90 (3H, m), 0.59-0.48 (2H, m), 0.41-0.34 (2H, m). MS (APCI+): 459. HPLC (Condition C): Rt 3.55 min (HPLC purity 98.4%).

Example 136

6-[cyclohexyl(cyclopropylmethyl)amino]-N-[4-(4-methyl-4H-1,2,4-triazol-3-yl)phenyl]pyrimidine-4-carboxamide

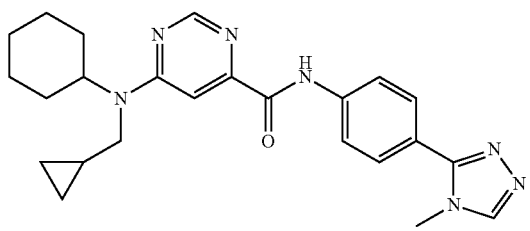 [SMILES: Cn1cnnc1-c1ccc(NC(=O)c2cc(N(CC3CC3)C3CCCCC3)ncn2)cc1]

A solution of 6-(cyclohexyl(cyclopropylmethyl)amino)pyrimidine-4-carboxylic acid (Intermediate 13, 100 mg; 0.36 mmol) in DCM (4 ml) was treated with polymer-supported Mukaiyama reagent (400 mg) followed by triethylamine (100 mL; 0.73 mmol) and 4-(4-methyl-4H-1,2,4-triazol-3-yl)aniline (Maybridge, 63.2 mg; 0.36 mmol). After stirring at RT for 24 hours the mixture was filtered and washed with saturated sodium bicarbonate solution. The organic phase was passed through a hydrophobic frit and the solvent removed in vacuo. The residue was purified by column chromatography (silica) eluting with petroleum ether containing increasing amounts of EtOAc to give the title compound as a white solid.

$^1$H NMR (400 MHz, CDCl3) δ 10.16 (1H, s), 8.60 (1H, s), 8.21 (1H, s), 7.93 (2H, d, J=8.3 Hz), 7.72 (2H, d, J=8.3 Hz), 7.45 (1H, s), 3.79 (3H, s), 3.39 (2H, s), 3.22-3.13 (1H, m), 1.86-1.10 (11H, m), 0.59 (2H, d, J=7.9 Hz), 0.40-0.34 (2H, m). MS (ESI+): 432. HPLC (Condition C): Rt 3.66 min (HPLC purity 99.4%).

Example 137

6-[cyclohexyl(cyclopropylmethyl)amino]-N-[4-(1H-1,2,4-triazol-1-ylmethyl)phenyl]pyrimidine-4-carboxamide

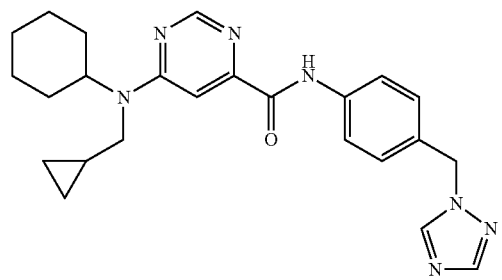 [SMILES: O=C(Nc1ccc(Cn2cncn2)cc1)c1cc(N(CC2CC2)C2CCCCC2)ncn1]

A solution of 6-(cyclohexyl(cyclopropylmethyl)amino) pyrimidine-4-carboxylic acid (Intermediate 13, 100 mg; 0.36 mmol) in DCM (4 ml) was treated with polymer-supported Mukaiyama reagent (400 mg) followed by triethylamine (100 mL; 0.73 mmol) and 4-((1H-1,2,4-triazol-1-yl)methyl) aniline (Maybridge, 63.2 mg; 0.36 mmol). After stirring at RT for 24 hours the mixture was filtered and washed with saturated sodium bicarbonate solution. The organic phase was passed through a hydrophobic frit and the solvent removed in vacuo. The residue was purified by column chromatography (silica) eluting with petroleum ether containing increasing amounts of EtOAc to give the title compound as a white solid.

$^1$H NMR (400 MHz, CDCl3) δ 10.03 (1H, s), 8.58 (1H, s), 8.05 (1H, s), 7.98 (1H, s), 7.79 (2H, d, J=8.3 Hz), 7.43 (1H, s), 7.31 (2H, d, J=8.3 Hz), 5.33 (2H, s), 3.65-3.05 (3H, m), 1.85-1.65 (5H, m), 1.64-1.38 (5H, m), 1.15 (1H, m), 0.58 (2H, d, J=7.9 Hz), 0.36 (2H, m). MS (ESI+): 432. HPLC (Condition C): Rt 4.06 min (HPLC purity 98.6%).

Example 138

1-{4-[({6-[(cyclopropylmethyl)(propyl)amino]pyrimidin-4-yl}carbonyl)amino]-3-methylbenzyl}piperidine-4-carboxylic Acid

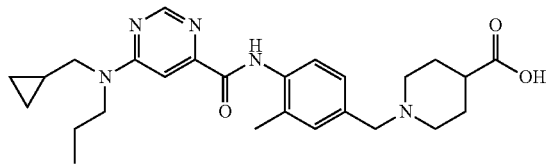 [SMILES: CCCN(CC1CC1)c1cc(C(=O)Nc2ccc(CN3CCC(C(=O)O)CC3)cc2C)ncn1]

Methyl piperidine-4-carboxylate (Aldrich, 41.1 μL; 0.3 mmol) was added to a stirred solution of 6-((cyclopropylmethyl)(propyl)amino)-N-(4-formyl-2-methylphenyl)pyrimidine-4-carboxamide (Intermediate 29, 100 mg; 0.27 mmol) in THF (4 mL). After stirring for 30 minutes sodium triacetoxyborohydride (87 mg; 0.41 mmol) was added and the reaction stirred for 18 hours. Additional sodium triacetoxyborohydride (174 mg; 0.82 mmol) was added and the mixture stirred for a further 18 hours. The THF was removed by evaporation. The residue was suspended in DCM (5 ml), washed with water (2 ml) and poured through a hydrophobic frit. The organic phase was collected and evaporated to give the product as colourless oil (130 mg). The oil was dissolved in THF (2 mL) and a solution of lithium hydroxide (30 mg; 1.25 mmol) in water (1 mL) added and the mixture stirred for 18 hours. The reaction was heated at 40° C. for 2 hours and then the solvent evaporated. The residue was dissolved in water (1 ml) and adjusted to pH 5 with HCl (2N). The colourless precipitate was collected by filtration washed with ice water and dried under vacuum to give the title compound.

$^1$H NMR (400 MHz, DMSO-d6, 105° C.) δ 10.0 (1H, br s), 8.51 (1H, s), 7.95 (1H, d, J=8.1 Hz), 7.35 (3H, m), 3.91 (2H, br s), 3.52 (2H, t, J=7.4 Hz), 3.40 (2H, d, J=6.5 Hz), 3.40-2.40 (6H, m), 2.35 (3H, s), 1.90 (4H, m), 1.75-1.67 (2H, m), 1.10 (1H, m), 0.95 (3H, t, J=7.4 Hz), 0.55 (2H, m), 0.45 (2H, m). MS (ESI+): 466. HPLC (Condition C): Rt 2.43 min (HPLC purity 98.1%).

Example 139

6-[(cyclopropylmethyl)(propyl)amino]-N-(4-{[(2R)-2-(methoxymethyl)pyrrolidin-1-yl]methyl}-2-methylphenyl)pyrimidine-4-carboxamide

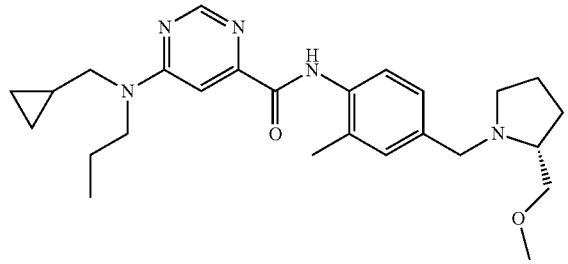 [SMILES: CCCN(CC1CC1)c1cc(C(=O)Nc2ccc(CN3CCC[C@@H]3COC)cc2C)ncn1]

(R)-2-(Methoxymethyl)pyrrolidine (Merck, 37.1 mL; 0.3 mmol) was added to a stirred solution of 6-((cyclopropylmethyl)(propyl)amino)-N-(4-formyl-2-methylphenyl)pyrimidine-4-carboxamide (Intermediate 29, 52.9 mg; 0.15 mmol) in DCM (1 mL). After stirring for 30 minutes sodium triacetoxyborohydride (95.4 mg; 0.45 mmol) was added and the reaction stirred for 18 hours. The reaction was diluted with DCM (6 ml), washed with water (2 ml) and poured through a hydrophobic frit. The organic phase was collected and evaporated to give the product as colourless oil. The crude product was dissolved in methanolic HCl and applied to an SCX cartridge. The cartridge was eluted with methanol followed by NH3 in Methanol to elute the product. Evaporation gave the title compound as a colourless oil (57 mg, 85%).

$^1$H NMR (400 MHz, CDCl3) δ 10.03 (1H, s), 8.57 (1H, d, J=1.1 Hz), 8.18 (1H, d, J=8.4 Hz), 7.37 (1H, s), 7.21 (2H, d, J=7.7 Hz), 4.05 (1H, d, J=13.0 Hz), 3.53-3.28 (11H, m), 2.97-2.91 (1H, m), 2.75-2.65 (1H, m), 2.39 (3H, s), 2.26-2.15 (1H, m), 1.99-1.86 (1H, m), 1.75-1.60 (4H, m), 1.09 (1H, d, J=8.9 Hz), 0.96 (3H, t, J=7.4 Hz), 0.56 (2H, d, J=7.8 Hz), 0.34-0.28 (2H, m). MS (ESI+): 452. HPLC (Condition C): Rt 2.56 min (HPLC purity 99.7%).

Example 140

6-[(cyclopropylmethyl)(propyl)amino]-N-{4-[(4-hydroxypiperidin-1-yl)methyl]-2-methylphenyl}pyrimidine-4-carboxamide

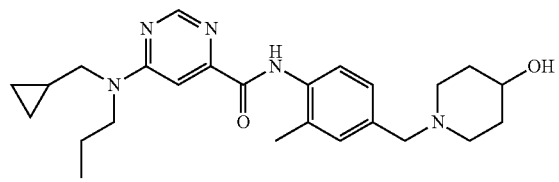 [SMILES: CCCN(CC1CC1)c1cc(C(=O)Nc2ccc(CN3CCC(O)CC3)cc2C)ncn1]

4-Piperidinol (Aldrich, 30.3 mL; 0.3 mmol) was added to a stirred solution of 6-((cyclopropylmethyl)(propyl)amino)-N-(4-formyl-2-methylphenyl)pyrimidine-4-carboxamide (Intermediate 29, 52.9 mg; 0.15 mmol) in DCM (1 mL). After stirring for 30 minutes sodium triacetoxyborohydride (95.4 mg; 0.45 mmol) was added and the reaction stirred for 18 hours. The reaction was diluted with DCM (6 ml), washed with water (2 ml) and poured through a hydrophobic frit. The organic phase was collected and evaporated to give the product as colourless oil. The crude product was dissolved in methanolic HCl and applied to an SCX cartridge. The cartridge was eluted with methanol followed by $NH_3$ in Methanol to elute the product. Evaporation gave the title compound as a colourless oil (59 mg, 90%).

$^1$H NMR (400 MHz, CDCl3) δ 10.04 (1H, s), 8.57 (1H, d, J=1.1 Hz), 8.19 (1H, d, J=8.0 Hz), 7.37 (1H, s), 7.19 (2H, d, J=9.3 Hz), 3.74-3.66 (1H, m), 3.53 (4H, s), 3.46 (2H, s), 2.81-2.71 (2H, m), 2.40 (3H, s), 2.15 (2H, t, J=10.7 Hz), 1.93-1.84 (2H, m), 1.80-1.35 (5H, m), 1.09 (1H, s), 0.96 (3H, t, J=7.4 Hz), 0.56 (2H, d, J=7.8 Hz), 0.35-0.29 (2H, m). MS (ESI+): 438. HPLC (Condition C): Rt 2.37 min (HPLC purity 98.5%).

Example 141

6-[(cyclopropylmethyl)(propyl)amino]-N-(4-{[3-(hydroxymethyl)piperidin-1-yl]methyl}-2-methylphenyl)pyrimidine-4-carboxamide

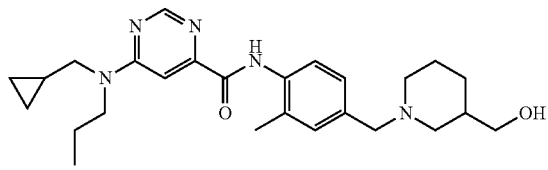 [SMILES: CCCN(CC1CC1)c1cc(C(=O)Nc2ccc(CN3CCCC(CO)C3)cc2C)ncn1]

3-Piperidinemethanol (Aldrich, 33.7 mL; 0.3 mmol) was added to a stirred solution of 6-((cyclopropylmethyl)(propyl)amino)-N-(4-formyl-2-methylphenyl)pyrimidine-4-carboxamide (Intermediate 29, 52.9 mg; 0.15 mmol) in DCM (1 mL). After stirring for 30 minutes sodium triacetoxyborohydride (95.4 mg; 0.45 mmol) was added and the reaction stirred for 18 hours. The reaction was diluted with DCM (6 ml), washed with water (2 ml) and poured through a hydrophobic frit. The organic phase was collected and evaporated to give the product as colourless oil. The crude product was dissolved in methanolic HCl and applied to an SCX cartridge. The cartridge was eluted with methanol followed by NH3 in Methanol to elute the product. Evaporation gave the title compound as a colourless oil (59 mg, 88%).

$^1$H NMR (400 MHz, CDCl3) δ 10.04 (1H, s), 8.57 (1H, d, J=1.1 Hz), 8.19 (1H, d, J=8.1 Hz), 7.37 (1H, s), 7.18 (2H, d, J=10.4 Hz), 3.65-3.45 (8H, m), 2.77 (1H, d, J=10.9 Hz), 2.58 (1H, m), 2.39 (3H, s), 2.20 (1H, s), 2.10 (1H, s), 1.79-1.51 (7H, m), 1.20 (1H, m), 1.09 (1H, m), 0.96 (3H, t, J=7.4 Hz), 0.56 (2H, d, J=7.7 Hz), 0.34-0.28 (2H, m). MS (ESI+): 452. HPLC (Condition C): Rt 2.41 min (HPLC purity 98.7%).

Example 142

6-[(cyclopropylmethyl)(propyl)amino]-N-{4-[(3-hydroxypyrrolidin-1-yl)methyl]-2-methylphenyl}pyrimidine-4-carboxamide

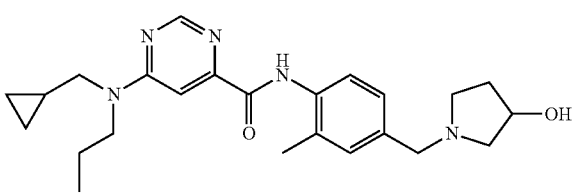 [SMILES: CCCN(CC1CC1)c1cc(C(=O)Nc2ccc(CN3CCC(O)C3)cc2C)ncn1]

3-Pyrrolidinol (Aldrich, 24.9 mL; 0.3 mmol) was added to a stirred solution of 6-((cyclopropylmethyl)(propyl)amino)-N-(4-formyl-2-methylphenyl)pyrimidine-4-carboxamide (Intermediate 29, 52.9 mg; 0.15 mmol) in DCM (1 mL). After stirring for 30 minutes sodium triacetoxyborohydride (95.4 mg; 0.45 mmol) was added and the reaction stirred for 18 hours. The reaction was diluted with DCM (6 ml), washed with water (2 ml) and poured through a hydrophobic frit. The organic phase was collected and evaporated to give the product as colourless oil. The crude product was dissolved in methanolic HCl and applied to an SCX cartridge. The cartridge was eluted with methanol followed by NH3 in methanol to elute the product. Evaporation gave the title compound as a colourless oil (61 mg, 96%).

$^1$H NMR (400 MHz, CDCl3) δ 10.04 (1H, s), 8.57 (1H, d, J=1.1 Hz), 8.21 (1H, d, J=8.6 Hz), 7.37 (1H, s), 7.12 (2H, m), 3.59 (2H, s), 3.53 (4H, s), 3.39 (4H, s), 2.39 (3H, s), 2.12 (2H, m), 1.67 (2H, m), 1.09 (1H, m), 0.96 (3H, t, J=7.4 Hz), 0.56 (2H, d, J=7.8 Hz), 0.32 (2H, m). MS (ESI+): 394. HPLC (Condition C): Rt 2.40 min (HPLC purity 99.1%).

Example 143

6-[(cyclopropylmethyl)(propyl)amino]-N-[3-(1H-1,2,4-triazol-1-yl)phenyl]pyrimidine-4-carboxamide

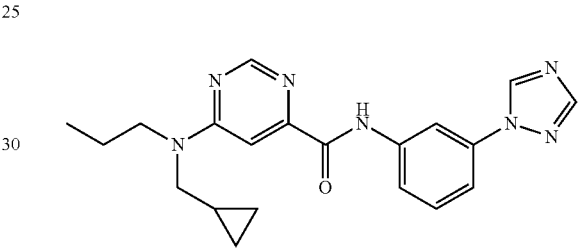

A cooled (0° C.) solution of 6-(cyclopropylmethyl(propyl)amino)pyrimidine-4-carboxylic acid (Intermediate 21, 112 mg; 0.45 mmol) in DCM was treated with diisopropylethylamine (78.4 mL; 0.52 mmol) and methyl chloroformate (36.2 mL; 0.47 mmol). After stirring at 0° C. for 15 minutes, 3-(1H-1,2,4-triazol-1-yl)aniline (Maybridge, 108 mg; 0.67 mmol) was added and the mixture stirred for 72 hours. The solvent was evaporated and the compound purified by preparative HPLC to give the title compound as a white solid. $^1$H NMR (400 MHz, CDCl3) δ 10.16 (1H, s), 8.60 (2H, d, J=18.1 Hz), 8.37 (1H, s), 8.11 (1H, s), 7.68-7.64 (1H, m), 7.53-7.48 (2H, m), 7.36 (1H, s), 3.54 (4H, s), 1.75-1.65 (2H, m), 1.10 (1H, s), 0.97 (3H, t, J=7.3 Hz), 0.58 (2H, d, J=7.7 Hz), 0.36-0.30 (2H, m). MS (ESI+) 387. HPLC (Condition C) Rt 3.77 min (HPLC purity 99.9%).

Example 144

6-[(cyclopropylmethyl)(propyl)amino]-N-[3-(2-methyl-1H-imidazol-1-yl)phenyl]pyrimidine-4-carboxamide

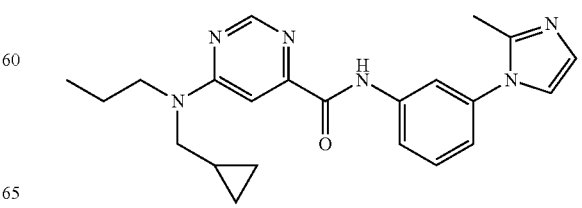

A cooled (0° C.) solution of 6-(cyclopropylmethyl(propyl) amino)pyrimidine-4-carboxylic acid (Intermediate 21, 112 mg; 0.45 mmol) in DCM was treated with diisopropylethylamine (78.4 mL; 0.52 mmol) and methyl chloroformate (36.2 mL; 0.47 mmol). After stirring at 0° C. for 15 minutes, 3-(2-methyl-1H-imidazol-1-yl)aniline (Maybridge, 117 mg; 0.67 mmol) was added and the mixture stirred for 72 hours. The solvent was evaporated and the compound purified by preparative HPLC to give the title compound as a white solid.

$^1$H NMR (400 MHz, CDCl3) δ 10.11 (1H, s), 8.57 (1H, s), 7.98 (1H, t, J=2.1 Hz), 7.64 (1H, dd, J=8.2, 2.0 Hz), 7.47 (1H, t, J=8.0 Hz), 7.35 (1H, s), 7.09-7.02 (3H, m), 3.53 (4H, s), 2.43 (3H, s), 1.76-1.64 (2H, m), 1.09 (1H, m), 0.97 (3H, t, J=7.3 Hz), 0.57 (2H, d, J=7.7 Hz), 0.35-0.29 (2H, m). MS (ESI+) 391. HPLC (Condition C) Rt 2.33 min (HPLC purity 99.8%).

Example 145

6-[(cyclopropylmethyl)(propyl)amino]-N-[4-(1H-1,2,4-triazol-1-ylmethyl)phenyl]pyrimidine-4-carboxamide

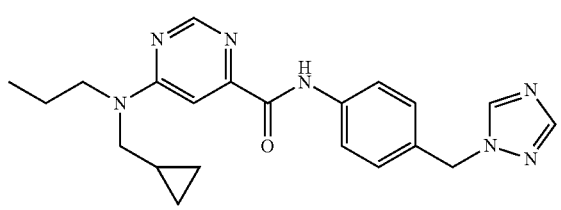 [SMILES: CCCN(CC1CC1)c1cc(C(=O)Nc2ccc(Cn3cncn3)cc2)ncn1]

A cooled (0° C.) solution of 6-(cyclopropylmethyl(propyl) amino)pyrimidine-4-carboxylic acid (Intermediate 21, 112 mg; 0.45 mmol) in DCM was treated with diisopropylethylamine (78.4 mL; 0.52 mmol) and methyl chloroformate (36.2 mL; 0.47 mmol). After stirring at 0° C. for 15 minutes, 4-(1H-1,2,4-triazol-1-ylmethyl)aniline (Maybridge, 117 mg; 0.67 mmol) was added and the mixture stirred for 72 hours. The solvent was evaporated and the compound purified by preparative HPLC to give the title compound as a white solid.

$^1$H NMR (400 MHz, CDCl3) δ 10.02 (1H, s), 8.56 (1H, d, J=1.1 Hz), 8.06 (1H, s), 7.98 (1H, s), 7.83-7.75 (2H, m), 7.35-7.28 (3H, m), 5.33 (2H, s), 3.52 (4H, s), 1.76-1.65 (2H, m), 1.01 (1H, m), 0.96 (3H, t, J=7.4 Hz), 0.57 (2H, d, J=7.7 Hz), 0.34-0.28 (2H, m). MS (ESI+) 392. HPLC (Condition C) Rt 3.46 min (HPLC purity 99.4%).

Example 146

6-[(cyclopropylmethyl)(propyl)amino]-N-[4-(1H-1,2,4-triazol-1-yl)phenyl]pyrimidine-4-carboxamide

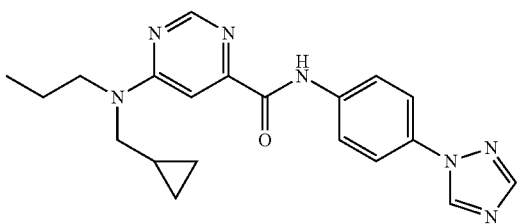 [SMILES: CCCN(CC1CC1)c1cc(C(=O)Nc2ccc(-n3cncn3)cc2)ncn1]

A cooled (0° C.) solution of 6-(cyclopropylmethyl(propyl) amino)pyrimidine-4-carboxylic acid (Intermediate 21, 112 mg; 0.45 mmol) in DCM was treated with diisopropylethylamine (78.4 mL; 0.52 mmol) and methyl chloroformate (36.2 mL; 0.47 mmol). After stirring at 0° C. for 15 minutes, 4-(1H-1,2,4-triazol-1-yl)aniline (Maybridge, 108 mg; 0.67 mmol) was added and the mixture stirred for 72 hours. The solvent was evaporated and the compound purified by preparative HPLC to give the title compound as a white solid.

$^1$H NMR (400 MHz, CDCl3) δ 10.13 (1H, s), 8.56 (2H, d, J=13.9 Hz), 8.11 (1H, s), 7.93 (2H, d, J=8.6 Hz), 7.70 (2H, d, J=8.6 Hz), 7.36 (1H, s), 3.53 (4H, s), 1.75-1.65 (2H, m), 1.10 (1H, s), 0.97 (3H, t, J=7.4 Hz), 0.58 (2H, d, J=7.7 Hz), 0.35-0.30 (2H, m). MS (ESI+) 378. HPLC (Condition C) Rt 3.70 min (HPLC purity 99.8%).

Example 147

6-[(cyclopropylmethyl)(propyl)amino]-N-[4-(1H-imidazol-1-ylmethyl)phenyl]pyrimidine-4-carboxamide

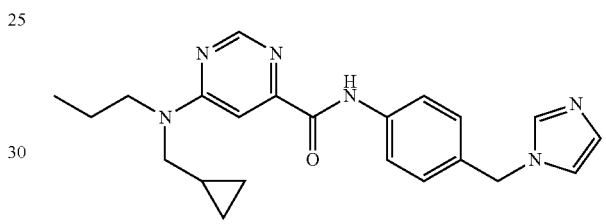

A cooled (0° C.) solution of 6-(cyclopropylmethyl(propyl) amino)pyrimidine-4-carboxylic acid (Intermediate 21, 112 mg; 0.45 mmol) in DCM was treated with diisopropylethylamine (78.4 mL; 0.52 mmol) and methyl chloroformate (36.2 mL; 0.47 mmol). After stirring at 0° C. for 15 minutes, 4-(1H-imidazol-1-ylmethyl)aniline (Maybridge, 117 mg; 0.67 mmol) was added and the mixture stirred for 72 hours. The solvent was evaporated and the compound purified by preparative HPLC to give the title compound as a white solid.

$^1$H NMR (400 MHz, CDCl3) δ 10.01 (1H, s), 8.56 (1H, s), 7.76 (2H, d, J=8.2 Hz), 7.55 (1H, s), 7.35 (1H, s), 7.19 (2H, d, J=8.2 Hz), 7.09 (1H, s), 6.91 (1H, s), 5.11 (2H, s), 3.52 (4H, s), 1.75-1.60 (2H, m), 1.08 (1H, m), 0.96 (3H, t, J=7.3 Hz), 0.57 (2H, d, J=7.7 Hz), 0.35-0.29 (2H, m). MS (ESI+) 391. HPLC (Condition C) Rt 2.32 min (HPLC purity 99.7%).

Example 148

6-[(cyclopropylmethyl)(propyl)amino]-N-[3-(1H-pyrazol-1-ylmethyl)phenyl]pyrimidine-4-carboxamide

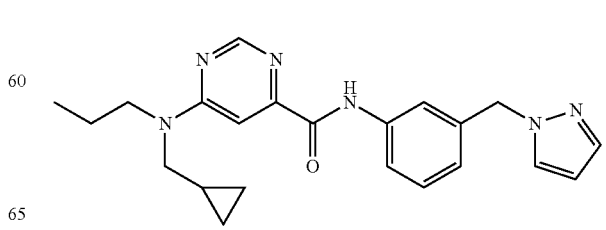

A cooled (0° C.) solution of 6-(cyclopropylmethyl(propyl) amino)pyrimidine-4-carboxylic acid (Intermediate 21, 112 mg; 0.45 mmol) in DCM was treated with diisopropylethylamine (78.4 mL; 0.52 mmol) and methyl chloroformate (36.2 mL; 0.47 mmol). After stirring at 0° C. for 15 minutes, 3-(1H-pyrazol-1-ylmethyl)aniline (Flrochem, 117 mg; 0.67 mmol) was added and the mixture stirred for 72 hours. The solvent was evaporated and the compound purified by preparative HPLC to give the title compound as a white solid.

$^1$H NMR (400 MHz, CDCl3) δ 9.97 (1H, s), 8.55 (1H, d, J=1.1 Hz), 7.69 (2H, d, J=9.6 Hz), 7.57 (1H, d, J=1.8 Hz), 7.43 (1H, d, J=2.3 Hz), 7.35 (2H, t, J=7.7 Hz), 6.99 (1H, d, J=7.6 Hz), 6.30 (1H, t, J=2.1 Hz), 5.35 (2H, s), 3.52 (4H, s), 1.74-1.63 (2H, m), 1.08 (1H, m), 0.96 (3H, t, J=7.4 Hz), 0.56 (2H, d, J=7.7 Hz), 0.34-0.28 (2H, m). MS (ESI+) 391. HPLC (Condition C) Rt 3.93 min (HPLC purity 99.4%).

Example 149

6-[(cyclopropylmethyl)(propyl)amino]-N-[3-(1H-pyrazol-3-yl)phenyl]pyrimidine-4-carboxamide

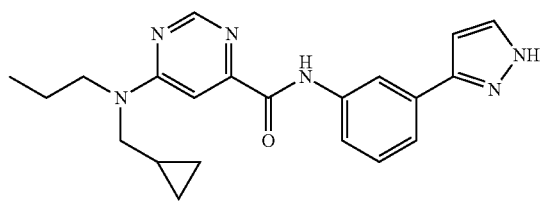 [SMILES: CCCN(CC1CC1)c1cc(C(=O)Nc2cccc(-c3cc[nH]n3)c2)ncn1]

A cooled (0° C.) solution of 6-(cyclopropylmethyl(propyl) amino)pyrimidine-4-carboxylic acid (Intermediate 21, 112 mg; 0.45 mmol) in DCM was treated with diisopropylethylamine (78.4 mL; 0.52 mmol) and methyl chloroformate (36.2 mL; 0.47 mmol). After stirring at 0° C. for 15 minutes, 3-(1H-pyrazol-3-yl)aniline (Apollo, 107 mg; 0.67 mmol) was added and the mixture stirred for 72 hours. The solvent was evaporated and the compound purified by preparative HPLC to give the title compound as a white solid.

$^1$H NMR (400 MHz, CDCl3) δ 10.08 (1H, br s), 8.58 (1H, s), 8.19 (1H, s), 7.76 (1H, d, J=8.0 Hz), 7.64 (1H, d, J=2.3 Hz), 7.57 (1H, d, J=7.7 Hz), 7.49-7.34 (2H, m), 6.67 (1H, d, J=2.3 Hz), 3.53 (4H, s), 1.75-1.63 (2H, m), 1.09 (1H, s), 0.97 (3H, t, J=7.4 Hz), 0.57 (2H, d, J=7.7 Hz), 0.35-0.29 (2H, m). MS (ESI-) 375. HPLC (Condition C) Rt 3.75 min (HPLC purity 99.9%).

Example 150

6-[(cyclopropylmethyl)(propyl)amino]-N-{4-[(2-oxo-1,3-oxazolidin-4-yl)methyl]phenyl}pyrimidine-4-carboxamide

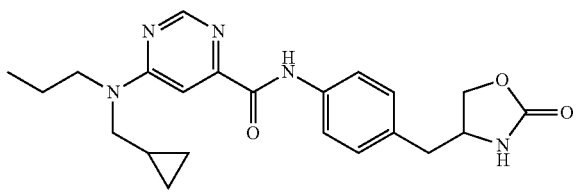 [SMILES: CCCN(CC1CC1)c1cc(C(=O)Nc2ccc(CC3COC(=O)N3)cc2)ncn1]

A cooled (0° C.) solution of 6-(cyclopropylmethyl(propyl) amino)pyrimidine-4-carboxylic acid (Intermediate 21, 112 mg; 0.45 mmol) in DCM was treated with diisopropylethylamine (78.4 mL; 0.52 mmol) and methyl chloroformate (36.2 mL; 0.47 mmol). After stirring at 0° C. for 15 minutes, 4-[(2-oxo-1,3-oxazolidin-4-yl)methyl]aniline (Specs, 130 mg; 0.67 mmol) was added and the mixture stirred for 72 hours. The solvent was evaporated and the compound purified by preparative HPLC to give the title compound as a white solid.

$^1$H NMR (400 MHz, CDCl3) δ 9.98 (1H, s), 8.57 (1H, s), 7.74 (2H, d, J=8.0 Hz), 7.35 (1H, s), 7.20 (2H, d, J=8.1 Hz), 5.02 (1H, s), 4.49 (1H, t, J=8.3 Hz), 4.20-4.06 (2H, m), 3.52 (4H, s), 2.93-2.80 (2H, m), 1.74-1.64 (2H, m), 1.08 (1H, s), 0.97 (3H, t, J=7.4 Hz), 0.56 (2H, s), 0.34-0.29 (2H, m). MS (ESI+) 410. HPLC (Condition C) Rt 3.48 min (HPLC purity 99.5%).

Example 151

6-[(cyclopropylmethyl)(propyl)amino]-N-(3-fluoro-4-morpholin-4-ylphenyl)pyrimidine-4-carboxamide

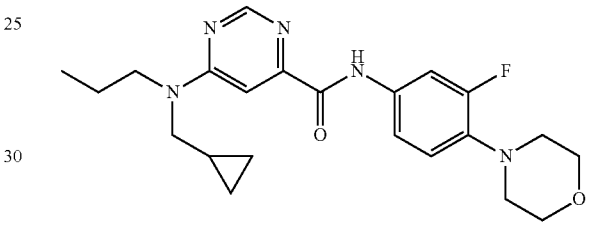

A cooled (0° C.) solution of 6-(cyclopropylmethyl(propyl) amino)pyrimidine-4-carboxylic acid (Intermediate 21, 112 mg; 0.45 mmol) in DCM was treated with diisopropylethylamine (78.4 mL; 0.52 mmol) and methyl chloroformate (36.2 mL; 0.47 mmol). After stirring at 0° C. for 15 minutes, 3-fluoro-4-morpholin-4-yl aniline (Bionet, 132 mg; 0.67 mmol) was added and the mixture stirred for 72 hours. The solvent was evaporated and the compound purified by preparative HPLC to give the title compound as a white solid.

$^1$H NMR (400 MHz, CDCl3) δ 9.91 (1H, s), 8.55 (1H, s), 7.71 (1H, dd, J=14.1, 2.1 Hz), 7.33 (2H, d, J=7.8 Hz), 6.94 (1H, t, J=8.9 Hz), 3.90-3.86 (4H, m), 3.52 (4H, s), 3.08 (4H, t, J=4.4 Hz), 1.74-1.64 (2H, m), 1.08 (1H, s), 0.96 (3H, t, J=7.3 Hz), 0.56 (2H, d, J=7.8 Hz), 0.31 (2H, d, J=5.3 Hz). MS (ESI+) 414. HPLC (Condition C) Rt 4.28 min (HPLC purity 99.5%).

Example 152

6-[(cyclopropylmethyl)(propyl)amino]-N-[3-(1H-1,2,4-triazol-1-ylmethyl)phenyl]pyrimidine-4-carboxamide

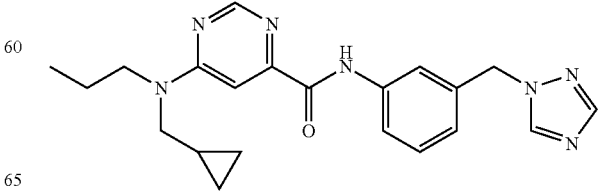

A cooled (0° C.) solution of 6-(cyclopropylmethyl(propyl) amino)pyrimidine-4-carboxylic acid (Intermediate 21, 112 mg; 0.45 mmol) in DCM was treated with diisopropylethylamine (78.4 mL; 0.52 mmol) and methyl chloroformate (36.2 mL; 0.47 mmol). After stirring at 0° C. for 15 minutes, 3-(1H-1,2,4-triazol-1-ylmethyl)aniline (Maybridge, 117 mg; 0.67 mmol) was added and the mixture stirred for 72 hours. The solvent was evaporated and the compound purified by preparative HPLC to give the title compound as a white solid.

$^1$H NMR (400 MHz, CDCl3) δ 10.01 (1H, s), 8.56 (1H, s), 8.10 (1H, s), 7.99 (1H, s), 7.83 (1H, s), 7.67 (1H, d, J=8.2 Hz), 7.44-7.32 (2H, m), 7.04 (1H, d, J=7.6 Hz), 5.37 (2H, s), 3.52 (4H, s), 1.76-1.59 (2H, m), 1.08 (1H, m), 0.97 (3H, t, J=7.4 Hz), 0.57 (2H, d, J=7.9 Hz), 0.35-0.29 (2H, m). MS (ESI+) 392. HPLC (Condition C) Rt 3.46 min (HPLC purity 97.8%).

Example 153

6-[(cyclopropylmethyl)(propyl)amino]-N-[3-(1H-imidazol-1-ylmethyl)phenyl]pyrimidine-4-carboxamide

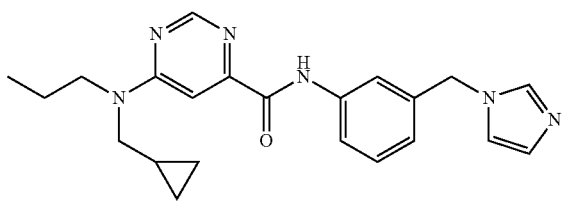

A cooled (0° C.) solution of 6-(cyclopropylmethyl(propyl) amino)pyrimidine-4-carboxylic acid (Intermediate 21, 112 mg; 0.45 mmol) in DCM was treated with diisopropylethylamine (78.4 mL; 0.52 mmol) and methyl chloroformate (36.2 mL; 0.47 mmol). After stirring at 0° C. for 15 minutes, 3-(1H-imidazol-1-ylmethyl)aniline (Maybridge, 117 mg; 0.67 mmol) was added and the mixture stirred for 72 hours. The solvent was evaporated and the compound purified by preparative HPLC to give the title compound as a white solid.

$^1$H NMR (400 MHz, CDCl3) δ 9.99 (1H, s), 8.56 (1H, s), 7.72 (1H, s), 7.67-7.56 (2H, m), 7.40-7.32 (2H, m), 7.11 (1H, s), 6.96-6.89 (2H, m), 5.14 (2H, s), 3.52 (4H, s), 1.74-1.64 (2H, m), 1.09 (1H, s), 0.97 (3H, t, J=7.3 Hz), 0.57 (2H, d, J=7.8 Hz), 0.34-0.29 (2H, m). MS (ESI+) 391. HPLC (Condition C) Rt 2.33 min (HPLC purity 95.7%).

Example 154

N-[4-(azetidin-1-ylmethyl)-2-methylphenyl]-6-[(cyclopropylmethyl)(propyl)amino]pyrimidine-4-carboxamide

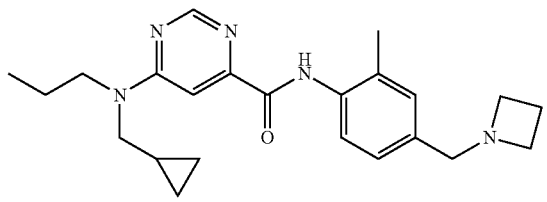 [SMILES: CCCN(CC1CC1)c1cc(C(=O)Nc2ccc(CN3CCC3)cc2C)ncn1]

Azetidine (Aldrich, 17.1 mg; 0.3 mmol) was added to a stirred solution of 6-((cyclopropylmethyl)(propyl)amino)-N-(4-formyl-2-methylphenyl)pyrimidine-4-carboxamide (Intermediate 29, 52.9 mg; 0.15 mmol) in DCM (1 mL). After stirring for 30 minutes sodium triacetoxyborohydride (95.4 mg; 0.45 mmol) was added and the reaction stirred for 18 hours. The reaction was diluted with DCM (6 ml), washed with water (2 ml) and poured through a hydrophobic frit. The organic phase was collected and evaporated to give the product as colourless oil. The crude product was dissolved in methanolic HCl and applied to an SCX cartridge. The cartridge was eluted with methanol followed by NH3 in methanol to elute the product. Evaporation gave the title compound as a colourless oil.

$^1$H NMR (400 MHz, CDCl3) δ 10.04 (1H, s), 8.57 (1H, s), 8.21 (1H, d, J=8.1 Hz), 7.37 (1H, s), 7.22-7.15 (2H, m), 3.59 (2H, s), 3.53 (4H, br s), 3.31 (4H, t, J=7.1 Hz), 2.39 (3H, s), 2.12 (2H, m), 1.67 (2H, m), 1.09 (1H, m), 0.96 (3H, t, J=7.3 Hz), 0.56 (2H, d, J=7.7 Hz), 0.32 (2H, m). MS (ESI+) 394. HPLC (Condition C) Rt 2.40 min (HPLC purity 99.1%).

Example 155

In Vitro Assays Receptor Binding Assay

Membranes were prepared from CHO cells expressing S1P1 or S1P3 for use in ligand and 355-GTPγS binding studies. Cells were suspended in 50 mM TRIS, pH 7.4, 2 mM EDTA, 250 mM Sucrose (buffer A) and 1× Complete protease inhibitor cocktail (Roche), and disrupted at 4° C. by nitrogen decompression using a cell disruption bomb (Parr Instrument). Following centrifugation at 1000 RPM for 10 min at 4° C., the supernatant was suspended in buffer A and centrifuged again at 19000 RPM for 60 min at 4° C. The pellet was then suspended in 10 mM HEPES, pH 7.4, 1 mM EDTA, 250 mM Sucrose (Buffer B), and 1× Complete EDTA-free protease inhibitor cocktail and homogenized using a potter. Membranes were flash frozen in liquid nitrogen and stored at −80° C. [33P]sphingosine 1-phosphate (3000 Ci/mmol; American Radiolabeled Chemicals, Inc.) was added to test compounds in DMSO. Membranes and WGA SPA beads (GE Healthcare) were added to give a final volume of 100 μl in 96-well plates with assay concentrations of 25 μM or 10 μM [33P]sphingosine 1-phosphate (respectively for S1P1 or S1P3), 50 mM HEPES, pH 7.5, 5 mM MgCl2, 100 mM NaCl, 0.4% fatty acid-free BSA, 1-5 μg/well of proteins and 100 μg/well of WGA SPA beads. Binding was performed for 60 min at room temperature on a shaker and bound radioactivity was measured on a PerkinElmer 1450 MicroBeta counter. Specific binding was calculated by subtracting remaining radioactivity in the presence of 1000-fold excess of unlabeled S1P. Binding data were analyzed using the GraphPad Prism program.

Measurements of $^{35}$S-GTPγS Binding: Membranes (1 to 10 μg protein) prepared as described above, were incubated in 96-well Scintiplates (PerkinElmer) with test compounds diluted in DMSO, in 180 μl of 20 mM HEPES, pH 7.4, 10 mM MgCl2, 2 μg/well Saponin, 0.2% fatty acid free BSA (Assay buffer), 140 mM NaCl and 1.7 μM GDP. The assay was initiated with the addition of 20 μl of 1.5 nM [35S]-GTPγS (1100 Ci/mmol; GE Healthcare) in assay buffer. After 60 min incubation at 30° C. on a shaker, plates were centrifuged for 10 min at 2000 RPM. Supernatant was discarded and membrane bound radioactivity was measured on a PerkinElmer 1450 MicroBeta counter. Triplicate samples were averaged and expressed as % response relative to SIP activation in absence of compound (n=2).

The examples disclosed herein have utility as immunoregulatory agents as demonstrated by their activity as potent and selective agonists of the S1P1 receptor over the S1P3 receptor as measured in the assays described above. In particular, the examples disclosed herein possess a selectivity for the S1P1 receptor over the S1P3 receptor as measured by the ratio of EC50 for the S1P1 receptor to the EC50 for the S1P3 receptor as evaluated in the $^{35}$S-GTPγS binding assay described above.

| Compound | | S1P1 Binding Ki (μM) | S1P1 GTPγS EC50 (μM) | S1P3 GTPγS EC50 (μM) |
|---|---|---|---|---|
| 1-1 | 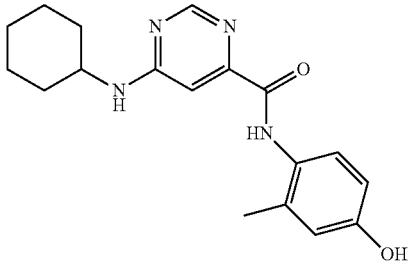 [SMILES: Cc1cc(O)ccc1NC(=O)c1cc(NC2CCCCC2)ncn1] | 0.55 | 1.16 | >30 |
| 1-2 | 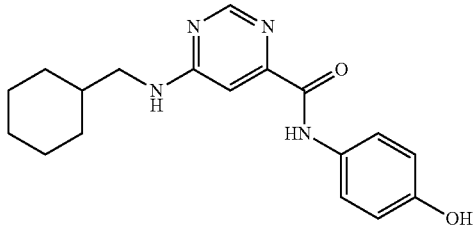 [SMILES: O=C(Nc1ccc(O)cc1)c1cc(NCC2CCCCC2)ncn1] | 3.23 | — | — |
| 1-3 | 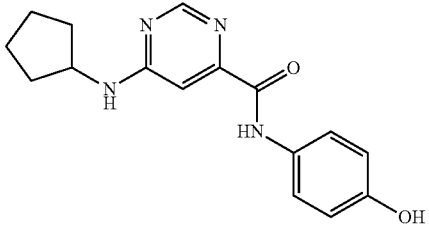 [SMILES: O=C(Nc1ccc(O)cc1)c1cc(NC2CCCC2)ncn1] | 2.13 | 16.70 | — |
| 1-4 | 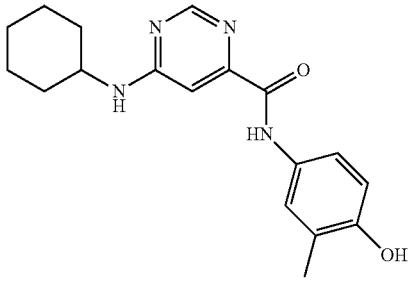 | 0.98 | 0.79 | — |
| 1-5 | 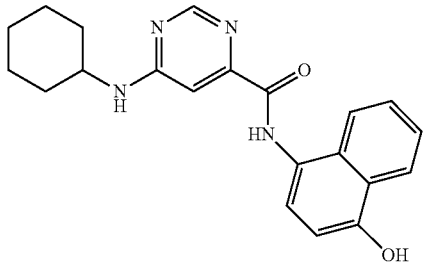 [SMILES: O=C(Nc1ccc(O)c2ccccc12)c1cc(NC2CCCCC2)ncn1] | 0.54 | 0.54 | >30 |

-continued

| Compound | | S1P1 Binding Ki (μM) | S1P1 GTPyS EC50 (μM) | S1P3 GTPyS EC50 (μM) |
|---|---|---|---|---|
| 1-6 | (cyclohexyl-NH-pyrimidine-C(=O)NH-phenyl(Cl)(OH)) | 0.50 | 1.14 | — |
| 1-7 | (cyclohexyl-NH-pyrimidine-C(=O)NH-phenyl(F)(OH)) | 0.34 | 0.44 | >30 |
| 1-8 | (cyclohexyl-NH-pyrimidine-C(=O)NH-phenyl(Cl)(OH)) | 0.38 | 0.39 | >30 |
| 1-9 | (cyclohexyl-NH-pyrimidine-C(=O)NH-dimethylphenyl-OH) | 0.65 | 1.04 | — |
| 1-10 | (cyclohexyl-NH-pyrimidine-C(=O)NH-dimethylphenyl-OH) | 0.74 | 1.44 | — |

-continued

| Compound | | S1P1 Binding Ki (μM) | S1P1 GTPγS EC50 (μM) | S1P3 GTPγS EC50 (μM) |
|---|---|---|---|---|
| 1-11 | (structure) | 3.45 | 3.87 | — |
| 1-12 | (structure) | 3.36 | 19.5 | — |
| 1-13 | (structure) | 0.28 | 0.96 | >30 |
| 1-14 | (structure) | — | 1.58 | — |
| 1-15 | (structure) | — | 0.38 | >30 |

-continued

| Compound | S1P1 Binding Ki (μM) | S1P1 GTPyS EC50 (μM) | S1P3 GTPyS EC50 (μM) |
|---|---|---|---|
| 1-16 | — | 1.07 | 5.23 |
| 1-17 | — | 1.99 | — |
| 1-18 | — | 0.44 | >30 |
| 1-19 | 0.81 | 0.70 | >30 |
| 1-20 | 0.84 | 2.10 | — |
| 1-21 | — | 0.66 | — |

-continued

| Compound | | S1P1 Binding Ki (μM) | S1P1 GTPyS EC50 (μM) | S1P3 GTPyS EC50 (μM) |
|---|---|---|---|---|
| 1-22 | [structure] | — | 0.37 | 2.32 |
| 1-23 | [structure] | — | 0.97 | — |
| 1-24 | [structure] | — | 1.68 | — |
| 1-25 | [structure] | — | 0.4 | >30 |
| 1-26 | [structure] | — | 0.24 | >30 |
| 1-27 | [structure] | — | 0.374 | — |

-continued
| Compound | S1P1 Binding Ki (μM) | S1P1 GTPyS EC50 (μM) | S1P3 GTPyS EC50 (μM) |
|---|---|---|---|
| 1-28 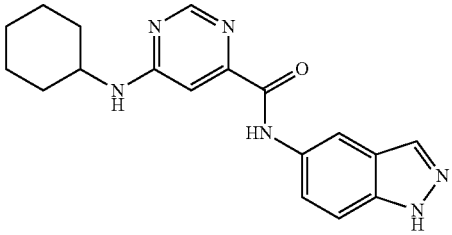 [SMILES: O=C(Nc1ccc2[nH]ncc2c1)c1cc(NC2CCCCC2)ncn1] | 0.458 | 2.71 | >30 |
| 1-29 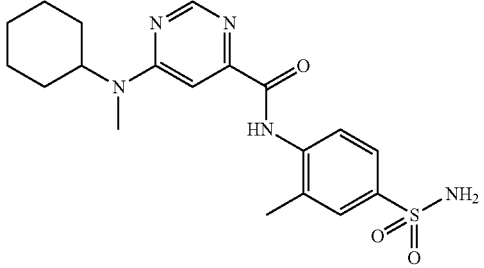 [SMILES: Cc1cc(S(N)(=O)=O)ccc1NC(=O)c1cc(N(C)C2CCCCC2)ncn1] | — | 0.065 | >30 |
| 1-30 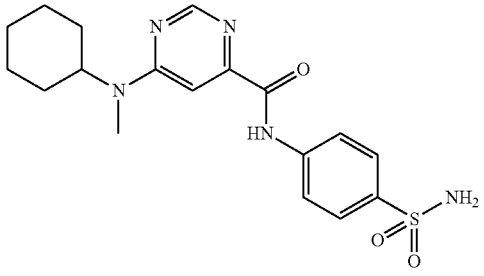 [SMILES: CN(c1cc(C(=O)Nc2ccc(S(N)(=O)=O)cc2)ncn1)C1CCCCC1] | — | 0.674 | — |
| 1-31 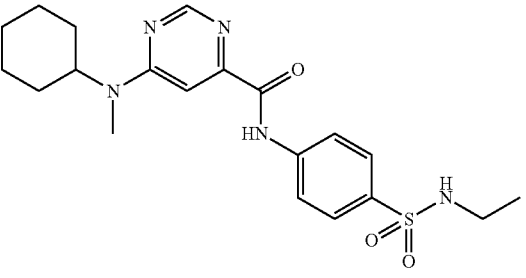 [SMILES: CCNS(=O)(=O)c1ccc(NC(=O)c2cc(N(C)C3CCCCC3)ncn2)cc1] | — | 2 | — |
| 1-32 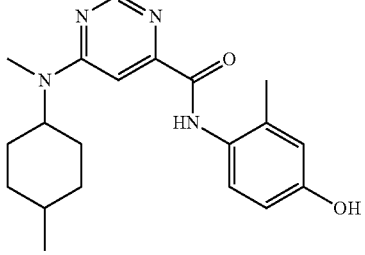 | — | 0.61 | — |

| Compound | S1P1 Binding Ki (μM) | S1P1 GTPyS EC50 (μM) | S1P3 GTPyS EC50 (μM) |
|---|---|---|---|
| 1-33 | — | 0.0246 | 100 |
| 1-34 | — | 0.132 | >20 |
| 1-35 | — | 0.418 | >20 |
| 1-36 | — | 2.92 | >20 |
| 1-37 | — | 0.907 | — |

-continued

| Compound | | S1P1 Binding Ki (μM) | S1P1 GTPyS EC50 (μM) | S1P3 GTPyS EC50 (μM) |
|---|---|---|---|---|
| 1-38 | [structure] | — | 0.002 | 47.5 |
| 1-39 | [structure] | — | 0.211 | 2.33 |
| 1-40 | [structure] | — | 1.52 | >20 |
| 1-41 | [structure] | — | 1.78 | 32 |
| 1-42 | [structure] | — | 2.28 | — |

| Compound | S1P1 Binding Ki (μM) | S1P1 GTPyS EC50 (μM) | S1P3 GTPyS EC50 (μM) |
|---|---|---|---|
| 1-43 | — | 1.35 | — |
| 1-44 | — | 0.009 | >20 |
| 1-45 | — | 0.013 | 0.416 |
| 1-46 | — | 0.019 | 1.16 |
| 1-47 | — | 0.006 | 3.27 |
| 1-48 | — | 0.039 | — |

-continued

| Compound | S1P1 Binding Ki (μM) | S1P1 GTPyS EC50 (μM) | S1P3 GTPyS EC50 (μM) |
|---|---|---|---|
| 1-49 | — | 0.107 | — |
| 1-50 | — | 0.073 | — |
| 1-51 | — | 0.060 | — |
| 1-52 | 2.00 | 4.45 | >30 |
| 1-53 | 1.68 | 1.78 | >30 |

-continued

| Compound | S1P1 Binding Ki (μM) | S1P1 GTPyS EC50 (μM) | S1P3 GTPyS EC50 (μM) |
|---|---|---|---|
| 1-54 | — | 0.0029 | 1.99 |
| 1-55 | 0.0032 | 0.0092 | — |
| 1-56 | 0.007 | 0.021 | >20 |
| 1-57 | — | 0.036 | >20 |
| 1-58 | — | 0.039 | >20 |
| 1-59 | — | 0.558 | — |

-continued

| Compound | | S1P1 Binding Ki (μM) | S1P1 GTPyS EC50 (μM) | S1P3 GTPyS EC50 (μM) |
|---|---|---|---|---|
| 1-60 | [structure] | — | 0.051 | >20 |
| 1-61 | [structure] | — | 0.012 | 0.259 |
| 1-62 | [structure] | 0.002 | 0.003 | 0.062 |
| 1-63 | [structure] | 0.008 | 0.02 | 1.31 |
| 1-64 | [structure] | 1.02 | 8.84 | — |
| 1-65 | [structure] | — | 13.3 | — |

-continued

| Compound | | S1P1 Binding Ki (μM) | S1P1 GTPyS EC50 (μM) | S1P3 GTPyS EC50 (μM) |
|---|---|---|---|---|
| 1-66 | | — | 0.032 | — |
| 1-67 | | — | 0.068 | — |
| 1-68 | | 0.003 | 0.0068 | — |
| 1-69 | | 0.01 | 0.019 | 0.666 |
| 1-70 | | — | 1.11 | — |
| 1-71 | | — | 0.012 | >20 |

-continued

| Compound | S1P1 Binding Ki (μM) | S1P1 GTPyS EC50 (μM) | S1P3 GTPyS EC50 (μM) |
|---|---|---|---|
| 1-72 | — | 0.497 | — |
| 1-73 | — | 0.724 | — |
| 1-74 | — | 2.16 | — |
| 1-75 | — | 2.69 | — |

-continued
| Compound | S1P1 Binding Ki (μM) | S1P1 GTPyS EC50 (μM) | S1P3 GTPyS EC50 (μM) |
|---|---|---|---|
| 1-76 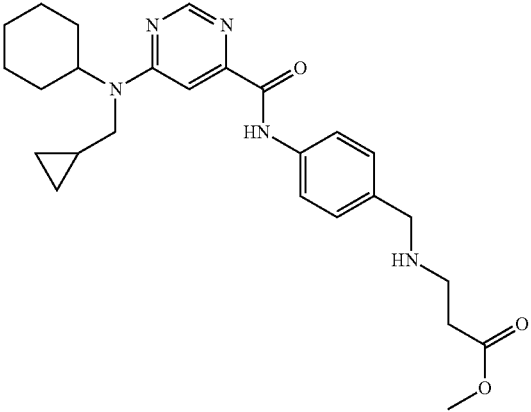 [SMILES: COC(=O)CCNCc1ccc(NC(=O)c2cc(N(CC3CC3)C3CCCCC3)ncn2)cc1] | — | 0.048 | 0.777 |
| 1-77 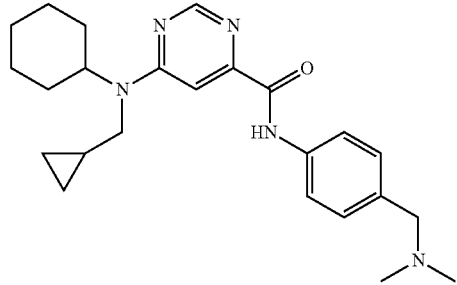 [SMILES: CN(C)Cc1ccc(NC(=O)c2cc(N(CC3CC3)C3CCCCC3)ncn2)cc1] | 0.051 | 0.104 | 1014 |
| 1-78 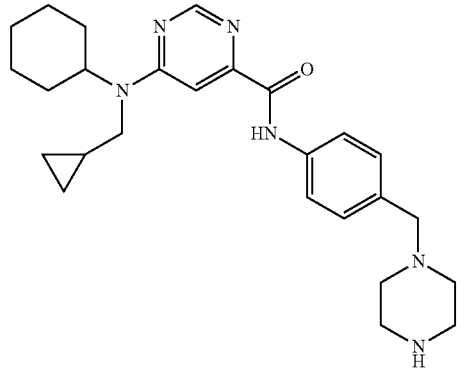 [SMILES: O=C(Nc1ccc(CN2CCNCC2)cc1)c1cc(N(CC2CC2)C2CCCCC2)ncn1] | — | 0.328 | — |
| 1-79 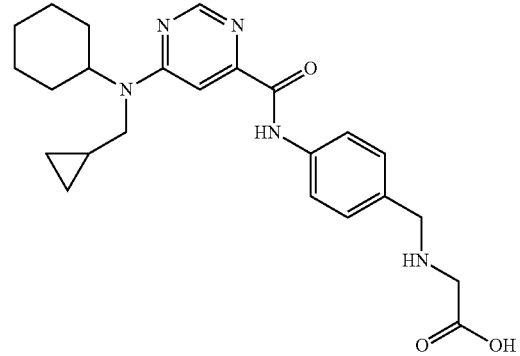 [SMILES: O=C(O)CNCc1ccc(NC(=O)c2cc(N(CC3CC3)C3CCCCC3)ncn2)cc1] | 0.012 | 0.035 | — |

-continued

| Compound | S1P1 Binding Ki (μM) | S1P1 GTPyS EC50 (μM) | S1P3 GTPyS EC50 (μM) |
|---|---|---|---|
| 1-80 | — | 0.287 | 4890 |
| 1-81 | 0.029 | 0.094 | — |
| 1-82 | 0.009 | 0.019 | 1094 |
| 1-83 | — | 1.155 | — |

-continued

| Compound | S1P1 Binding Ki (μM) | S1P1 GTPyS EC50 (μM) | S1P3 GTPyS EC50 (μM) |
|---|---|---|---|
| 1-84 | 0.007 | 0.0029 | 0.236 |
| 1-85 | 0.043 | 0.118 | >20 |
| 1-86 | 2.455 | — | — |
| 1-87 | — | 0.216 | — |
| 1-88 | — | 0.101 | — |

-continued

| Compound | S1P1 Binding Ki (μM) | S1P1 GTPyS EC50 (μM) | S1P3 GTPyS EC50 (μM) |
|---|---|---|---|
| 1-89 | — | 1.49 | — |
| 1-90 | 0.023 | 0.069 | — |
| 1-91 | — | 0.145 | — |
| 1-92 | — | 0.236 | — |
| 1-93 | — | 1.47 | — |
| 1-94 | — | 0.265 | — |

-continued

| Compound | | S1P1 Binding Ki (μM) | S1P1 GTPyS EC50 (μM) | S1P3 GTPyS EC50 (μM) |
|---|---|---|---|---|
| 1-95 | | — | 0.821 | — |
| 1-96 | | — | 0.391 | — |
| 1-97 | | 0.009 | 0.033 | — |
| 1-98 | | — | 0.706 | — |
| 1-99 | | 0.006 | 0.033 | 5.65 |
| 1-100 | | 0.008 | 0.045 | >20 |
| 1-101 | | — | 0.127 | — |

-continued

| Compound | S1P1 Binding Ki (μM) | S1P1 GTPyS EC50 (μM) | S1P3 GTPyS EC50 (μM) |
|---|---|---|---|
| 1-102 | — | 1.230 | — |
| 1-103 | — | 0.208 | — |
| 1-104 | — | 0.517 | — |
| 1-105 | — | 0.0058 | 2.47 |
| 1-106 | — | 0.202 | — |
| 1-107 | — | 0.019 | 3.3 |

-continued

| Compound | S1P1 Binding Ki (μM) | S1P1 GTPyS EC50 (μM) | S1P3 GTPyS EC50 (μM) |
|---|---|---|---|
| 1-108 | — | 0.238 | — |
| 1-109 | — | 0.063 | >20 |
| 1-110 | — | 2.34 | — |
| 1-111 | — | 0.567 | — |
| 1-112 | — | 0.193 | — |
| 1-113 | 0.025 | 0.056 | >20 |

| Compound | S1P1 Binding Ki (μM) | S1P1 GTPyS EC50 (μM) | S1P3 GTPyS EC50 (μM) |
|---|---|---|---|
| 1-114 | — | 1.32 | — |
| 1-115 | — | 2.845 | — |
| 1-116 | — | 3.265 | — |
| 1-117 | — | 1.07 | — |
| 1-118 | — | 6.35 | — |
| 1-119 | — | 5.05 | — |

-continued

| Compound | | S1P1 Binding Ki (μM) | S1P1 GTPyS EC50 (μM) | S1P3 GTPyS EC50 (μM) |
|---|---|---|---|---|
| 1-120 | | — | 0.596 | — |
| 1-121 | | — | 1.015 | — |
| 1-122 | | — | 4.36 | — |
| 1-123 | | — | 0.86 | — |
| 1-124 | | — | 1.5 | — |
| 1-125 | | — | 2.755 | — |
| 1-126 | | — | 0.006 | >20 |

-continued

| Compound | S1P1 Binding Ki (μM) | S1P1 GTPyS EC50 (μM) | S1P3 GTPyS EC50 (μM) |
|---|---|---|---|
| 1-127 | — | 0.048 | >20 |
| 1-128 | — | 0.816 | — |
| 1-129 | — | 1.71 | — |
| 1-130 | — | 0.537 | — |
| 1-131 | — | 1.68 | — |
| 1-132 | — | 0.040 | 0.085 |

-continued

| Compound | S1P1 Binding Ki (μM) | S1P1 GTPyS EC50 (μM) | S1P3 GTPyS EC50 (μM) |
|---|---|---|---|
| 1-133 | — | 0.226 | — |
| 1-134 | — | 0.594 | — |
| 1-135 | — | 3.125 | — |
| 1-136 | — | 2.04 | — |
| 1-137 | — | 0.346 | — |
| 1-138 | — | 0.443 | — |

-continued

| Compound | S1P1 Binding Ki (μM) | S1P1 GTPyS EC50 (μM) | S1P3 GTPyS EC50 (μM) |
|---|---|---|---|
| 1-139 | — | 2.48 | — |
| 1-140 | — | 1.41 | — |
| 1-141 | — | 2.29 | — |
| 1-142 | — | 0.465 | — |
| 1-143 | — | 0.079 | — |
| 1-144 | — | 1.54 | — |
| 1-145 | — | 0.055 | — |

-continued

| Compound | S1P1 Binding Ki (μM) | S1P1 GTPyS EC50 (μM) | S1P3 GTPyS EC50 (μM) |
|---|---|---|---|
| 1-146 | — | 0.279 | — |
| 1-147 | — | 0.038 | — |
| 1-148 | — | 1.05 | — |
| 1-149 | — | 0.481 | — |
| 1-150 | — | 0.268 | — |
| 1-151 | — | 0.604 | — |
| 1-152 | — | 1.12 | — |

| Compound | S1P1 Binding Ki (µM) | S1P1 GTPyS EC50 (µM) | S1P3 GTPyS EC50 (µM) |
|---|---|---|---|
| 1-153 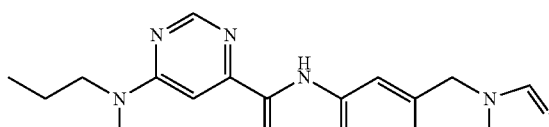 | — | 0.481 | — |
| 1-154 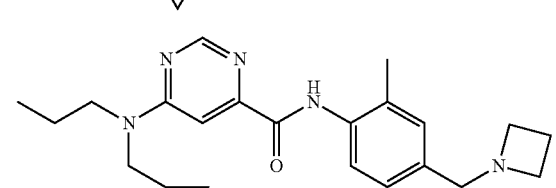 | — | 0.807 | — |

Example 156

Animal Models Evaluating the IN Vivo Efficacy of S1P Agonists Model OF S1P Agonists-Induced Lymphopenia in Mice Female C57BL/6 mice (Elevage Janvier) (8 week old) receive S1P agonists by oral route. Blood is sampled in heparinized (100 IU/kg, ip) mice by intracardiac or retroorbital puncture under isoflurane anesthesia 2 to 120 hrs after drug treatment. The white blood cells (lymphocytes and neutrophils) are counted using a Beckman/Coulter counter. The quality of blood sampling is assessed by counting erythrocytes and platelets.

Model of MOG-Induced Experimental Autoimmune Encephalomyelytis (EAE) in Mice EAE was induced in 9 weeks old female mice (C57BL/6, Elevage Janvier) by an immunization against MOG. The mice received Pertussis toxin (Alexis, 300 ng/mouse in 200 µl of PBS) by ip route and 100 µl of an emulsion containing MOG35-55 peptide (NeoMPS, 200 µg/mouse), *Mycobacterium Tuberculosis* (0.25 mg/mouse) in Complete Freund's Adjuvant (DIFCO) by subcutaneous injection into the back. Two days later an additional injection of Pertussis toxin (Alexis, 300 ng/mouse in 200 µl of PBS) was done by ip route. After EAE induction, mice were weighed daily and the neurological impairment was quantified using a 15-points clinical scale assessing the paralysis (tail, hind limbs and fore limbs), the incontinency and the death.

Clinical Score

1—Tail
  Score=0 A normal mouse holds its tail erect when moving.
  Score=1 If the extremity of the tail is flaccid with a tendency to fall.
  Score=2 If the tail is completely flaccid and drags on the table.

2—Hind Limbs
  Score=0 A normal mouse has an energetic walk and doesn't drag his paws.
  Score=1 Either one of the following tests is positive:
  a—Flip test: while holding the tail between thumb and index finger, flip the animal on his back and observe the time it takes to right itself. A healthy mouse will turn itself immediately. A delay suggests hind-limb weakness.
  b—Place the mouse on the wire cage top and observe as it crosses from one side to the other. If one or both limbs frequently slip between the bars we consider that there is a partial paralysis.
  Score=2 Both previous tests are positive.
  Score=3 One or both hind limbs show signs of paralysis but some movements are preserved; for example: the animal can grasp and hold on to the underside of the wire cage top for a short moment before letting go.
  Score=4 When both hind legs are paralyzed and the mouse drags them when moving.

3—Fore Limbs:
  Score=0 A normal mouse uses his front paws actively for grasping and walking and holds his head erect.
  Score=1 Walking is possible but difficult due to a weakness in one or both of the paws, for example, the front paws are considered weak when the mouse has difficulty grasping the underside of the wire top cage. Another sign of weakness is head drooping.
  Score=2 When one forelimb is paralyzed (impossibility to grasp and the mouse turns around the paralyzed limb). At this time the head has also lost much of its muscle tone.
  Score=3 Mouse cannot move, and food and water are unattainable.

4—Bladder:
  Score=0 A normal mouse has full control of his bladder.
  Score=1 A mouse is considered incontinent when his lower body is soaked with urine.

5—Death:
  Score=15

The final score for each animal is determined by the addition of all the above-mentioned categories. The maximum score for live animals is 10.

At day 12 (first signs of paralysis) the mice were stratified in experimental groups (n=10) according to the clinical score and the body weight loss. The semi-curative treatment started at day 14.

The following examples relate to pharmaceutical compositions:

Example A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C

Solution

A solution is prepared from 1 g of an active ingredient of the formula I, 9.38 g of NaH2PO4.2H2O, 28.48 g of Na2HPO4.12 H2O and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active ingredient of the formula I are mixed with 99.5 g of Vaseline under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

Example F

Coated Tablets

Tablets are pressed analogously to Example E and subsequently coated in a conventional manner with a coating of sucrose, potato starch, talc, traga-canth and dye.

Example G

Capsules 2 kg of active ingredient of the formula I are introduced into hard gelatine capsules in a conventional manner in such a way that each capsule con-tains 20 mg of the active ingredient.

Example H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

We claim:
1. A method of treating an immunoregulatory abnormality comprising the administration of a composition to a subject having said abnormality, said composition comprising compound according to formula (I):

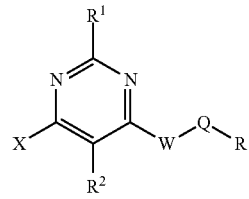

wherein
X is $NR^aR^b$, $SR^b$ or Hal,
$R^a$ is H or A,
$R^b$ is A,
A is a branched or linear alkyl having 1 to 12 C-atoms, wherein one or more H-atoms may be replaced by Hal, $OR^3$, $COOR^3$, CN or $N(R^3)_2$ and wherein one or more non-adjacent $CH_2$-groups may be replaced by O, $NR^3$, S or $SO_2$ and/or by —CH═CH—groups, or A is a cycloalkyl or cycloalkylalkylene having 3-7 ring C atoms,
Hal is F, Cl, Br or I,
W is C═O, C═S, $SO_2$ or SO,
Q is $NR^3$, —O— or —S—, R is Het,
Het denotes a bicyclic, aromatic heterocyclic ring having 2 N atoms which may be unsubstituted, monosubstituted, disubstituted or trisubstituted by Hal, A, $OR^3$, —$[C(R^3)_2]_n$—$OR^3$, $N(R^3)_2$, —$[C(R^3)_2]_n$—$N(R^3)_2$, $NO_2$, CN, $COOR^3$, $CF_3$, $OCF_3$, $CON(R^3)_2$, $NR^3COA$, $NR^3CON(R^3)_2$, —$[C(R^3)_2]_n$—Het, —$[C(R^3)_2]_n$—Ar, —$[C(R^3)_2]_n$cycloalkyl, —$[C(R^3)_2]_n$—$CON(R^3)_2$, $[C(R^3)_2]_n$—$COOR^3$, —$[C(R^3)_2]_n$—$NR^3$—$[C(R^3)_2]_n$—$CO_2R^3$, —$[C(R^3)_2]_n$—$NR^3$—$[C(R^3)_2]_n$—$OR^3$, —$SO_2$—$[C(R^3)_2]_n$—$CO_2R^3$, —$SO_2$—$N(R^3)_24[C(R^3)_2]_n$—$CO_2R^3$, —$[C(R^3)_2]_n$—$SO_2$—$[C(R^3)_2]_n$—$CO_2R^3$, —$SO_2$—$[C(R^3)_2]_n$—$OR^3$, —$SO_2$—$N(R^3)_2$—$[C(R^3)_2]_n$—$OR^3$, —$[C(R^3)_2]_n$—$SO_2$—$[C(R^3)_2]_n$—$OR^3$, $NR^3CON(R^3)_2$, $NR^3SO_2A$, $COR^3$, $SO_2N(R^3)_2$, $SO_2N(R^3)A$, SOA, $SONR^3A$, or $SO_2A$, and/or —O[$C(R^3)_2]_n$—$COOR^3$, R$^a$ is H or A,
R$^2$ is H, A or Hal,
R$^3$ is H or A, and
N is 0, 1, 2, 3, 4, 5, 6, 7 or 8, or pharmaceutically acceptable derivatives, solvates, tautomers, salts, stereoisomers or mixtures thereof.

2. The method according to claim 1, wherein the immunoregulatory abnormality is an autoimmune or chronic inflammatory disease selected from the group consisting of: chronic rheumatoid arthritis, multiple sclerosis, and rheumatoid arthritis.

3. The method according to claim 1, wherein Het denotes one of the following groups:

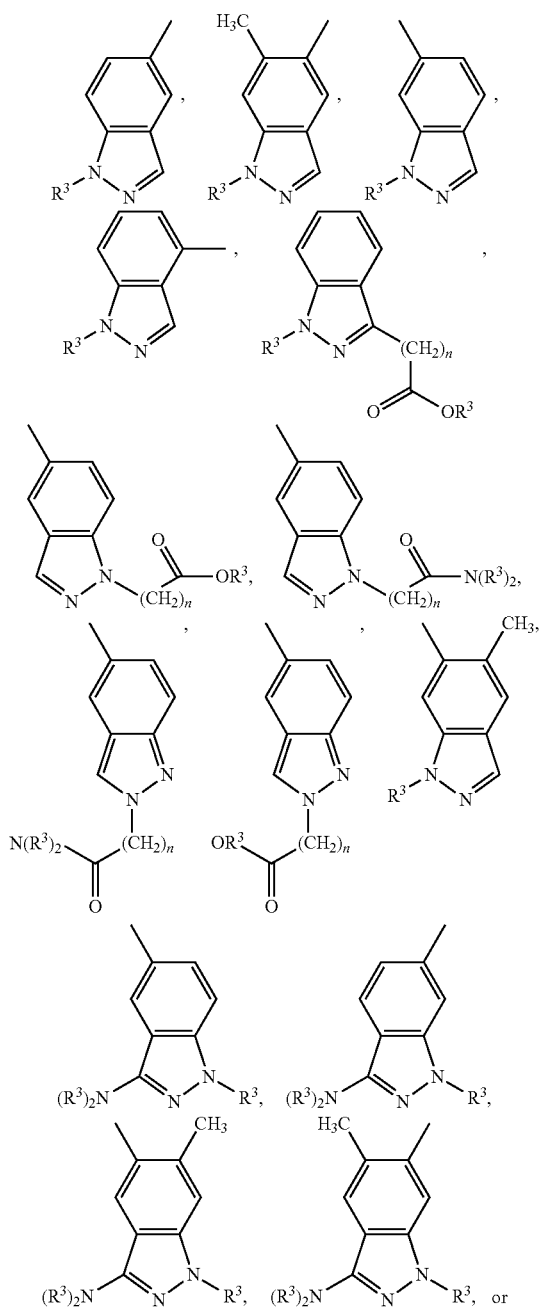

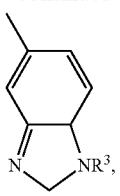

wherein m is 1, 2, or 3, n is 0, 1, 2 or 3, and R$^3$ is as defined in claim 1.

4. The method according to claim 1, wherein said compound is:

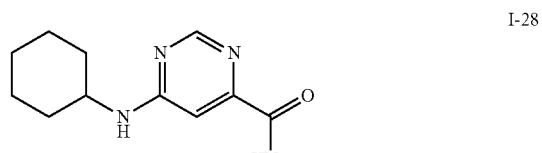

I-28

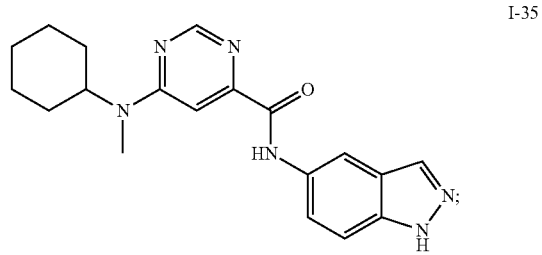 [SMILES: CN(c1cc(C(=O)Nc2ccc3[nH]ncc3c2)ncn1)C1CCCCC1]

I-35

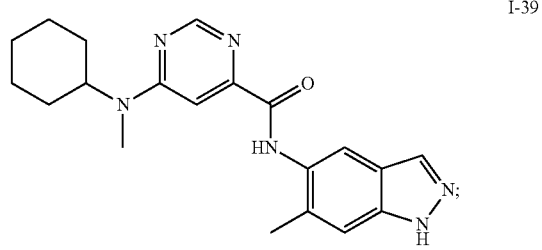 [SMILES: Cc1cc2[nH]ncc2cc1NC(=O)c1cc(N(C)C2CCCCC2)ncn1]

I-39

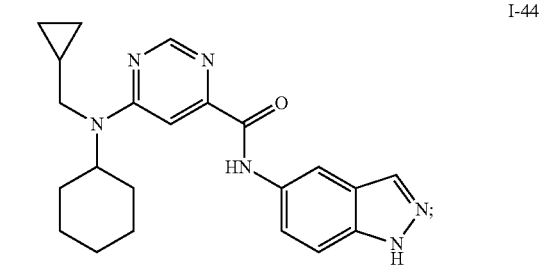

I-44

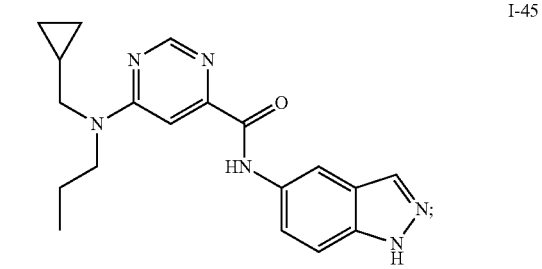

I-45

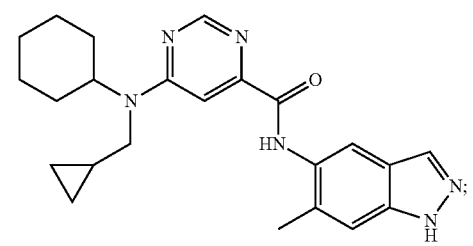
I-47
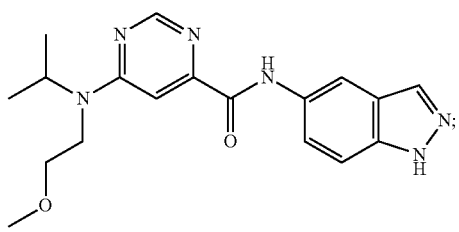
I-87
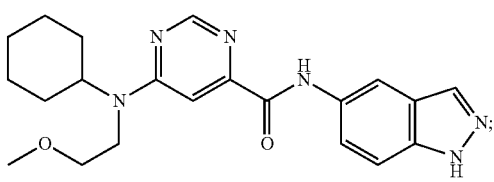
I-66
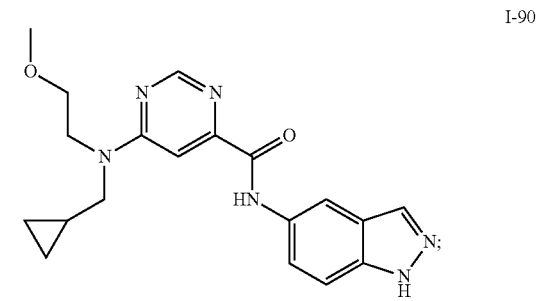
I-90
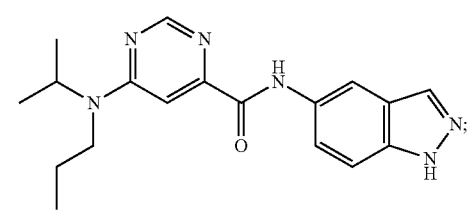
I-67
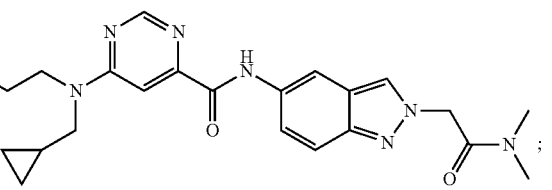
I-114
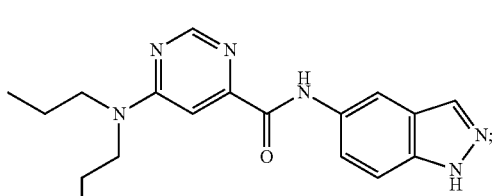
I-68
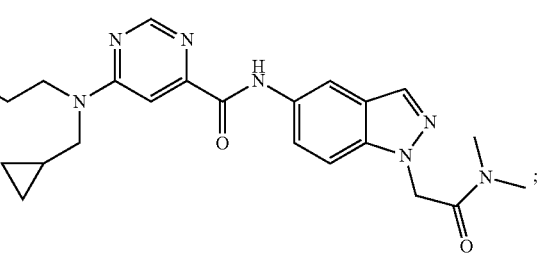
I-115
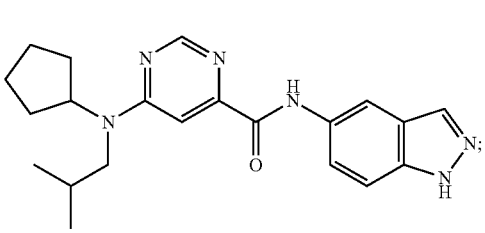
I-69
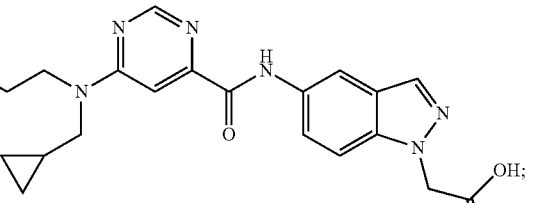
I-116
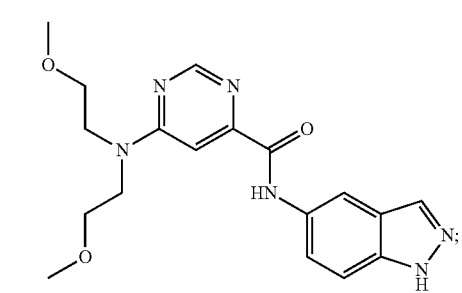
I-70
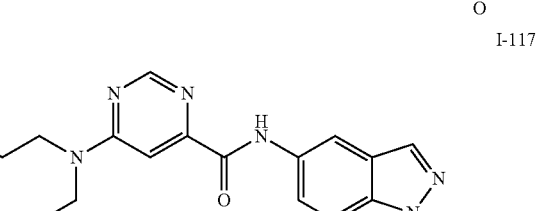
I-117
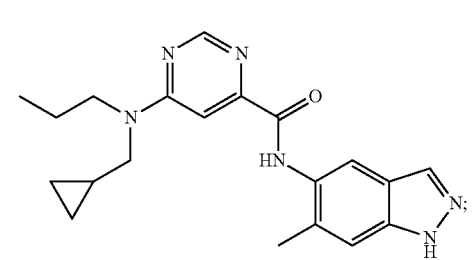
I-71

-continued
I-118
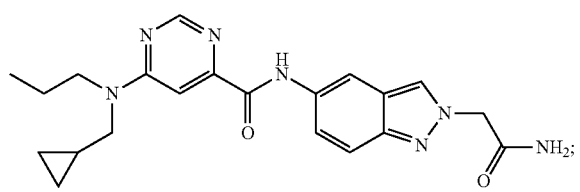
I-120
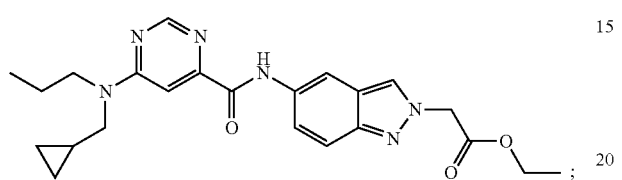
I-121
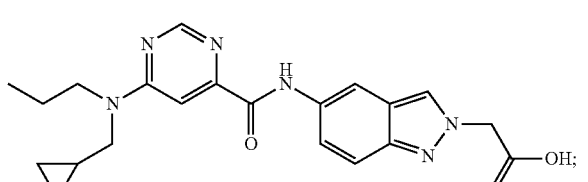
I-123
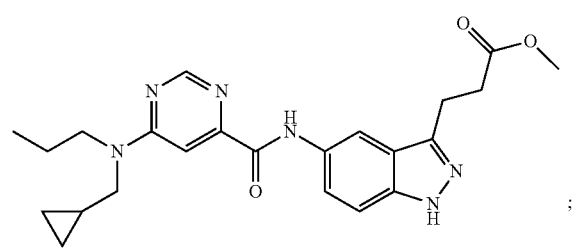
-continued
I-125
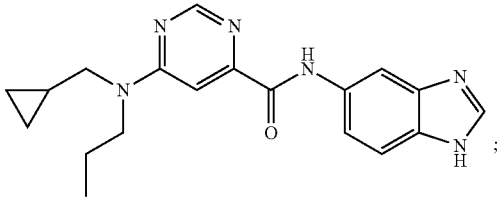
I-127
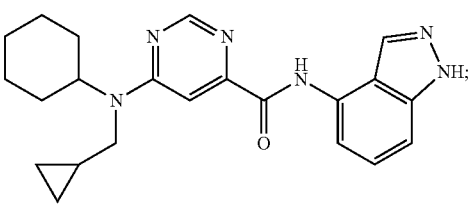
I-129
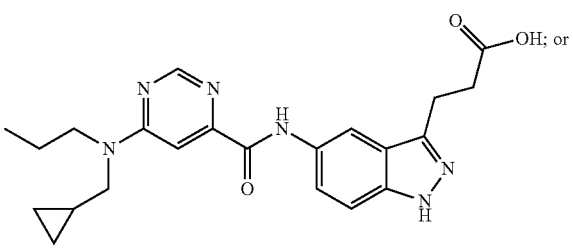
I-134
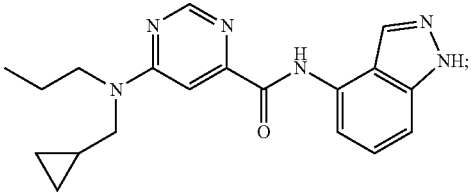
or pharmaceutically acceptable derivatives, solvates, tautomers, salts, stereoisomers or mixtures thereof.
* * * * *